(12) United States Patent
Dai et al.

(10) Patent No.: US 9,243,002 B2
(45) Date of Patent: Jan. 26, 2016

(54) TETRACYCLIC HETEROCYCLE COMPOUNDS AND METHODS OF USE THEREOF FOR THE TREATMENT OF HEPATITIS C

(71) Applicant: Merck Sharp & Dohme Corp., Rahway, NJ (US)

(72) Inventors: Xing Dai, Cranford, NJ (US); Hong Liu, Hillsborough, NJ (US); Anandan Palani, Bridgewater, NJ (US); Shuwen He, Fanwood, NJ (US); Linda L. Brockunier, Orange, NJ (US); Ravi Nargund, East Brunswick, NJ (US); Karen Marcantonio, New York, NY (US); Nicolas Zorn, Durmenach (FR); Dong Xiao, Warren, NJ (US); Xuanjia Peng, Shanghai (CN); Peng Li, Shanghai (CN); Tao Guo, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/766,462

(22) PCT Filed: Feb. 3, 2014

(86) PCT No.: PCT/US2014/014361
§ 371 (c)(1),
(2) Date: Aug. 7, 2015

(87) PCT Pub. No.: WO2014/123793
PCT Pub. Date: Aug. 14, 2014

(65) Prior Publication Data
US 2015/0361101 A1    Dec. 17, 2015

(30) Foreign Application Priority Data

Feb. 7, 2013   (CN) .................. PCT/CN2013/000128

(51) Int. Cl.
| | | |
|---|---|---|
| A61K 31/4375 | (2006.01) |
| C07D 471/12 | (2006.01) |
| C07D 519/00 | (2006.01) |
| A61K 45/06 | (2006.01) |
| C07D 471/14 | (2006.01) |
| A61K 31/5025 | (2006.01) |
| A61K 31/519 | (2006.01) |
| A61K 31/55 | (2006.01) |
| C07D 471/22 | (2006.01) |
| C07D 471/04 | (2006.01) |
| C07D 471/20 | (2006.01) |
| A61K 31/438 | (2006.01) |

(52) U.S. Cl.
CPC .......... *C07D 519/00* (2013.01); *A61K 31/438* (2013.01); *A61K 31/4375* (2013.01); *A61K 31/5025* (2013.01); *A61K 31/519* (2013.01); *A61K 31/55* (2013.01); *A61K 45/06* (2013.01); *C07D 471/04* (2013.01); *C07D 471/14* (2013.01); *C07D 471/20* (2013.01); *C07D 471/22* (2013.01)

(58) Field of Classification Search
USPC ............. 514/285, 257, 214; 546/70; 544/246; 540/579
See application file for complete search history.

(56) References Cited

U.S. PATENT DOCUMENTS

| | | |
|---|---|---|
| 6,777,392 B2 | 8/2004 | Maurya et al. |
| 7,105,499 B2 | 9/2006 | Carroll et al. |
| 7,112,600 B1 | 9/2006 | Hashimoto et al. |
| 7,125,855 B2 | 10/2006 | Bhat et al. |
| 7,202,224 B2 | 4/2007 | Eldrup et al. |
| 2003/0203948 A1 | 10/2003 | Fujishita et al. |
| 2004/0067901 A1 | 4/2004 | Bhat et al. |
| 2004/0110717 A1 | 6/2004 | Carroll et al. |

(Continued)

FOREIGN PATENT DOCUMENTS

| | | |
|---|---|---|
| WO | WO0147883 | 7/2001 |
| WO | WO0177091 | 10/2001 |

(Continued)

OTHER PUBLICATIONS

Carroll et al., Inhibition of Hepatitis C Virus RNA Replication by 2′-Modified Nucleoside Analogs, J. Biol. Chem., 2003, 11979-11984, 278(14).

*Primary Examiner* — Charanjit Aulakh
(74) *Attorney, Agent, or Firm* — Anna L. Cocuzzo; Alysia A. Finnegan

(57) ABSTRACT

The present invention relates to compounds of formula I that are useful as hepatitis C virus (HCV) NS5B polymerase inhibitors, the synthesis of such compounds, and the use of such compounds for inhibiting HCV NS5B polymerase activity, for treating or preventing HCV infections and for inhibiting HCV viral replication and/or viral production in a cell-based system.

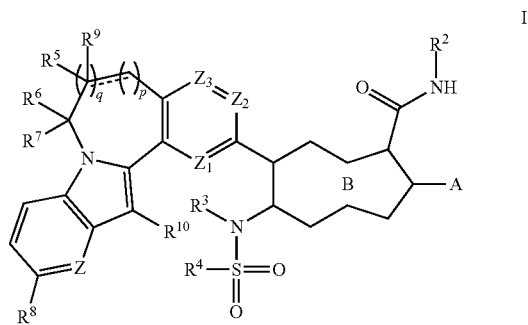

17 Claims, No Drawings

(56) References Cited

U.S. PATENT DOCUMENTS

| | | |
|---|---|---|
| 2006/0100262 A1 | 5/2006 | Conte et al. |
| 2008/0045498 A1 | 2/2008 | Griffith et al. |
| 2009/0048239 A1 | 2/2009 | Conte et al. |
| 2010/0093694 A1 | 4/2010 | Yeung et al. |
| 2011/0256099 A1 | 10/2011 | Yeung et al. |
| 2012/0328569 A1 | 12/2012 | McComas et al. |

FOREIGN PATENT DOCUMENTS

| | | |
|---|---|---|
| WO | WO0204425 | 1/2002 |
| WO | WO0206246 | 1/2002 |
| WO | WO0220497 | 3/2002 |
| WO | WO0257287 | 7/2002 |
| WO | WO0257425 | 7/2002 |
| WO | WO03068244 | 8/2003 |
| WO | WO2004000858 | 12/2003 |
| WO | WO2004003138 | 1/2004 |
| WO | WO2004007512 | 1/2004 |
| WO | WO2004041201 | 5/2004 |
| WO | WO2005003147 | 1/2005 |
| WO | WO2005016927 | 2/2005 |
| WO | WO2006020082 | 2/2006 |
| WO | WO2006066079 | 6/2006 |
| WO | WO2006066080 | 6/2006 |
| WO | WO2008075103 | 6/2008 |
| WO | WO2009010783 | 1/2009 |
| WO | WO2009010785 | 1/2009 |
| WO | WO2011106992 | 9/2011 |
| WO | WO2013033971 | 3/2013 |
| WO | WO2013034048 | 3/2013 |
| WO | WO2014123794 | 8/2014 |
| WO | WO2014123795 | 8/2014 |

TETRACYCLIC HETEROCYCLE COMPOUNDS AND METHODS OF USE THEREOF FOR THE TREATMENT OF HEPATITIS C

FIELD OF THE INVENTION

The present disclosure relates to antiviral compounds that are useful as inhibitors of the hepatitis C virus (HCV) NS5B (non-structural protein 5B) polymerase, compositions comprising such compounds, the use of such compounds for treating HCV infection and/or reducing the likelihood or severity of symptoms of HCV infection, methods for inhibiting the function of the NS5B polymerase, and methods for inhibiting HCV viral replication and/or viral production.

CROSS-REFERENCE TO RELATED APPLICATIONS

This application is a §371 National Stage Application of PCT/US2014/014361, international filing date of Feb. 3, 2014, which claims the benefit of International Application No. PCT/CN2013/000128, filed Feb. 7, 2013, now expired.

BACKGROUND OF THE INVENTION

Hepatitis C virus (HCV) infection is a major health problem that leads to chronic liver disease, such as cirrhosis and hepatocellular carcinoma, in a substantial number of infected individuals. Current treatments for HCV infection include immunotherapy with recombinant interferon-α alone or in combination with the nucleoside analog ribavirin.

Several virally-encoded enzymes are putative targets for therapeutic intervention, including a metalloprotease (NS2-3), a serine protease (NS3, amino acid residues 1-180), a helicase (NS3, full length), an NS3 protease cofactor (NS4A), a membrane protein (NS4B), a zinc metalloprotein (NS5A) and an RNA-dependent RNA polymerase (NS5B).

One identified target for therapeutic intervention is HCV NS5B polymerase. Sven-Erik Behrens et al., *Identification and properties of the RNA-dependent RNA polymerase of heptatitis C virus*, 15(1) EMBO J. 12-22 (1996). Antagonists of NS5B activity are inhibitors of HCV replication. Steven S. Carroll et al., *Inhibition of Hepatitis C Virus RNA Replication by 2'-Modified Nucleoside Analogs*, 278 (14) J. BIOL. CHEM. 11979-84 (2003).

There is a clear and long-felt need to develop effective therapeutics for treatment of HCV infection. Specifically, there is a need to develop compounds that selectively inhibit HCV viral replication and that would be useful for treating HCV-infected patients.

SUMMARY OF THE INVENTION

The present disclosure relates to novel compounds of formula I and/or pharmaceutically acceptable salts thereof. These compounds are useful, either as compounds or their pharmaceutically acceptable salts (when appropriate), in the inhibition of HCV (hepatitis C virus) NS5B (non-structural 5B) polymerase, the prevention or treatment of one or more of the symptoms of HCV infection, the inhibition of HCV viral replication and/or HCV viral production, and/or as pharmaceutical composition ingredients. As pharmaceutical composition ingredients, these compounds and their salts may be the primary active therapeutic agent, and, when appropriate, may be combined with other therapeutic agents including but not limited to other HCV antivirals, anti-infectives, immuno-modulators, antibiotics or vaccines, as well as the present Standard of Care treatment options for HCV.

In one aspect, the present invention relates to a compound of formula I:

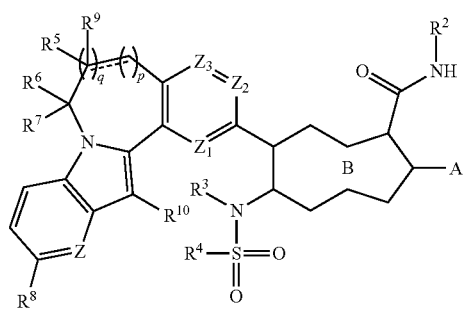

or a pharmaceutically acceptable salt thereof, wherein:

A is a $C_3$-$C_6$ cycloalkyl or an aromatic ring system selected from:
  (i) 5-6 membered monocyclic ring with 0, 1, 2 or 3 heteroatom ring atoms selected from N, S or O, optionally substituted with 1 or 2 substituents independently selected from $C_1$-$C_6$ alkyl, $C_1$-$C_6$ alkoxy, $C_1$-$C_6$ haloalkyl, cyano, oxo, halo, —O—$C_1$-$C_6$ haloalkyl, $C_1$-$C_6$ hydroxyalkyl, $C_3$-$C_6$cycloalkyl, phenyl, pyrrolidinyl, and —O—$C_3$-$C_6$cycloalkyl; and
  (ii) 8-10 membered bicyclic rings with 2 or 3 heteroatom ring atoms selected from N and O;

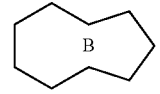

is

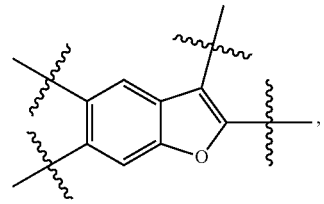

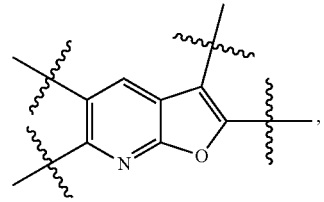

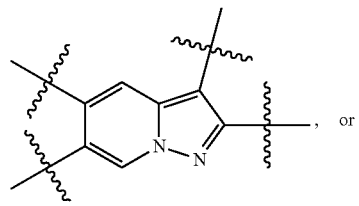

Z is N or CR$^a$;

$Z_1$, $Z_2$ and $Z_3$ are independently selected from CH and N, wherein 1 or 2 of $Z_1$, $Z_2$ and $Z_3$ are N;

p is 0, 1, or 2;

q is 0 or 1;

$R^2$ is hydrogen, $C_1$-$C_6$ alkyl or —O—$C_1$-$C_6$ alkyl;

$R^3$ is hydrogen or $C_1$-$C_6$ alkyl;

$R^4$ is $C_1$-$C_6$ alkyl or —O—$C_1$-$C_6$ alkyl;

$R^5$ is hydrogen, $C_1$-$C_6$ alkyl, —OH, halo, or a 4- to 7-membered heterocycloalkyl substituted with halo;

$R^9$ is hydrogen; or $R^5$ and $R^9$ together with the C to which they are attached form a $C_3$-$C_6$ cycloalkyl, $R^6$ is hydrogen, —OH, $C_1$-$C_6$ alkyl, $C_1$-$C_6$ haloalkyl, $C_1$-$C_6$ hydroxyalkyl, —CH$_2$SO$_2$CH$_3$, —$C_1$-$C_6$-(4- to 6-membered monocyclic heterocycloalkyl);

wherein the 4- to 6-membered monocyclic heterocycloalkyl is optionally substituted with one or two F substituents;

$R^7$ is hydrogen or $C_1$-$C_6$ alkyl;

or $R^6$ and $R^7$ together with the C to which they are attached form an oxo; $R^8$ is hydrogen, halo or —OR$^b$;

$R^{10}$ is hydrogen or $C_1$-$C_6$ alkyl;

$R^a$ is hydrogen, halo, or cyano;

each $R^b$ is independently H or $C_1$-$C_6$ alkyl;

wherein when q is 0, p is 0 or 1;

when q is 1 and p is 2, ≡≡≡ is a single bond; and when ≡≡≡ is a double bond, $R^7$ and $R^9$ are absent.

The present invention also includes pharmaceutical compositions containing a compound of the present invention and methods of preparing such pharmaceutical compositions. The present invention further includes methods of treating or reducing the likelihood or severity of HCV infection, methods for inhibiting the activity of the NS5B polymerase, and methods for inhibiting HCV viral replication and/or viral production.

Other embodiments, aspects and features of the present invention are either further described in or will be apparent from the ensuing description, examples and appended claims.

DETAILED DESCRIPTION OF THE INVENTION

The present invention includes compounds of formula I above, and pharmaceutically acceptable salts thereof. The compounds of formula I are HCV NS5B polymerase inhibitors.

For purposes of illustration, the portion of formula I represented by can be

In a first embodiment of the invention, $R^2$ and $R^4$ are independently $C_1$-$C_6$ alkyl. In this embodiment, all other groups are as provided in the general formula above.

In a second embodiment of the invention, $R^2$, $R^3$ and $R^4$ are methyl. In this embodiment, all other groups are as provided in the general formula above and/or in the first embodiment.

In a third embodiment of the invention, each halo is F. In this embodiment, all other groups are as provided in the general formula above and/or in the first or second embodiments.

In a fourth embodiment of the invention, the compound of the invention has the formula:

(Ia)

(Ib)

-continued

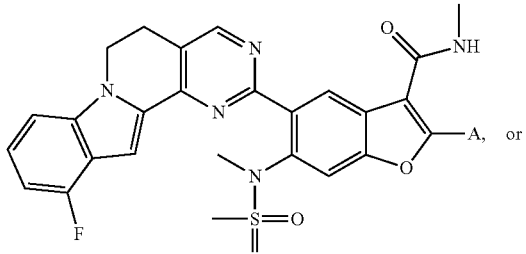
(Ic)

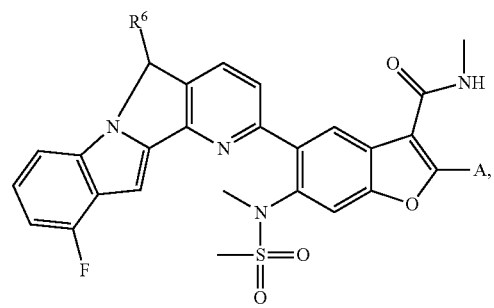
(Id)

or a pharmaceutically acceptable salt thereof. In this embodiment, all other groups are as provided in the general formula above and/or in the first through third embodiments.

In a fifth embodiment of the invention, $R^5$ is hydrogen or methyl;

$R^6$ is hydrogen, methyl, —$CH_2OH$, —$CH_2CH_2OH$, —$CH_2SO_2CH_3$,

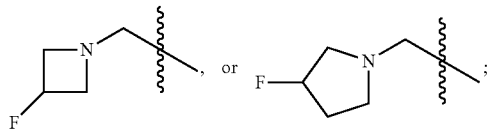 [SMILES: *CN1CC(F)C1 ; *CN1CCC(F)C1]

and $R^7$ is hydrogen or methyl.

In this embodiment, all other groups are as provided in the general formula above and/or in the first through fourth embodiments.

In a sixth embodiment of the invention, A is $C_3$-$C_6$ cycloalkyl, or a 5-6 membered aromatic monocyclic ring with 0, 1, 2 or 3 heteroatom ring atoms selected from N and S, optionally substituted with 1 or 2 substituents independently selected from $C_1$-$C_6$ alkyl, $C_1$-$C_6$ alkoxy, $C_1$-$C_6$ haloalkyl, oxo, halo, and —O—$C_1$-$C_6$ haloalkyl. In an aspect of this seventh embodiment, A is cyclopropyl,

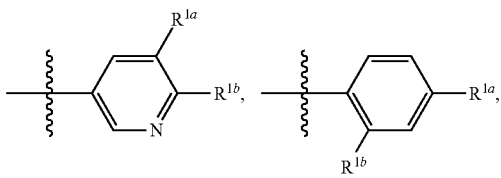

-continued

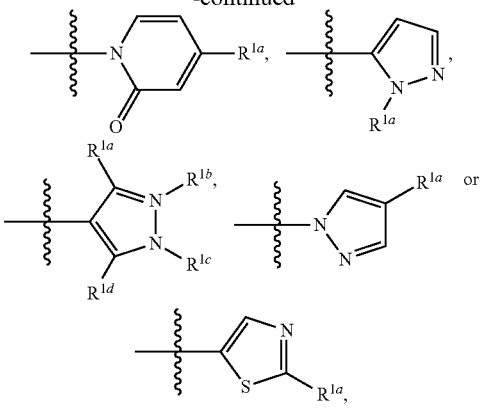

wherein $R^{1a}$, $R^{1b}$, $R^{1c}$ and $R^{1d}$ are independently selected from hydrogen, F, methyl, ethyl, hydroxymethyl, isopropyl, methoxy, ethoxy, —$OCHF_2$, —$OCH_2CF_3$, cyclopropyl, phenyl, pyrrolidinyl, —O-cyclopropyl, —$CHF_2$, cyano, —$CF_3$ and —$CH_2CF_3$. In another aspect of this embodiment, A is

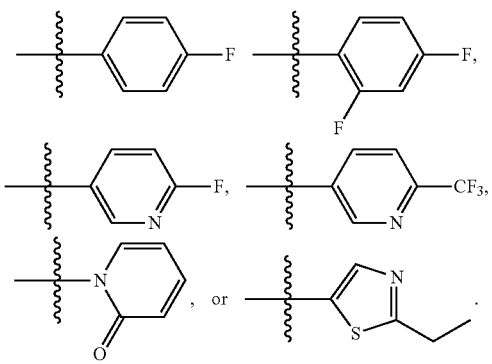

In this embodiment, all other groups are as provided in the general formula above and/or in the first through fifth embodiments.

In another embodiment of the invention, the compound of the invention is selected from the exemplary species depicted in Examples 1 through 99 shown below, and pharmaceutically acceptable salts thereof In another embodiment of the invention, the compound of the invention is selected from the exemplary species depicted in Examples 1, 15, 30, 34, 38, 42, 45, 46, 54, 55, 56, 60, 63, 64, 65, 82, 85, 88, 90 and 94 shown below, and pharmaceutically acceptable salts thereof Other embodiments of the present invention include the following:

(a) A pharmaceutical composition comprising an effective amount of a compound of formula I and a pharmaceutically acceptable carrier.

(b) The pharmaceutical composition of (a), further comprising a second therapeutic agent selected from the group consisting of HCV antiviral agents, immunomodulators, and anti-infective agents.

(c) The pharmaceutical composition of (b), wherein the HCV antiviral agent is an antiviral selected from the group consisting of direct inhibitors of HCV, including but not limited to NS3 and NS3/4A protease inhibitors, NS5A inhibitors and HCV NS5B polymerase inhibitors.

(d) A pharmaceutical combination that is (i) a compound of formula I and (ii) a second therapeutic agent selected from the group consisting of HCV antiviral agents, immunomodulators, and anti-infective agents; wherein the compound of formula I and the second therapeutic agent are each employed in an amount that renders the combination effective for inhibiting HCV NS5B activity, or for inhibiting HCV viral replication, or for treating HCV infection and/or reducing the likelihood or severity of symptoms of HCV infection.

(e) The combination of (d), wherein the HCV antiviral agents are one or more antiviral agents selected from the group consisting of direct inhibitors of HCV, including but not limited to NS3 and NS3/4A protease inhibitors, NS5A inhibitors and HCV NS5B polymerase inhibitors.

(f) A use of a compound of formula I in the preparation of a medicament for inhibiting HCV NS5B activity in a subject in need thereof (g) A use of a compound of formula I in the preparation of a medicament for preventing and/or treating infection by HCV in a subject in need thereof (h) A method of treating HCV infection and/or reducing the likelihood or severity of symptoms of HCV infection in a subject in need thereof, which comprises administering to the subject an effective amount of a compound of formula I.

(i) The method of (h), wherein the compound of formula I is administered in combination with an effective amount of at least one second therapeutic agent selected from the group consisting of HCV antiviral agents, immunomodulators, and anti-infective agents.

(j) The method of (i), wherein the HCV antiviral agent is an antiviral selected from the group consisting of direct inhibitors of HCV, including but not limited to NS3 and NS3/4A protease inhibitors, NS5A inhibitors and HCV NS5B polymerase inhibitors.

(k) A method of inhibiting HCV viral replication and/or HCV viral production in a cell-based system, which comprises administering to the subject an effective amount of a compound of formula I in combination with an effective amount of at least one second therapeutic agent selected from the group consisting of HCV antiviral agents, immunomodulators, and anti-infective agents.

(l) The method of (k), wherein the HCV antiviral agent is an antiviral selected from the group consisting of direct inhibitors of HCV, including but not limited to NS3 and NS3/4A protease inhibitors, NS5A inhibitors and HCV NS5B polymerase inhibitors.

(m) A method of inhibiting HCV NS5B activity in a subject in need thereof, which comprises administering to the subject the pharmaceutical composition of (a), (b), or (c) or the combination of (d) or (e).

(n) A method of treating HCV infection and/or reducing the likelihood or severity of symptoms of HCV infection in a subject in need thereof, which comprises administering to the subject the pharmaceutical composition of (a), (b), or (c) or the combination of (d) or (e).

In the embodiments of the compounds and salts provided above, it is to be understood that each embodiment may be combined with one or more other embodiments, to the extent that such a combination provides a stable compound or salt and is consistent with the description of the embodiments. It is further to be understood that the embodiments of compositions and methods provided as (a) through (n) above are understood to include all embodiments of the compounds and/or salts, including such embodiments as result from combinations of embodiments.

Additional embodiments of the invention include the pharmaceutical compositions, combinations, uses and methods set forth in (a) through (n) above, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

The present invention also includes a compound of the present invention for use (i) in, (ii) as a medicament for, or (iii) in the preparation of a medicament for: (a) inhibiting HCV NS5B activity, or (b) inhibiting HCV viral replication, or (c) treating HCV infection and/or reducing the likelihood or severity of symptoms of HCV infection, or (d) use in medicine. In these uses, the compounds of the present invention can optionally be employed in combination with one or more second therapeutic agents selected from HCV antiviral agents, anti-infective agents, and immunomodulators.

Chemical names, common names, and chemical structures may be used interchangeably to describe the same structure. If a chemical compound is referred to using both a chemical structure and a chemical name and an ambiguity exists between the structure and the name, the structure is understood to predominate.

As used herein, the term "administration" and variants thereof (e.g., "administering" a compound) in reference to a compound of the invention mean providing the compound to the individual in need of treatment. When a compound of the invention is provided in combination with one or more other active agents (e.g., antiviral agents useful for treating HCV infection), "administration" and its variants are each understood to include concurrent and sequential provision of the compound or salt and other agents.

The term "alkoxy" refers to an "alkyl-O-" group. Alkoxy groups may be substituted as indicated.

The term "alkyl" refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 3 carbon atoms ($C_1$-$C_3$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "aryl" (or "aryl ring system") refers to aromatic mono- and poly-carbocyclic ring systems wherein the individual carbocyclic rings in the polyring systems are fused or attached to each other via a single bond. As used herein, the term aryl includes aromatic mono- and poly-carbocyclic ring systems that include from 0 to 4 heteroatoms (non-carbon atoms) that are independently chosen from N, O and S. Suitable aryl groups include phenyl, naphthyl, biphenylenyl, pyridinyl, pyrimidinyl and pyrrolyl, as well as those discussed below. Aryl groups may be substituted as indicated. Aryl ring systems may include, where appropriate, an indication of the variable to which a particular ring atom is attached. Unless otherwise indicated, substituents to the aryl ring systems can be attached to any ring atom, provided that such attachment results in formation of a stable ring system.

The term "carbocycle" (and variations thereof such as "carbocyclic") as used herein, unless otherwise indicated, refers to (i) a $C_5$ to $C_7$ monocyclic, saturated or unsaturated ring, or (ii) a $C_8$ to $C_{10}$ bicyclic saturated or unsaturated ring system. Each ring in (ii) is either independent of, or fused to, the other ring, and each ring is saturated or unsaturated. Carbocycle groups may be substituted as indicated. When the carbocycles contain one or more heteroatoms independently chosen from N, O and S, the carbocycles may also be referred to as "heterocycles," as defined below. The carbocycle may be attached to the rest of the molecule at any carbon or nitrogen atom that results in a stable compound. The fused bicyclic carbocycles are a subset of the carbocycles; i.e., the term "fused bicyclic carbocycle" generally refers to a $C_8$ to $C_{10}$ bicyclic ring system in which each ring is saturated or unsaturated and two adjacent carbon atoms are shared by each of the rings in the ring system. A fused bicyclic carbocycle in which both rings are saturated is a saturated bicyclic ring system. Saturated carbocyclic rings are also referred to as cycloalkyl rings, e.g., cyclopropyl, cyclobutyl, etc. A fused bicyclic carbocycle in which one or both rings are unsaturated is an unsaturated bicyclic ring system. Carbocycle ring systems may include, where appropriate, an indication of the variable to which a particular ring atom is attached. Unless otherwise indicated, substituents to the ring systems can be attached to any ring atom, provided that such attachment results in formation of a stable ring system.

The term "composition" is intended to encompass a product comprising the specified ingredients, as well as any product which results, directly or indirectly, from combining the specified ingredients.

The term "compound" is intended to encompass chemical agents described by generic formula I in all forms, including hydrates and solvates of such chemical agents.

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment, a cycloalkyl group is unsubstituted. The term "3 to 7-membered cycloalkyl" refers to a cycloalkyl group having from 3 to 7 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

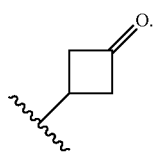 [SMILES: *C1CC(=O)C1]

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of one or more symptoms of the disease or condition being treated. In another embodiment, the effective amount is a "prophylactically effective amount" for reduction of the severity or likelihood of one or more symptoms of the disease or condition. In another embodiment, the effective amount is a "therapeutically effective amount" for inhibition of HCV viral replication and/or HCV viral production. The term also includes herein the amount of active compound sufficient to inhibit HCV NS5B activity and thereby elicit the response being sought (i.e., an "inhibition effective amount"). When the active compound (i.e., active ingredient) is administered as the salt, references to the amount of active ingredient are to the free acid or free base form of the compound.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —$CH_2F$, —$CHF_2$, —$CF_3$, —$CH_2Cl$ and —$CCl_3$. The term "$C_1$-$C_6$ haloalkyl" refers to a haloalkyl group having from 1 to 6 carbon atoms.

The term "halogen" (or "halo") refers to atoms of fluorine, chlorine, bromine and iodine (alternatively referred to as fluoro, chloro, bromo, and iodo).

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic and has 9 or 10 ring atoms. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. The term "heteroaryl" also encompasses any fused polycyclic ring system containing at least one ring heteroatom selected from N, O and S, wherein at least one ring of the fused polycyclic ring system is aromatic. For example, the term "9 to 10-membered bicyclic heteroaryl" encompasses a non-aromatic 5 membered heterocyclic ring that is fused to a benzene or pyridyl ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring. Unless otherwise indicated, a heteroaryl group is unsubstituted.

As used herein, the term "heterocycle" (and variations thereof such as "heterocyclic" or "heterocyclyl") broadly refers to (i) a stable 5- to 7-membered, saturated or unsaturated monocyclic ring, or (ii) a stable 8- to 10-membered bicyclic ring system, wherein each ring in (ii) is independent of, or fused to, the other ring or rings and each ring is saturated or unsaturated, and the monocyclic ring or bicyclic ring system contains one or more heteroatoms (e.g., from 1 to 6 heteroatoms, or from 1 to 4 heteroatoms) independently selected from N, O and S and a balance of carbon atoms (the monocyclic ring typically contains at least one carbon atom and the bicyclic ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Heterocycle groups may be substituted as indicated, and unless otherwise specified, the substituents may be attached to any atom in the ring, whether a heteroatom or a carbon atom, provided that a stable chemical structure results. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

The term "heterocycloalkyl," as used herein, refers to a non-aromatic saturated monocyclic or multicyclic ring system comprising 3 to about 11 ring atoms, wherein from 1 to 4 of the ring atoms are independently O, S, or N, and the remainder of the ring atoms are carbon atoms. A heterocycloalkyl group can be joined via a ring carbon or ring nitrogen atom. In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, a heterocycloalkyl group is monocyclic has from about 5 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone and the like, and all isomers thereof.

A ring carbon atom of a heterocycloalkyl group may be functionalized as a carbonyl group. Illustrative example of such heterocycloalkyl groups, include:

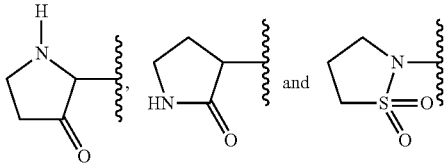

In one embodiment, a heterocycloalkyl group is a 5-membered monocyclic heterocycloalkyl. In another embodiment, a heterocycloalkyl group is a 6-membered monocyclic heterocycloalkyl. The term "3 to 7-membered monocyclic cycloalkyl" refers to a monocyclic heterocycloalkyl group having from 3 to 7 ring atoms. The term "4 to 7-membered monocyclic cycloalkyl" refers to a monocyclic heterocycloalkyl group having from 4 to 7 ring atoms. The term "5 to 7-membered monocyclic cycloalkyl" refers to a monocyclic heterocycloalkyl group having from 5 to 7 ring atoms. The term "7 to 11-membered bicyclic heterocycloalkyl" refers to a bicyclic heterocycloalkyl group having from 7 to 11 ring atoms. Unless otherwise indicated, an heterocycloalkyl group is unsubstituted.

The term "hydroxyalkyl," as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$. The term "C$_1$-C$_6$ hydroxyalkyl" refers to a hydroxyalkyl group having from 1 to 6 carbon atoms.

As used herein, the term "oxo" or "=O" forms a carbonyl moiety with the carbon atom to which it is attached.

By "pharmaceutically acceptable" is meant that the ingredients of the pharmaceutical composition must be compatible with each other and not deleterious to the recipient thereof.

The term "preventing," as used herein with respect to an HCV viral infection or HCV-virus related disorder, refers to reducing the likelihood of HCV infection.

The term "ring system substituent," as used herein, refers to a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O— alkylene-aryl, acyl, —C(O)-aryl, halo, —NO$_2$, —CN, —SF$_5$, —C(O)OH, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, —S(O)$_2$-alkylene-aryl, —S(O)$_2$-alkylene-heteroaryl, cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), —N(Y$_1$)(Y$_2$), -alkylene-N(Y$_1$)(Y$_2$), —C(O)N(Y$_1$)(Y$_2$) and —S(O)$_2$N(Y$_1$)(Y$_2$), wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

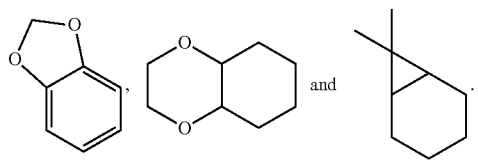

The term "subject" (alternatively referred to herein as "patient"), as used herein, refers to an animal, preferably a mammal, most preferably a human.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture.

In the compounds of formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of formula I. For example, different isotopic forms of hydrogen (H) include protium ($^1$H) and deuterium ($^2$H or D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within formula I can be prepared without undue experimentation by conventional techniques well known to those skilled in the art or by processes analogous to those described in the Schemes and Examples herein using appropriate isotopically-enriched reagents and/or intermediates.

Unless expressly stated to the contrary, all ranges cited herein are inclusive. For example, a heteroaryl ring described as containing from "0 to 3 heteroatoms" means the ring can contain 0, 1, 2, or 3 heteroatoms. It is also to be understood that any range cited herein includes within its scope all of the sub-ranges within that range. The oxidized forms of the heteroatoms N and S are also included within the scope of the present invention.

When any variable (for example, R$^1$ or R$^3$) occurs more than one time in any constituent or in formula I or in any other formula depicting and describing compounds of the invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom provided such substitution is chemically allowed and results in a stable compound. A "stable" compound is a compound that can be prepared and isolated and whose structure and properties remain or can be caused to remain essentially unchanged for a period of time sufficient to allow use of the compound for the purposes described herein (e.g., therapeutic or prophylactic administration to a subject).

As a result of the selection of substituents and substituent patterns, certain of the compounds of the present invention can have asymmetric centers and can occur as mixtures of stereoisomers, or as individual diastereomers, or enantiomers. All isomeric forms of these compounds, whether isolated or in mixtures, are within the scope of the present invention.

As would be recognized by one of ordinary skill in the art, certain of the compounds of the present invention can exist as tautomers. For the purposes of the present invention a reference to a compound of formula I is a reference to the compound per se, or to any one of its tautomers per se, or to mixtures of two or more tautomers.

The compounds of the present inventions are useful in the inhibition of HCV replication (e.g., HCV NS5B activity), the treatment of HCV infection and/or reduction of the likelihood or severity of symptoms of HCV infection. For example, the compounds of this invention are useful in treating infection by HCV after suspected past exposure to HCV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for identifying resistant HCV replicon cell lines harboring mutations within NS5B, which are excellent screening tools for more powerful antiviral compounds. Furthermore, the compounds of this invention are useful in establishing or determining the binding site of other antivirals to the HCV replicase.

The compounds of the present invention may be administered in the form of pharmaceutically acceptable salts. The term "pharmaceutically acceptable salt" refers to a salt that possesses the effectiveness of the parent compound and that is not biologically or otherwise undesirable (e.g., is neither toxic nor otherwise deleterious to the recipient thereof). Suitable salts include acid addition salts that may, for example, be formed by mixing a solution of the compound of the present invention with a solution of a pharmaceutically acceptable acid such as hydrochloric acid, sulfuric acid, acetic acid, trifluoroacetic acid, or benzoic acid. Many of the compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates ("mesylates"), naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Prop-*

*erties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quaternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

For the purposes of inhibiting HCV NS5B polymerase, treating HCV infection and/or reducing the likelihood or severity of symptoms of HCV infection and inhibiting HCV viral replication and/or HCV viral production, the compounds of the present invention, optionally in the form of a salt, can be administered by any means that produces contact of the active agent with the agent's site of action. They can be administered by one or more conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered by one or more of the following: orally, parenterally (including subcutaneous injections, intravenous, intramuscular, intrasternal injection or infusion techniques), by inhalation (such as in a spray form), or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as solubility aids. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in *Remington's Pharmaceutical Sciences*, 18$^{th}$ edition (ed. A. R. Gennaro, Mack Publishing Co., 1990).

The compounds of this invention can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 mg of the active ingredient, particularly 1, 5, 10, 15, 20, 25, 50, 75, 100, 150, 200, 250, 300, 400, and 500 mg of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, HCV viral genotype, viral resistance, and the host undergoing therapy.

As noted above, the present invention also relates to a method of inhibiting HCV NS5B activity, inhibiting HCV viral replication and/or HCV viral production, treating HCV infection and/or reducing the likelihood or severity of symptoms of HCV infection with a compound of the present invention in combination with one or more therapeutic agents and a pharmaceutical composition comprising a compound of the present invention and one or more therapeutic agents selected from the group consisting of a HCV antiviral agent, an immunomodulator, and an anti-infective agent. Such therapeutic agents active against HCV include, but are not limited to, ribavirin, levovirin, viramidine, thymosin alpha-1, R7025 (an enhanced interferon (Roche)), interferon-β, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as ROFERON interferon available from Hoffmann-LaRoche, Nutley, N.J.), pegylated interferon-α2a (PEGASYS), interferon-α2b (such as INTRON-A interferon available from Schering Corp., Kenilworth, N.J.), pegylated interferon-α2b (PEGINTRON), a recombinant consensus interferon (such as interferon alphacon-1), albuferon (interferon-α bound to human serum albumin (Human Genome Sciences)), and a purified interferon-α product. Amgen's recombinant consensus interferon has the brand name INFERGEN. Levovirin is the L-enantiomer of ribavirin which has shown immunomodulatory activity similar to ribavirin. Viramidine represents an analog of ribavirin disclosed in International Patent Application Publication WO 01/60379. In accordance with the method of the present invention, the individual components of the combination can be administered separately at different times during the course of therapy or concurrently in divided or single combination forms.

For the treatment of HCV infection, the compounds of the invention may also be administered in combination with the antiviral agent NS5B polymerase inhibitor R7128 (Roche). The compounds of the present invention also may be combined for the treatment of HCV infection with antiviral 2'-C-branched ribonucleosides disclosed in Rogers E. Harry-O'Kuru et al., *A Short, Flexible Route toward 2'-C-Branched Ribonucleosides*, 62 J. ORG. CHEM. 1754-59 (1997); Michael S. Wolfe & Rogers E. Harry-O'Kuru, *A Concise Synthesis of 2'-C-Methylribonucleosides*, 36 (42) TETRAHEDRON LETTERS 7611-14 (1995); U.S. Pat. No. 3,480,613; and International Patent Application Publications WO 01/90121, WO 01/92282, WO 02/32920, WO 04/002999, WO 04/003000 and WO 04/002422; the entire contents of each of which are incorporated by reference. Such 2'-C-branched ribonucleosides include, but are not limited to, 2'-C-methyl-cytidine, 2'-C-methyl-uridine, 2'-C-methyl-adenosine, 2'-C-methyl-guanosine, and 9-(2-C-methyl-β-D-ribofuranosyl)-2,6-diaminopurine, and the corresponding amino acid ester of the ribose C-2', C-3', and C-5' hydroxyls and the corresponding optionally substituted cyclic 1,3-propanediol esters of the 5'-phosphate derivatives.

For the treatment of HCV infection, the compounds of the present invention may also be administered in combination with an agent that is an inhibitor of HCV NS3 serine protease. HCV NS3 serine protease is an essential viral enzyme and has been described to be an excellent target for inhibition of HCV replication. Exemplary substrate and non-substrate based inhibitors of HCV NS3 protease inhibitors are disclosed in International Patent Application Publications WO 98/22496, WO 98/46630, WO 99/07733, WO 99/07734, WO 99/38888, WO 99/50230, WO 99/64442, WO 00/09543, WO 00/59929, WO 02/48116, WO 02/48172, WO 2008/057208 and WO 2008/057209, in British Patent No. GB 2 337 262, and in U.S. Pat. Nos. 6,323,180 and 7,470,664.

The compounds of the present invention may also be combined for the treatment of HCV infection with nucleosides having anti-HCV properties, such as those disclosed in International Patent Application Publications WO 02/51425, WO 01/79246, WO 02/32920, WO 02/48165 and WO 2005/003147 (including R1656, (2'R)-2'-deoxy-2'-fluoro-2'-C-methylcytidine, shown as compounds 3-6 on page 77); WO 01/68663; WO 99/43691; WO 02/18404 and WO 2006/021341, and U.S. Patent Application Publication US 2005/0038240, including 4'-azido nucleosides such as R1626,4'-azidocytidine; U.S. Patent Application Publications US 2002/0019363, US 2003/0236216, US 2004/0006007, US 2004/0063658 and US 2004/0110717; U.S. Pat. Nos. 7,105,499, 7,125,855, 7,202,224; and International Patent Application Publications WO 02/100415, WO 03/026589, WO 03/026675, WO 03/093290, WO 04/011478, WO 04/013300 and WO 04/028481; the content of each is incorporated herein by reference in its entirety.

For the treatment of HCV infection, the compounds of the present invention may also be administered in combination with an agent that is an inhibitor of HCV NS5B polymerase. Such HCV NS5B polymerase inhibitors that may be used as combination therapy include, but are not limited to, those disclosed in International Patent Application Publications WO 02/057287, WO 02/057425, WO 03/068244, WO 2004/000858, WO 04/003138 and WO 2004/007512; U.S. Pat. Nos. 6,777,392, 7,105,499, 7,125,855, 7,202,224 and U.S. Patent Application Publications US 2004/0067901 and US 2004/0110717; the content of each is incorporated herein by reference in its entirety. Other such HCV polymerase inhibitors include, but are not limited to, valopicitabine (NM-283; Idenix) and 2'-F-2'-beta-methylcytidine (see also WO 2005/003147).

In one embodiment, additional nucleoside HCV NS5B polymerase inhibitors that are used in combination with the present HCV NS5B inhibitors are selected from the following compounds: 4-amino-7-(2-C-methyl-β-D-arabinofuranosyl)-7H-pyrrolo[2,3-d]pyrimidine; 4-amino-7-(2-C-methyl-β-D-ribofuranosyl)-7H-pyrrolo[2,3-d]pyrimidine; 4-methylamino-7-(2-C-methyl-β-D-ribofuranosyl)-7H-pyrrolo[2,3-d]pyrimidine; 4-dimethylamino-7-(2-C-methyl-β-D-ribofuranosyl)-7H-pyrrolo[2,3-d]pyrimidine; 4-cyclopropylamino-7-(2-C-methyl-β-D-ribofuranosyl)-7H-pyrrolo[2,3-d]pyrimidine; 4-amino-7-(2-C-vinyl-β-D-ribofuranosyl)-7H-pyrrolo[2,3-d]pyrimidine; 4-amino-7-(2-C-hydroxymethyl-β-D-ribofuranosyl)-7H-pyrrolo[2,3-d]pyrimidine; 4-amino-7-(2-C-fluoromethyl-β-D-ribofuranosyl)-7H-pyrrolo[2,3-d]pyrimidine; 4-amino-5-methyl-7-(2-C-methyl-β-D-ribofuranosyl)-7H-pyrrolo[2,3-d]pyrimidine; 4-amino-7-(2-C-methyl-β-D-ribofuranosyl)-7H-pyrrolo[2,3-d]pyrimidine-5-carboxylic acid; 4-amino-5-bromo-7-(2-C-methyl-β-D-ribofuranosyl)-7H-pyrrolo[2,3-d]pyrimidine; 4-amino-5-chloro-7-(2-C-methyl-β-D-ribofuranosyl)-7H-pyrrolo[2,3-d]pyrimidine; 4-amino-5-fluoro-7-(2-C-methyl-β-D-ribofuranosyl)-7H-pyrrolo[2,3-d]pyrimidine; 2,4-diamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidine; 2-amino-4-cyclopropylamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidin-4(3H)-one; 4-amino-7-(2-C-ethyl-β-D-ribofuranosyl)-7H-pyrrolo[2,3-d]pyrimidine; 4-amino-7-(2-β-O-dimethyl-β-D-ribofuranosyl)-7H-pyrrolo[2,3-d]pyrimidine; 7-(2-C-methyl-β-D-ribofuranosyl)-7H-pyrrolo[2,3-d]pyrimidin-4(3H)-one; 2-amino-5-methyl-7-(2-C, 2-O-dimethyl-β-D-ribofuranosyl)-7H-pyrrolo[2,3-d]pyrimidin-4 (3H)-one; 4-amino-7-(3-deoxy-2-C-methyl-β-D-ribofuranosyl)-7H-pyrrolo[2,3-d]pyrimidine; 4-amino-7-(3-deoxy-2-C-methyl-β-D-arabinofuranosyl)-7H-pyrrolo[2,3-d]pyrimidine; 4-amino-2-fluoro-7-(2-C-methyl-β-D-ribofuranosyl)-7H-pyrrolo[2,3-d]pyrimidine; 4-amino-7-(3-C-methyl-(3-D-ribofuranosyl)-7H-pyrrolo[2,3-d]pyrimidine; 4-amino-7-(3-C-methyl-β-D-xylofuranosyl)-7H-pyrrolo[2,3-d]pyrimidine; 4-amino-7-(2,4-di-C-methyl-β-D-ribofuranosyl)-7H-pyrrolo[2,3-d]pyrimidine; 4-amino-7-(3-deoxy-3-fluoro-2-C-methyl-β-D-ribofuranosyl)-7H-pyrrolo[2,3-d]pyrimidine; and the corresponding 5'-triphosphates; or a pharmaceutically acceptable salt thereof The compounds of the present invention may also be combined for the treatment of HCV infection with non-nucleoside inhibitors of HCV polymerase such as those disclosed in U.S. Patent Application Publications US 2006/0100262 and US 2009/0048239; International Patent Application Publications WO 01/77091, WO 01/47883, WO 02/04425, WO 02/06246, WO 02/20497, WO 2005/016927 (in particular JTK003), WO 2004/041201, WO 2006/066079, WO 2006/066080, WO 2008/075103, WO 2009/010783 and WO 2009/010785; the content of each is incorporated herein by reference in its entirety.

In one embodiment, additional non-nucleoside HCV NS5B polymerase inhibitors that are used in combination with the present HCV NS5B inhibitors are selected from the following compounds: 14-cyclohexyl-6-[2-(dimethylamino)ethyl]-7-oxo-5,6,7,8-tetrahydroindolo[2,1-a][2,5]benzodiazocine-11-carboxylic acid; 14-cyclohexyl-6-(2-morpholin-4-ylethyl)-5,6,7,8-tetrahydroindolo[2,1-a][2,5]benzodiazocine-11-carboxylic acid; 14-cyclohexyl-6-[2-(dimethylamino)ethyl]-3-methoxy-5,6,7,8-tetrahydroindolo[2,1-a][2,5]benzodiazocine-11-carboxylic acid; 14-cyclohexyl-3-methoxy-6-methyl-5,6,7,8-tetrahydroindolo[2,1-a][2,5]benzodiazocine-11-carboxylic acid; methyl ({[(14-cyclohexyl-3-methoxy-6-methyl-5,6,7,8-tetrahydroindolo[2,1-a][2,5]benzodiazocin-11-yl)carbonyl]amino}sulfonyl)acetate; ({[(14-cyclohexyl-3-methoxy-6-methyl-5,6,7,8-tetrahydroindolo[2,1-a][2,5]benzodiazocin-11-yl)carbonyl]amino}sulfonyl)acetic acid; 14-cyclohexyl-N-[(dimethylamino)sulfonyl]-3-methoxy-6-methyl-5,6,7,8-tetrahydroindolo[2,1-a][2,5]benzodiazocine-11-carboxamide; 3-chloro-14-cyclohexyl-6-[2-(dimethylamino)ethyl]-7-oxo-5,6,7,8-tetrahydroindolo[2,1-a][2,5]benzodiazocine 11-carboxylic acid; N'-(11-carboxy-14-cyclohexyl-7,8-dihydro-6H-indolo[1,2-e][1,5]benzoxazocin-7-yl)-N,N-dimethylethane-1,2-diaminium bis (trifluoroacetate); 14-cyclohexyl-7,8-dihydro-6H-indolo[1,2-e][1,5]benzoxazocine-11-carboxylic acid; 14-cyclohexyl-6-methyl-7-oxo-5,6,7,8-tetrahydroindolo[2,1-a][2,5]benzodiazocine-11-carboxylic acid; 14-cyclohexyl-3-methoxy-6-methyl-7-oxo-5,6,7,8-tetrahydroindolo[2,1-a][2,5]benzodiazocine-11-carboxylic acid; 14-cyclohexyl-6-[2-(dimethylamino)ethyl]-3-methoxy-7-oxo-5,6,7,8-tetrahydroindolo[2,1-a][2,5]benzodiazocine-11-carboxylic acid; 14-cyclohexyl-6-[3-(dimethylamino)propyl]-7-oxo-5,6,7,8-tetrahydroindolo[2,1-a][2,5]benzodiazocine-11-carboxylic acid; 14-cyclohexyl-7-oxo-6-(2-piperidin-1-ylethyl)-5,6,7,8-tetrahydroindolo[2,1-a][2,5]benzodiazocine-11-carboxylic acid; 14-cyclohexyl-6-(2-morpholin-4-ylethyl)-7-oxo-5,6,7,8-tetrahydroindolo[2,1-a][2,5]benzodiazocine-11-carboxylic acid; 14-cyclohexyl-6-[2-(diethylamino)ethyl]-7-oxo-5,6,7,8-tetrahydroindolo[2,1-a][2,5]benzodiazocine-11-carboxylic acid; 14-cyclohexyl-6-(1-methylpiperidin-4-yl)-7-oxo-5,6,7,8-tetrahydroindolo[2,1-a][2,5]benzodiazocine-11-carboxylic acid; 14-cyclohexyl-N-[(dimethylamino)sulfonyl]-7-oxo-6-(2-piperidin-1-ylethyl)-5,6,7,8-tetrahydroindolo[2,1-a][2,5]benzodiazocine-11-carboxamide; 14-cyclohexyl-6-[2-(dimethylamino)ethyl]-N-[(dimethylamino)sulfonyl]-7-oxo-5,6,7,8-tetrahydroindolo[2,1-a][2,5]benzodiazocine-11-carboxamide; 14-cyclopentyl-6-[2-(dimethylamino)ethyl]-7-oxo-5,6,7,8-tetrahydroindolo[2,1-a][2,5]benzodiazocine-11-carboxylic acid; 14-cyclohexyl-5,6,7,8-tetrahydroindolo[2,1-a][2,5]benzodiazocine-11-carboxylic acid; 6-allyl-14-cyclohexyl-3-methoxy-5,6,7,8-tetrahydroindolo[2,1-a][2,5]benzodiazocine-11-carboxylic acid; 14-cyclopentyl-6-[2-(dimethylamino)ethyl]-5,6,7,8-tetrahydroindolo[2,1-a][2,5]benzodiazocine-11-carboxylic acid; 14-cyclohexyl-6-[2-(dimethylamino)ethyl]-5,6,7,8-tetrahydroindolo[2,1-a][2,5]benzodiazocine-11-carboxylic acid; 13-cyclohexyl-5-methyl-4,5,6,7-tetrahydrofuro[3',2':6,7][1,4]diazocino[1,8-a]indole-10-carboxylic acid; 15-cyclohexyl-6-[2-(dimethylamino)ethyl]-7-oxo-6,7,8,9-tetrahydro-5H-indolo[2,1-a][2,6]benzodiazonine-12-carboxylic acid; 15-cyclohexyl-8-oxo-6,7,8,9-tetrahydro-5H-indolo[2,1-a][2,5]benzodiazonine-12-carboxylic acid; 13-cyclohexyl-6-oxo-6,7-dihydro-5H-indolo[1,2-d][1,4]benzodiazepine-10-carboxylic acid; and pharmaceutically acceptable salts thereof In another embodiment, the present HCV NS5B polymerase inhibitors are used in combination with non-nucleoside HCV NS5A inhibitors and pharmaceutically acceptable salts thereof The HCV NS5B inhibitory activity of the present compounds may be tested using assays known in the art. The HCV NS5B polymerase inhibitors described herein have activities in a genotype 1b replicon assay as described in the Examples. The assay is performed by incubating a replicon harboring cell-line in the presence of inhibitor for a set period of time and measuring the effect of the inhibitor on HCV replicon replication either directly by quantifying replicon RNA level, or indirectly by measuring enzymatic activity of a co-encoded reporter enzyme such as luciferase or β-lactamase. By performing a series of such measurements at different inhibitor concentrations, the effective inhibitory concentration of the inhibitor ($EC_{50}$ or $EC_{90}$) is determined See Jan M. Vrolijk et al., *A replicons-based bioassay for the measurement of interferons in patients with chronic hepatitis C*, 110 J. VIROLOGICAL METHODS 201 (2003). Such assays may also be run in an automated format for high through-put screening. See Paul Zuck et al., *A cell-based β-lactamase reporter gene assay for the identification of inhibitors of hepatitis C virus replication*, 334 ANALYTICAL BIOCHEMISTRY 344 (2004).

The present invention also includes processes for making compounds of formula I. The Compounds of Formula (I) may be prepared from known or readily prepared starting materials, following methods known to one skilled in the art of organic synthesis. Methods useful for making the Compounds of Formula (I) are set forth in the Examples below and generalized in Schemes 1-6 below. Alternative synthetic pathways and analogous structures will be apparent to those skilled in the art of organic synthesis. All stereoisomers and tautomeric forms of the compounds are contemplated.

Some commercially available starting materials and intermediates used for the synthesis of the Compounds of Formula (I) are available. These starting materials and intermediates are available from commercial suppliers such as Sigma-Aldrich (St. Louis, Mo.) and Acros Organics Co. (Fair Lawn, N.J.). Such starting materials and intermediates compounds are used as received.

Scheme 1 shows methods useful for making the intermediates of formula A and B, which can be converted to intermediate C.

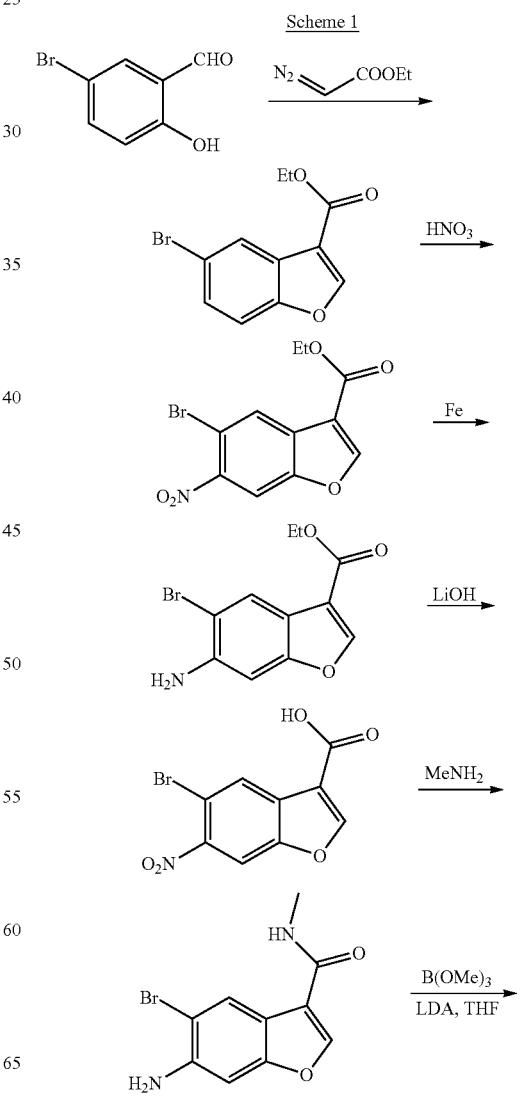

Scheme 1

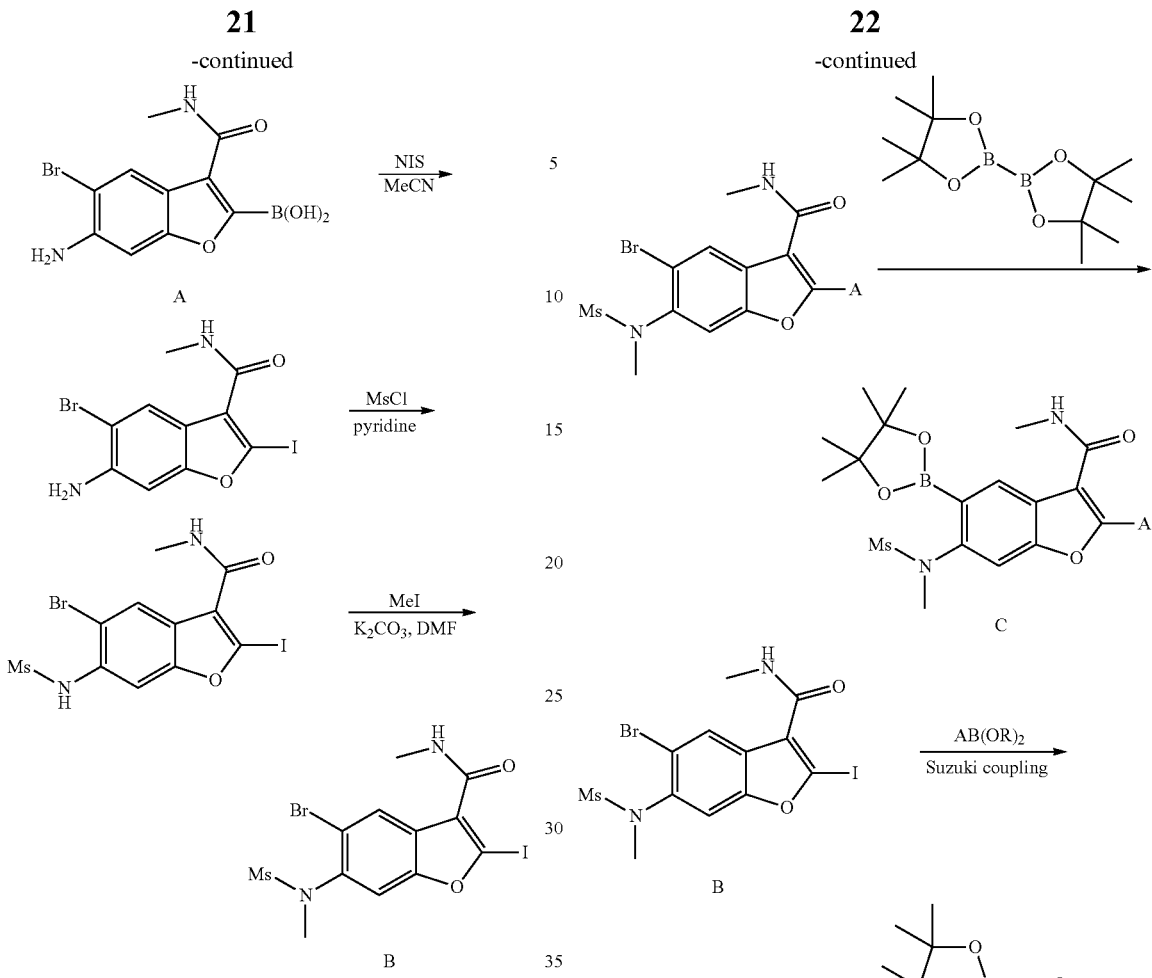
Scheme 2 shows a method useful for converting intermediate of formula A or B to intermediate C, which can be converted to Compounds of Formula (I).
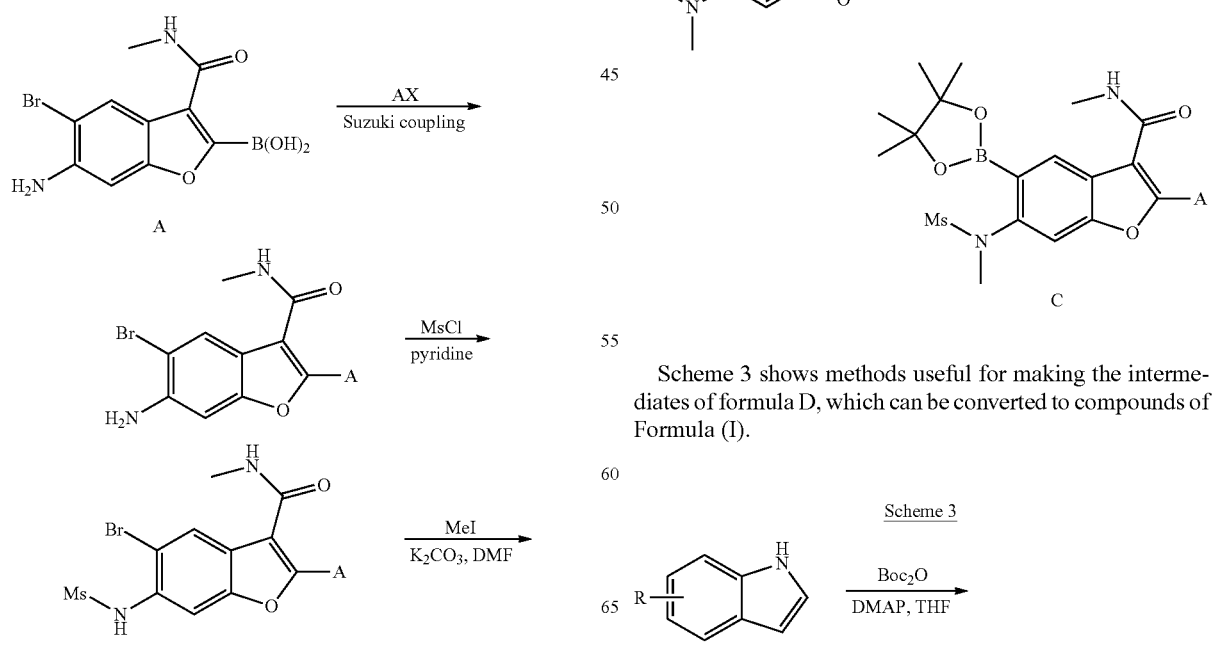
Scheme 3 shows methods useful for making the intermediates of formula D, which can be converted to compounds of Formula (I).

23
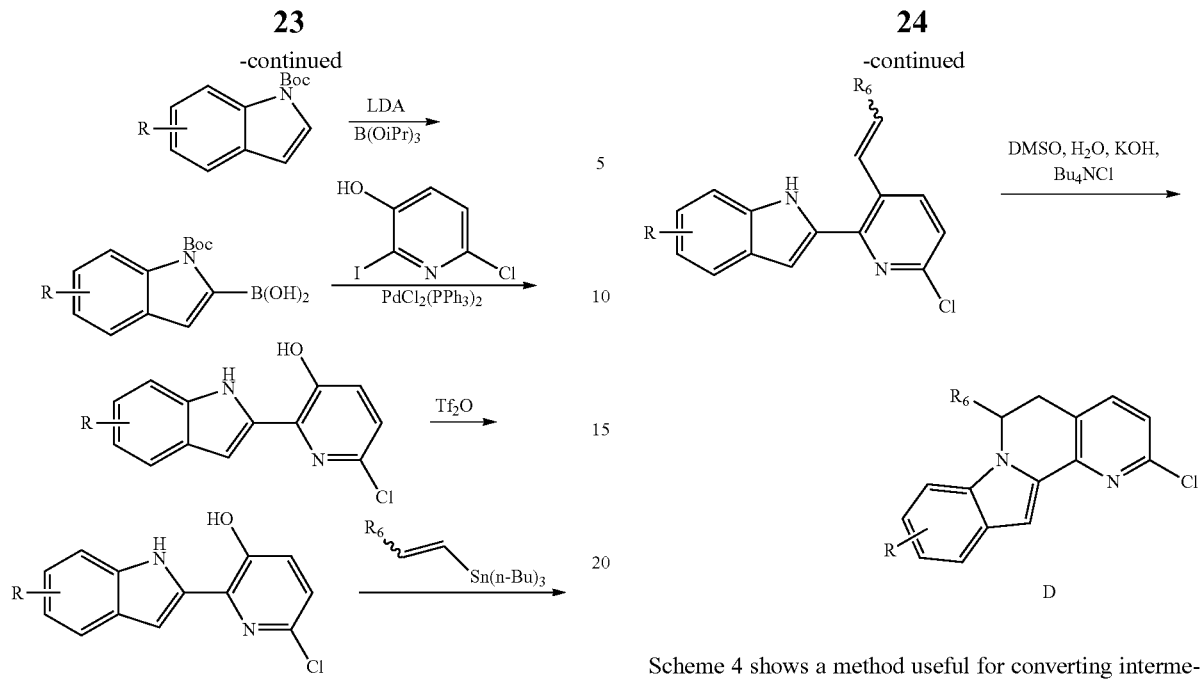
24
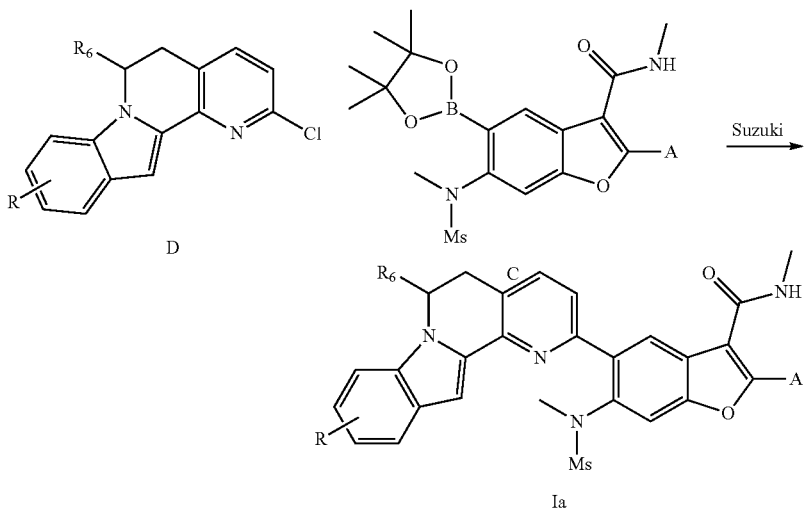
Scheme 4 shows a method useful for converting intermediate of formula D to compounds of formula (Ia).
Scheme 5 shows an alternative route to compounds of formula (Ia), when $R_6$ is H.
Scheme 5
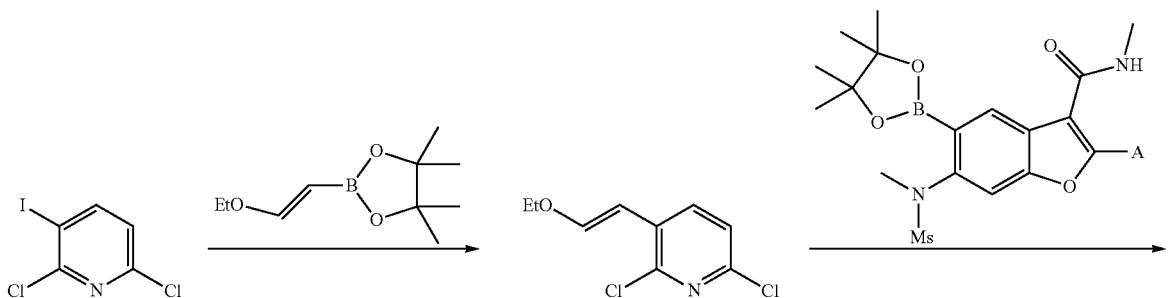

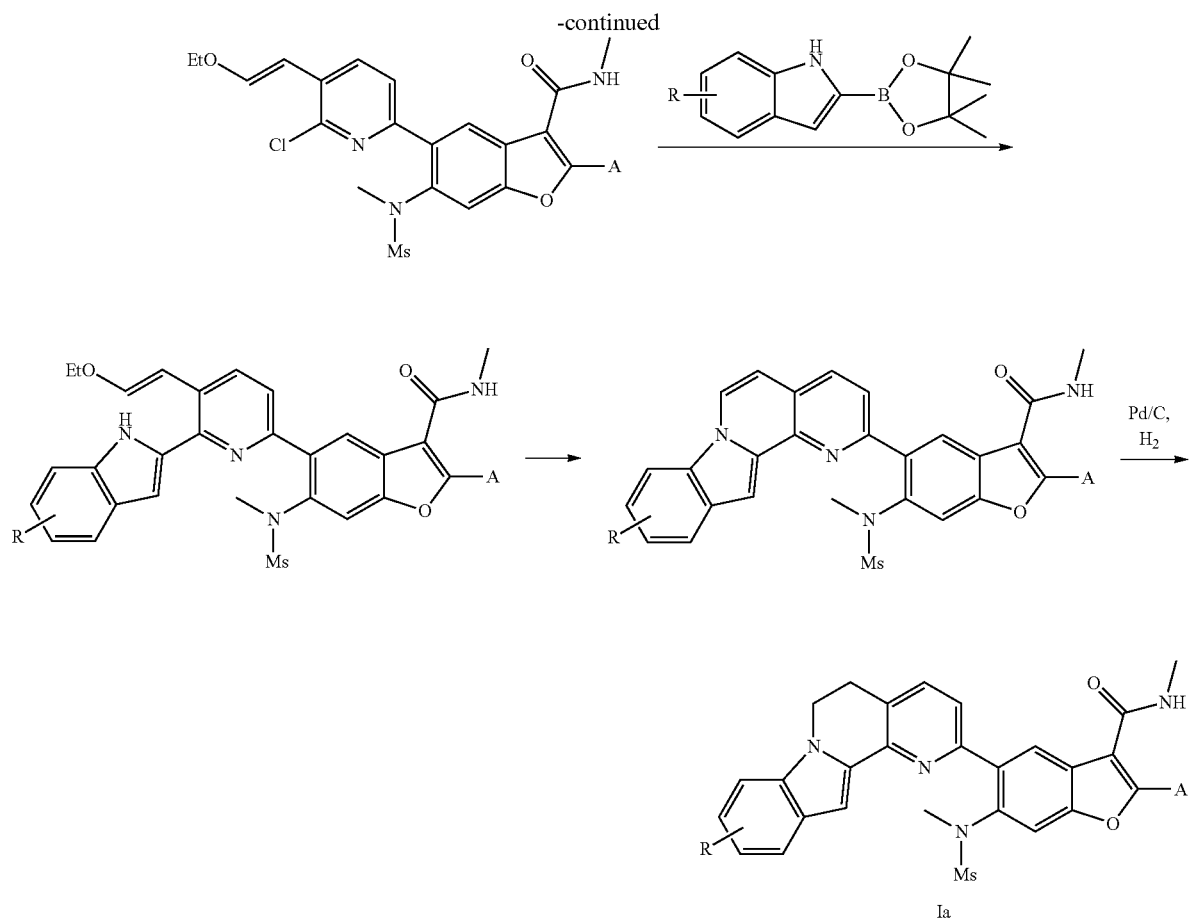
Scheme 6 shows an alternative route to compounds of formula (Ia), when $R_6$ is H, n is 0, 1, 2 or 3.
Scheme 6
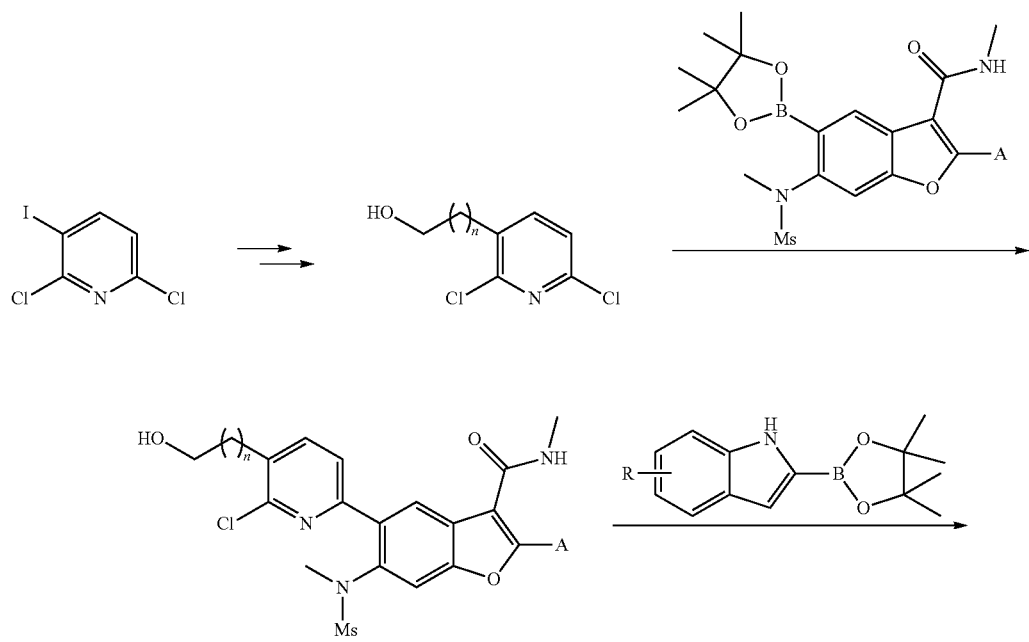

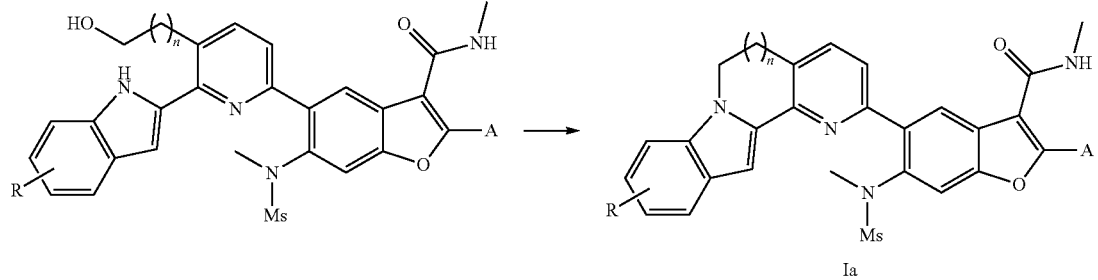
-continued

LIST OF ABBREVIATIONS

AIBN 2,2'-azoisobutyronitrile
a.q., aq Aqueous
$Al_2O_3$ Aluminum oxide
$Ar_2$ Argon
ATM Atmosphere
$BH_3$-DMS Borane methyl sulfide
Boc t-butyloxycarbonyl
$Boc_2O$ Di-tert-butyl-dicarbonate
n-Bu n-butyl
n-BuLi n-butyllithium
$Bu_3SnH$ Tributylin hydride
$Bu_4NCl$ Tetrabutylammonium chloride
conc. concentrated
$CDCl_3$ Trichloro($^2$H)methane or deuterio-trichloromethane
$CHCl_3$ Chloroform
$CH_3SNa$ Sodium thiomethoxide
CO Carbon monoxide
$Cs_2CO_3$ Cesium carbonate
DAST Diethylaminosulfur trifluoride
DCM, $CH_2Cl_2$ Dichloromethane
DEAD Diethyl azodicarboxylate
DIAD Diisopropyl azodicarboxylate
DIBAL-H Diisobutylaluminium hydride
DIPEA, DIEA N,N-Diisopropylethylamine
DMAc Dimethylacetamide
DMAP 4-dimethylaminopyridine
DMF Dimethylformamide
DMSO Dimethylsulfoxide
EDCI N-(3-Dimethylaminopropyl)-N'-ethylcarbodiimide (also EDC)
Et Ethyl
$Et_3N$ Triethylamine
EtOAc, EA Ethyl acetate
EtOH Ethanol
Fe Iron
HATU (Dimethylamino)-N,N-dimethyl(3H-[1,2,3]triazolo[4,5-b]pyridin-3-yloxy)methaniminium hexafluorophosphate
$HBF_4$ Fluoroboric acid
HCl Hydrochloric acid
$H_2$ Hydrogen gas or atmosphere
$HNO_3$ Nitric acid
$H_2O$ Water
$H_2O_2$ Hydrogen peroxide
$H_2SO_4$ Sulfuric acid
HOBT 1-Hydroxy benzotriazole
$^1$H-NMR Proton Nuclear Magnetic Resonance
HPLC High Performance Liquid Chromatography
IPA Isopropyl alcohol
KCN Potassium cyanide
$K_2CO_3$ Potassium carbonate
$K_3CO_3$ Potassium bicarbonate
KOAc Potassium acetate
KOH Potassium hydroxide
$K_3PO_4$ Potassium Phosphate
LDA Lithium diisopropylamide
LiCl Lithium chloride
LiOH Lithium hydroxide
$MeNH_2$, $CH_3NH_2$ Methylamine
MeCN, $CH_3CN$ Acetonitrile
Met, $CH_3I$ Methyl iodide
MeOD Methan($^2$H)ol
MeOH, $CH_3OH$ Methanol
MS Mass spectroscopy
Ms Methanesulfonyl (or mesyl) group
MsCl Methanesulfonyl chloride
$N_2$ Nitrogen gas or atmosphere
$NaBH_4$ Sodium borohydride
$NaBO_3$ Sodium perborate
NaCN Sodium cyanide
$Na_2CO_3$ Sodium carbonate
$NaHCO_3$ Sodium bicarbonate
$NaIO_4$ Sodium periodate
$Na(OAc)_3BH$ Sodium triactetoxy borohydride
$Na_2SO_4$ Sodium sulfate (anhydrous)
$Na_2S_2O_3$ Sodium thiosulfate
NaH Sodium hydride
NCS N-chlorosuccinimide
$NH_4Cl$ Ammonium chloride
$NH_2NH_2.H_2SO_4$ Hydrazine sulfate
NIS N-iodosuccinimide
NMO N-methylmorpholine-N-oxide
$OPPh_3$ Triphenyl phosphine oxide
$OsO_4$ Osmium tetroxide
Pd Palladium
Pd/C Palladium on carbon
$PdCl_2$ Palladium(II) chloride
$Pd_2(dba)_3$ Tris(dibenzylideneacetone)dipalladium(0)
$Pd(dppf)Cl_2$ 1,1'-bis(diphenylphosphino)ferrocene-palladium(II)dichloride
$Pd(dtbpf)Cl_2$, DTBPF 1,1'-bis(di-tert-butylphosphino)ferrocene-dichloropalladium(II)
$PdCl_2$ Palladium(II)chloride
$Pd(OAc)_2$ Palladium(II)acetate
$Pd(PPh_3)_2Cl_2$ 1,1'-bis(tetrakis(triphenylphosphine))palladium(II)dichloride
PE Petroleum ether
Ph Phenyl
$PPh_3$ Triphenylphosphine
$POCl_3$ Phosphoryl chloride
Py Pyridine
RT Room temperature, approximately 25° C.

sat saturated
SFC Supercritical fluid chromatography
TBAc Tert-butyl acetate
TEA Triethylamine
TFA Trifluoroacetic acid
THF Tetrahydrofuran
TLC Thin layer chromatography
TMSCl Trimethylsilyl chloride

EXAMPLES

Example 1

5-(11-fluoro-5,6-dihydroindolo[1,2-h][1,7]naphthyridin-2-yl)-N-methyl-6-(N-methylmethylsulfonamido)-2-(4-(trifluoromethyl)phenyl)benzofuran-3-carboxamide

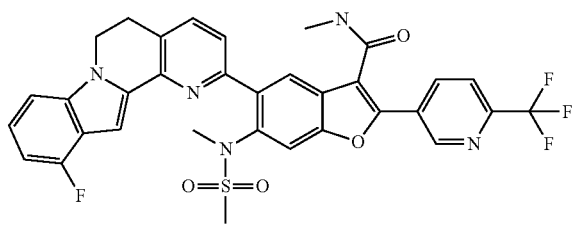 [SMILES: CNC(=O)c1c(-c2ccc(C(F)(F)F)nc2)oc2cc(N(C)S(C)(=O)=O)c(-c3ccc4c(n3)-c3cc5c(F)cccc5n3CC4)cc12]

Step 1—Synthesis of ethyl 5-bromobenzofuran-3-carboxylate

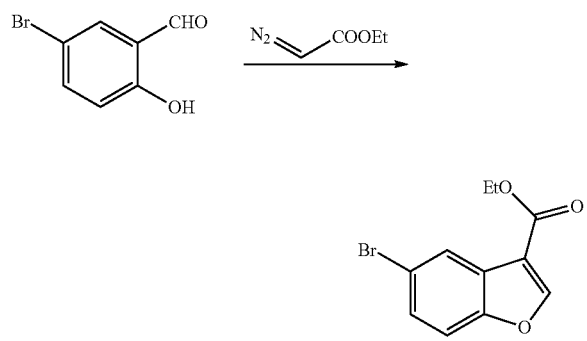

HBF$_4$·Et$_2$O (16.2 g, 99.5 mmol) was added to a solution of 5-bromo-2-hydroxybenzaldehyde (200 g, 995 mmol) in CH$_2$Cl$_2$ (500 mL), and then a solution of ethyl diazoacetate (180 g, 1.42 mol) in CH$_2$Cl$_2$ (500 mL) was introduced as evolution of N$_2$ gas while the reaction was not allowed over 38° C. Once gas evolution ceased, the reaction mixture was concentrated by rotary evaporator and conc. H$_2$SO$_4$ (129 g, 1.29 mol, 98%) was added to the mixture while stirring. After 20 minutes, the acidic mixture was neutralized with Na$_2$CO$_3$ (a.q). After the mixture was stored and crystallized overnight, ethyl 5-bromobenzofuran-3-carboxylate (100 g, yield: 75%) was obtained by filtration. $^1$H-NMR (CDCl$_3$, 400 MHz) δ 8.25 (s, 1H), 8.15~8.21 (m, 1H), 7.44~7.50 (m, 1H), 7.37~7.42 (m, 1H), 4.41 (q, J=7.2 Hz, 2H), 1.43 (t, J=7.2 Hz, 3H). MS (M+H)$^+$: 269/271.

Step 2—Synthesis of ethyl 5-bromo-6-nitrobenzofuran-3-carboxylate

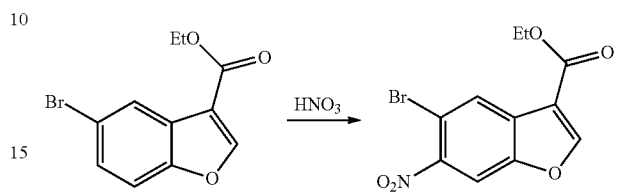

To a solution of ethyl 5-bromobenzofuran-3-carboxylate (95 g, 353 mmol) in CHCl$_3$ (1000 mL), fuming HNO$_3$ (192 mL, 95%) was added dropwise at −20° C. over 90 min and stirred at 0° C. for 1 hour. The reaction mixture was added to ice water and extracted with CH$_2$Cl$_2$. The organic layer was washed with NaHCO$_3$ and brine. The solvent was removed by distillation to provide the crude product of ethyl 5-bromo-6-nitrobenzofuran-3-carboxylate (95 g, yield: 85%). It was used for the next step without further purification.

Step 3—Synthesis of ethyl 6-amino-5-bromobenzofuran-3-carboxylate

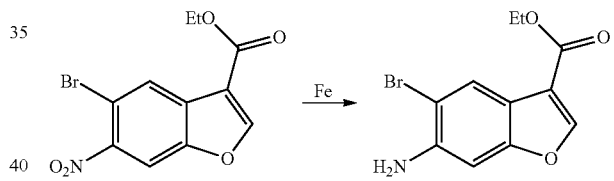

A mixture of crude ethyl 5-bromo-6-nitrobenzofuran-3-carboxylate (95 g, 302 mmol), iron filings (50.67 g, 907 mmol) and NH$_4$Cl (97 g, 1.82 mol) in MeOH-THF—H$_2$O (2:2:1, 1000 mL) were stirred at refluxing for 3 hours. After filtered and concentrated in vacuum, the residue was purified by column chromatography (eluted with PE:EA from 20:1 to 10:1) to furnish the pure product of ethyl 6-amino-5-bromobenzofuran-3-carboxylate (58.0 g, yield: 68%). $^1$H-NMR (DMSO-d$_6$, 400 MHz) δ 8.46 (s, 1H), 7.85 (s, 1H), 7.03 (s, 1H), 5.55 (br s, 2H), 4.31 (q, J=7.2 Hz, 2H), 1.32 (t, J=7.2 Hz, 3H). MS (M+H)$^+$: 284/286.

Step 4—Synthesis of 6-amino-5-bromobenzofuran-3-carboxylic acid

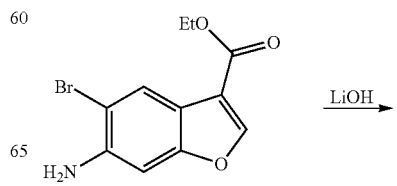

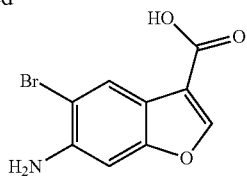

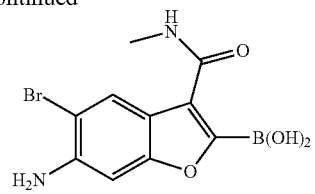

To a solution of ethyl 6-amino-5-bromobenzofuran-3-carboxylate (58 g, 204 mmol) in 1,4-dioxane and H₂O (850 mL and 150 mL) was add LiOH.H₂O (42.8 g, 1.02 mol). The reaction mixture was refluxed for 2 hours, and then 400 mL H₂O was added to the reaction mixture. After acidifying to pH 4~5 with HCl, the resulting solid was filtered to give the product of 6-amino-5-bromobenzofuran-3-carboxylic acid (51 g, yield: 97%). ¹H-NMR (DMSO-d₆, 400 MHz) δ 8.36 (s, 1H), 7.87 (s, 1H), 7.02 (s, 1H), 5.51 (br s, 2H). MS (M+H)⁺: 256/258.

To a solution of LDA in THF (62.5 mmol, 70 mL, freshly prepared), 6-amino-5-bromo-N-methylbenzofuran-3-carboxamide (4 g, 14.86 mmol) in THF (60 mL) was added dropwise at −78° C. under N₂. After the mixture was stirred for 1 hour, trimethyl borate (6.18 g, 59.5 mmol) was added dropwise at −78° C. After the mixture was stirred for 1 hour, NH₄Cl (a.q.) was added, and the mixture was extracted with EtOAc (100 mL×3), dried over Na₂SO₄, filtrated and concentrated to give (6-amino-5-bromo-3-(methylcarbamoyl)benzofuran-2-yl)boronic acid (3.3 g, yield: 70%). ¹H-NMR (DMSO-d₆, 400 MHz) δ 9.56 (s, 2H), 8.46 (d, J=4.8 Hz, 1H), 8.00 (s, 1H), 6.95 (s, 1H), 5.20~5.82 (br s, 2H), 2.87 (d, J=4.8 Hz, 3H). MS (M+H)⁺: 313/315.

Step 5—Synthesis of 6-amino-5-bromo-N-methylbenzofuran-3-carboxamide

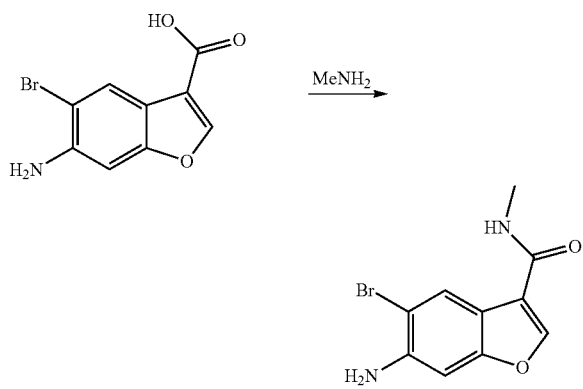

Step 7—Synthesis of 6-amino-5-bromo-2-iodo-N-methylbenzofuran-3-carboxamide

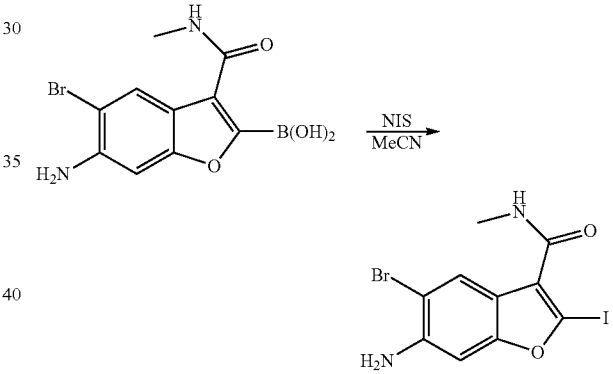

To a solution of 6-amino-5-bromobenzofuran-3-carboxylic acid (51 g, 199 mmol) in dry DMF (500 mL) was added EDCI (53.1 g, 298.77 mmol) and HOBT (40.4 g, 299 mmol). The reaction mixture was stirred at room temperature for 2 h, and then Et₃N (60.5 g, 598 mmol) and MeNH₂.HCl (40.3 g, 598 mmol) were added to the reaction mixture. After stirring for another 2 hours, the reaction mixture was concentrated in vacuum and then 300 mL Na₂CO₃ (sat., a.q.) was added to the mixture. The resulting solid was filtered to give the crude product, which was purified by column chromatography (DCM:MeOH=30:1) to give the product 6-amino-5-bromo-N-methylbenzofuran-3-carboxamide (38 g, yield: 71%). ¹H-NMR (DMSO-d₆, 400 MHz) δ 8.19~8.21 (m, 2H), 7.98 (s, 1H), 6.97 (s, 1H), 5.46 (br s, 2H), 2.75 (d, J=4.4 Hz, 3H). MS (M+H)⁺: 269/271.

To a solution of (6-amino-5-bromo-3-(methylcarbamoyl)benzofuran-2-yl)boronic acid (2 g, 6.4 mmol) in MeCN (20 mL) was added NIS (1.44 g, 6.4 mmol) at 0° C., and then the mixture was stirred at 25° C. overnight. After concentrated in vacuum, the residue was purified by column chromatography (DCM:EtOAc=10:1) to give to give pure 6-amino-5-bromo-2-iodo-N-methylbenzofuran-3-carboxamide (2 g, yield: 80%). ¹H-NMR (CDCl₃, 400 MHz) δ 7.84 (s, 1H), 6.80 (s, 1H), 6.45 (s, 1H), 2.92 (s, 3H). MS (M+H)⁺: 395/397.

Step 6—Synthesis of (6-amino-5-bromo-3-(methylcarbamoyl)benzofuran-2-yl)boronic acid Step 8—Synthesis of 5-bromo-2-iodo-N-methyl-6-(methylsulfonamido)benzofuran-3-carboxamide

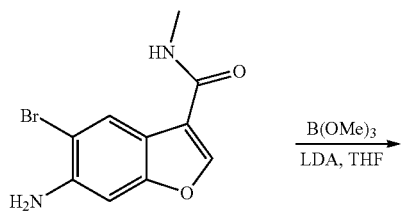

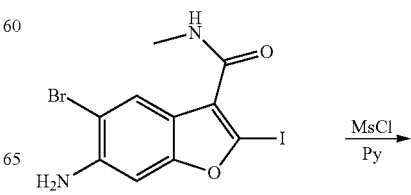

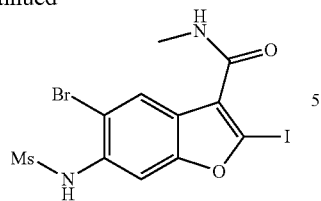

To a solution of 6-amino-5-bromo-2-iodo-N-methylbenzofuran-3-carboxamide (1 g, 2.53 mmol) in pyridine, MsCl (580 mg, 5.06 mmol) was added dropwise at 0° C. The mixture was allowed to warm to room temperature and stirred for 1.5 h. After the solvent was removed in vacuo, the reaction mixture was adjusted to pH=5-6 with 1 N HCl aq. After filtration, the solid was dissolved in THF:H$_2$O=5:1 (15 mL) and then LiOH.H$_2$O (800 mg, 20 mmol) was added. The mixture was stirred for 30 minutes at room temperature. After the solvent was removed in vacuo, the reaction mixture was adjusted to pH=5-6 with 1 N HCl aq. Finally the precipitate was collected to give 5-bromo-2-iodo-N-methyl-6-(methylsulfonamido)benzofuran-3-carboxamide (800 mg, 90% purity by HPLC, yield: 60%), which was used for the next step without further purification. $^1$H-NMR (CDCl$_3$, 400 MHz) δ 8.37 (s, 1H), 7.84 (s, 1H), 6.86 (s, 1H), 6.29 (s, 1H), 3.07 (d, J=4.8 Hz, 3H), 2.99 (s, 3H). MS (M+H)$^+$: 473/475.

Step 9—Synthesis of 5-bromo-2-iodo-N-methyl-6-(N-methylmethylsulfonamido)benzofuran-3-carboxamide

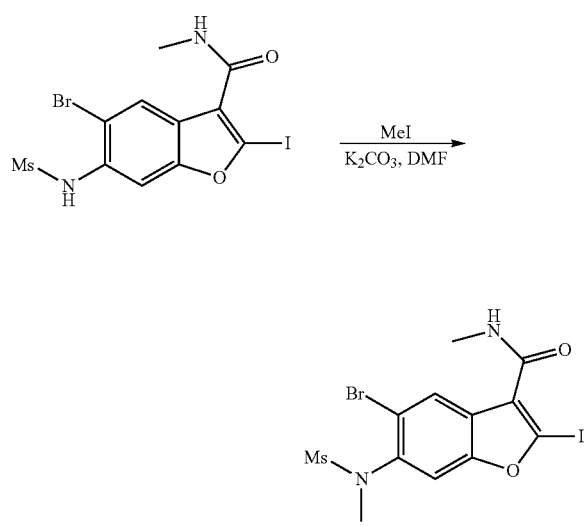

To a suspension of 5-bromo-2-iodo-N-methyl-6-(methylsulfonamido)benzofuran-3-carboxamide (177 mg, 90% purity, 0.34 mmol) and K$_2$CO$_3$ (140 mg, 1.01 mmol) in DMF (3 mL) was added dropwise CH$_3$I (79 mg, 0.68 mol) at 0° C. under N$_2$, and then the mixture was stirred at 80° C. for 1 hour. After concentrated in vacuum, the residue was suspended in H$_2$O and extracted with DCM. The residue was purified by column chromatography (eluted with DCM: EtOAc from 10:1 to 2:1) to give 5-bromo-2-iodo-N-methyl-6-(N-methylmethylsulfonamido)benzofuran-3-carboxamide (150 mg, yield: 90%). $^1$H-NMR (CDCl$_3$, 400 MHz) δ 8.38 (s, 1H), 7.66 (s, 1H), 6.27 (s, 1H), 3.32 (s, 3H), 3.08 (d, J=4.8 Hz, 3H), 2.89 (s, 3H). MS (M+H)$^+$: 487/489.

Step 10—Synthesis of 5-bromo-N-methyl-6-(N-methylmethylsulfonamido)-2-(6-(trifluoromethyl)pyridin-3-yl)benzofuran-3-carboxamide

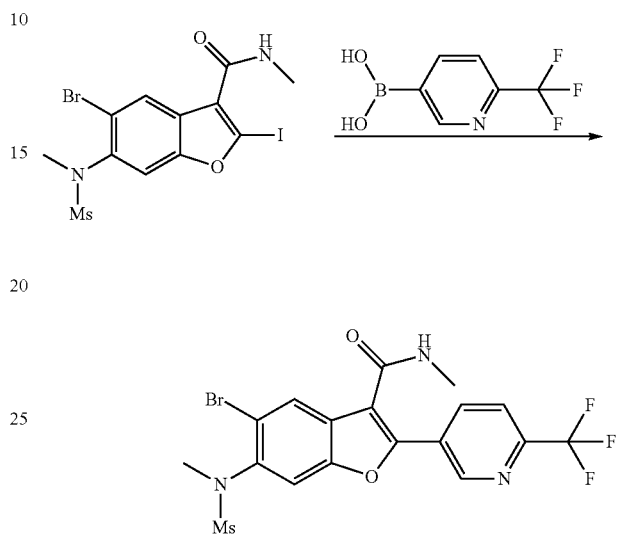

A mixture of 5-bromo-2-iodo-N-methyl-6-(N-methylmethylsulfonamido)benzofuran-3-carboxamide (1.5 g, 3.1 mmol), (6-(trifluoromethyl)pyridin-3-yl)boronic acid (705 mg, 3.7 mmol), Pd(dppf)Cl$_2$ (245 mg, 0.3 mmol) and Na$_2$CO$_3$ (985 mg, 9.3 mmol) in dioxane/H$_2$O (20 mL/4 mL) was stirred at 80° C. for 6 h. Water was added and the mixture was extracted with EtOAc. The organic phase was dried over Na$_2$SO$_4$ and concentrated in vacuum. The residue was purified by column chromatography (PE:EA=1:1) to give the product of 5-bromo-N-methyl-6-(N-methylmethylsulfonamido)-2-(6-(trifluoromethyl)pyridin-3-yl)benzofuran-3-carboxamide (1.4 g, yield: 90%). $^1$H-NMR (DMSO-d$_6$, 400 MHz) δ 9.24 (s, 1H), 8.65 (d, J=4.4 Hz, 1H), 8.56 (d, J=8.0 Hz, 1H), 8.17 (s, 1H), 8.12 (d, J=8.0 Hz, 1H), 8.08 (s, 1H), 3.23 (s, 3H), 3.22 (s, 3H), 2.85 (d, J=4.4 Hz, 3H). MS (M+H)$^+$: 506/508.

Step 11—Synthesis of N-methyl-6-(N-methylmethylsulfonamido)-5-(4,4,5,5-tetramethyl-1,3,2-dioxaborolan-2-yl)-2-(6-(trifluoromethyl)pyridin-3-yl)benzofuran-3-carboxamide

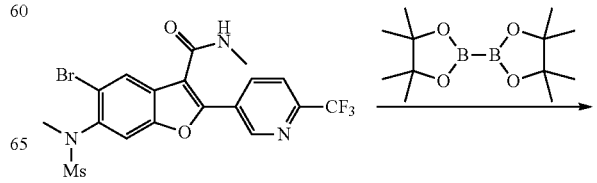

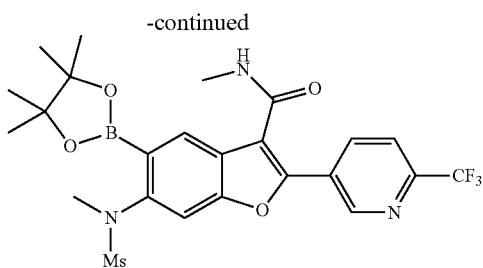

A mixture of 5-bromo-N-methyl-6-(N-methylmethylsulfonamido)-2-(6-(trifluoromethyl)pyridin-3-yl)benzofuran-3-carboxamide (1.4 g, 2.7 mmol), bis(pinacolato)diboron (3.5 g, 13.8 mmol), Pd(dppf)Cl$_2$ (226 mg, 0.27 mmol) and KOAc (814 mg, 8.3 mmol) in dioxane/H$_2$O (10 mL/1 mL) was stirred at 120° C. for 5 h. Water was added and the mixture was extracted with EtOAc. The organic phase was dried over Na$_2$SO$_4$ and concentrated in vacuum. The residue was purified by column chromatography (PE:EA=1:1) to give the product of N-methyl-6-(N-methylmethylsulfonamido)-5-(4,4,5,5-tetramethyl-1,3,2-dioxaborolan-2-yl)-2-(6-(trifluoromethyl)pyridin-3-yl)benzofuran-3-carboxamide (1.3 g, yield: 87%). $^1$H-NMR (MeOD, 400 MHz) δ 9.22 (s, 1H), 8.54 (d, J=8.4 Hz, 1H), 8.11 (s, 1H), 7.97 (d, J=8.4 Hz, 1H), 7.79 (s, 1H), 3.38 (s, 3H), 3.01 (s, 3H), 3.00 (s, 3H), 1.39 (s, 12H). MS (M+H)$^+$: 554.

Step 12—Synthesis of tert-butyl 4-fluoro-1H-indole-1-carboxylate

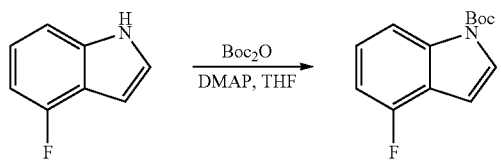 [SMILES: "Boc2O" ; Fc1cccc2[nH]ccc12 ; CC(C)(C)OC(=O)n1ccc2c(F)cccc21]

To a solution of 4-fluoro-1H-indole (150 g, 1.11 mol) and DMAP (4.5 g, 3% Wt) in THF (2.5 L) was added (Boc)$_2$O (255 g, 1.16 mol) dropwise. The mixture was stirred at room temperature overnight. The organic solvent was removed in vacuum, and the residue was purified by column chromatography (PE) to give tert-butyl 4-fluoro-1H-indole-1-carboxylate (250 g, yield: 96%). $^1$H-NMR (CDCl$_3$, 400 MHz) δ 7.92 (d, J=8.4 Hz, 1H), 7.55 (d, J=3.6 Hz, 1H), 7.23 (m, 1H), 6.90 (m, 1H), 6.66 (d, J=3.6 Hz, 1H), 1.67 (s, 9H). MS (M+H)$^+$: 236.

Step 13—Synthesis of (1-(tert-butoxycarbonyl)-4-fluoro-1H-indol-2-yl)boronic acid

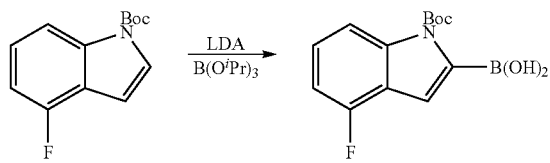 [SMILES: CC(C)(C)OC(=O)n1ccc2c(F)cccc21 ; "LDA" ; CC(C)(C)OC(=O)n1c(B(O)O)cc2c(F)cccc21 ; "B(OiPr)3"]

To a solution of diisopropylamine (175 mL, 1.25 mol) in THF (800 mL) at 0° C. was added n-BuLi (500 mL, 1.25 mol, 2.5 M in hexane) dropwise. The mixture was stirred at 0° C. for 40 min. Then the mixture was cooled to −78° C. Tert-butyl 4-fluoro-1H-indole-1-carboxylate (118 g, 0.50 mol) in THF (300 mL) was added dropwise slowly, followed by triisopropyl borate (231 mL, 1.00 mol). The mixture was stirred at −78° C. for another 40 min. The reaction was monitored by HPLC. When the reaction was completed, the reaction was quenched with NH$_4$Cl (sat. 500 mL). Then the mixture was adjusted to pH=6 with 1 N HCl. Extracted with EtOAc (2000 mL) and the combined organic layers were washed with brine (500 mL), dried over Na$_2$SO$_4$, filtered and concentrated. The obtained solid was recrystallized with EtOAc and PE to give (1-(tert-butoxycarbonyl)-4-fluoro-1H-indol-2-yl)boronic acid (93 g, yield: 64%, store in fridge). $^1$H-NMR (CDCl$_3$, 400 MHz) δ 7.77 (d, J=8.4 Hz, 1H), 7.57 (s, 1H), 7.44 (s, 2H), 7.24 (m, 1H), 6.90 (m, 1H), 1.66 (s, 9H). MS (M+H)$^+$: 280.

Step 14—Synthesis of 6-chloro-2-iodopyridin-3-ol

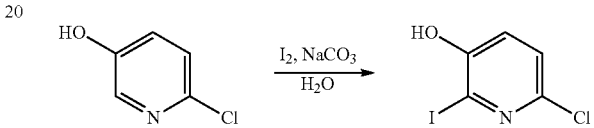

6-chloropyridin-3-ol (5.0 g, 38.60 mmol) was dissolved in water (50 mL) and placed under an N$_2$ atmosphere. Na$_2$CO$_3$ (8.2 g, 77.37 mmol) was added followed by iodine (9.8 g, 38.81 mmol). The reaction mixture was stirred at room temperature for 2 h. The mixture was poured into 1 M Na$_2$S$_2$O$_3$ and extracted with EtOAc. The combined organic phases were washed with brine, dried over Na$_2$SO$_4$ and concentrated to give the product of 6-chloro-2-iodopyridin-3-ol (7.0 g, yield: 70.9%). $^1$H-NMR (CDCl$_3$, 400 MHz) δ 7.17 (d, J=8.4 Hz, 1H), 7.06 (d, J=8.4 Hz, 1H). MS (M+H)$^+$: 256/258.

Step 15—Synthesis of 6-chloro-2-(4-fluoro-1H-indol-2-yl)pyridin-3-ol

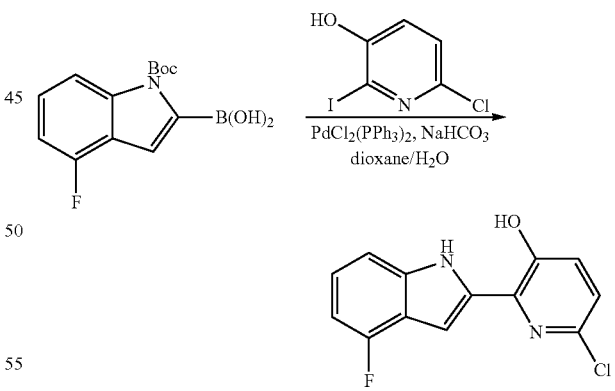

To a solution of (1-(tert-butoxycarbonyl)-4-fluoro-1H-indol-2-yl)boronic acid (126 g, 0.45 mol) and 6-chloro-2-iodopyridin-3-ol (96 g, 0.37 mmol) in 1,4-dioxane (1.8 L) and water (0.2 L) were added Pd(PPh$_3$)$_2$Cl$_2$ (13.2 g, 18.6 mmol) and NaHCO$_3$ (94.8 g, 1.13 mol) under nitrogen atmosphere, and the mixture was heated at 90° C. under N$_2$ for 16 h. The reaction mixture was cooled to room temperature, diluted with EtOAc (900 mL), filtered and concentrated. The residue was diluted with H$_2$O (400 mL) and EtOAc (800 mL), and the layer was separated, the aqueous layer was extracted with EtOAc (3*400 mL). The combined organic layers were washed with brine (800 mL), dried over Na₂SO₄, filtered and concentrated. The residue was purified by column chromatography (PE:EtOAc=20:1~3:1) to give 6-chloro-2-(4-fluoro-1H-indol-2-yl)pyridin-3-ol (70 g, yield: 70.1%). ¹H-NMR (MeOD, 400 MHz) δ 7.36 (s, 1H), 7.23~7.27 (m, 2H), 7.03~7.11 (m, 2H), 6.63~6.68 (m, 1H). MS (M+H)⁺: 263 (M+H).

Step 16—Synthesis of 6-chloro-2-(4-fluoro-1H-indol-2-yl)pyridin-3-yl trifluoromethanesulfonate

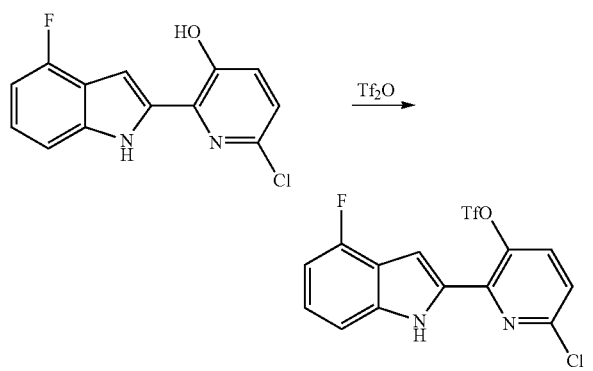

DIPEA (1.96 g, 15.2 mmol) and DMAP (18 mg, 0.15 mmol) were added to a suspension of 6-chloro-2-(4-fluoro-1H-indol-2-yl)pyridin-3-ol (2 g, 7.6 mmol) in anhydrous DCM (20 mL) under N₂. The reaction mixture was cooled to 0° C., and then trifluoromethanesulfonic anhydride (4.28 g, 15.2 mmol) was added dropwise. After stirred at RT for 1 h, the mixture was diluted with water and extracted with CH₂Cl₂. The organic layers were washed with brine, dried over Na₂SO₄, and concentrated. The mixture was purified by column chromatography (PE:EA=200:1) to give 6-chloro-2-(4-fluoro-1H-indol-2-yl)pyridin-3-yl trifluoromethanesulfonate (2.5 g, yield: 83%). ¹H-NMR (DMSO-d₆, 400 MHz) δ 12.12 (br s, 1H), 8.14 (d, J=8.6 Hz, 1H), 7.64 (d, J=8.8 Hz, 1H), 7.36 (d, J=8.2 Hz, 1H), 7.24~7.11 (m, 2H), 6.83 (dd, J=8.0, 10.4 Hz, 1H). MS (M+H)⁺: 395.

Step 17—Synthesis of 6-chloro-2-(4-fluoro-1H-indol-2-yl)pyridin-3-yl trifluoromethanesulfonate

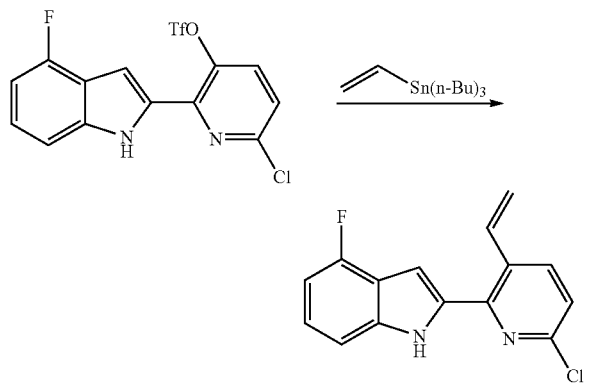

To a mixture of 6-chloro-2-(4-fluoro-1H-indol-2-yl)pyridin-3-yl trifluoromethanesulfonate (2.50 g, 6.3 mmol), tributyl(vinyl)stannane (2.41 g, 7.6 mmol) and anhydrous LiCl (805 mg, 19.0 mmol) in DMF (50 mL), Pd(PPh₃)₂Cl₂ (222 mg, 0.3 mmol) was added under N₂ protection. The reaction mixture was stirred at 60° C. for 1 h. Then it was concentrated in vacuo, the residue was purified by column chromatography (PE:EA=400:1-100:1) to give the product of 2-(6-chloro-3-vinylpyridin-2-yl)-4-fluoro-1H-indole (1.20 g, yield: 69%). ¹H-NMR (CDCl₃, 400 MHz) δ 9.63 (br s, 1H), 7.75 (d, J=8.4 Hz, 1H), 7.28~7.11 (m, 4H), 7.04 (s, 1H), 6.84~6.72 (m, 1H), 5.77 (d, J=17.2 Hz, 1H), 5.60 (d, J=11.2 Hz, 1H). MS (M+H)⁺: 273.

Step 18—Synthesis of 2-chloro-11-fluoro-5,6-dihydroindolo[1,2-h][1,7]naphthyridine

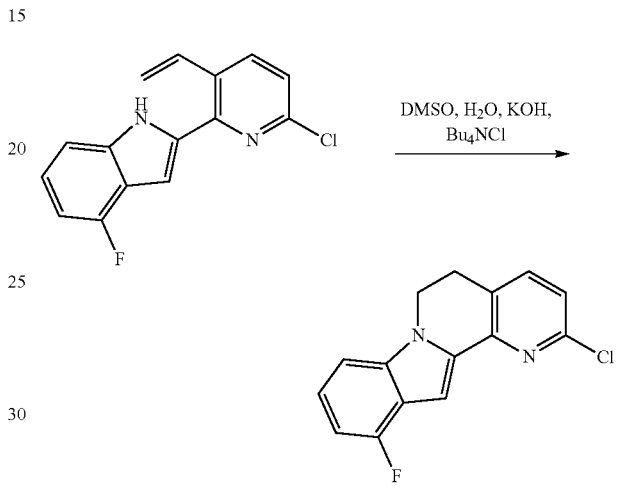

A mixture of 2-(6-chloro-3-vinylpyridin-2-yl)-4-fluoro-1H-indole (1.0 g, 3.7 mmol), DMSO (2.5 mL), TBAC (0.3 mL, 50% aq. solution) and KOH (10 mL, 60% a.q. solution) was stirred under N₂ at 100° C. for 4 h. After cooled to RT and extracted with CH₂Cl₂, the organic layer was washed with water, brine, dried over Na₂SO₄ and concentrated on a rotary evaporator. The residue was purified by column chromatography (PE:EA=100:1~10:1) to give the product of 2-chloro-11-fluoro-5,6-dihydroindolo[1,2-h][1,7]naphthyridine (0.5 g, yield: 50%). And 150 mg of un-reacted 2-(6-chloro-3-vinylpyridin-2-yl)-4-fluoro-1H-indole was recycled during the column purification. ¹H-NMR (CDCl₃, 400 MHz) δ 7.50 (d, J=7.8 Hz, 1H), 7.38 (s, 1H), 7.22~7.04 (m, 3H), 6.86~6.71 (m, 1H), 4.27 (t, J=6.8 Hz, 2H), 3.22 (t, J=6.8 Hz, 2H). MS (M+H)⁺: 273.

Step 19—Synthesis of 5-(11-fluoro-5,6-dihydroindolo[1,2-h][1,7]naphthyridin-2-yl)-N-methyl-6-(N-methylmethylsulfonamido)-2-(4-(trifluoromethyl)phenyl)benzofuran-3-carboxamide

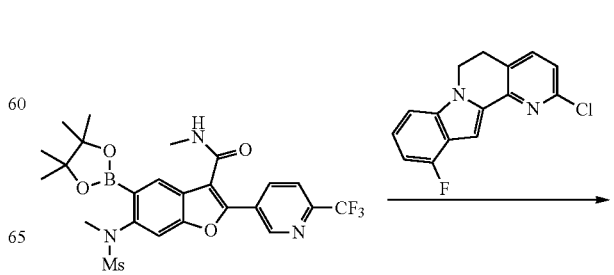

-continued

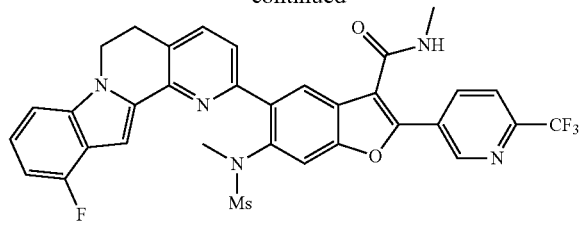

A mixture of N-methyl-6-(N-methylmethylsulfonamido)-5-(4,4,5,5-tetramethyl-1,3,2-dioxaborolan-2-yl)-2-(6-(trifluoromethyl)pyridin-3-yl)benzofuran-3-carboxamide (121 mg, 0.22 mmol), 2-chloro-11-fluoro-5,6-dihydroindolo[1,2-h][1,7]naphthyridine (50 mg, 0.18 mmol) and $K_2CO_3$ (51 mg, 0.37 mmol) in dioxane/water (2 mL/0.4 mL) was stirred at room temperature for 10 min under $N_2$ protection. Then $Pd_2$(dba)$_3$ (18 mg, 0.02 mmol) and X-Phos (17 mg, 0.04 mmol) were added to the reaction solution. The mixture was stirred at 90° C. for 2 hours under $N_2$ protection. The mixture was then cooled to room temperature, added EA (10 mL) and then filtered through a Celite pad. The combined organic phase was washed with water and brine, dried over $Na_2SO_4$ and concentrated. The residue was purified by prep-HPLC to afford the desired product (crude: 70 mg, yield: 58%).
$^1$H-NMR (CDCl$_3$, 400 MHz) δ 9.29 (s, 1H), 8.63 (d, J=7.2 Hz, 1H), 7.95 (s, 1H), 7.67~7.79 (m, 3H), 7.45 (d, J=7.6 Hz, 3H), 7.14~7.24 (m, 3H), 6.78~6.80 (m, 1H), 6.14~6.15 (m, 1H), 4.33 (t, J=6.8 Hz, 1H), 3.29~3.33 (m, 5H), 3.02 (d, J=4.8 Hz, 3H), 2.74 (s, 3H). MS (M+H)$^+$: 663.

Examples 2-16

Examples 2-16, depicted in the table below, were prepared in accordance with the method described in Example 1.

| Example | Structure | NMR | MS (M + H)$^+$ |
|---|---|---|---|
| 2 | 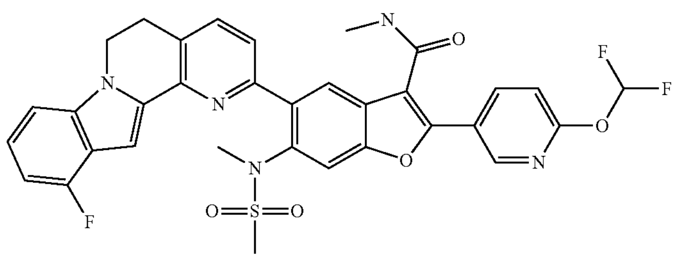 [SMILES: CNC(=O)c1c(-c2ccc(OC(F)F)nc2)oc2cc(N(C)S(C)(=O)=O)c(-c3ccc4c(n3)-c3cc5c(F)cccc5n3CC4)cc12] | $^1$H-NMR (CDCl$_3$, 400 MHz) δ 8.65 (s, 1H), 8.36 (d, J = 8.8 Hz, 1H), 7.89 (s, 1H), 7.67 (s, 0.25H), 7.61~7.64 (m, 2H), 7.49 (s, 0.5H), 7.40 (d, J = 8.0 Hz, 1H), 7.35 (s, 0.25H), 7.23 (s, 1H), 7.10~7.15 (m, 2H), 6.96 (d, J = 8.4 Hz, 1H), 6.61~6.72 (m, 1H), 5.95 (s, 1H), 4.28~4.31 (m, 2H), 3.30 (s, 1H), 3.21~3.29 (m, 2H), 2.99 (d, J = 4.8 Hz, 3H), 2.68 (s, 3H). | 662 |
| 3 | 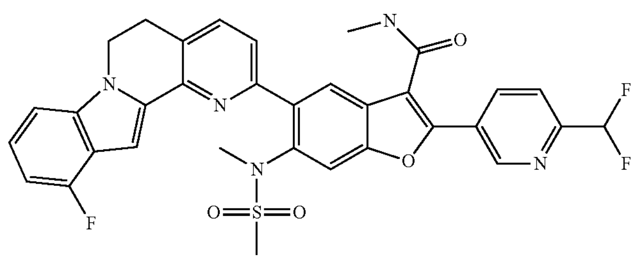 [SMILES: CNC(=O)c1c(-c2ccc(C(F)F)nc2)oc2cc(N(C)S(C)(=O)=O)c(-c3ccc4c(n3)-c3cc5c(F)cccc5n3CC4)cc12] | $^1$H-NMR (CDCl$_3$, 400 MHz) δ 9.22 (s, 1H), 8.55 (dd, J = 8.0, 1.6 Hz, 1H), 7.95 (s, 1H), 7.71~7.76 (m, 2H), 7.67 (d, J = 7.6 Hz, 1H), 7.45 (d, J = 7.6 Hz, 1H), 7.24 (s, 1H), 7.13~7.18 (m, 2H), 6.76~6.82 (m, 1H), 6.68 (s, 1H), 6.13 (d, J = 3.6 Hz, 1H), 4.33 (t, J = 6.8 Hz, 2H), 3.34 (s, 3H), 3.29~3.33 (m, 2H), 3.02 (d, J = 5.2 Hz, 3H), 2.73 (s, 3H). | 646 |
| 4 | 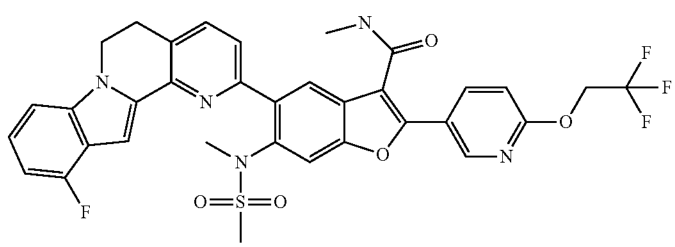 [SMILES: CNC(=O)c1c(-c2ccc(OCC(F)(F)F)nc2)oc2cc(N(C)S(C)(=O)=O)c(-c3ccc4c(n3)-c3cc5c(F)cccc5n3CC4)cc12] | $^1$H-NMR (CDCl$_3$, 400 MHz) δ 8.81 (d, J = 1.6 Hz, 1H), 8.35 (dd, J = 8.8, 1.6 Hz, 1H), 7.98 (s, 1H), 7.68~7.74 (m, 2H), 7.48 (d, J = 7.6 Hz, 1H), 7.31 (s, 1H), 7.15~7.22 (m, 2H), 7.01 (d, J = 8.8 Hz, 1H), 6.77~6.85 (m, 1H), 6.05 (d, J = 3.6 Hz, 1H), 4.86 (q, J = 8.8 Hz, 2H), 4.37 (t, J = 6.4 Hz, 2H), 3.38 (s, 3H), 3.34 (t, J = 6.4 Hz, 2H), 3.04 (d, J = 5.2 Hz, 3H), 2.74 (s, 3H). | 694 |
| 5 | 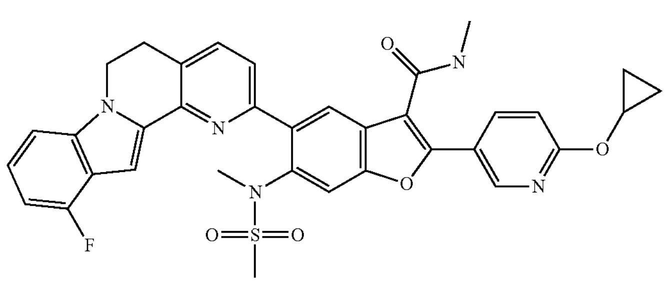 [SMILES: CNC(=O)c1c(-c2ccc(OC3CC3)nc2)oc2cc(N(C)S(C)(=O)=O)c(-c3ccc4c(n3)-c3cc5c(F)cccc5n3CC4)cc12] | $^1$H-NMR (CDCl$_3$, 400 MHz) δ 8.80 (d, J = 1.6 Hz, 1H), 8.22 (dd, J = 2.4, 8.8 Hz, 1H), 7.97 (s, 1H), 7.64~7.69 (m, 2H), 7.44 (d, J = 7.6 Hz, 1H), 7.24 (s, 1H), 7.12~7.17 (m, 2H), 6.88 (d, J = 8.8 Hz, 1H), 6.78 (dd, J = 7.2, 8.61 Hz, 1H), 6.02 (d, J = 4.4 Hz, 1H), 4.33 (t, J = 6.4 Hz, 2H), 4.28 (dt, J = 3.2, 5.6 Hz, 1H), 3.36 (s, 3H), 3.30 (t, J = 6.4 Hz, 2H), 2.98 (d, J = 5.2 Hz, 3H), 2.69 (s, 3H), 0.83 (d, J = 3.6 Hz, 2H), 0.81 (br s., 2H). | 652 |

| Example | Structure | NMR | MS (M + H)+ |
|---|---|---|---|
| 6 | 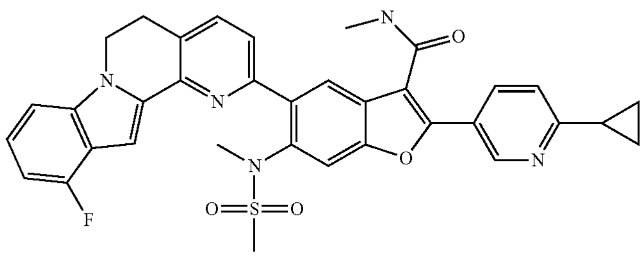 [SMILES: CNC(=O)c1c(-c2ccc(C3CC3)nc2)oc2cc(N(C)S(C)(=O)=O)c(-c3ccc4c(n3)-c3cc5c(F)cccc5n3CC4)cc12] | ¹H-NMR (CDCl₃, 400 MHz) δ 8.94~8.97 (m, 1H), 8.14 (dd, J = 2.0, 8.0 Hz, 1H), 7.98 (s, 1H), 7.64~7.68 (m, 2H), 7.44 (d, J = 8.0 Hz, 1H), 7.25~7.29 (m, 2H), 7.12~7.18 (m, 2H), 6.74~6.81 (m, 1H), 6.01 (d, J = 4.4 Hz, 1H), 4.33 (t, J = 6.8 Hz, 2H), 3.36 (s, 3H), 3.30 (t, J = 6.4 Hz, 2H), 2.98 (d, J = 4.8 Hz, 3H), 2.69 (s, 3H), 2.06~2.13 (m, 1H), 1.11 (dd, J = 2.4, 4.4 Hz, 2H), 1.04~1.09 (m, 2H). | 636 |
| 7 | 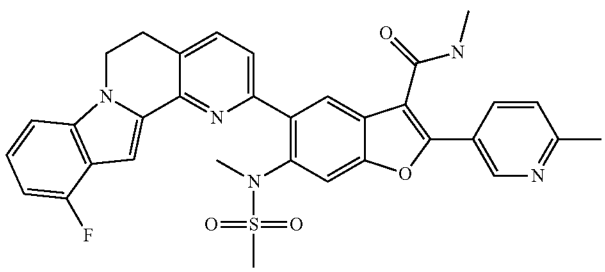 [SMILES: CNC(=O)c1c(-c2ccc(C)nc2)oc2cc(N(C)S(C)(=O)=O)c(-c3ccc4c(n3)-c3cc5c(F)cccc5n3CC4)cc12] | ¹H-NMR (CDCl₃, 400 MHz) δ 9.00 (s, 1H), 8.18~8.20 (m, 1H), 7.97 (s, 1H), 7.64~7.67 (m, 2H), 7.42 (d, J = 7.6 Hz, 1H), 7.27 (d, J = 2.8 Hz, 2H), 7.13~7.19 (m, 2H), 6.76-6.80 (m, 1H), 6.20 (br s, 1H), 4.31~4.34 (m, 2H), 3.36 (s, 3H), 3.28~3.31 (m, 2H), 2.98 (d, J = 4.8 Hz, 3H), 2.69 (s, 3H), 2.61 (m., 3H). | 610 |
| 8 | 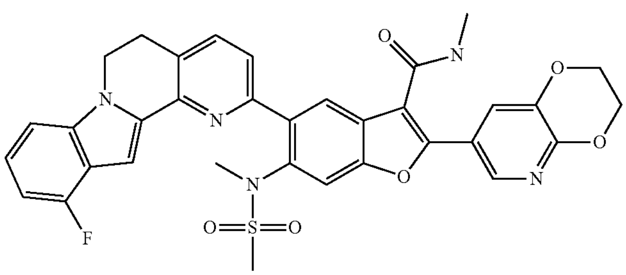 [SMILES: CNC(=O)c1c(-c2cnc3c(c2)OCCO3)oc2cc(N(C)S(C)(=O)=O)c(-c3ccc4c(n3)-c3cc5c(F)cccc5n3CC4)cc12] | ¹H-NMR (DMSO-d₆, 400 MHz) δ 8.36 (s, 1H), 7.94 (s, 1H), 7.82 (s, 1H), 7.62 (s, 2H), 7.40 (d, J = 8.0 Hz, 1H), 7.23 (s, 2H), 7.09 (s, 2H), 6.74 (d, J = 8.0 Hz, 0.4H), 5.91 (s, 0.4H), 4.46 (s, 2H), 4.27~4.29 (m, 4H), 3.32 (s, 2H), 3.27 (d, J = 6.0 Hz, 2H), 2.95 (d, J = 4.8 Hz, 3H), 2.65 (s, 3H). | 654 |
| 9 | 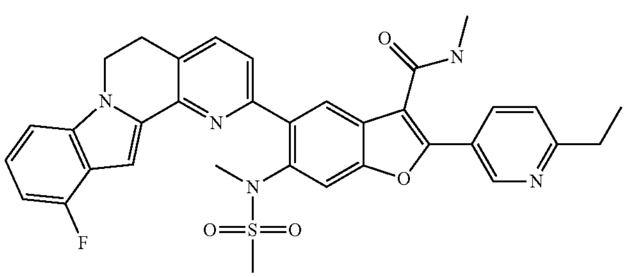 [SMILES: CCc1ccc(-c2oc3cc(N(C)S(C)(=O)=O)c(-c4ccc5c(n4)-c4cc6c(F)cccc6n4CC5)cc3c2C(=O)NC)cn1] | ¹H-NMR (CDCl₃, 400 MHz) δ 9.05 (s, 1H), 8.23 (dd, J₁ = 8.4 Hz, J₂ = 2.0 Hz, 1H), 7.99 (s, 1H), 7.69 (s, 1H), 7.66 (d, J = 8.0 Hz, 1H), 7.44 (d, J = 8.0 Hz, 1H), 7.24~7.31 (m, 2H), 7.12~7.16 (m, 2H), 6.77~6.80 (m, 1H), 5.96 (br s, 1H), 4.33 (t, J = 6.4 Hz, 2H), 3.36 (s, 3H), 3.31 (t, J = 6.4 Hz, 2H), 2.99 (d, J = 4.8 Hz, 3H), 2.87~2.92 (m, 2H), 2.70 (s, 3H), 1.35 (t, J = 7.2 Hz, 3H). | 624 |
| 10 | 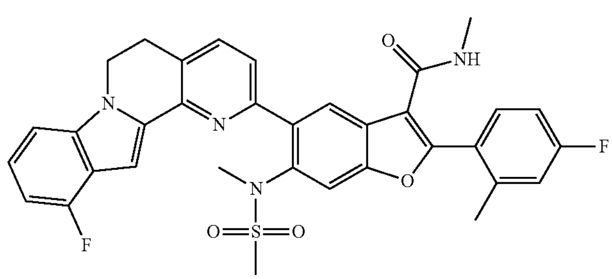 [SMILES: CNC(=O)c1c(-c2ccc(F)cc2C)oc2cc(N(C)S(C)(=O)=O)c(-c3ccc4c(n3)-c3cc5c(F)cccc5n3CC4)cc12] | ¹H-NMR (CDCl₃, 400 MHz) δ 8.29 (s, 1H), 7.61 (d, J = 8.0 Hz, 2H), 7.40~7.47 (m, 2H), 7.22 (s, 1H), 7.02~7.10 (m, 4H), 6.74 (d, J = 7.8 Hz, 1H), 5.43 (br s, 1H), 4.29 (t, J = 6.4 Hz, 2H), 3.37 (s, 3H), 3.23~3.28 (m, 2H), 2.77 (d, J = 4.8 Hz, 3H), 2.57 (s, 3H), 2.30 (s, 3H). | 627 |

| Example | Structure | NMR | MS (M + H)+ |
|---|---|---|---|
| 11 | 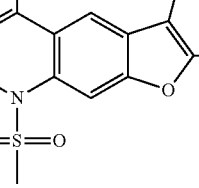 | ¹H-NMR (CDCl₃, 400 MHz) δ 8.69 (d, J = 4.4 Hz, 1H), 8.64 (d, J = 5.2 Hz, 1H), 8.10 (s, 1H), 7.85 (d, J = 4.8 Hz, 2H), 7.74 (s, 1H), 7.66 (d, J = 4.8 Hz, 1H), 7.52 (d, J = 8.0 Hz, 1H), 7.40 (d, J = 8.0 Hz, 1H), 7.15~7.18 (m, 1H), 7.07 (s, 1H), 6.83~6.86 (m, 1H), 4.39 (t, J = 6.4 Hz, 2H), 3.25~3.32 (m, 5H), 3.05~3.12 (m, 1H), 2.93 (s, 3H), 2.82 (d, J = 4.8 Hz, 3H), 1.26 (d, J = 6.8 Hz, 6H). | 638 |
| 12 | 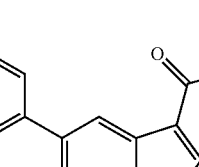 | ¹H-NMR (CDCl₃, 400 MHz) δ 8.22 (s, 1H), 7.66~7.69 (m, 3H), 7.47 (d, J = 8.0 Hz, 1H), 7.32~7.35 (m, 1H), 7.28 (s, 1H), 7.16~7.18 (m, 3H), 6.79~6.81 (m, 1H), 5.64 (br s, 1H), 4.33~4.36 (m, 2H), 3.40 (s., 3H), 3.30~3.33 (m, 2H), 2.90 (d, J = 4.8 Hz, 3H), 2.67 (s, 3H). | 647 |
| 13 | 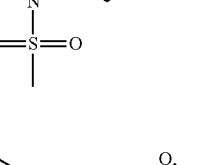 | ¹H-NMR (CDCl₃, 400 MHz) δ 8.03 (s, 1H), 7.89~8.00 (m, 1H), 7.75 (s, 1H), 7.70~7.72 (m, 1H), 7.47~7.55 (m, 3H), 7.31 (s, 1H), 7.14~7.19 (m, 2H), 6.80~6.81 (m, 1H), 6.11~6.12 (m, 1H), 4.37 (t, J = 6.8 Hz, 2H), 3.37 (s, 3H), 3.34 (t, J = 6.8 Hz, 2H), 3.02 (d, J = 4.8 Hz, 3H), 2.77 (s, 3H). | 638 |
| 14 | 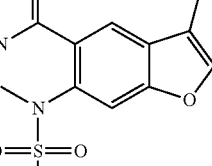 | ¹H-NMR (CDCl₃, 400 MHz) δ 8.82 (s, 1H), 8.05 (d, J = 8.0 Hz, 1H), 7.89 (s, 1H), 7.56~7.69 (m, 2H), 7.39 (d, J = 4.8 Hz, 1H), 7.22 (s, 1H), 7.07~7.12 (m, 2H), 6.73 (t, J = 8.0 Hz, 1H), 6.17 (br s, 1H), 4.28 (t, J = 6.0 Hz, 2H), 3.29 (s, 3H), 3.25 (t, J = 6.0 Hz, 2H), 2.96 (d, J = 4.8 Hz, 3H), 2.67 (s, 3H), 2.53 (s, 3H). | 628 |
| 15 | 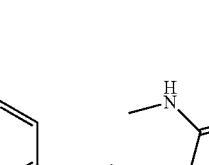 | ¹H-NMR (CDCl₃, 400 MHz) δ 8.85 (s, 1H), 8.55~8.59 (m, 1H), 7.95 (s, 1H), 7.67~7.71 (m, 2H), 7.46 (d, J = 8.0 Hz, 1H), 7.28 (s, 1H), 7.13~7.18 (m, 2H), 7.05~7.08 (m, 1H), 6.78~6.81 (m, 1H), 6.06 (br s, 1H), 4.34 (t, J = 6.4 Hz, 2H), 3.35 (s, 3H), 3.33 (d, J = 6.4 Hz, 2H), 3.02 (d, J = 4.8 Hz, 3H), 2.73 (s, 3H). | 614 |

| Example | Structure | NMR | MS (M + H)+ |
|---|---|---|---|
| 16 | 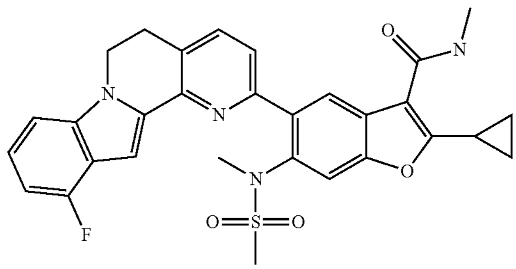 [SMILES: CNC(=O)c1c(C2CC2)oc2cc(N(C)S(C)(=O)=O)c(-c3ccc4c(n3)-c3cc5c(F)cccc5n3CC4)cc12] | $^1$H-NMR (CDCl$_3$, 400 MHz) δ 7.85 (s, 1H), 7.65 (d, J = 7.6 Hz, 1H), 7.50 (s, 1H), 7.43 (d, J = 7.6 Hz, 1H), 7.28 (s, 1H), 7.11~7.19 (m, 2H), 6.76~6.83 (m, 1H), 6.12 (d, J = 3.6 Hz, 1H), 4.33 (t, J = 6.4 Hz, 2H), 3.33 (s, 3H), 3.29 (t, J = 6.4 Hz, 2H), 3.02 (d, J = 4.8 Hz, 3H), 2.80~2.87 (m, 1H), 2.69 (s, 3H), 1.25 (d, J = 2.4 Hz, 2H), 1.15~1.21 (m, 2H). | 559 |

Example 17

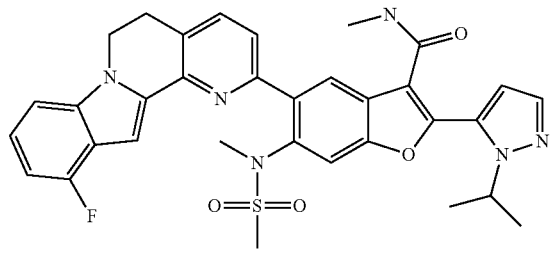 [SMILES: CNC(=O)c1c(-c2ccnn2C(C)C)oc2cc(N(C)S(C)(=O)=O)c(-c3ccc4c(n3)-c3cc5c(F)cccc5n3CC4)cc12]

Step 1—Synthesis of 5-bromo-2-(1-isopropyl-1H-pyrazol-5-yl)-N-methyl-6-(N-methylmethylsulfonamido)benzofuran-3-carboxamide

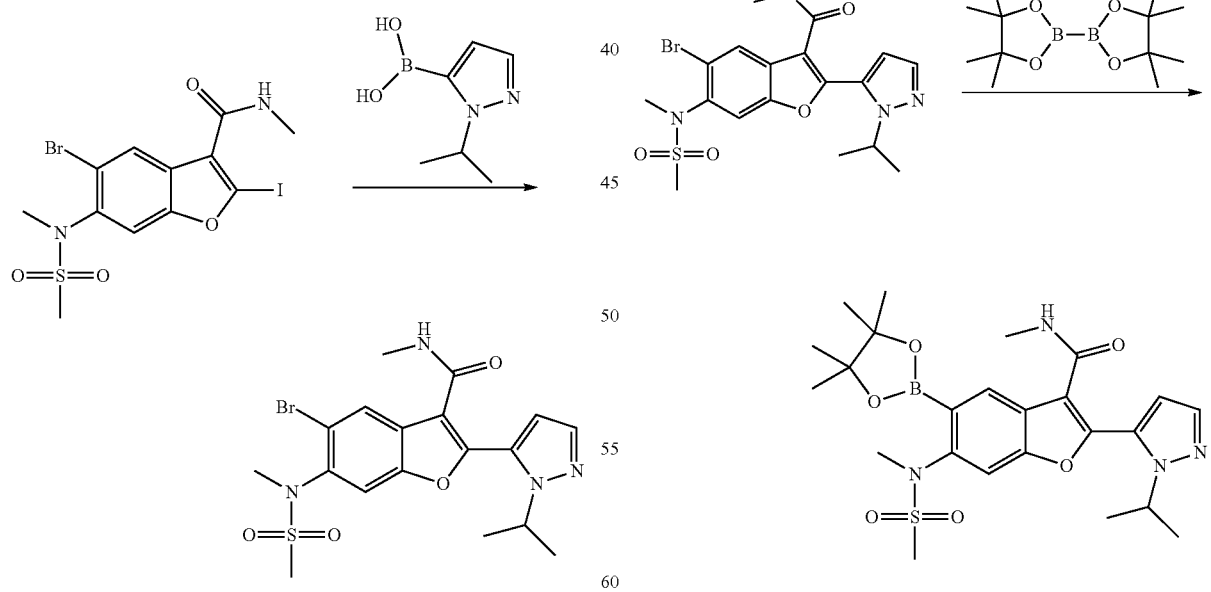

To a solution of 5-bromo-2-iodo-N-methyl-6-(N-methylmethylsulfonamido)benzofuran-3-carboxamide (50 mg, 0.12 mmol), (1-isopropyl-1H-pyrazol-5-yl)boronic acid (23 mg, 0.12 mmol) and Na$_2$CO$_3$ (22 mg, 0.25 mmol) in 1,4-dioxane (0.5 mL) and water (0.05 mL) was added Pd (dppf)Cl$_2$ (10 mg) under nitrogen. The mixture was heated at 100° C. for 4 hour and filtered through the Celite pad. The filtrate was extracted with EtOAc, and then the combined organic phase was washed with brine, dried over Na$_2$SO$_4$ and concentrated in vacuo. The crude product was purified by the prep-TLC (PE:EA=1:1) to give 5-bromo-2-(1-isopropyl-1H-pyrazol-5-yl)-N-methyl-6-(N-methylmethylsulfonamido)benzofuran-3-carboxamide (25 mg, yield: 50%). $^1$H-NMR (CDCl$_3$, 400 MHz) δ 8.50 (s, 1H), 7.66 (s, 1H), 7.64 (s, 1H), 6.58 (d, J=2.0 Hz, 1H), 5.74 (d, J=3.6 Hz, 1H), 4.45~4.52 (m, 1H), 3.28 (s, 3H), 3.04 (s, 3H), 2.82 (d, J=4.8 Hz, 3H), 1.51 (s, 6H). MS (M+H)+: 469/471.

Step 2—Synthesis of 2-(1-isopropyl-1H-pyrazol-5-yl)-N-methyl-6-(N-methylmethylsulfonamido)-5-(4,4,5,5-tetramethyl-1,3,2-dioxaborolan-2-yl)benzofuran-3-carboxamide To a degassed solution of 5-bromo-2-(1-isopropyl-1H-pyrazol-5-yl)-N-methyl-6-(N-methylmethylsulfonamido)benzofuran-3-carboxamide (60 mg, 0.12 mmol) and bis(pinacolato)diboron (100 mg, 0.42 mmol) in 1,4-dioxane (1.0 mL)

was added Pd(dppf)Cl$_2$ (5 mg) and KOAc (50 mg, 0.50 mmol) under N$_2$. The mixture was heated at a pre-heated oil-bath at 110° C. for 3 h. The reaction mixture was concentrated in vacuo and it was extracted with EtOAc. The residue was washed with H$_2$O, brine, and dried over Na$_2$SO$_4$. After concentration, the crude product was purified by prep-TLC (PE: EA=2:1) to give of 2-(1-isopropyl-1H-pyrazol-5-yl)-N-methyl-6-(N-methylmethylsulfonamido)-5-(4,4,5,5-tetramethyl-1,3,2-dioxaborolan-2-yl)benzofuran-3-carboxamide (25 mg, yield: 30%). $^1$H-NMR (CDCl$_3$, 400 MHz) δ 8.58 (s, 1H), 7.62 (s, 1H), 7.55 (s, 1H), 6.59 (d, J=1.6 Hz, 1H), 5.74 (s, 1H), 4.49~4.56 (m, 1H), 3.30 (s, 3H), 2.93 (s, 3H), 2.84 (d, J=4.8 Hz, 3H), 1.44 (d, J=6.4 Hz, 6H), 1.30 (s, 12H). MS (M+H)$^+$: 517.

Step 3—Synthesis of 5-(11-fluoro-5,6-dihydroindolo [1,2-h][1,7]naphthyridin-2-yl)-2-(1-isopropyl-1H-pyrazol-5-yl)-N-methyl-6-(N-methylmethylsulfonamido)benzofuran-3-carboxamide

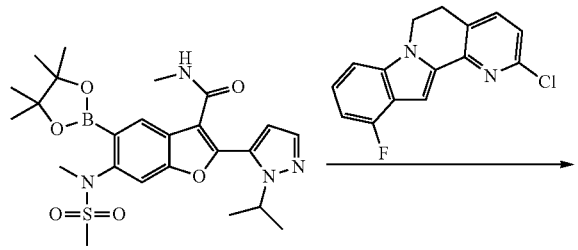

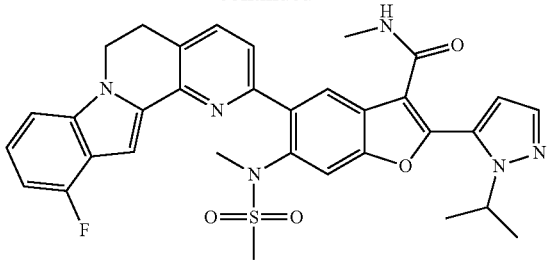

To a solution of 2-(1-isopropyl-1H-pyrazol-5-yl)-N-methyl-6-(N-methylmethylsulfonamido)-5-(4,4,5,5-tetramethyl-1,3,2-dioxaborolan-2-yl)benzofuran-3-carboxamide (78 mg, 0.14 mmol), 2-chloro-11-fluoro-5,6-dihydroindolo [1,2-h][1,7]naphthyridine (35 mg, 0.13 mmol) and K$_2$CO$_3$ (27 mg, 0.19 mmol) in 1,4-dioxane (0.8 mL) and water (0.05 mL) were added X-Phos (10 mg) and Pd$_2$(dba)$_3$ (20 mg) under nitrogen. The mixture was heated at 120° C. for 2 hours and filtered through the Celite pad. The filtrate was extracted with EtOAc, then the combined organic phase was washed with brine, dried over Na$_2$SO$_4$ and concentrated in vacuo. The crude product was purified by the prep-HPLC to give the desired compound (30 mg, yield: 42%). $^1$H-NMR (CDCl$_3$, 400 MHz) δ 8.41 (s, 1H), 7.72 (s, 1H), 7.69 (d, J=7.6 Hz, 1H), 7.47 (d, J=7.6 Hz, 1H), 7.28 (s, 1H), 7.17~7.19 (m, 2H), 6.79~6.83 (m, 1H), 6.69 (s, 1H), 5.85 (s, 1H), 4.61~4.64 (m, 1H), 4.35~4.38 (m, 2H), 3.44 (s, 3H), 3.32~3.56 (m, 2H), 2.90 (d, J=5.2 Hz, 3H), 2.64 (s, 3H). MS (M+H)$^+$: 627.

Examples 18-27

Examples 18~27, depicted in the table below, were prepared in accordance with the method described in Example 17.

| Example | Structure | NMR | MS (M + H)$^+$ |
|---|---|---|---|
| 18 | 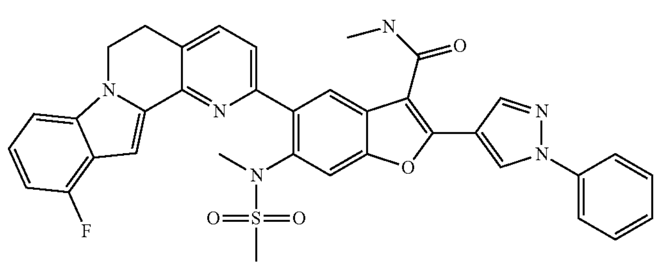 [SMILES: CNC(=O)c1c(-c2cnn(-c3ccccc3)c2)oc2cc(N(C)S(C)(=O)=O)c(-c3ccc4c(n3)-c3cc5c(F)cccc5n3CC4)cc12] | $^1$H-NMR (CDCl$_3$, 400 MHz) δ 8.99 (s, 1H), 8.30 (s, 1H), 7.85 (s, 1H), 7.74 (d, J = 8.0 Hz, 2H), 7.42~7.46 (m, 3H), 7.20~7.30 (m, 1H), 7.15 (s, 1H), 7.08~7.15 (m, 2H), 6.74 (t, J = 8.4 Hz, 1H), 6.08 (s, 1H), 4.30 (t, J = 6.4 Hz, 2H), 3.30 (s, 3H), 3.26 (d, J = 6.4 Hz, 2H), 3.01 (d, J = 4.8 Hz, 3H), 2.72 (s, 3H). | 661 |
| 19 | 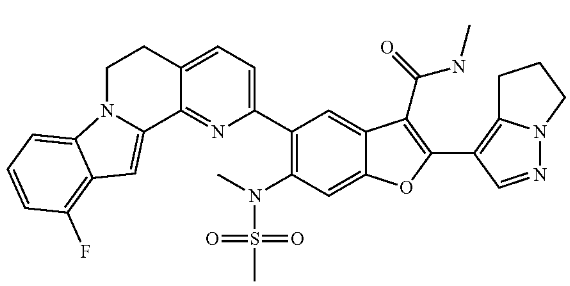 [SMILES: CNC(=O)c1c(-c2cnn3c2CCC3)oc2cc(N(C)S(C)(=O)=O)c(-c3ccc4c(n3)-c3cc5c(F)cccc5n3CC4)cc12] | $^1$H-NMR (CDCl$_3$, 400 MHz) δ 8.14 (s, 1H), 7.90 (s, 1H), 7.61 (d, J = 7.6 Hz, 1H), 7.55 (s, 1H), 7.39 (d, J = 8.0 Hz, 1H), 7.22 (s, 1H), 7.08 (d, J = 6.4 Hz, 2H), 6.73 (t, J = 7.2 Hz, 1H), 5.95 (s, 1H), 4.29 (t, J = 6.4 Hz, 2H), 4.17 (t, J = 6.4 Hz, 2H), 3.32 (s, 3H), 3.26 (t, J = 6.4 Hz, 2H), 3.14 (t, J = 6.4 Hz, 2H), 2.96 (d, J = 4.2 Hz, 3H), 2.67 (t, J = 6.4 Hz, 2H), 2.61 (s, 3H). | 625 |

| Example | Structure | NMR | MS (M + H)+ |
|---|---|---|---|
| 20 | 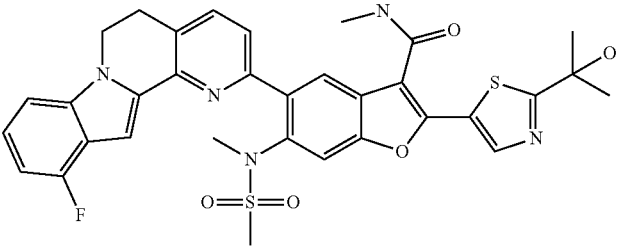 | ¹H-NMR (CDCl₃, 400 MHz) δ 8.08 (s, 1H), 7.85 (s, 1H), 7.64 (d, J = 7.60 Hz, 1H), 7.57 (s, 1H), 7.44 (d, J = 8.00 Hz, 1H), 7.29 (s, 1H), 7.12~7.19 (m, 2H), 6.76~6.80 (m, 1H), 6.23 (br s, 1H), 4.31~4.34 (m, 2H), 3.53~3.55 (m, 4H), 3.34 (s, 3H), 3.28~3.31 (m, 2H), 3.02 (d, J = 4.80 Hz, 3H), 2.75 (s, 3H), 2.09~2.14 (m, 4H). | 660 |
| 21 | 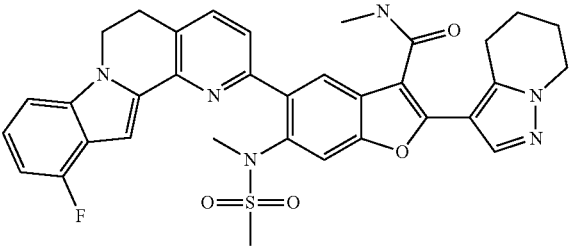 [SMILES: CNC(=O)c1c(-c2cnn3c2CCCC3)oc2cc(N(C)S(C)(=O)=O)c(-c3ccc4c(n3)-c3cc5c(F)cccc5n3CC4)cc12] | ¹H-NMR (CDCl₃, 400 MHz) δ 8.06 (s, 1H), 8.02 (s, 1H), 7.65 (d, J = 8.0 Hz, 1H), 7.61 (s, 1H), 7.43 (d, J = 8.0 Hz, 1H), 7.24 (s, 1H), 7.09~7.19 (m, 2H), 6.73~6.81 (m, 1H), 6.01 (d, J = 3.6 Hz, 1H), 4.33 (t, J = 6.0 Hz, 2H), 4.22 (t, J = 5.6 Hz, 2H), 3.38 (s, 3H), 3.30 (t, J = 6.0 Hz, 2H), 3.06 (t, J = 5.6 Hz, 2H), 2.97 (d, J = 4.4 Hz, 3H), 2.63 (s, 3H), 2.10 (d, J = 4.8 Hz, 2H), 1.94 (d, J = 4.8 Hz, 2H). | 639 |
| 22 | 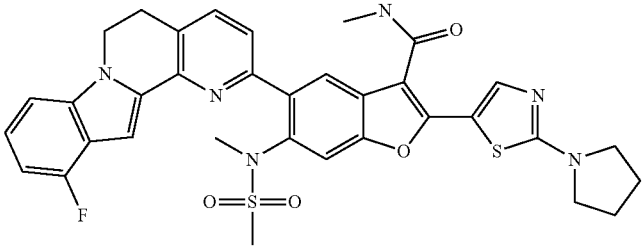 [SMILES: CNC(=O)c1c(-c2cnc(N3CCCC3)s2)oc2cc(N(C)S(C)(=O)=O)c(-c3ccc4c(n3)-c3cc5c(F)cccc5n3CC4)cc12] | ¹H-NMR (CDCl₃, 400 MHz) δ 8.08 (s, 1H), 7.85 (s, 1H), 7.64 (d, J = 7.60 Hz, 1H), 7.57 (s, 1H), 7.44 (d, J = 8.00 Hz, 1H), 7.29 (s, 1H), 7.12~7.19 (m, 2H), 6.76~6.80 (m, 1H), 6.23 (br s, 1H), 4.31~4.34 (m, 2H), 3.53~3.55 (m, 4H), 3.34 (s, 3H), 3.28~3.31 (m, 2H), 3.02 (d, J = 4.80 Hz, 3H), 2.75 (s, 3H), 2.09~2.14 (m, 4H). | 671 |
| 23 | 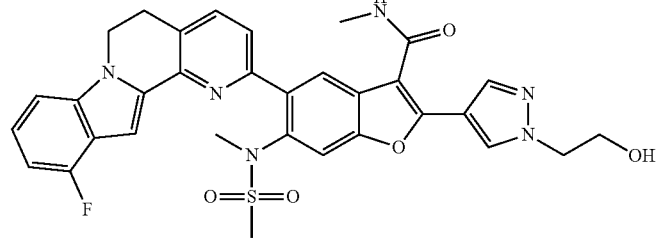 | ¹H-NMR (CDCl₃, 400 MHz) δ 8.45 (s, 1H), 8.07 (s, 1H), 7.80 (s, 1H), 7.15 (d, J = 7.2 Hz, 1H), 7.54 (s, 1H), 7.25 (d, J = 8.0 Hz, 1H), 7.25 (s, 1H), 7.10 (d, J = 6.0 Hz, 2H), 6.71~6.75 (m, 1H), 6.21 (d, J = 4.0 Hz, 1H), 4.28 (d, J = 6.8 Hz, 2H), 4.23~4.26 (m, 2H), 3.99 (s, 2H), 3.28 (s, 3H), 3.25 (s, 2H), 2.96 (d, J = 4.8 Hz, 3H), 2.70 (s, 3H). | 629 |
| 24 | 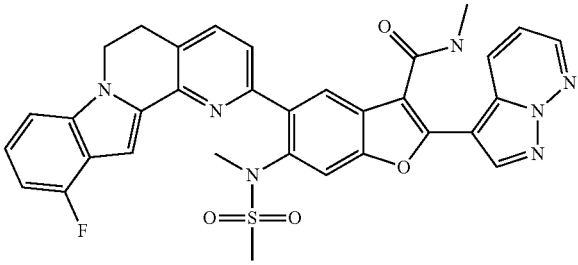 [SMILES: CNC(=O)c1c(-c2cnn3ncccc23)oc2cc(N(C)S(C)(=O)=O)c(-c3ccc4c(n3)-c3cc5c(F)cccc5n3CC4)cc12] | ¹H-NMR (CDCl₃, 400 MHz) δ 8.89 (s, 1H), 8.55 (d, J = 8.8 Hz, 1H), 8.39 (d, J = 3.6 Hz, 1H), 7.95 (s, 1H), 7.64-7.72 (m, 2H), 7.44 (d, J = 8.0 Hz, 1H), 7.21 (dd, J = 4.4, 9.2 Hz, 2H), 7.14 (br s., 2H), 6.74~6.81 (m, 1H), 6.11 (d, J = 3.6 Hz, 1H), 4.34 (t, J = 6.4 Hz, 2H), 3.36 (s, 3H), 3.31 (t, J = 6.4 Hz, 2H), 3.02 (d, J = 4.8 Hz, 3H), 2.69 (s, 3H). | 636 |
| 25 | 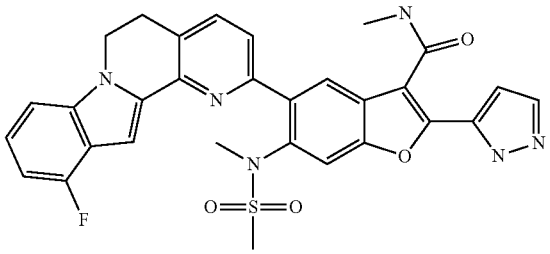 [SMILES: CNC(=O)c1c(-c2ccn[nH]2)oc2cc(N(C)S(C)(=O)=O)c(-c3ccc4c(n3)-c3cc5c(F)cccc5n3CC4)cc12] | ¹H-NMR (CDCl₃, 400 MHz) δ 10.15 (s, 1H), 8.48 (s, 1H), 8.00~8.09 (m, 2H), 7.86 (s, 1H), 7.51 (m, J = 8.4 Hz, 1H), 7.40 (s, 1H), 7.16 (d, J = 8.4 Hz, 1H), 7.07 (s, 1H), 6.95 (s, 1H), 6.84 (s, 1H), 4.40 (t, J = 8.4 Hz, 2H), 2.93 (s, 3H), 2.88 (d, J = 4.8 Hz, 3H), 2.53 (s, 3H), 2.50 (t, J = 8.4 Hz, 2H). | 585 |

| Example | Structure | NMR | MS (M + H)+ |
|---|---|---|---|
| 26 | 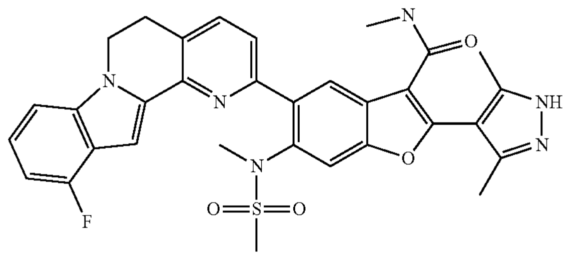 [SMILES: CNC(=O)c1c(-c2c(C)n[nH]c2C)oc2cc(N(C)S(C)(=O)=O)c(-c3ccc4c(n3)-c3cc5c(F)cccc5n3CC4)cc12] | ¹H-NMR (CDCl₃, 400 MHz) δ 8.26 (s, 1H), 7.60 (d, J = 8.0 Hz, 1H), 7.59 (s, 1H), 7.40 (d, J = 8.0 Hz, 1H), 7.20 (s, 1H), 7.09~7.12 (m 2H), 6.70~6.74 (m 1H), 5.76 (br s, 1H), 4.28 (t, J = 6.4 Hz, 2H), 3.37 (s, 3H), 3.25 (t, J = 6.4 Hz, 2H), 2.84 (d, J = 4.8 Hz, 3H), 2.56 (s, 3H), 2.29 (s, 6H). | 613 |
| 27 | 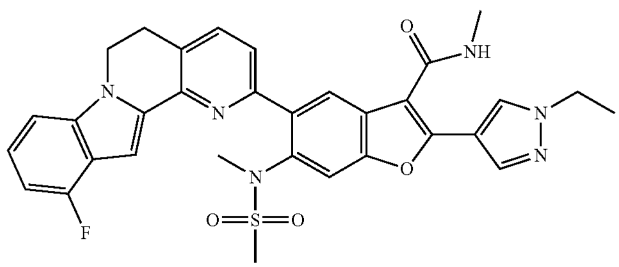 [SMILES: CCn1cc(-c2oc3cc(N(C)S(C)(=O)=O)c(-c4ccc5c(n4)-c4cc6c(F)cccc6n4CC5)cc3c2C(=O)NC)cn1] | ¹H-NMR (DMSO-d₆, 400 MHz) δ 8.50 (s, 1H), 8.14 (s, 1H), 7.89 (s, 1H), 7.67 (d, J = 8.0 Hz, 1H), 7.62 (s, 1H), 7.48 (d, J = 8.0 Hz, 1H), 7.31 (s, 1H), 7.14~7.19 (m, 2H), 6.80 (t, J = 8.0 Hz, 1H) 6.20 (br s, 1H), 4.34 (t, J = 6.8 Hz, 2H), 4.25 (dd, J₁ = 14.4 Hz, J₂ = 7.6 Hz, 2H), 3.35 (s, 3H), 3.31 (t, J = 6.8 Hz, 2H), 3.03 (d, J = 4.8 Hz, 3H), 2.76 (s, 3H), 1.56 (t, J = 7.2 Hz, 3H). | 613 |
| 28 | 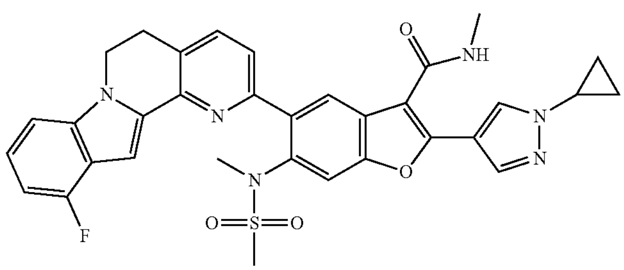 [SMILES: CNC(=O)c1c(-c2cnn(C3CC3)c2)oc2cc(N(C)S(C)(=O)=O)c(-c3ccc4c(n3)-c3cc5c(F)cccc5n3CC4)cc12] | ¹H-NMR (CDCl₃, 400 MHz) δ 8.89 (s, 1H), 7.92 (s, 1H), 7.56~7.65 (m, H), 7.38 (d, J = 8.0 Hz, 1H), 7.16~7.23 (m, 2H), 7.05~7.13 (m, 2H), 6.68~6.75 (m, 1H), 5.90~6.01 (br s, 1H), 4.28 (t, J = 6.4 Hz, 2H), 3.30 (s, 3H), 3.23 (t, J = 6.4 Hz, 2H), 2.91 (d, J = 4.8 Hz, 3H), 2.63 (s, 3H), 1.98~2.10 (m, 1H), 0.98~1.09 (m, 4H). | 625 |

Example 29

Step 1—Synthesis of 5-bromo-2-(4-formylphenyl)-N-methyl-6-(N-methylmethylsulfonamido)benzofuran-3-carboxamide

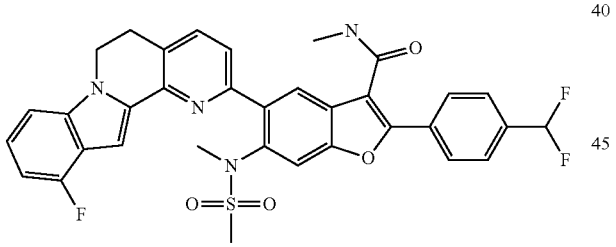

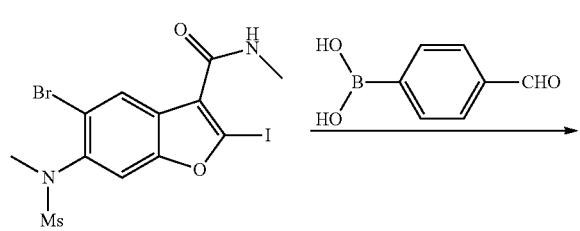

To a degassed solution of 5-bromo-2-iodo-N-methyl-6-(N-methylmethylsulfonamido)benzofuran-3-carboxamide (400 mg, 0.82 mmol), (4-formylphenyl) boronic acid (110 mg, 0.74 mmol) and Na₂CO₃ (174 mg, 1.6 mmol) in DMF (4 mL) was added Pd(dppf)Cl₂ (20 mg) under N₂, and the mixture was stirred at 100° C. for 2 h. After the solvent was removed, the residue was purified by column chromatography (DCM: EtOAc=10:1) to give the product of 5-bromo-2-(4-formylphenyl)-N-methyl-6-(N-methylmethylsulfonamido) benzofuran-3-carboxamide (200 mg, yield: 52%). ¹H-NMR (CDCl₃, 400 MHz) δ 10.09 (s, 1H), 8.09~8.15 (m, 3H), 8.02

(s, 2H), 7.75 (s, 1H), 5.90 (br s., 1H), 3.36 (s, 3H), 3.11 (s, 3H), 3.05 (d, J=4.8 Hz, 3H). MS (M+H)+: 465/467.

Step 2—Synthesis of 5-bromo-2-(4-(difluoromethyl) phenyl)-N-methyl-6-(N-methylmethylsulfonamido) benzofuran-3-carboxamide

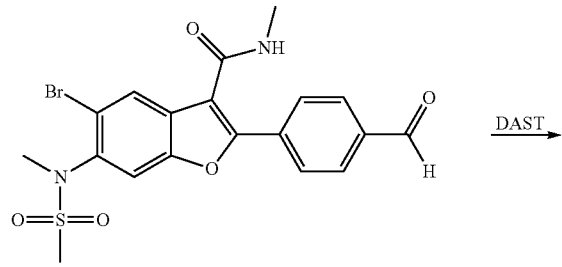

To a solution of 5-bromo-2-(4-formylphenyl)-N-methyl-6-(N-methylmethylsulfonamido)benzofuran-3-carboxamide (50 mg, 0.1 mmol) in DCM (1 mL) was added dropwise DAST (0.2 mL) at −78° C. Then the mixture was stirred at 25° C. for 5 hours. Then MeOH (3 ml) was added, the pH of mixture was adjusted to 7 and extracted with DCM (10 ml). The organic phase was dried over Na$_2$SO$_4$. After concentrated in vacuo, the residue was purified by prep-TLC (DCM:EtOAc=10:1) to give the product of 5-bromo-2-(4-(difluoromethyl)phenyl)-N-methyl-6-(N-methylmethylsulfonamido) benzofuran-3-carboxamide (26 mg, yield: 50%). $^1$H-NMR (CDCl$_3$, 400 MHz) δ 8.16 (s, 1H), 7.99 (d, J=8.0 Hz, 2H), 7.73 (s, 1H), 7.66 (d, J=8.0 Hz, 2H), 6.56~6.88 (m, 1H), 5.85 (br s., 1H), 3.35 (s, 3H), 3.10 (s, 3H), 3.02 (d, J=5.2 Hz, 3H). MS (M+H)+: 487/489.

Step 3—Synthesis of 2-(4-(difluoromethyl)phenyl)-N-methyl-6-(N-methylmethylsulfonamido)-5-(4,4,5,5-tetramethyl-1,3,2-dioxaborolan-2-yl)benzofuran-3-carboxamide

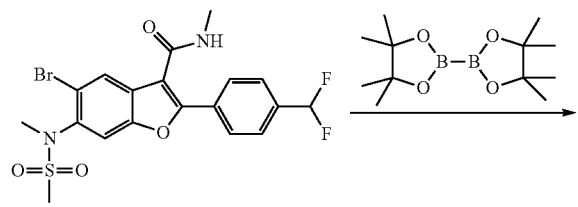

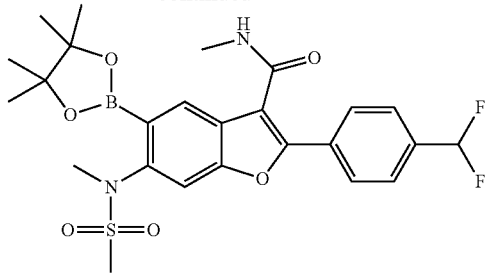

To a degassed solution of 5-bromo-2-(4-(difluoromethyl)phenyl)-N-methyl-6-(N-methylmethylsulfonamido)benzofuran-3-carboxamide (50 mg, 0.1 mmol), KOAc (30 mg, 0.3 mmol) and bis(pinacolato)diboron (130 mg, 0.5 mmol) in 1,4-dioxane (2 mL) and H$_2$O (0.1 mL) was added Pd(dppf)Cl$_2$ (5 mg) under N$_2$, and the mixture was stirred at 130° C. for 3 hours. After the solvent was removed, the residue was purified by column chromatography (DCM:EtOAc=10:1) to give the product of 2-(4-(difluoromethyl)phenyl)-N-methyl-6-(N-methylmethylsulfonamido)-5-(4,4,5,5-tetramethyl-1,3,2-dioxaborolan-2-yl)benzofuran-3-carboxamide (30 mg, yield: 55%). $^1$H-NMR (CDCl$_3$, 400 MHz) δ 8.16 (s, 1H), 7.99 (d, J=8.0 Hz, 2H), 7.73 (s, 1H), 7.66 (d, J=80 Hz, 2H), 6.56~6.88 (m, 1H), 5.85 (br s., 1H), 3.35 (s, 3H), 3.10 (s, 3H), 3.02 (d, J=5.2 Hz, 3H), 1.33 (s, 12H). MS (M+H)+: 535.

Step 4—Synthesis of 2-(4-(difluoromethyl)phenyl)-5-(11-fluoro-5,6-dihydroindolo[1,2-h][1,7]naphthyridin-2-yl)-N-methyl-6-(N-methylmethylsulfonamido)benzofuran-3-carboxamide

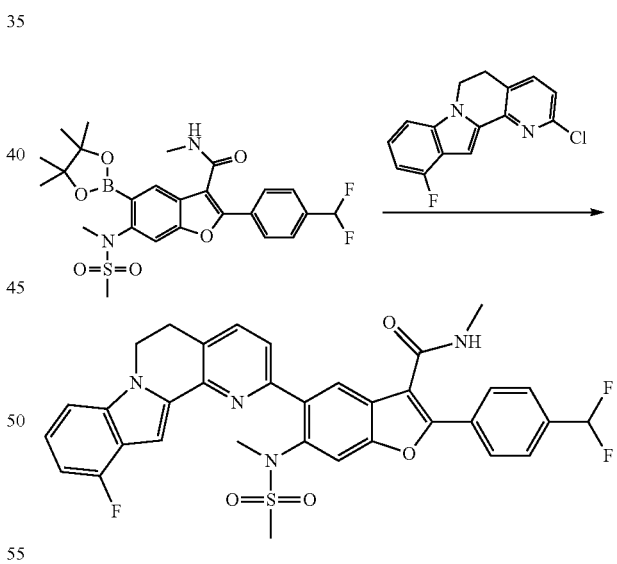

To a degassed solution of 2-(4-(difluoromethyl)phenyl)-N-methyl-6-(N-methylmethylsulfonamido)-5-(4,4,5,5-tetramethyl-1,3,2-dioxaborolan-2-yl)benzofuran-3-carboxamide (120 mg, 0.22 mmol), 2-chloro-11-fluoro-5,6-dihydroindolo[1,2-h][1,7]naphthyridine (64 mg, 0.22 mmol), Na$_2$CO$_3$ (62 mg, 0.45 mmol), in 1,4-dioxane (3 mL) and H$_2$O (0.1 mL) was added Pd$_2$(dba)$_3$ (5 mg) and X-Phos (5 mg) under N$_2$. Then the mixture was stirred at 100° C. for 2 hours. The reaction mixture was cooled to RT and filtered. The filtrate was washed with H$_2$O and dried over Na$_2$SO$_4$. After concentrated, the residue was purified by prep-HPLC to give the product (30 mg, yield: 21%). $^1$H-NMR (CDCl$_3$, 400 MHz) δ 8.08 (d, J=8.0 Hz, 2H), 8.03 (s, 1H), 7.74~7.64 (m, 4H), 7.47

(d, J=7.6 Hz, 1H), 7.30 (s, 1H), 7.22~7.14 (m, 2H), 6.89~6.81 (m, 1H), 6.81~6.73 (m, 1H), 6.00 (d, J=4.4 Hz, 1H), 4.37 (t, J=6.4 Hz, 2H), 3.40 (s, 3H), 3.34 (t, J=6.4 Hz, 2H), 3.02 (d, J=4.8 Hz, 3H), 2.72 (s, 3H). MS (M+H)⁺: 645.

Example 30

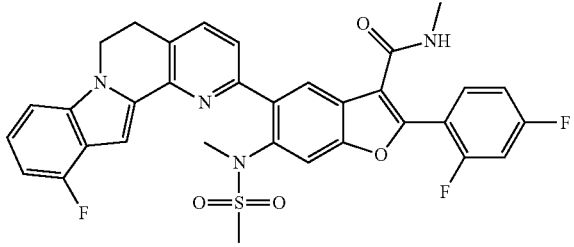 [SMILES: CNC(=O)c1c(-c2ccc(F)cc2F)oc2cc(N(C)S(C)(=O)=O)c(-c3ccc4c(n3)-c3cc5c(F)cccc5n3CC4)cc12]

Step 1—Synthesis of 6-amino-5-bromo-2-(2,4-difluorophenyl)-N-methylbenzofuran-3-carboxamide

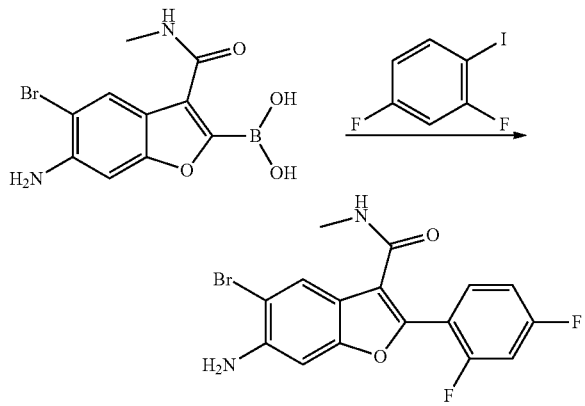

To a mixture of (6-amino-5-bromo-3-(methylcarbamoyl)benzofuran-2-yl)boronic acid (4.78 g, 11.46 mmol), K$_3$PO$_4$·3H$_2$O (8.32 g, 31.25 mmol) and 2,4-difluoro-1-iodobenzene (2.50 g, 10.42 mmol) in DMF (25 mL) was added Pd(dppf)Cl$_2$ (380 mg, 0.52 mmol) under N$_2$, and then the mixture was stirred at 15° C. for 3 hours. After the solvent was removed, EtOAc/H$_2$O (10 mL/20 mL) was added to the mixture. After stirring 15 minutes, the resulting solid was filtered to give the product of 6-amino-5-bromo-2-(2,4-difluorophenyl)-N-methylbenzofuran-3-carboxamide (2.80 g, yield: 70%). $^1$H-NMR (DMSO-d$_6$, 400 MHz) δ 8.06 (d, J=1.6 Hz, 1H), 7.74 (d, J=10.4 Hz, 1H), 7.70 (s, 1H), 7.41 (s, 1H), 7.24 (s, 1H), 7.00 (s, 1H), 5.58 (br s, 2H), 2.76 (s, 3H). MS (M+H)⁺: 281/283

Step 2—Synthesis of 5-bromo-2-(2,4-difluorophenyl)-N-methyl-6-(methylsulfonamido)benzofuran-3-carboxamide

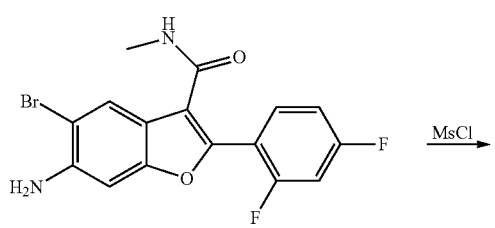

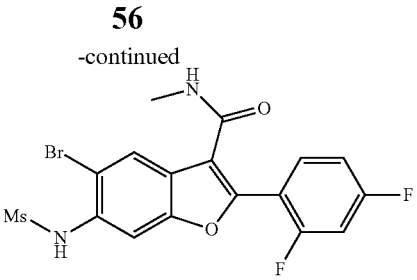

To a mixture of (6-amino-5-bromo-3-(methylcarbamoyl)benzofuran-2-yl)boronic acid (400 mg, 1.01 mmol) and pyridine (830 mg, 10.49 mmol) in DCM (15 mL), MsCl (601 mg, 5.25 mmol) was added dropwise at 0° C. The mixture was allowed to room temperature and stirred overnight. The reaction mixture was quenched with NaHCO$_3$ and extracted with DCM. The organic phase was washed with brine, dried over Na$_2$SO$_4$, and concentrated. The residue was dissolved in THF:H$_2$O=5:1 (15 mL) and LiOH·H$_2$O (800 mg, 0.02 mmol) was added. The mixture was stirred for 1 hour at room temperature. EtOAc (300 mL) was added, and the organic phase washed with NH$_4$Cl(a.q.), brine, dried over Na$_2$SO$_4$, filtrated and concentrated in vacuo. The residue was purified by column chromatography (eluted with DCM/EtOAc=10/1 to 2/1) to give 5-bromo-2-(2,4-difluorophenyl)-N-methyl-6-(methylsulfonamido)benzofuran-3-carboxamide (210 mg, yield: 43%). $^1$H-NMR (CDCl$_3$, 400 MHz) δ 8.32 (s, 1H), 7.91 (s, 1H), 7.64~7.90 (m, 1H), 7.06 (d, J=3.0 Hz, 1H), 7.03 (d, J=3.0 Hz, 1H), 6.88 (s, 1H), 3.02 (s, 3H), 2.97 (d, J=4.8 Hz, 3H). MS (M+H)⁺: 459/461

Step 3—Synthesis of 5-bromo-2-(2,4-difluorophenyl)-N-methyl-6-(N-methylmethylsulfonamido)benzofuran-3-carboxamide

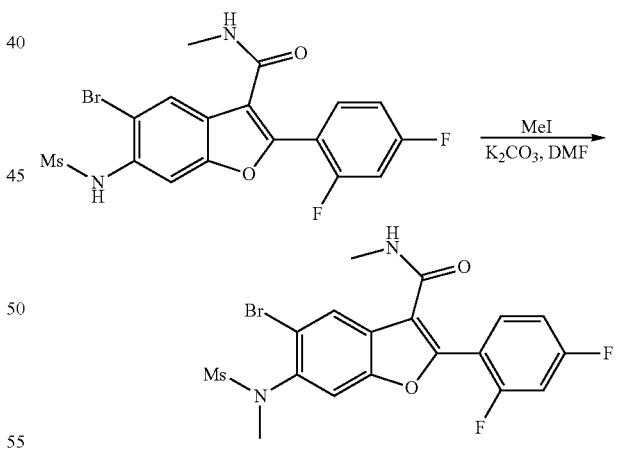

To a mixture of 5-bromo-2-(2,4-difluorophenyl)-N-methyl-6-(methylsulfonamido)benzofuran-3-carboxamide (653 mg, 1.38 mmol), K$_2$CO$_3$ (406 mg, 2.94 mmol) in DMF (10 mL) was added MeI (519 mg, 3.66 mmol), then the mixture was stirred at 80° C. After 3 hours, the solvent was removed by vacuum, the mixture was washed with H$_2$O (20 mL) and extract with DCM (50 mL×3), dried over Na$_2$SO$_4$ and concentrated to give the desired product of 5-bromo-2-(2,4-difluorophenyl)-N-methyl-6-(N-methylmethylsulfonamido)benzofuran-3-carboxamide (600 mg, yield: 89%). $^1$H-NMR (CDCl$_3$, 400 MHz) δ 8.24 (s, 1H), 7.69~7.75 (m, 2H), 7.05~7.10 (m, 1H), 6.98~7.03 (m, 1H), 5.64 (d, J=3.0 Hz, 1H), 3.09 (s, 3H), 2.97 (s, 3H), 2.95 (d, J=3.6 Hz, 3H). MS (M+H)+: 473/475.

Step 4—Synthesis of 2-(2,4-difluorophenyl)-N-methyl-6-(N-methylmethylsulfonamido)-5-(4,4,5,5-tetramethyl-1,3,2-dioxaborolan-2-yl)benzofuran-3-carboxamide

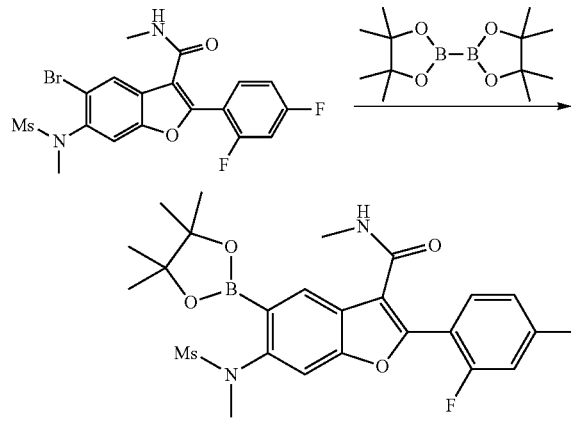

To a degassed mixture of 5-bromo-2-(2,4-difluorophenyl)-N-methyl-6-(N-methylmethylsulfonamido)benzofuran-3-carboxamide (400 mg, 0.85 mmol), bis(pinacolato)diboron (1 g, 4.23 mmol), KOAc (249 mg, 2.54 mmol) in 1,4-Dioxane (5 mL) and H₂O (1 mL) was added Pd(dppf)Cl₂ (5 mg), then the mixture was stirred at 130° C. After 3 hours, the solvent was removed by vacuum, and the mixture was washed with H₂O (20 mL), extract with DCM (50 mL×3), dried over Na₂SO₄. After concentrated, the residue was purified by column chromatography (PE/EtOAc=2/1) to give the product of 2-(2,4-difluorophenyl)-N-methyl-6-(N-methylmethylsulfonamido)-5-(4,4,5,5-tetramethyl-1,3,2-dioxaborolan-2-yl)benzofuran-3-carboxamide (240 mg, yield: 54%). ¹H-NMR (CDCl₃, 400 MHz) δ 8.26 (s, 1H), 7.73 (d, J=6.8 Hz, 1H), 7.56 (s, 1H), 7.05 (t, J=6.8 Hz, 1H), 6.96 (q, J=6.8 Hz, 1H), 5.96 (s, 1H), 3.33 (s, 3H), 2.97 (s, 3H), 2.93 (d, J=4.8 Hz, 3H), 1.20 (s, 12H). MS (M+H)+: 521.

Step 5—Synthesis of 2-(2,4-difluorophenyl)-5-(11-fluoro-5,6-dihydroindolo[1,2-h][1,7]naphthyridin-2-yl)-N-methyl-6-(N-methylmethylsulfonamido)benzofuran-3-carboxamide

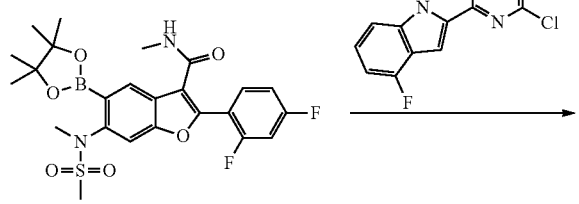

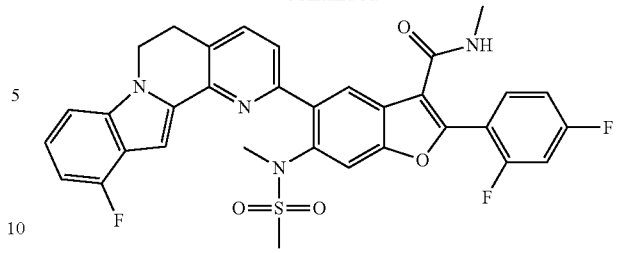

To a solution of 2-(2,4-difluorophenyl)-N-methyl-6-(N-methylmethylsulfonamido)-5-(4,4,5,5-tetramethyl-1,3,2-dioxaborolan-2-yl)benzofuran-3-carboxamide (500 mg, 0.96 mmol), 2-chloro-11-fluoro-5,6-dihydroindolo[1,2-h][1,7] naphthyridine (240 mg, 0.87 mmol) and K₂CO₃ (241 mg, 1.75 mmol) in 1,4-dioxane (5 mL) and H₂O (5 drop) were added X-Phos (10 mg) and Pd₂(dba)₃ (10 mg) under N₂. The reaction mixture was stirred at 100° C. for 10 hours and concentrated in vacuo to remove 1,4-dioxane. The reaction mixture was extracted with EtOAc. The organic phase was washed with brine, dried over Na₂SO₄, filtered and concentrated in vacuo. The residue was purified by prep-HPLC to give the product (230 mg, yield: 42%). ¹H-NMR (CDCl₃, 400 MHz) δ 8.08 (s, 1H), 7.7~57.81 (m, 1H), 7.66~7.69 (m, 2H), 7.46 (d, J=8.0 Hz, 1H), 7.28 (s, 1H), 7.15~7.18 (m, 2H), 6.98~7.09 (m, 2H), 6.79 (t, J=8.4 Hz, 1H), 5.81 (br s, 1H), 4.35 (t, J=6.4 Hz, 2H), 3.39 (s, 3H), 3.32 (t, J=6.4 Hz, 2H), 2.96 (d, J=4.8 Hz, 3H), 2.68 (s, 3H). MS (M+H)+: 631.

Example 31

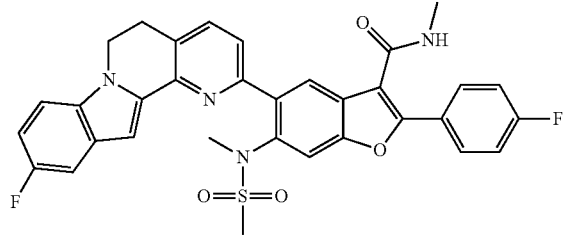 [SMILES: CNC(=O)c1c(-c2ccc(F)cc2)oc2cc(N(C)S(C)(=O)=O)c(-c3ccc4c(n3)-c3cc5cc(F)ccc5n3CC4)cc12]

Step 1—Synthesis of 6-chloro-2-(5-fluoro-1H-indol-2-yl)pyridin-3-ol

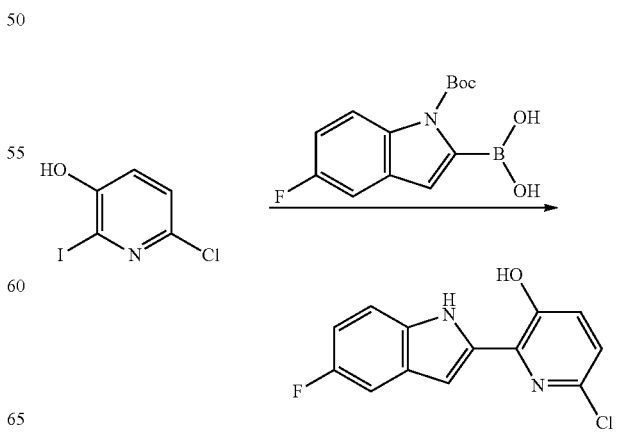

To a degassed solution of 6-chloro-2-iodopyridin-3-ol (1.0 g, 3.91 mmol) and (1-(tert-butoxycarbonyl)-5-fluoro-1H-indol-2-yl)boronic acid (prepared using the method described in Example 1, 1.3 g, 4.66 mmol) in 1,4-dioxane-H$_2$O (20 mL, 10:1), Pd(PPh$_3$)$_2$Cl$_2$ (120 mg) and NaHCO$_3$ (1.0 g, 11.90 mmol) were added under N$_2$. The mixture was heated to 100° C. overnight. The reaction mixture was cooled to room temperature, filtered and washed with EtOAc. The filtrate was washed with H$_2$O, brine, dried over Na$_2$SO$_4$. After concentrated, the residue was purified by column chromatography (PE:EA 5:1) to give the product of 6-chloro-2-(5-fluoro-1H-indol-2-yl)pyridin-3-ol (600 mg, yield: 58.2%). $^1$H-NMR (DMSO-d$_6$, 400 MHz) δ 11.37 (br s, 1H), 11.03 (s, 1H), 7.51 (dd, J=8.8, 4.8 Hz, 1H), 7.41 (d, J=8.4 Hz, 1H), 7.34 (dd, J=10.0, 2.4 Hz, 1H), 7.30 (d, J=1.2 Hz, 1H), 7.26 (d, J=8.4 Hz, 1H), 6.94~6.99 (m, 1H). MS (M+H)$^+$: 263/265.

Step 2—Synthesis of 6-chloro-2-(5-fluoro-1H-indol-2-yl)pyridin-3-yl trifluoromethanesulfonate

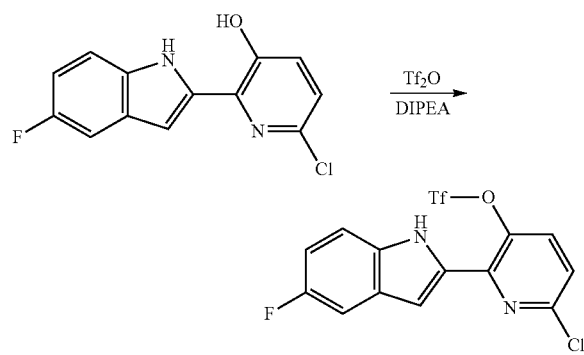

To a degassed solution of 6-chloro-2-(5-fluoro-1H-indol-2-yl)pyridin-3-ol (600 mg, 2.28 mmol) and DIPEA (1.0 g, 7.74 mmol) in DCM (10 mL), Tf$_2$O (1.3 g, 4.61 mmol) were added dropwise under N$_2$ at 0° C. The mixture was stirred at RT for 2 hours. The mixture was diluted with water and extracted with DCM. The organic layers were washed with brine, dried over Na$_2$SO$_4$, and concentrated. The mixture was purified by column chromatography (PE:EA=10:1) to give 6-chloro-2-(5-fluoro-1H-indol-2-yl)pyridin-3-yl trifluoromethanesulfonate (700 mg, yield: 77.6%). $^1$H-NMR (DMSO-d$_6$, 400 MHz) δ 11.91 (br s, 1H), 8.17 (d, J=8.8 Hz, 1H), 7.66 (d, J=8.8 Hz, 1H), 7.51~7.58 (m, 1H), 7.42~7.50 (m, 1H), 7.18 (d, J=1.6 Hz, 1H), 7.06~7.14 (m, 1H). MS (M+H)$^+$: 395/397.

Step 3—Synthesis of 2-(6-chloro-3-vinylpyridin-2-yl)-5-fluoro-1H-indole

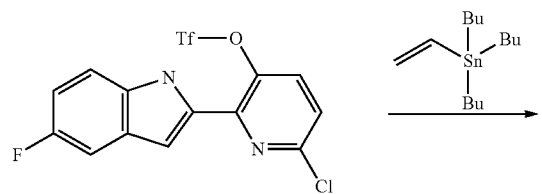

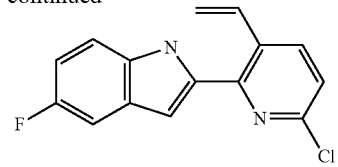

To a mixture of 6-chloro-2-(5-fluoro-1H-indol-2-yl)pyridin-3-yl trifluoromethanesulfonate (200 mg, 0.51 mmol), tributyl(vinyl)stannane (170 mg, 0.54 mmol) and anhydrous LiCl (70 mg, 1.65 mmol) in DMF (2 mL), Pd(PPh$_3$)$_2$Cl$_2$ (30 mg, 0.04 mmol) was added under N$_2$ protection. The reaction mixture was stirred at 50° C. for 1 h. Then it was filtered and concentrated in vacuo, the residue was purified by column chromatography (PE: EA=20:1) to give the product of 2-(6-chloro-3-vinylpyridin-2-yl)-5-fluoro-1H-indole (100 mg, yield: 72.4%). $^1$H-NMR (CDCl$_3$, 400 MHz) δ 11.67 (br s, 1H), 8.05 (d, J=8.4 Hz, 1H), 7.45~7.55 (m, 2H), 7.38 (d, J=10.0 Hz, 1H), 7.15 (dd, J=17.2, 11.2 Hz, 1H), 7.00~7.06 (m, 1H), 6.84 (d, J=2.0 Hz, 1H), 5.93 (d, J=17.2 Hz, 1H), 5.59 (d, J=11.2 Hz, 1H). MS (M+H)$^+$: 273/275.

Step 4—Synthesis of 2-(6-chloro-3-vinylpyridin-2-yl)-5-fluoro-1H-indole

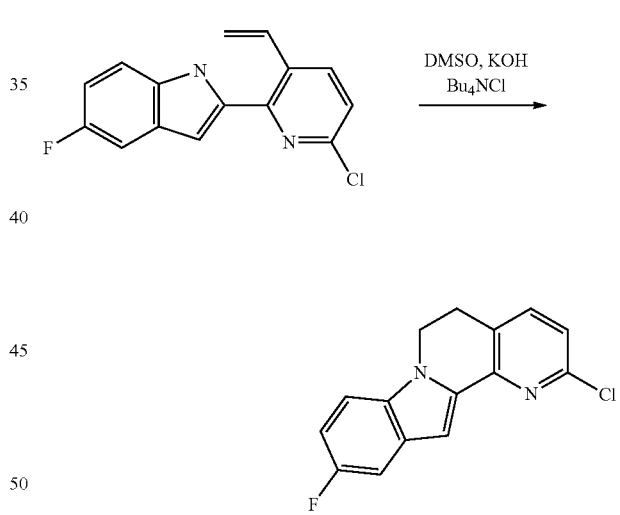

A mixture of 2-(6-chloro-3-vinylpyridin-2-yl)-5-fluoro-1H-indole (100 mg, 0.36 mmol), DMSO (0.5 mL), TBAC (0.1 mL of 50% a.q. solution) and KOH (1.0 mL of 60% a.q. solution) was stirred under N$_2$ at 100° C. for 4 h. After cooled and extracted with EtOAc, the organic layer was washed with water, brine, dried over Na$_2$SO$_4$, and concentrated. The residue was purified by prep-TLC (PE:EA=10:1) to give the product of 2-chloro-10-fluoro-5,6-dihydroindolo[1,2-h][1,7]naphthyridine (50 mg, yield: 50.0%). $^1$H-NMR (CDCl$_3$, 400 MHz) δ 7.51 (d, J=8.0 Hz, 1H), 7.25~7.38 (m, 3H), 7.15 (d, J=8.0 Hz, 1H), 6.98~7.04 (m, 1H), 4.26 (d, J=6.4 Hz, 2H), 3.22 (d, J=6.4 Hz, 2H). MS (M+H)+: 273/275.

Step 5—Synthesis of 5-(10-fluoro-5,6-dihydroindolo[1,2-h][1,7]naphthyridin-2-yl)-2-(4-fluorophenyl)-N-methyl-6-(N-methylmethylsulfonamido)benzofuran-3-carboxamide

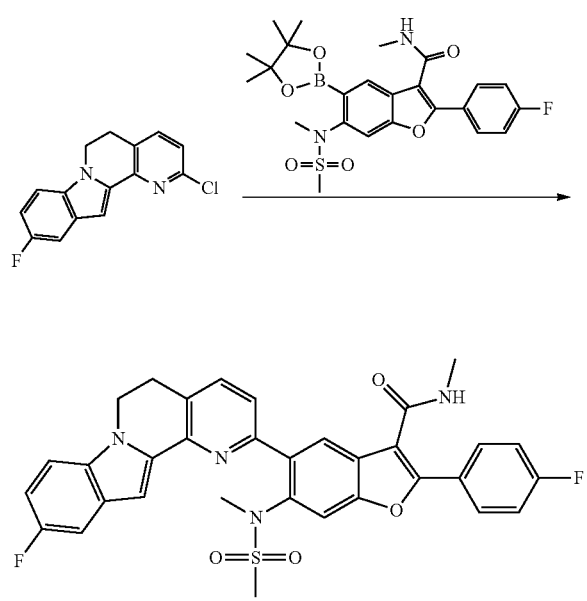

To a degassed solution of 2-chloro-10-fluoro-5,6-dihydroindolo[1,2-h][1,7]naphthyridine (50 mg, 0.18 mmol) and 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (80 mg, 0.16 mmol) in 1,4-dioxane (5 mL), Pd$_2$(dba)$_3$ (10 mg), X-Phos (10 mg) and K$_3$PO$_4$ (100 mg, 0.38 mmol) were added under N$_2$. After heated to 100° C. for 1 hour, the reaction mixture was cooled to RT, filtered and washed with EtOAc. The filtrate was washed with H$_2$O, brine, dried over Na$_2$SO$_4$. After concentrated, the residue was purified by prep-HPLC to give the product (60 mg, yield: 61.5%). $^1$H-NMR (CDCl$_3$, 400 MHz) δ 7.99 (s, 1H), 7.92~7.98 (m, 2H), 7.65~7.67 (m, 2H), 7.43 (d, J=7.6 Hz, 1H), 7.28~7.32 (m, 2H), 7.15~7.24 (m, 3H), 6.98~7.03 (m, 1H), 6.05 (br s, 1H), 4.31 (t, J=6.4 Hz, 2H), 3.36 (s, 3H), 3.30 (t, J=6.4 Hz, 2H), 2.97 (d, J=4.8 Hz, 3H), 2.68 (s, 3H). MS (M+H)+: 613.

Example 32

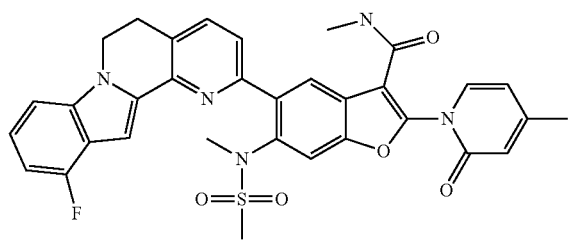 [SMILES: CNC(=O)c1c(-n2ccc(C)cc2=O)oc2cc(N(C)S(C)(=O)=O)c(-c3ccc4c(n3)-c3cc5c(F)cccc5n3CC4)cc12]

Step 1—Synthesis of 5-bromo-N-methyl-2-(4-methyl-2-oxopyridin-1 (2H)-yl)-6-(N-methylmethylsulfonamido)benzofuran-3-carboxamide

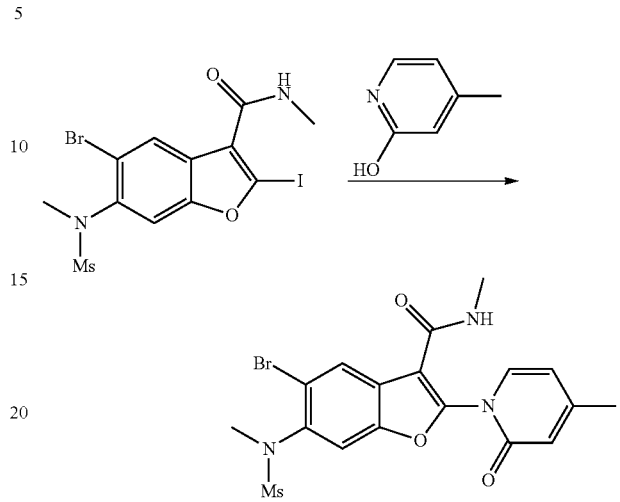

To a mixture of 5-bromo-2-iodo-N-methyl-6-(N-methylmethylsulfonamido)benzofuran-3-carboxamide (500 mg, 1.03 mmol), 4-methylpyridin-2-ol (168 mg, 1.54 mmol) and K$_2$CO$_3$ (283 mg, 2.05 mmol) in DMF (5 mL) was stirred at 80° C. for 10 hours and concentrated in vacuo to remove DMF. The reaction mixture was extracted with EtOAc, washed with brine, dried over Na$_2$SO$_4$, filtered and concentrated in vacuo. The residue was purified by column chromatography (PE:EtOAc=1:1) to give the product of 5-bromo-N-methyl-2-(4-methyl-2-oxopyridin-1 (2H)-yl)-6-(N-methylmethylsulfonamido)benzofuran-3-carboxamide (400 mg, yield: 83%). $^1$H-NMR (CDCl$_3$, 400 MHz) δ 8.32 (s, 1H), 7.85 (s, 1H), 7.67 (s, 1H), 7.22 (d, J=7.2 Hz, 1H), 6.52 (s, 1H), 6.28 (d, J=1.6 Hz, 1H), 3.32 (s, 3H), 3.06 (s, 3H), 2.89 (d, J=4.8 Hz, 3H), 2.31 (s, 3H). MS (M+H)+: 468/470.

Step 2—Synthesis of N-methyl-2-(4-methyl-2-oxopyridin-1 (2H)-yl)-6-(N-methylmethylsulfonamido)-5-(4,4,5,5-tetramethyl-1,3,2-dioxaborolan-2-yl)benzofuran-3-carboxamide

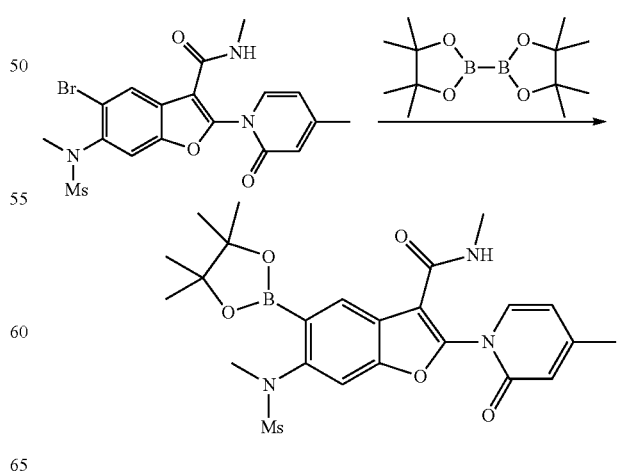

To a mixture of 5-bromo-N-methyl-2-(4-methyl-2-oxopyridin-1 (2H)-yl)-6-(N-methylmethylsulfonamido)benzofuran-3-carboxamide (400 mg, 0.85 mmol), bis(pinacolato)diboron (1.08 mg, 4.27 mmol) and KOAc (168 mg, 1.71 mmol) in 1,4-dioxane/H$_2$O (5 mL/0.5 mL) was added Pd(dppf)Cl$_2$ (10 mg) under N$_2$. The reaction mixture was stirred at 120° C. for 5 hours and concentrated in vacuo to remove 1,4-dioxane. The reaction mixture was extracted with EtOAc, washed with brine, dried over Na$_2$SO$_4$, filtered and concentrated in vacuo. The residue was purified by column chromatography (PE:EA=1:1) to give the product of N-methyl-2-(4-methyl-2-oxopyridin-1 (2H)-yl)-6-(N-methylmethylsulfonamido)-5-(4,4,5,5-tetramethyl-1,3,2-dioxaborolan-2-yl)benzofuran-3-carboxamide (200 mg, yield: 45%). $^1$H-NMR (CDCl$_3$, 400 MHz) δ 8.45 (s, 1H), 7.75 (d, J=4.4 Hz, 1H) 7.56 (s, 1H), 7.23 (s, 1H), 6.51 (s, 1H), 6.25 (d, J=7.2 Hz, 1H), 3.34 (s, 3H), 2.96 (s, 3H), 2.91 (d, J=4.8 Hz, 3H), 2.30 (s, 3H), 1.35 (s, 12H). MS (M+H)$^+$: 516.

Step 3—Synthesis of 5-(11-fluoro-5,6-dihydroindolo[1,2-h][1,7]naphthyridin-2-yl)-N-methyl-2-(4-methyl-2-oxopyridin-1 (2H)-yl)-6-(N-methylmethylsulfonamido)benzofuran-3-carboxamide

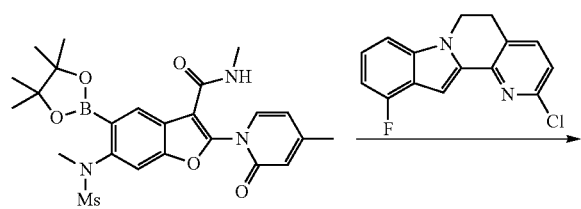

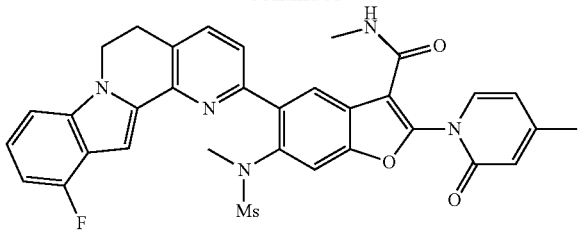

To a mixture of N-methyl-2-(4-methyl-2-oxopyridin-1 (2H)-yl)-6-(N-methylmethylsulfonamido)-5-(4,4,5,5-tetramethyl-1,3,2-dioxaborolan-2-yl)benzofuran-3-carboxamide (100 mg, 0.19 mmol), 2-chloro-11-fluoro-5,6-dihydroindolo[1,2-h][1,7]naphthyridine (63 mg, 0.23 mmol) and K$_2$CO$_3$ (54 mg, 0.39 mmol) in 1,4-dioxane/H$_2$O (3 mL/0.1 mL) were added X-Phos (10 mg) and Pd$_2$(dba)$_3$ (10 mg) under N$_2$. The reaction mixture was stirred at 80° C. for 5 hours and concentrated in vacuo to remove 1,4-dioxane. The reaction mixture was extracted with EtOAc, washed with brine, dried over Na$_2$SO$_4$, filtered and concentrated in vacuo. The residue was purified by prep-HPLC to give the product (30 mg, yield: 24%). $^1$H-NMR (CDCl$_3$, 400 MHz) δ 8.17 (s, 1H), 7.83~7.85 (m, 1H), 7.66~7.68 (m, 2H), 7.44 (d, J=8.0 Hz, 1H), 7.26~7.18 (m, 2H), 7.14~7.18 (m, 2H), 6.77~6.81 (m, 1H), 6.53 (s, 1H), 6.29 (d, J=8.0 Hz, 1H), 4.34 (t, J=6.4 Hz, 2H), 3.40 (s, 3H), 3.31 (t, J=6.4 Hz, 2H), 2.90 (d, J=4.8 Hz, 3H), 2.61 (s, 3H), 2.32 (s, 3H). MS (M+H)$^+$: 626.

Examples 33-34

Examples 33 and 34, depicted in the table below, were prepared in accordance with the method described in Example 32.

| Example | Structure | NMR | MS (M + H)$^+$ |
|---|---|---|---|
| 33 | 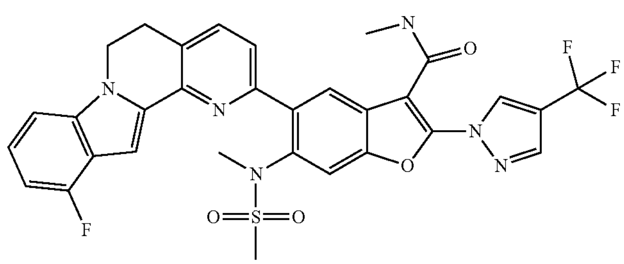 [SMILES: CNC(=O)c1c(-n2cc(C(F)(F)F)cn2)oc2cc(N(C)S(C)(=O)=O)c(-c3ccc4c(n3)-c3cc5c(F)cccc5n3CC4)cc12] | $^1$H-NMR (CDCl$_3$, 400 MHz) δ 9.31 (s, 1H), 8.59 (s, 1H), 8.50 (s, 1H), 8.04 (s, 1H), 7.62 (s, 2H), 7.40 (d, J = 7.6 Hz, 1H), 7.09 (s, 3H), 6.75 (d, J = 5.2 Hz, 1H), 4.29 (d, J = 6.8 Hz, 2H), 3.37 (s, 3H), 3.26 (t, J = 6.8 Hz, 2H), 2.95 (d, J = 4.4 Hz, 3H), 2.53 (s, 3H). | 653 |
| 34 | 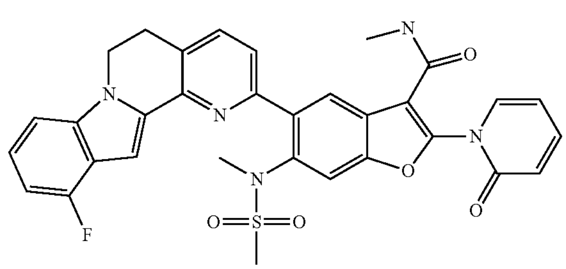 [SMILES: CNC(=O)c1c(-n2ccccc2=O)oc2cc(N(C)S(C)(=O)=O)c(-c3ccc4c(n3)-c3cc5c(F)cccc5n3CC4)cc12] | $^1$H-NMR (CDCl$_3$, 400 MHz) δ 8.17 (s, 1H), 7.67 (t, J = 3.6 Hz, 3H), 7.53~7.59 (m, 1H), 7.45 (d, J = 8.0 Hz, 1H), 7.40 (d, J = 5.6 Hz, 1H), 7.24~7.26 (m, 1H), 7.13~7.20 (m, 2H), 6.73~6.83 (m, 2H), 6.45 (t, J = 6.4 Hz, 1H), 4.35 (t, J = 6.4 Hz, 2H), 3.41 (s, 3H), 3.32 (t, J = 6.4 Hz, 2H), 2.91 (d, J = 4.8 Hz, 3H), 2.62 (s, 3H). | 612 |

Example 35

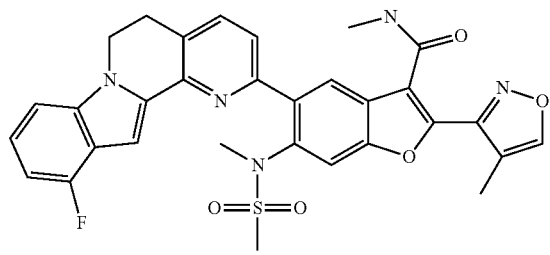 [SMILES: CNC(=O)c1c(-c2nocc2C)oc2cc(N(C)S(C)(=O)=O)c(-c3ccc4c(n3)-c3cc5c(F)cccc5n3CC4)cc12]

Step 1—Synthesis of methyl 5-bromo-3-(methylcarbamoyl)-6-(N-methylmethylsulfonamido)benzofuran-2-carboxylate

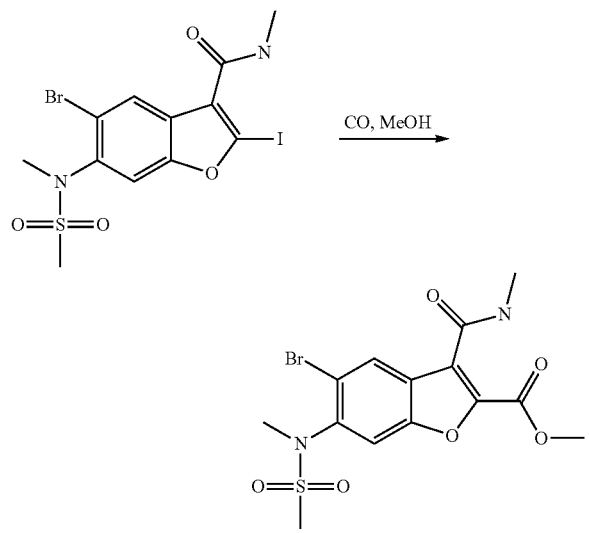

To a solution of 5-bromo-2-iodo-N-methyl-6-(N-methylmethylsulfonamido)benzofuran-3-carboxamide (4.0 g, 8.21 mmol) in MeOH (10 mL) and DMSO (35 mL) was added Pd(PPh$_3$)$_2$Cl$_2$ under Ar$_e$. The suspension was degassed under vacuum and purged with CO 4 times. The mixture was stirred under CO (50 psi) at 50° C. for 16 h. Then 30 mL MeOH was added to the mixture. The resulting solid was filtered to give the product of methyl 5-bromo-3-(methylcarbamoyl)-6-(N-methylmethylsulfonamido)benzofuran-2-carboxylate (2.90 g, yield: 84%). $^1$H-NMR (CDCl$_3$, 400 MHz) δ 9.39 (br s, 1H), 8.94 (s, 1H), 7.74 (s, 1H), 4.08 (s, 3H), 3.34 (s, 3H), 3.08 (s, 3H), 3.04 (d, J=4.8 Hz, 3H). (M+H)$^+$: 419/421

Step 2—Synthesis of 5-bromo-3-(methylcarbamoyl)-6-(N-methylmethylsulfonamido)benzofuran-2-carboxylic acid

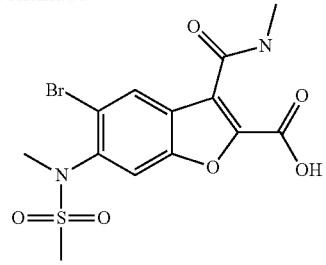

To a suspension of methyl 5-bromo-3-(methylcarbamoyl)-6-(N-methylmethylsulfonamido)benzofuran-2-carboxylate (2.90 g, 6.92 mmol) in 1,4-dioxane/H$_2$O (30 mL/5 mL) was added LiOH.H$_2$O (870 mg, 20.75 mmol). The mixture was stirred at room temperature overnight. Then it was concentrated in vacuo, diluted with water, acidized with HCl (aq. 2 M) and extracted with EtOAc. The organic layer was washed with brine, dried over Na$_2$SO$_4$ and concentrated give the product of 5-bromo-3-(methylcarbamoyl)-6-(N-methylmethylsulfonamido)benzofuran-2-carboxylic acid (2.50 g, yield: 89%). It was used for the next step without further purification. $^1$H-NMR (DMSO-d$_6$, 400 MHz) δ 9.16 (br s, 1H), 8.27 (s, 1H), 8.16 (s, 1H), 3.17 (s., 6H), 2.82 (d, J=4.4 Hz, 3H). (M+H)$^+$: 405/407.

Step 3—Synthesis of 5-bromo-N$^2$-methoxy-N$^2$,N$^3$-dimethyl-6-(N-methylmethylsulfonamido)benzofuran-2,3-dicarboxamide

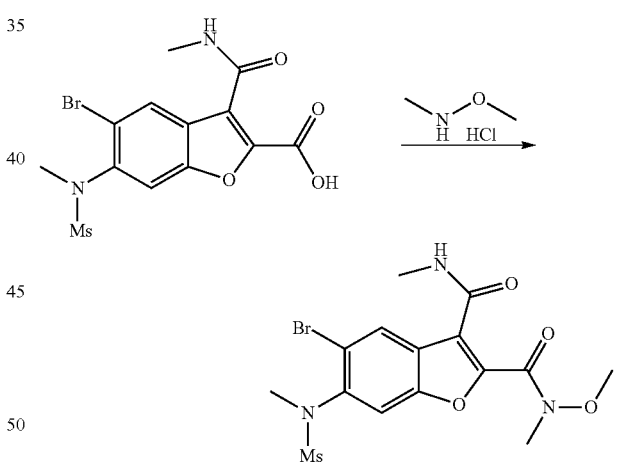

A mixture of 5-bromo-3-(methylcarbamoyl)-6-(N-methylmethylsulfonamido)benzofuran-2-carboxylic acid (1 g, 2.47 mmol), HOBT (500 mg, 3.70 mmol) and EDCI (946 mg, 4.94 mmol) in DMF (20 mL) was stirred at room temperature under N$_2$ for 2 h. Et$_3$N (1.25 g, 12.34 mmol) and N,O-dimethylhydroxylamine hydrochloride (1.03 g, 12.34 mmol) were added, then the mixture was stirred for 18 h. The mixture was concentrated, diluted with water, extracted with EA, the organic layers were washed with Na$_2$CO$_3$ (a.q.), brine, dried over Na$_2$SO$_4$, concentrated. The residue was purified by column chromatography (DCM:EA=20:1) to get product 5-bromo-N$^2$-methoxy-N$^2$,N$^3$-dimethyl-6-(N-methylmethylsulfonamido)benzofuran-2,3-dicarboxamide (0.68 g, yield: 62%). $^1$H-NMR (CDCl$_3$, 400 MHz) δ 8.83 (s, 1H), 8.74 (s, 1H), 7.72 (s, 1H), 3.89 (s, 3H), 3.42 (s, 3H), 3.34 (s, 3H), 3.08 (s, 3H), 2.98 (d, J=4.8 Hz, 3H). MS (M+H)+: 448/450.

Step 4—Synthesis of ethyl 5-bromo-6-nitrobenzofuran-3-carboxylate

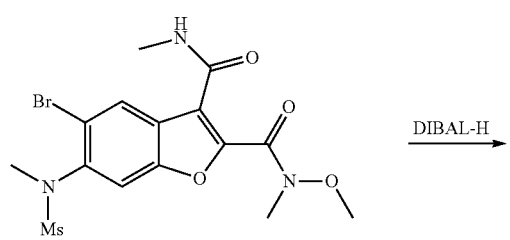

To a mixture of 5-bromo-N²-methoxy-N²,N³-dimethyl-6-(N-methylmethylsulfonamido)benzofuran-2,3-dicarboxamide (1 g, 2.3 mmol) in THF (10 mL) was added DIBAL-H (11.5 mL, 11.5 mmol) at −78° C. dropwise. The mixture was stirred at −15° C. for 2 h. Then it was quenched with HCl (a.q.), extracted with CH₂Cl₂, dried over Na₂SO₄, concentrated. The residue was crude product of 5-bromo-2-formyl-N-methyl-6-(N-methylmethylsulfonamido)benzofuran-3-carboxamide (700 mg, yield: 74%). ¹H-NMR (CDCl₃, 400 MHz) δ 10.07 (s, 1H), 9.14 (br s, 1H), 9.00 (s, 1H), 7.80 (s, 1H), 3.35 (s, 3H), 3.10 (s, 3H), 3.05 (d, J=4.4 Hz, 3H). MS (M+H)+: 389/391.

Step 5—Synthesis of 5-bromo-2-((hydroxyimino)methyl)-N-methyl-6-(N-methylmethylsulfonamido)benzofuran-3-carboxamide

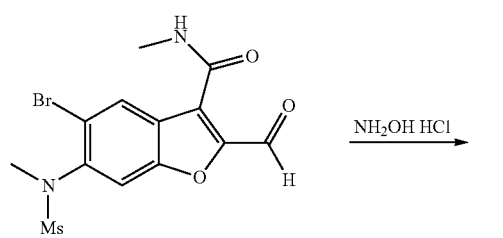

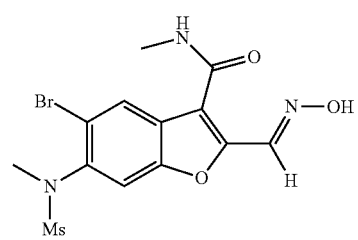

A mixture of 5-bromo-2-formyl-N-methyl-6-(N-methylmethylsulfonamido)benzofuran-3-carboxamide (700 mg, 1.8 mmol), hydroxylamine hydrochloride (280 mg, 4.05 mmol) and pyridine (284 mg, 3.6 mmol) in DMSO (5 mL) was stirred at room temperature for 2 h. The mixture was diluted with water, then filtered, the residue was crude product of 5-bromo-2-((hydroxyimino)methyl)-N-methyl-6-(N-methylmethylsulfonamido)benzofuran-3-carboxamide (650 mg, yield: 75%). ¹H-NMR (DMSO-d₆, 400 MHz) δ 12.26 (s, 1H), 8.46 (s, 1H), 8.41 (d, J=4.4 Hz, 1H), 8.18 (s, 1H), 8.06 (s, 1H), 3.20 (s, 3H), 3.19 (s, 3H), 2.83 (d, J=4.4 Hz, 3H). MS (M+H)+: 404/406.

Step 6—Synthesis of 5-bromo-N-hydroxy-3-(methylcarbamoyl)-6-(N-methylmethylsulfonamido)benzofuran-2-carbimidoyl chloride

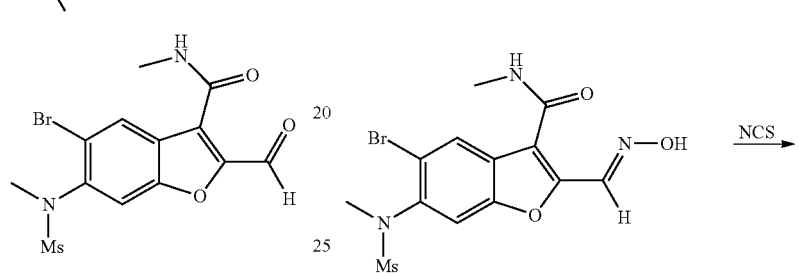

A mixture of 5-bromo-2-((hydroxyimino)methyl)-N-methyl-6-(N-methylmethylsulfonamido)benzofuran-3-carboxamide (100 mg, 0.25 mmol) and NCS (40 mg, 0.30 mmol) in DMF (2 mL) was stirred at 60° C. for 18 h. The mixture was used for the next step without purification, 5-bromo-N-hydroxy-3-(methylcarbamoyl)-6-(N-methylmethylsulfonamido)benzofuran-2-carbimidoyl chloride was obtained (90 mg, yield: 65%). ¹H-NMR (DMSO-d₆, 400 MHz) δ 13.33 (s, 1H), 8.65 (d, J=4 Hz, 1H), 8.13 (s, 1H), 8.05 (s, 1H), 3.20 (s, 6H), 2.80 (d, J=4.8 Hz, 3H). MS (M+H)+: 438/440.

Step 7—Synthesis of 5-bromo-2-(5-ethoxy-4-methyl-4,5-dihydroisoxazol-3-yl)-N-methyl-6-(N-methylmethylsulfonamido)benzofuran-3-carboxamide

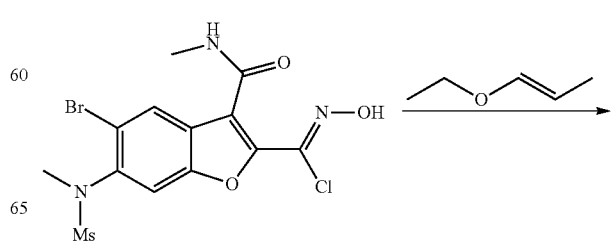

-continued

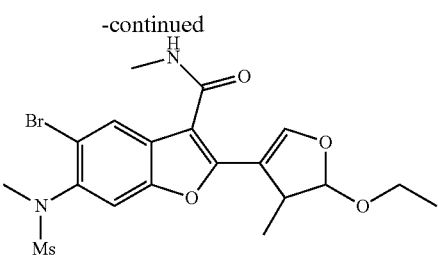

A mixture of 5-bromo-N-hydroxy-3-(methylcarbamoyl)-6-(N-methylmethylsulfonamido)benzofuran-2-carbimidoyl chloride (400 mg, 0.91 mmol), 1-ethoxyprop-1-ene (392 mg, 4.56 mmol) and NaHCO$_3$ (153 mg, 1.82 mmol) in DMF (10 mL) was stirred at room temperature for 16 h. It was concentrated, diluted with water, extracted with EtOAc, the organic layers were washed with brine, dried over Na$_2$SO$_4$, and concentrated. The residue was purified by column chromatography (PE:EA=2:1) to get product 5-bromo-2-(5-ethoxy-4-methyl-4,5-dihydroisoxazol-3-yl)-N-methyl-6-(N-methylmethylsulfonamido)benzofuran-3-carboxamide (370 mg, yield: 83%). MS (M+H)$^+$: 488/490.

Step 8—Synthesis of 5-bromo-N-methyl-2-(4-methylisoxazol-3-yl)-6-(N-methylmethylsulfonamido)benzofuran-3-carboxamide

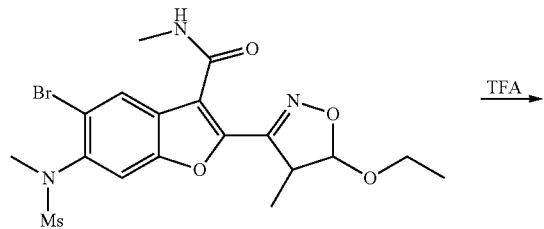

A mixture of 5-bromo-2-(5-ethoxy-4-methyl-4,5-dihydroisoxazol-3-yl)-N-methyl-6-(N-methylmethylsulfonamido)benzofuran-3-carboxamide (50 mg, 0.10 mmol) in DCM/TFA (1 mL/2 mL) was stirred at reflux for 16 h. It was washed with water, brine, dried over Na$_2$SO$_4$, and concentrated. The residue was purified by prep-TLC (DCM:MeOH=20:1) to get 5-bromo-N-methyl-2-(4-methylisoxazol-3-yl)-6-(N-methylmethylsulfonamido)benzofuran-3-carboxamide (40 mg, yield: 88%). $^1$H-NMR (CDCl$_3$, 400 MHz) δ 9.14 (br s, 1H), 8.84 (s, 1H), 8.39 (s, 1H), 7.76 (s, 1H), 3.35 (s, 3H), 3.10 (s, 3H), 3.04 (d, J=4.8 Hz, 3H), 2.36 (s, 3H). MS (M+H)$^+$: 442/444.

Step 9—Synthesis of N-methyl-2-(4-methylisoxazol-3-yl)-6-(N-methylmethylsulfonamido)-5-(4,4,5,5-tetramethyl-1,3,2-dioxaborolan-2-yl)benzofuran-3-carboxamide

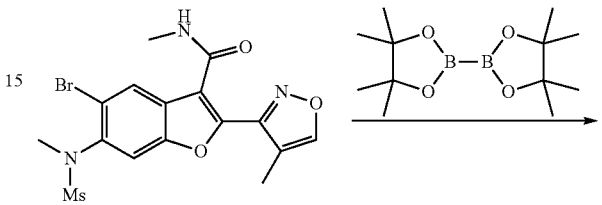

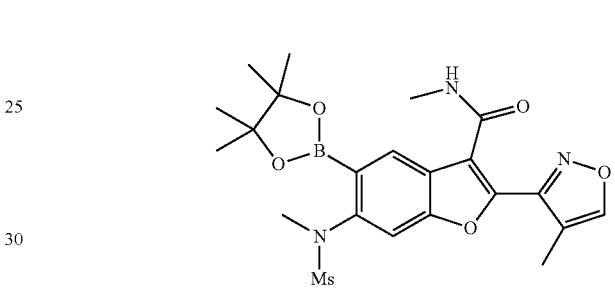

To a mixture of 5-bromo-N-methyl-2-(4-methylisoxazol-3-yl)-6-(N-methylmethylsulfonamido)benzofuran-3-carboxamide (250 mg, 0.57 mmol), bis(pinacolato)diboron (719 mg, 2.83 mmol) and KOAc (169 mg, 1.7 mmol) in dioxane (5 mL) was added Pd(dppf)Cl$_2$ (43 mg, 0.06 mmol) under N$_2$. The mixture was stirred at 85° C. for 3 h, then it was cooled to room temperature, diluted with water, extracted with EA, dried over Na$_2$SO$_4$, and concentrated. The residue was purified by prep-TLC (DCM:MeOH=60:1) to get crude product of N-methyl-2-(4-methylisoxazol-3-yl)-6-(N-methylmethylsulfonamido)-5-(4,4,5,5-tetramethyl-1,3,2-dioxaborolan-2-yl)benzofuran-3-carboxamide (64 mg, yield: 20%). $^1$H-NMR (CDCl$_3$, 400 MHz) δ 9.01 (br s, 1H), 8.97 (s, 1H), 8.36 (s, 1H), 7.76 (s, 1H), 3.36 (s, 3H), 3.04 (d, J=4.8 Hz, 3H), 2.99 (s, 3H), 2.36 (s, 3H), 1.36 (s, 12H). MS (M+H)$^+$: 490.

Step 10—Synthesis of 5-(11-fluoro-5,6-dihydroindolo[1,2-h][1,7]naphthyridin-2-yl)-N-methyl-2-(4-methylisoxazol-3-yl)-6-(N-methylmethylsulfonamido)benzofuran-3-carboxamide

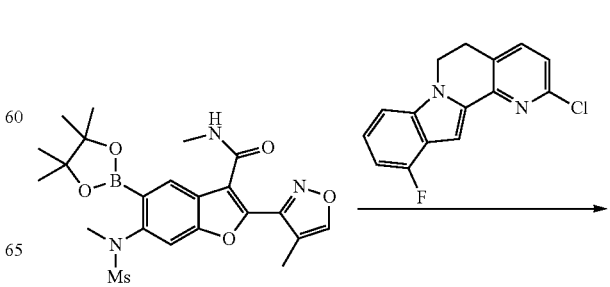

71

-continued

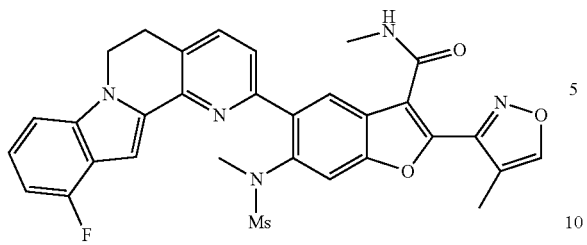

To a mixture of N-methyl-2-(4-methylisoxazol-3-yl)-6-(N-methylmethylsulfonamido)-5-(4,4,5,5-tetramethyl-1,3,2-dioxaborolan-2-yl)benzofuran-3-carboxamide (60 mg, 0.12 mmol), 2-chloro-11-fluoro-5,6-dihydroindolo[1,2-h][1,7]naphthyridine (50 mg, 0.18 mmol) and K$_3$PO$_4$·3H$_2$O (98 mg, 0.37 mmol) in dioxane/H$_2$O (1.5 mL/0.5 mL) was added Pd$_2$(dba)$_3$ (8 mg, 0.008 mmol) and X-Phos (8 mg, 0.016 mmol) under N$_2$. The mixture was stirred at 85° C. for 3 h. It was concentrated, diluted with water, extracted with EtOAc, and dried over Na$_2$SO$_4$. The residue was purified by prep-TLC (DCM:MeOH=60:1) to get the product (35 mg, yield: 48%). $^1$H-NMR (CDCl$_3$, 400 MHz) δ 9.12 (d, J=3.6 Hz, 1H), 8.68 (s, 1H), 8.40 (s, 1H), 7.76 (s, 1H), 7.68 (d, J=7.6 Hz, 1H), 7.48 (d, J=7.6 Hz, 1H), 7.28~7.26 (m, 1H), 7.21~7.12 (m, 2H), 6.85~6.75 (m, 1H), 4.36 (t, J=6.4 Hz, 2H), 3.46 (s, 3H), 3.33 (t, J=6.4 Hz, 2H), 3.03 (d, J=4.8 Hz, 3H), 2.60 (s, 3H), 2.40 (s, 3H). MS (M+H)$^+$: 600.

Example 36

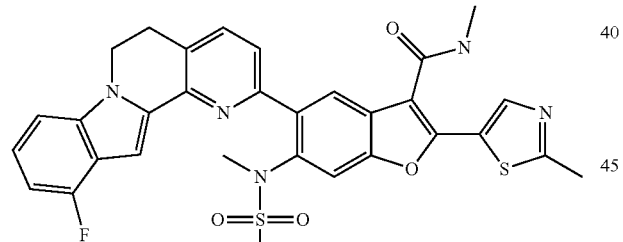

Step 1—Synthesis of 5-bromo-N-methyl-6-(N-methylmethylsulfonamido)-2-(2-methylthiazol-5-yl)benzofuran-3-carboxamide

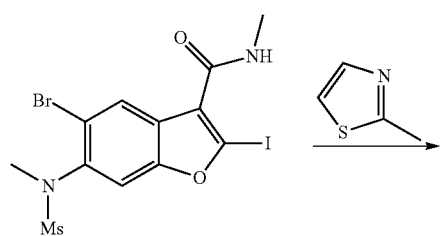

72

-continued

To a degassed solution of compound 5-bromo-2-iodo-N-methyl-6-(N-methylmethylsulfonamido)benzofuran-3-carboxamide (600 mg, 1.2 mmol), 2-methylthiazole (244 mg, 2.5 mmol) and Na$_2$CO$_3$ (261 mg, 2.5 mmol) in DMF (6 mL) was added Pd(dppf)Cl$_2$ (50 mg) under N$_2$, and the mixture was stirred at 80° C. for 12 h. After the solvent was removed, the residue was purified by column chromatography (DCM:EtOAc=2:1) to give the product of 5-bromo-N-methyl-6-(N-methylmethylsulfonamido)-2-(2-methylthiazol-5-yl)benzofuran-3-carboxamide (240 mg, yield: 42%). $^1$H-NMR (CDCl$_3$, 400 MHz) δ 8.36 (s, 1H), 7.98~8.01 (m, 1H), 7.68 (s, 1H), 6.06 (br s., 1H), 3.33 (s, 3H), 3.10 (s, 3H), 3.08 (d, J=5.2 Hz, 3H), 2.78 (s, 3H). MS (M+H)$^+$: 458/460.

Step 2—Synthesis of N-methyl-6-(N-methylmethylsulfonamido)-2-(2-methylthiazol-5-yl)-5-(4,4,5,5-tetramethyl-1,3,2-dioxaborolan-2-yl)benzofuran-3-carboxamide

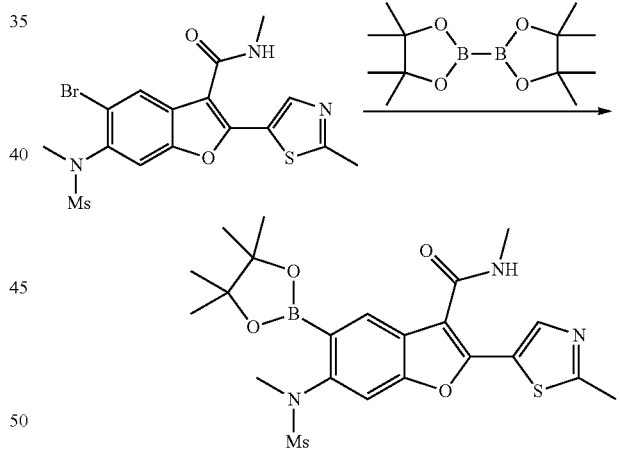

To a degassed solution of 5-bromo-N-methyl-6-(N-methylmethylsulfonamido)-2-(2-methylthiazol-5-yl)benzofuran-3-carboxamide (240 mg, 0.52 mmol), KOAc (154 mg, 1.6 mmol) and dis(pinacolato)diboron (665 mg, 2.6 mmol) in 1,4-dioxane (5 mL) and H$_2$O (0.1 mL) was added Pd(dppf)Cl$_2$ (10 mg) under N$_2$, and the mixture was stirred at 130° C. for 3 hours. After the solvent was removed, the residue was purified by prep-TLC (DCM:EtOAc=2:1) to give the product of N-methyl-6-(N-methylmethylsulfonamido)-2-(2-methylthiazol-5-yl)-5-(4,4,5,5-tetramethyl-1,3,2-dioxaborolan-2-yl)benzofuran-3-carboxamide (120 mg, yield: 45%). $^1$H-NMR (CDCl$_3$, 400 MHz) δ 8.39 (s, 1H), 8.08 (s, 1H), 7.55 (s, 1H), 6.34 (br s., 1H), 3.36 (s, 3H), 3.09 (d, J=4.4 Hz, 3H), 2.95 (s, 3H), 2.75 (s, 3H), 1.38 (s, 12H). MS (M+H)$^+$: 506.

Step 3—Synthesis of 5-(11-fluoro-5,6-dihydroindolo [1,2-h][1,7]naphthyridin-2-yl)-N-methyl-6-(N-methylmethylsulfonamido)-2-(2-methylthiazol-5-yl)benzofuran-3-carboxamide

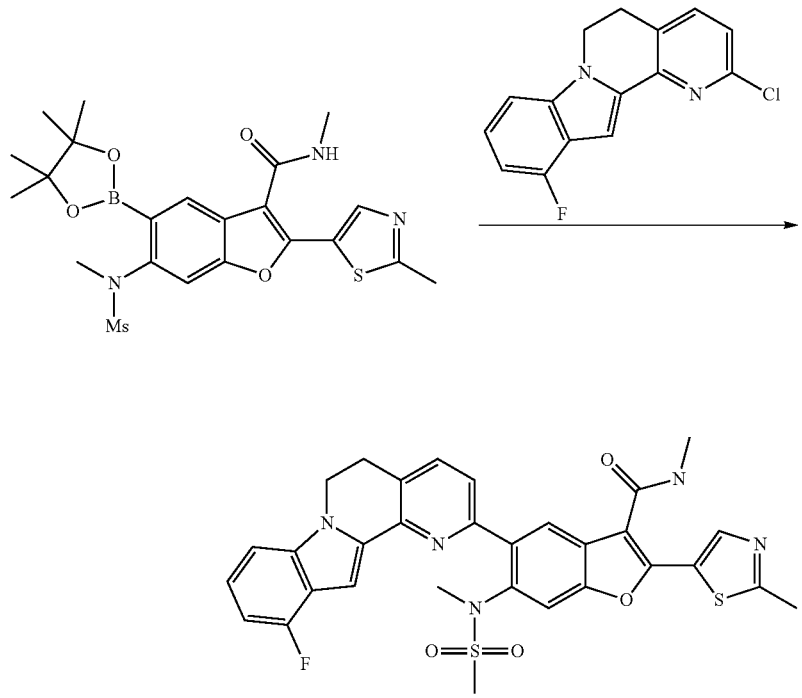

To a degassed solution of N-methyl-6-(N-methylmethylsulfonamido)-2-(2-methylthiazol-5-yl)-5-(4,4,5,5-tetramethyl-1,3,2-dioxaborolan-2-yl)benzofuran-3-carboxamide (200 mg, 0.40 mmol), 2-chloro-11-fluoro-5,6-dihydroindolo [1,2-h][1,7]naphthyridine (113 mg, 0.41 mmol), $Na_2CO_3$ (84 mg, 0.79 mmol), $K_2CO_3$ (109 mg, 0.79 mmol) in 1,4-dioxane (5 mL) and $H_2O$ (0.1 mL) were added $Pd_2(dba)_3$ (10 mg) and X-Phos (10 mg) under $N_2$. Then the mixture was stirred at 100° C. for 2 hours. The reaction mixture was cooled to RT and filtered. The filtrate was washed with $H_2O$ and dried over $Na_2SO_4$. After concentrated, the residue was purified by prep-HPLC to give the product (30 mg, yield: 12%). $^1$H-NMR (CDCl$_3$, 400 MHz) δ 8.41 (s, 1H), 7.89 (s, 1H), 7.62~7.68 (m, 2H), 7.45 (d, J=7.6 Hz, 1H), 7.24 (s, 1H), 7.12~7.20 (m, 2H), 6.74~6.81 (m, 1H), 6.22 (d, J=4.0 Hz, 1H), 4.32 (t, J=6.4 Hz, 2H), 3.32 (s, 3H), 3.27~3.31 (m, 2H), 3.02 (d, J=4.8 Hz, 3H), 2.75 (s, 3H), 2.74 (s, 3H). MS (M+H)$^+$: 616.

Examples 37 and 38

Examples 37 and 38, depicted in the table below, were prepared in accordance with the method described in Example 36.

| Example | Structure | NMR | MS (M + H)$^+$ |
|---|---|---|---|
| 37 | 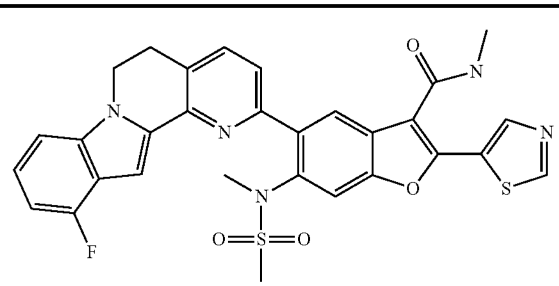 | $^1$H-NMR (CDCl$_3$, 400 MHz) δ 8.93 (s, 1H), 8.72 (s, 1H), 7.93 (s, 1H), 7.73~7.65 (m, 2H), 7.47 (d, J = 7.6 Hz, 1H), 7.29 (s, 1H), 7.22~7.11 (m, 2H), 6.79 (dd, J = 7.2, 9.2 Hz, 1H), 6.25 (br s, 1H), 4.34 (t, J = 6.5 Hz, 2H), 3.38~3.28 (m, 5H), 3.05 (d, J = 4.8 Hz, 3H), 2.77 (s, 3H). | 602 |

| Example | Structure | NMR | MS (M + H)+ |
|---|---|---|---|
| 38 | 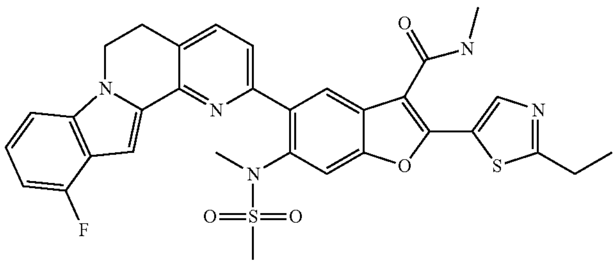 [SMILES: CCc1ncc(-c2oc3cc(N(C)S(C)(=O)=O)c(-c4ccc5c(n4)-c4cc6c(F)cccc6n4CC5)cc3c2C(=O)NC)s1] | ¹H-NMR (CDCl₃, 400 MHz) δ 8.41 (s, 1H), 7.89 (s, 1H), 7.62~7.66 (m, 2H), 7.43 (d, J = 7.6 Hz, 1H), 7.23 (s, 1H), 7.10~7.15 (m, 2H), 6.76 (dd, J = 7.6, 8.8 Hz, 1H), 6.17 (d, J = 3.6 Hz, 1H), 4.31 (t, J = 6.4 Hz, 2H), 3.31 (s, 3H), 3.26~3.30 (m, 2H), 3.05~3.10 (m, 2H), 3.01 (d, J = 4.8 Hz, 3H), 2.73 (s, 3H), 1.43 (t, J = 7.6 Hz, 3H). | 630 |

Example 39

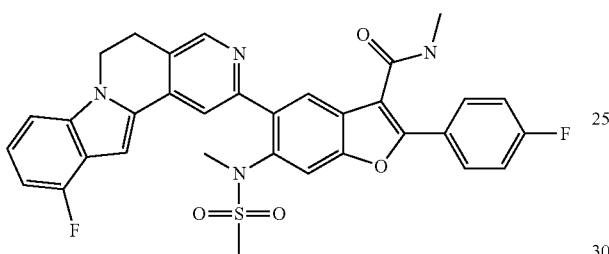

Step 1—Synthesis of 6-chloro-4-(4-fluoro-1H-indol-2-yl)pyridin-3-yl trifluoromethanesulfonate

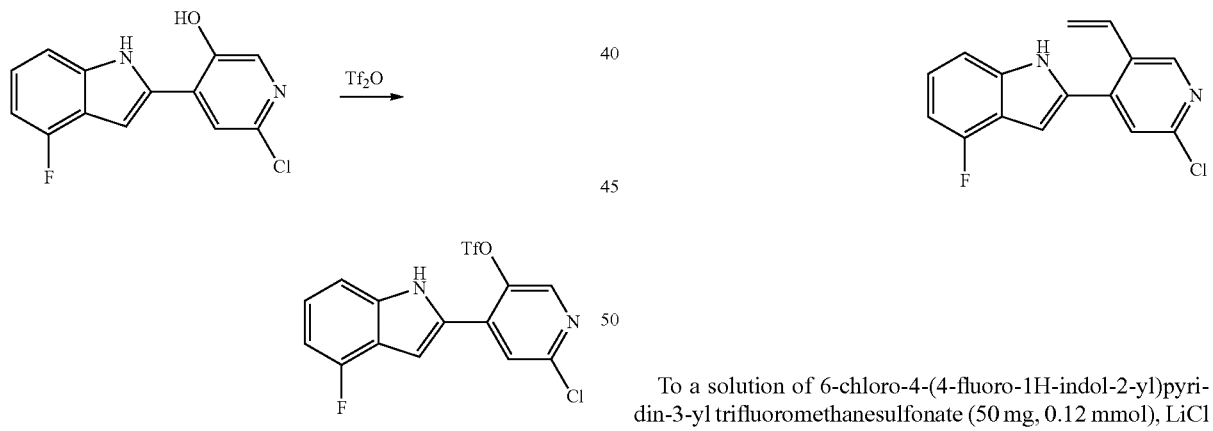

To a solution of 6-chloro-4-(4-fluoro-1H-indol-2-yl)pyridin-3-ol (prepared using similar method described in Example 1, 500 mg, 1.9 mmol), DIPEA (490 mg, 3.8 mmol) and DMAP (5 mg, 0.02 mmol) in DCM (2 mL) was added Tf₂O (1.07 g, 3.8 mmol) dropwise at 0° C. under nitrogen. The mixture was stirred at 25° C. for 5 hours. The mixture was diluted with H₂O extracted with EtOAc, then the combined organic phase was washed with brine, dried over Na₂SO₄ and concentrated in vacuo to give the crude product. It was purified by column (PE:EA=5:1) to obtain the product of 6-chloro-4-(4-fluoro-1H-indol-2-yl)pyridin-3-yl trifluoromethanesulfonate (600 mg, yield: 80%). ¹H-NMR (CDCl₃, 400 MHz) δ 8.71 (s, 1H), 8.39 (s, 1H), 7.64 (s, 1H), 7.18~7.20 (m, 3H), 6.77~6.82 (m, 1H). MS (M+H)⁺: 395/397.

Step 2—Synthesis of 2-(2-chloro-5-vinylpyridin-4-yl)-4-fluoro-1H-indole

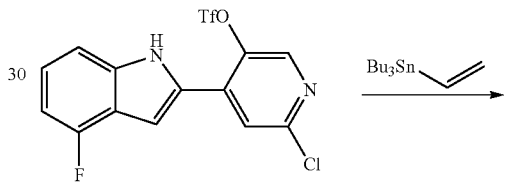

To a solution of 6-chloro-4-(4-fluoro-1H-indol-2-yl)pyridin-3-yl trifluoromethanesulfonate (50 mg, 0.12 mmol), LiCl (8 mg, 0.19 mmol) in DMF (0.8 mL) was added tributyl (vinyl)stannane (80 mg, 0.25 mmol) dropwise at 25° C. under nitrogen. The mixture was stirred at 65° C. for 10 hours. The mixture was diluted with H₂O, extracted with EtOAc, then the combined organic phase was washed with brine, dried over Na₂SO₄ and concentrated in vacuo to give the crude product. It was purified by column (PE:EA=5:1) to obtain the product of 2-(2-chloro-5-vinylpyridin-4-yl)-4-fluoro-1H-indole (150 mg, yield: 40%). ¹H-NMR (CDCl₃, 400 MHz) δ 8.45 (s, 1H), 7.41 (s, 1H), 7.15 (d, J=2.4 Hz, 1H), 6.88 (d, J=6.0 Hz, 1H), 6.79 (t, J=6.0 Hz, 1H), 6.35~6.41 (m, 1H), 6.07~6.10 (m, 1H), 5.77 (d, J=17.6 Hz, 1H), 5.49~5.62 (m, 2H). MS (M+H)⁺: 273/275.

Step 3—Synthesis of 2-chloro-11-fluoro-5,6-dihydroindolo[2,1-a][2,6]naphthyridine

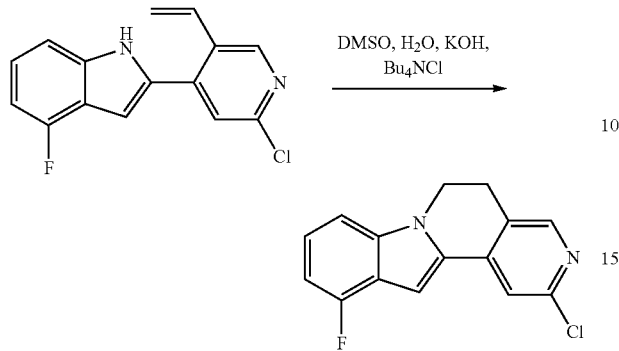

A solution of 2-(2-chloro-5-vinylpyridin-4-yl)-4-fluoro-1H-indole (50 mg, 0.18 mmol), Bu$_4$NCl (0.07 mL of 50% a.q. solution), DMSO (0.25 mL) and KOH (0.6 mL of 60% a.q. solution) was stirred at 100° C. for 3 hours. Then the mixture was diluted with H$_2$O, extracted with EtOAc, then the combined organic phase was washed with brine, dried over Na$_2$SO$_4$ and concentrated in vacuo to give the crude product. It was purified by column (PE:EA=3:1) to obtain the product of 2-chloro-11-fluoro-5,6-dihydroindolo[2,1-a][2,6]naphthyridine (11 mg, yield: 20%). $^1$H-NMR (CDCl$_3$, 400 MHz) δ 8.30 (s, 1H), 7.62 (s, 1H), 7.18~7.21 (m, 2H), 7.12 (s, 1H), 6.81 (t, J=8.4 Hz, 1H), 4.29 (t, J=6.0 Hz, 2H), 3.20 (t, J=6.0 Hz, 2H). MS (M+H)$^+$: 273/275.

Step 4—Synthesis of 5-(11-fluoro-5,6-dihydroindolo[2,1-a][2,6]naphthyridin-2-yl)-2-(4-fluorophenyl)-N-methyl-6-(N-methylmethylsulfonamido)benzofuran-3-carboxamide

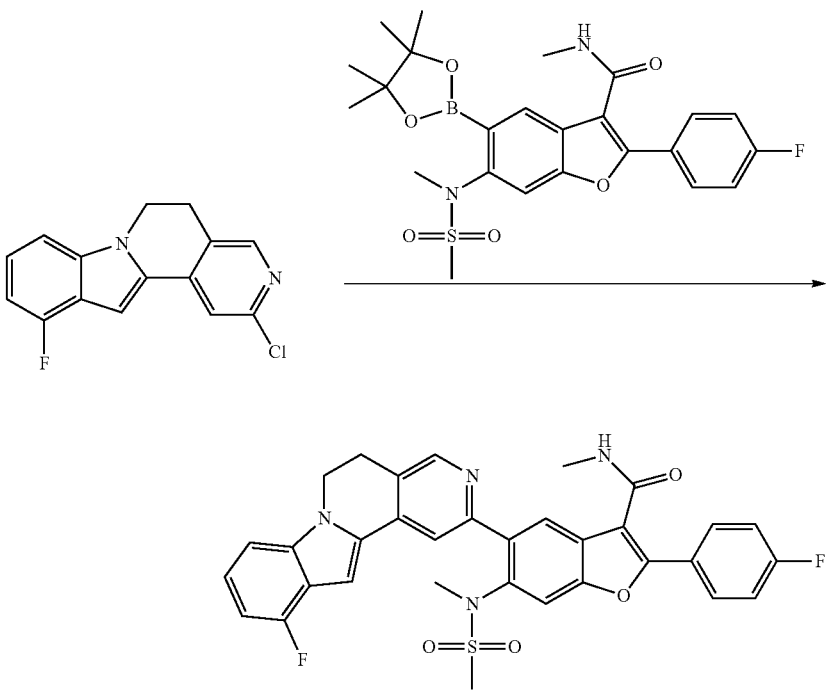

To a solution of compound 2-chloro-11-fluoro-5,6-dihydroindolo[2,1-a][2,6]naphthyridine (70 mg, 0.26 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (155 mg, 0.31 mmol) and K$_2$CO$_3$ (53 mg, 0.38 mmol) in 1,4-dioxane (2 mL) and water (0.05 mL) were added X-Phos (10 mg) and Pd$_2$(dba)$_3$ (10 mg) under nitrogen. The mixture was heated at 120° C. for 3 hours and filtered through the celite pad. The filtrate was extracted with EtOAc, then the combined organic phase was washed with brine, dried over Na$_2$SO$_4$ and concentrated. The crude product was purified by prep-HPLC to give the desired compound (50 mg, yield: 30%). $^1$H-NMR (CDCl$_3$, 400 MHz) δ 8.54 (s, 1H), 7.91~7.98 (m, 4H), 7.62 (s, 1H), 7.09~7.16 (m, 5H), 6.74 (t, J=8.8 Hz, 1H), 5.95 (s, 1H), 4.29 (t, J=6.0 Hz, 2H), 3.23 (t, J=6.0 Hz, 2H), 3.17 (s, 3H), 2.95 (d, J=4.0 Hz, 3H), 2.83 (s, 3H). MS (M+H)$^+$: 613.

Example 40

Example 40, depicted in the table below, was prepared in accordance with the method described in Example 39.

| Compound ID | Structure | NMR | MS (M + H)+ |
|---|---|---|---|
| 40 | 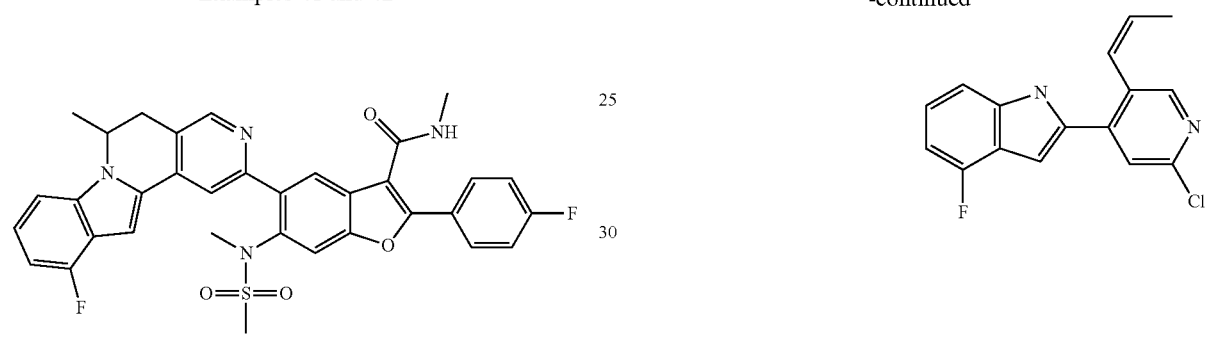 | $^1$H-NMR (CDCl$_3$, 400 MHz) δ 8.96 (s, 1H), 8.68 (s, 1H), 8.53 (d, J = 3.6 Hz, 1H), 8.19 (s, 1H), 8.16 (s, 1H), 8.06 (s, 1H), 7.94 (s, 1H), 7.44 (d, J = 6.4 Hz, 2H), 7.25 (s, 1H), 7.19 (t, J = 4.8 Hz, 1H), 6.87 (t, J = 8.0 Hz, 1H), 4.38-4.43 (m, 2H), 3.18-3.52 (m, 2H), 3.22 (m, 3H), 3.05 (s, 3H), 2.81 (d, J = 4.0 Hz, 3H), 2.55 (s, 3H). | 610 |

Examples 41 and 42

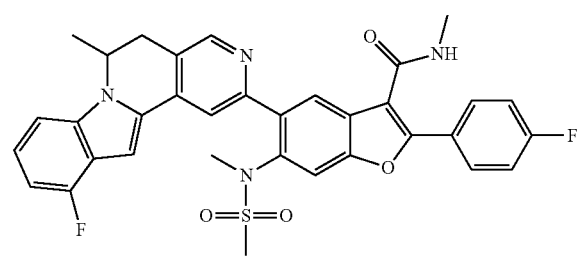

41 (Enantiomer 1, peak 1 on SFC)

42 (Enantiomer 2, peak 2 on SFC)

41 (Enantiomer 1, peak 1 on SFC) 42 (Enantiomer 2, peak 2 on SFC)

Step 1—Synthesis of (Z)-2-(2-chloro-5-(prop-1-en-1-yl)pyridin-4-yl)-4-fluoro-1H-indole

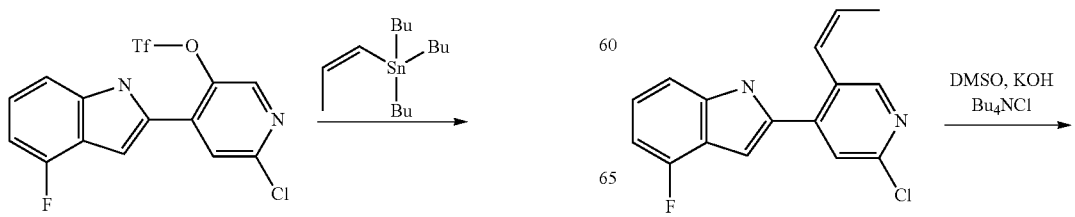

To a mixture of 6-chloro-4-(4-fluoro-1H-indol-2-yl)pyridin-3-yl trifluoromethanesulfonate (200 mg, 0.51 mmol), (Z)-tributyl (prop-1-en-1-yl) stannane (170 mg, 0.51 mmol) and anhydrous LiCl (70 mg, 1.65 mmol) in DMF (2 mL), Pd(PPh$_3$)$_2$Cl$_2$ (30 mg, 0.04 mmol) was added under N$_2$ protection. The reaction mixture was stirred at 100° C. for 10 h. Then it was filtered and concentrated in vacuo. The residue was purified by column chromatography (PE:EA=10:1) to give the product of (Z)-2-(2-chloro-5-(prop-1-en-1-yl)pyridin-4-yl)-4-fluoro-1H-indole (90 mg, yield: 61.9%). $^1$H-NMR (CDCl$_3$, 400 MHz) δ 12.02 (br s, 1H), 8.33 (s, 1H), 7.87 (s, 1H), 7.31 (d, J=7.6 Hz, 1H), 7.16~7.21 (m, 1H), 6.98 (d, J=1.2 Hz, 1H), 6.85 (dd, J=10.8, 7.6 Hz, 1H), 6.57 (dd, J=11.2, 1.6 Hz, 1H), 6.06~6.16 (m, 1H), 1.78 (dd, J=6.8, 1.6 Hz, 3H). MS (M+H)+: 287.

Step 2—Synthesis of 2-chloro-11-fluoro-6-methyl-5,6-dihydroindolo[2,1-a][2,6]naphthyridine -continued

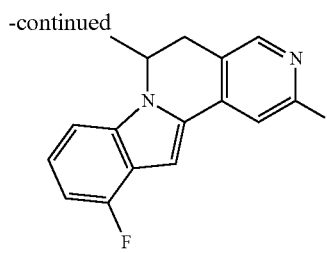

A mixture of (Z)-2-(2-chloro-5-(prop-1-en-1-yl)pyridin-4-yl)-4-fluoro-1H-indole (90 mg, 0.31 mmol), DMSO (0.5 mL), TBAC (0.1 mL of 50% a.q. solution) and KOH (1.0 mL of 60% aq. solution) was stirred under $N_2$ at 100° C. for 5 h. After cooling and extraction with EtOAc, the organic layer was washed with water, brine, dried over $Na_2SO_4$, and concentrated.

The residue was purified by prep-TLC (PE:EA=5:1) to give the product of 2-chloro-11-fluoro-6-methyl-5,6-dihydroindolo[2,1-a][2,6]naphthyridine (30 mg, yield: 33.3%). $^1$H-NMR (CDCl$_3$, 400 MHz) δ 8.31 (s, 1H), 7.62 (s, 1H), 7.14~7.22 (m, 2H), 7.11 (s, 1H), 6.81~6.82 (m, 1H), 4.92~4.98 (m, 1H), 3.35~3.41 (m, 1H), 2.99 (d, J=15.2 Hz, 1H), 1.24 (d, J=6.4 Hz, 3H). MS (M+H)$^+$: 287.

Step 3—Synthesis of (R or S)-5-(11-fluoro-6-methyl-5,6-dihydroindolo[2,1-a][2,6]naphthyridin-2-yl)-2-(4-fluorophenyl)-N-methyl-6-(N-methylmethylsulfonamido)benzofuran-3-carboxamide and (S or R)-5-(11-fluoro-6-methyl-5,6-dihydroindolo[2,1-a][2,6]naphthyridin-2-yl)-2-(4-fluorophenyl)-N-methyl-6-(N-methylmethylsulfonamido)benzofuran-3-carboxamide

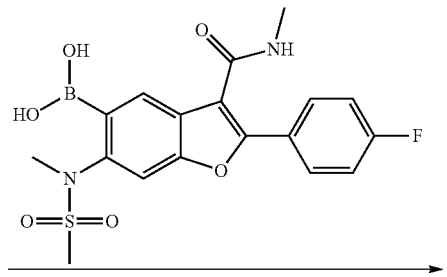

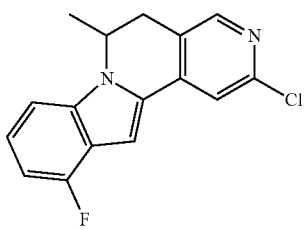

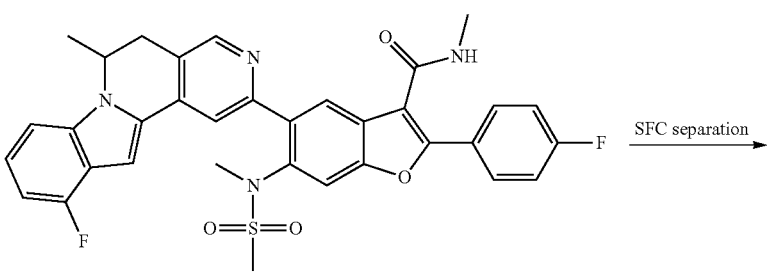

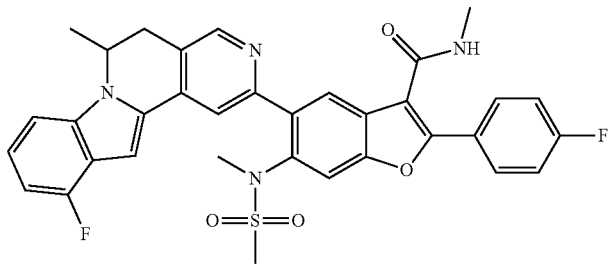

41 (Enantiomer 1, peak 1 on SFC)

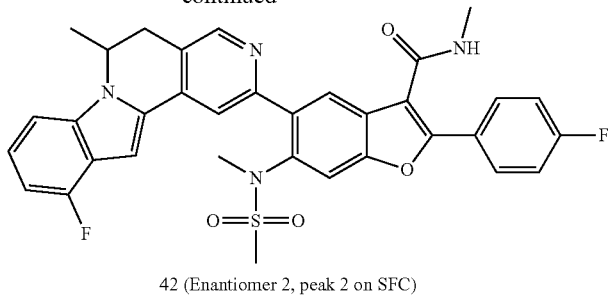

42 (Enantiomer 2, peak 2 on SFC)

To a degassed solution of 2-chloro-11-fluoro-6-methyl-5,6-dihydroindolo[2,1-a][2,6]naphthyridine (80 mg, 0.28 mmol) and (2-(4-fluorophenyl)-3-(methylcarbamoyl)-6-(N-methylmethylsulfonamido)benzofuran-5-yl)boronic acid (130 mg, 0.26 mmol) in 1,4-dioxane (5 mL), Pd$_2$(dba)$_3$ (10 mg), X-Phos (10 mg) and K$_3$PO$_4$ (200 mg, 0.75 mmol) were added under N$_2$. The mixture was heated to 80° C. for 2 hours. The reaction mixture was cooled to RT, filtered and washed with EtOAc. The filtrate was washed with H$_2$O, brine, dried over Na$_2$SO$_4$. After being concentrated, the residue was purified by prep-HPLC and SFC to give two single enantiomers.

Compound 41 (enantiomer 1, peak 1 on SFC, AS-H_S_3_5_40_3ML_8MIN_15CM, HPLC_RT=4.47 min) (40 mg, yield: 24.7%). $^1$H-NMR (CDCl$_3$, 400 MHz) δ 8.59 (s, 1H), 8.05 (s, 1H), 7.92~8.02 (m, 3H), 7.67 (s, 1H), 7.14~7.24 (m, 5H), 6.78~6.82 (m, 1H), 6.13 (br s, 1H), 4.99 (q, J=6.4 Hz, 1H), 3.49 (dd, J=15.6, 6.4 Hz, 1H), 3.23 (s, 3H), 2.96~3.08 (m, 4H), 2.85 (s, 3H), 1.28 (d, J=6.4 Hz, 3H). MS (M+H)$^+$: 628.

Compound 42 (enantiomer 2, peak 2 on SFC, AS-H_S_3_5_40_3ML_8MIN_15CM, HPLC_RT=5.24 min) (40 mg, yield: 24.7%). $^1$H-NMR (CDCl$_3$, 400 MHz) δ 8.59 (s, 1H), 8.05 (s, 1H), 7.92~8.02 (m, 3H), 7.67 (s, 1H), 7.14~7.24 (m, 5H), 6.78~6.82 (m, 1H), 6.13 (br s, 1H), 4.99 (q, J=6.4 Hz, 1H), 3.49 (dd, J=15.6, 6.4 Hz, 1H), 3.23 (s, 3H), 2.96~3.08 (m, 4H), 2.85 (s, 3H), 1.28 (d, J=6.4 Hz, 3H). MS (M+H)$^+$: 628.

Example 43

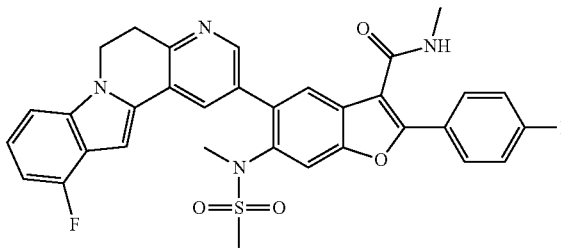

Step 1—Synthesis of 5-bromo-3-(4-fluoro-1H-indol-2-yl)pyridin-2-ol

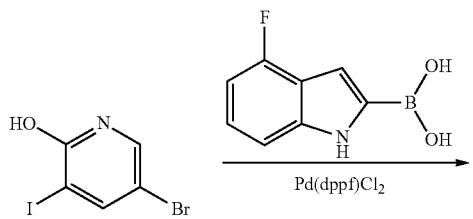

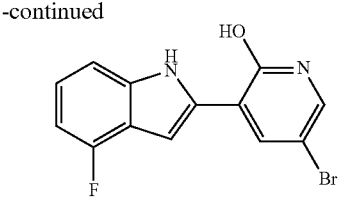

A mixture of 5-bromo-3-iodopyridin-2-ol (5 g, 16.7 mmol), (4-fluoro-1H-indol-2-yl)boronic acid (4.48 g, 25.0 mmol), sodium carbonate (3.53 g, 33.4 mmol) and Pd(dppf)Cl$_2$ (200 mg) in 1,4-dioxane (50 mL) was stirred at 100° C. for 16 hours under nitrogen atmosphere. The mixture was filtered through celite and concentrated, and the residue was diluted with water and EA. After extracted with EA, the combined organic phase was washed with brine, dried over sodium sulfate and concentrated to afford crude 5-bromo-3-(4-fluoro-1H-indol-2-yl)pyridin-2-ol (3.5 g) through the column chromatography (DCM:EA=5:1). Finally the pure 5-bromo-3-(4-fluoro-1H-indol-2-yl)pyridin-2-ol (2.7 g, yield: 52%) was obtained by recrystallized from DCM:MeOH (10:1). $^1$H-NMR (DMSO-d$_6$, 400 MHz) δ 12.36 (br s, 1H), 11.79 (s, 1H), 8.25 (s, $^1$H), 7.70 (s, 1H), 7.39 (s, 1H), 7.30 (d, J=8.00 Hz, 1H), 7.04~7.07 (m, 1H), 6.74~6.78 (m, 1H). MS (M+H)$^+$: 307/309.

Step 2—Synthesis of 5-bromo-3-(4-fluoro-1H-indol-2-yl)pyridin-2-yl trifluoromethanesulfonate

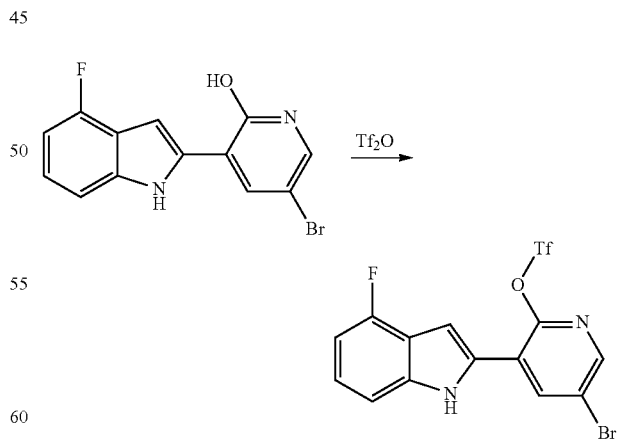

To a mixture of 5-bromo-3-(4-fluoro-1H-indol-2-yl)pyridin-2-ol (1.0 g, 3.26 mmol), DIPEA (1.26 g, 9.77 mmol) and DMAP (80 mg, 0.65 mmol) in 15 mL of DCM was added Tf$_2$O (1.84 g, 6.51 mmol) at 0 dropwise. After stirring at room temperature for 3 hours, the mixture was suspended in water and extracted with DCM. Then the combined organic phase was washed with brine, dried over sodium sulfate and concentrated. After column chromatography (PE:EA=20:1), 5-bromo-3-(4-fluoro-1H-indol-2-yl)pyridin-2-yl trifluoromethanesulfonate (1.0 g, yield: 52%) was obtained. $^1$H-NMR (DMSO-d$_6$, 400 MHz) δ 12.28 (s, 1H), 8.81 (s, 1H), 8.60 (s, 1H), 7.32 (d, J=8.40 Hz, 1H), 7.18~7.22 (m, 1H), 7.05 (s, 1H), 6.84~6.87 (m, 1H). MS (M+H)$^+$: 439/441.

Step 3—Synthesis of 2-(5-bromo-2-vinylpyridin-3-yl)-4-fluoro-1H-indole

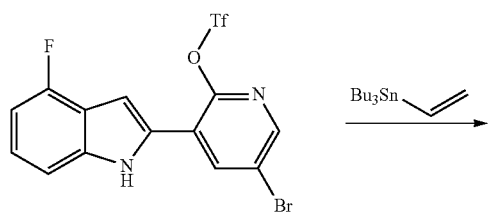

A mixture of 5-bromo-3-(4-fluoro-1H-indol-2-yl)pyridin-2-yl trifluoromethanesulfonate (700 mg, 1.59 mmol), tributyl(vinyl)stannane (556 mg, 1.75 mmol), LiCl (202 mg, 4.78 mmol) and Pd(PPh$_3$)$_2$Cl$_2$ (100 mg) in DMF (20 mL) was stirred at 60° C. for 3 hours under nitrogen atmosphere. The mixture was filtered through celite and concentrated in vacuo to remove DMF, and then the residue was suspended in water/EA. After extracted with EA, the combined organic phase was washed with brine, dried over sodium sulfate and concentrated to afford 2-(5-bromo-2-vinylpyridin-3-yl)-4-fluoro-1H-indole (400 mg, yield: 79%) through the column chromatography (PE:EA=20:1). $^1$H-NMR (CDCl$_3$, 400 MHz) δ 8.64 (s, 1H), 8.46 (s, 1H), 7.93 (s, 1H), 7.14~7.22 (m, 2H), 7.00~7.07 (m, 1H), 6.82~6.86 (m, 1H), 6.76 (s, 1H), 6.43~6.47 (m, 1H), 5.54~5.58 (m, 1H). MS (M+H)$^+$: 317/319.

Step 4—Synthesis of 2-(5-bromo-2-(2-chloroethyl)pyridin-3-yl)-4-fluoro-1H-indole

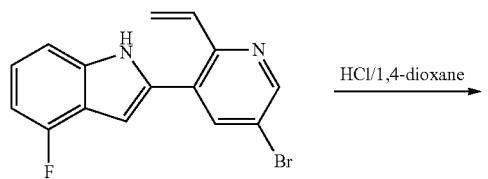

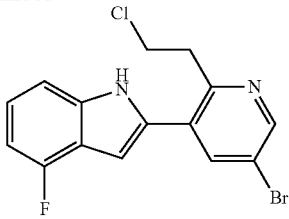

A solution of 2-(5-bromo-2-vinylpyridin-3-yl)-4-fluoro-1H-indole (800 mg, 2.52 mmol) in 20 mL of HCl/1,4-dioxane (4 mol/L) was heated at 80° C. for 2 hours and then the mixture was concentrated in vacuo to give the crude 2-(5-bromo-2-(2-chloroethyl)pyridin-3-yl)-4-fluoro-1H-indole (800 mg, yield: 90%) which was used directly in the next step without further purification. $^1$H-NMR (CDCl$_3$, 400 MHz) δ 8.76 (s, 1H), 8.66 (s, 1H), 7.93 (s, 1H), 7.14~7.22 (m, 2H), 6.73~6.86 (m, 1H), 6.72 (s, 1H), 4.07~4.10 (m, 2H), 3.35~3.36 (m, 2H). MS (M+H)$^+$: 353/355.

Step 5—Synthesis of 2-bromo-11-fluoro-5,6-dihydroindolo[2,1-f][1,6]naphthyridine

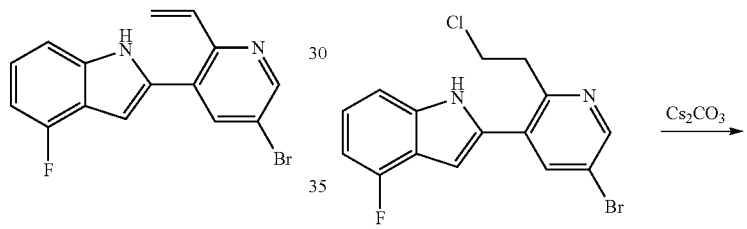

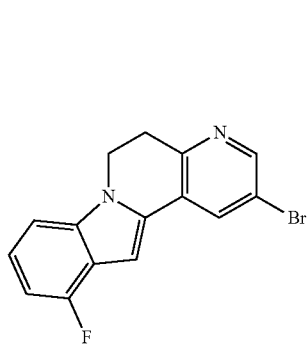

A solution of 2-(5-bromo-2-(2-chloroethyl)pyridin-3-yl)-4-fluoro-1H-indole (800 mg, 2.26 mmol) and cesium carbonate (1.47 g, 4.52 mmol) in 25 mL of DMF was heated at 80° C. for 1 hour. The mixture was concentrated in vacuo to remove DMF, and then the residue was suspended in water and EA. After extraction with EA, the combined organic phase was washed with brine, dried over sodium sulfate and concentrated to afford crude 2-bromo-11-fluoro-5,6-dihydroindolo[2,1-f][1,6]naphthyridine (600 mg, yield: 83.6%) which was used directly in the next step without further purification. $^1$H-NMR (CDCl$_3$, 400 MHz) δ 8.48 (s, 1H), 8.11

(s, 1H), 7.11~7.17 (m, 2H), 6.97 (s, 1H), 6.78~6.82 (m, 1H), 4.34~4.37 (m, 2H), 3.34~3.37 (m, 2H). MS (M+H)+: 317/319.

Step 6—Synthesis of 5-(11-fluoro-5,6-dihydroindolo[2,1-f][1,6]naphthyridin-2-yl)-2-(4-fluorophenyl)-N-methyl-6-(N-methylmethylsulfonamido)benzofuran-3-carboxamide water and EA. After extraction with EA, the combined organic phase was washed with brine, dried over sodium sulfate and concentrated to afford the desired product (40 mg, yield: 41.7%) through the prep-HPLC. $^1$H-NMR (CDCl$_3$, 400 MHz) δ 8.50 (s, 1H), 8.19 (s, 1H), 7.93~7.96 (m, 2H), 7.90 (s, 1H), 7.65 (s, 1H), 7.19~7.24 (m, 2H), 7.15~7.17 (m, 2H), 7.02 (s, 1H), 6.77~6.82 (m, 1H), 5.88 (br s, 1H), 4.41~4.44 (m, 2H), 3.45~3.49 (m, 2H), 3.18 (s, 3H), 2.99 (d, J=4.80 Hz, 3H), 2.84 (s, 3H). MS (M+H)+: 613.

Example 44

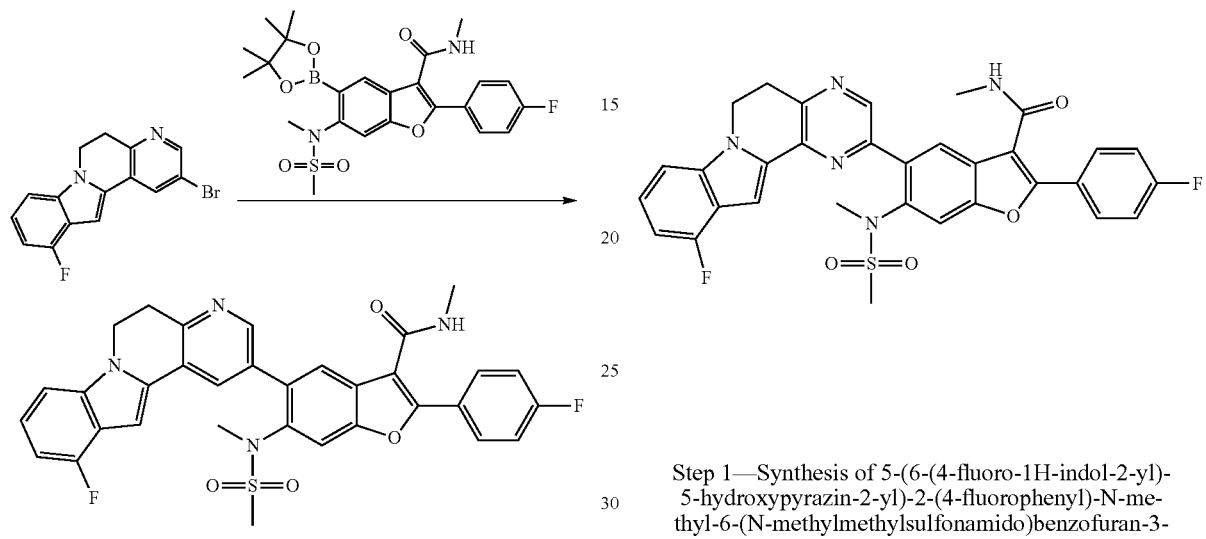

Step 1—Synthesis of 5-(6-(4-fluoro-1H-indol-2-yl)-5-hydroxypyrazin-2-yl)-2-(4-fluorophenyl)-N-methyl-6-(N-methylmethylsulfonamido)benzofuran-3-carboxamide

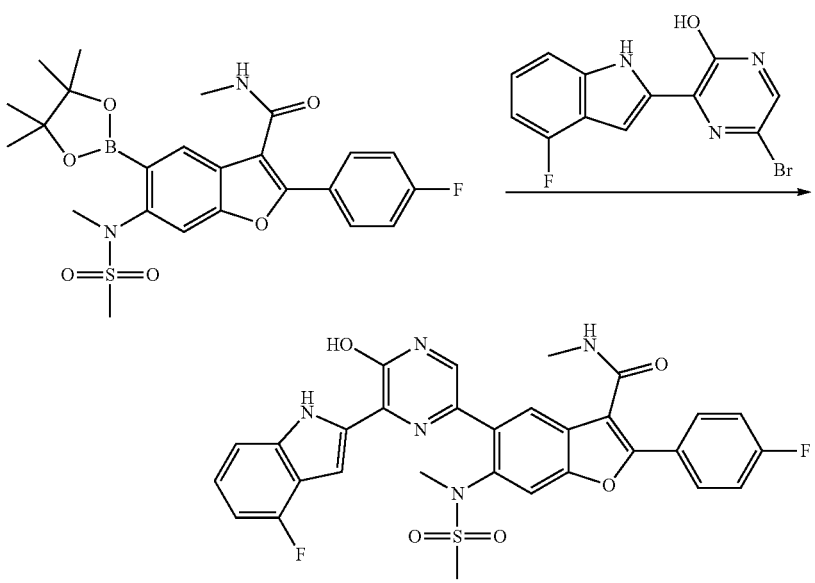

A mixture of 2-bromo-11-fluoro-5,6-dihydroindolo[2,1-f][1,6]naphthyridine (50 mg, 0.16 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (87 mg, 0.17 mmol), potassium carbonate (43 mg, 0.32 mmol) and Pd(dtbpf)Cl$_2$ (10 mg) in 1,4-dioxane/water (1/0.1 mL) was stirred at 100° C. for 6 hours under nitrogen atmosphere. The mixture was filtered through Celite pad and concentrated, and then the residue was diluted with To a degassed solution of 5-bromo-3-(4-fluoro-1H-indol-2-yl)pyrazin-2-ol (prepared using similar method described in Example 1, 1.23 g, 3.98 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (2 g, 3.98 mmol) and K$_3$PO$_4$.3H$_2$O (2.12 g, 7.96 mmol) in IPA (20 mL) and H$_2$O (2 mL) was added Pd$_2$(dba)$_3$ (50 mg) and X-Phos (50 mg) under nitrogen atmosphere. The reaction mixture was stirred at 100° C. for 16 h, concentrated in vacuo to remove IPA. The residue was diluted with H₂O and extracted with DCM. Then the combined organic layers were washed with brine (100 mL), dried over Na₂SO₄, filtered, concentrated and purified by column chromatography (PE:EA=1:2) to give 5-(6-(4-fluoro-1H-indol-2-yl)-5-hydroxy-pyrazin-2-yl)-2-(4-fluorophenyl)-N-methyl-6-(N-methylmethylsulfonamido)benzofuran-3-carboxamide (1 g, yield: 41%). ¹H-NMR (CDCl₃, 400 MHz) δ 8.52 (d, J=4.0 Hz, 1H), 8.06 (s, 1H), 8.02 (s, 1H), 7.71 (s, 1H), 7.66 (s, 1H), 7.42 (t, J=8.8 Hz, 2H), 7.33~7.36 (m, 2H), 7.11~7.18 (m, 2H), 6.80 (dd, J₁=10.4 Hz, J₂=8.0 Hz, 2H), 3.27 (s, 3H), 3.10 (s, 3H), 2.85 (d, J=4.8 Hz, 3H). MS (M+H)⁺: 604.

Step 2—Synthesis of 3-(4-fluoro-1H-indol-2-yl)-5-(2-(4-fluorophenyl)-3-(methylcarbamoyl)-6-(N-methylmethylsulfonamido)benzofuran-5-yl)pyrazin-2-yl trifluoromethanesulfonate

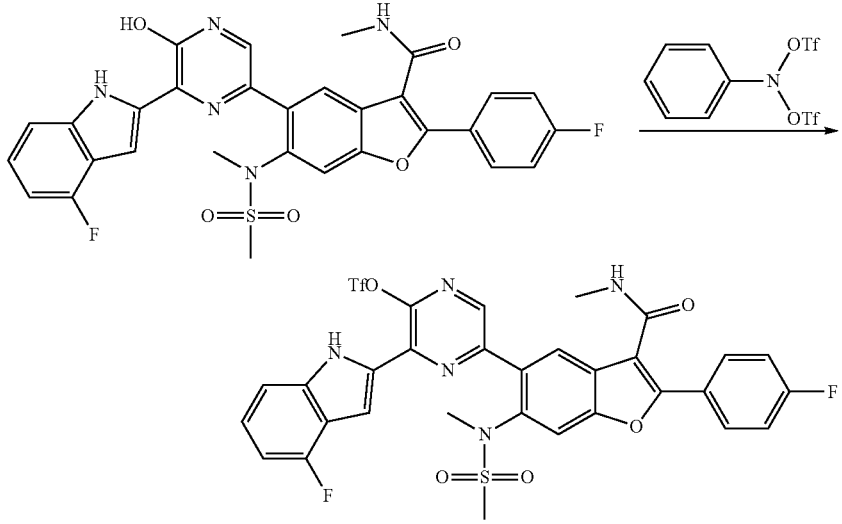

To a solution of 5-(6-(4-fluoro-1H-indol-2-yl)-5-hydroxy-pyrazin-2-yl)-2-(4-fluorophenyl)-N-methyl-6-(N-methylmethylsulfonamido)benzofuran-3-carboxamide (400 mg, 0.68 mmol) and N-phenyl-O-(((trifluoromethyl)sulfonyl)-N-(((trifluoromethyl)sulfonyl)oxy) hydroxylamine (400 mg, 1.03 mmol) in THF (10 mL) was added Et₃N (276 mg, 2.73 mmol) under nitrogen atmosphere. The reaction mixture was stirred at room temperature overnight, diluted with H₂O and extracted with DCM. The combined organic layers were washed with brine (100 mL), dried over Na₂SO₄, filtered, concentrated and purified by column chromatography (PE:EA=1:1) to give 3-(4-fluoro-1H-indol-2-yl)-5-(2-(4-fluorophenyl)-3-(methylcarbamoyl)-6-(N-methylmethylsulfonamido)benzofuran-5-yl)pyrazin-2-yl trifluoromethanesulfonate (150 mg, yield: 36%). ¹H-NMR (CDCl₃, 400 MHz) δ 8.40 (s, 1H), 8.17 (s, 1H), 7.89~7.93 (m, 2H), 7.64 (s, 1H), 7.48 (s, 1H), 7.33~7.36 (m, 2H), 7.13~7.21 (m, 3H), 6.78 (dd, J=8.8 Hz, 6.8 Hz, 1H), 5.87 (br s, 1H), 3.19 (s, 3H), 3.02 (s, 3H), 2.98 (d, J=4.8 Hz, 3H). MS (M+H)⁺: 736.

Step 3—Synthesis of 5-(6-(4-fluoro-1H-indol-2-yl)-5-vinylpyrazin-2-yl)-2-(4-fluorophenyl)-N-methyl-6-(N-methylmethylsulfonamido)benzofuran-3-carboxamide

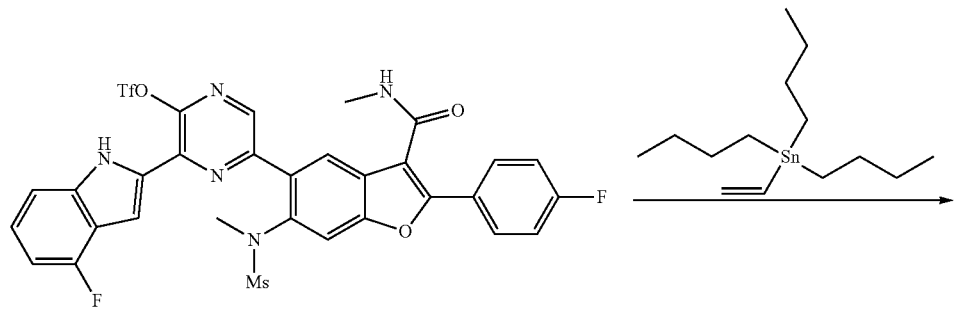

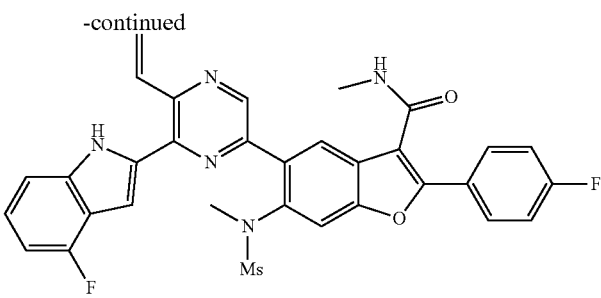

To a mixture of 3-(4-fluoro-1H-indol-2-yl)-5-(2-(4-fluorophenyl)-3-(methylcarbamoyl)-6-(N-methylmethylsulfonamido)benzofuran-5-yl)pyrazin-2-yl trifluoromethanesulfonate (30 mg, 0.04 mmol), tributyl(vinyl)stannane (16 mg, 0.05 mmol) and LiCl (5 mg, 0.12 mmol) in DMF (1 mL) was added Pd(PPh$_3$)$_2$Cl$_2$ (5 mg) under nitrogen atmosphere. The reaction mixture was stirred at 60° C. for 1 h, concentrated and purified by prep-TLC (PE:EA=1:1) to give 5-(6-(4-fluoro-1H-indol-2-yl)-5-vinylpyrazin-2-yl)-2-(4-fluorophenyl)-N-methyl-6-(N-methylmethylsulfonamido) benzofuran-3-carboxamide (15 mg, yield: 60%). $^1$H-NMR (CDCl$_3$, 400 MHz) δ 8.66 (s, 1H), 8.10 (s, 1H), 7.86~7.89 (m, 2H), 7.57~7.61 (m, 2H), 7.38~7.44 (m, 3H), 7.04~7.19 (m, 3H), 6.71 (t, J=8.0 Hz, 1H), 6.50~6.54 (m, 1H), 5.89 (br s, 1H), 5.71~5.74 (m, 1H), 3.11 (s, 3H), 2.91 (s, 6H). MS (M+H)$^+$: 614.

Step 4—Synthesis of 5-(11-fluoro-5,6-dihydropyrazino[2',3':3,4]pyrido[1,2-a]indol-2-yl)-2-(4-fluorophenyl)-N-methyl-6-(N-methylmethylsulfonamido)benzofuran-3-carboxamide

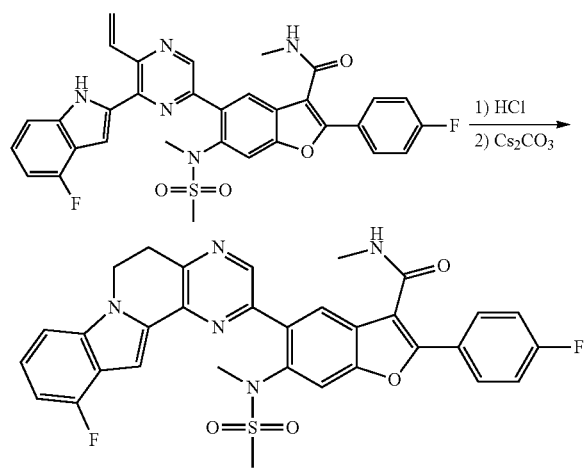

A solution of 5-(6-(4-fluoro-1H-indol-2-yl)-5-vinylpyrazin-2-yl)-2-(4-fluorophenyl)-N-methyl-6-(N-methylmethylsulfonamido)benzofuran-3-carboxamide (50 mg, 0.08 mmol) in HCl/1,4-dioxane (1 mL) was stirred at 80° C. for 1 h under nitrogen atmosphere. The reaction mixture was concentrated; then the residue was used to the next step reaction without purification. To the residue in DMF, Cs$_2$CO$_3$ was added (53 mg, 0.16 mmol), the reaction mixture was stirred at 80° C. for 1 h under nitrogen atmosphere, concentrated and purified by prep-TLC (PE:EA=1:2) to give the desired product (10 mg, yield: 20%). $^1$H-NMR (CDCl$_3$, 400 MHz) δ 8.56 (s, 1H), 8.03 (s, 1H), 7.90 (dd, J=9.2 Hz, 5.2 Hz, 2H), 7.64 (s, 1H), 7.29 (s, 1H), 7.09~7.17 (m, 4H), 6.74~6.78 (m, 1H), 5.85 (br s, 1H), 4.41 (t, J=6.8 Hz, 2H), 3.47 (t, J=6.8 Hz, 2H), 3.34 (s, 3H), 2.94 (d, J=4.8 Hz, 3H), 2.73 (s, 3H). MS (M+H)$^+$: 614.

Example 45

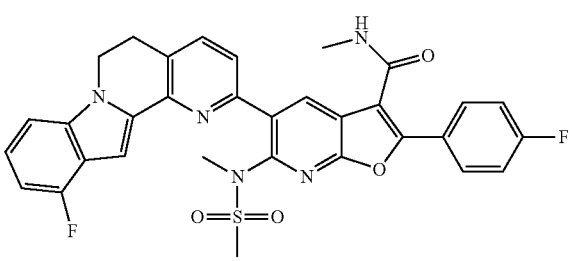 [SMILES: CNC(=O)c1c(-c2ccc(F)cc2)oc2nc(N(C)S(C)(=O)=O)c(-c3ccc4c(n3)-c3cc5c(F)cccc5n3CC4)cc12]

Step 1—Synthesis of (2-(4-fluorophenyl)-3-(methylcarbamoyl)-6-(N-methylmethylsulfonamido) furo[2,3-b]pyridin-5-yl)boronic acid

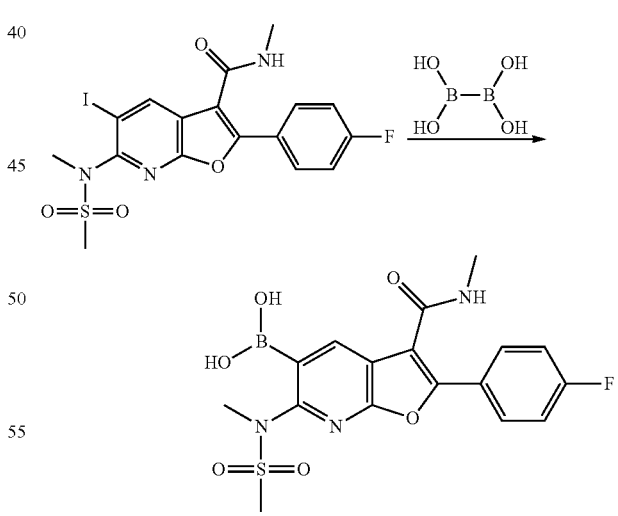

To a degassed solution of 2-(4-fluorophenyl)-5-iodo-N-methyl-6-(N-methylmethylsulfonamido)furo[2,3-b]pyridine-3-carboxamide (prepared according to International Patent Application Publication No. WO2011131709, 3.0 g, 6 mmol), hypodiboric acid (1.08 g, 1.2 mmol) and KOAc (1.8 g, 1.8 mmol) in EtOH (60 mL) was added Pd(OAc)$_2$ (50 mg) and Ad$_2$n-BuP (50 mg) under nitrogen atmosphere. The reaction mixture was stirred at 80° C. for 5 h, concentrated in vacuo to remove EtOH. The residue was purified by column chromatography (EA:DCM=1:1~DCM:MeOH=5:1) to afford the desired product of (2-(4-fluorophenyl)-3-(methylcarbamoyl)-6-(N-methylmethylsulfonamido)furo[2,3-b]pyridin-5-yl)boronic acid (1 g, yield: 40%). ¹H-NMR (DMSO-d₆, 400 MHz) δ 8.53 (d, J=4.4 Hz, 1H), 8.24 (s, 1H), 8.00~8.04 (m, 3H), 7.40 (t, J=8.8 Hz, 2H), 4.08 (br s, 1H), 3.17 (s, 3H), 3.06 (s, 3H), 2.85 (d, J=4.8 Hz, 3H). MS (M+H)⁺: 422.

Step 2—Synthesis of 5-(11-fluoro-5,6-dihydroindolo[1,2-h][1,7]naphthyridin-2-yl)-2-(4-fluorophenyl)-N-methyl-6-(N-methylmethylsulfonamido)furo[2,3-b]pyridine-3-carboxamide

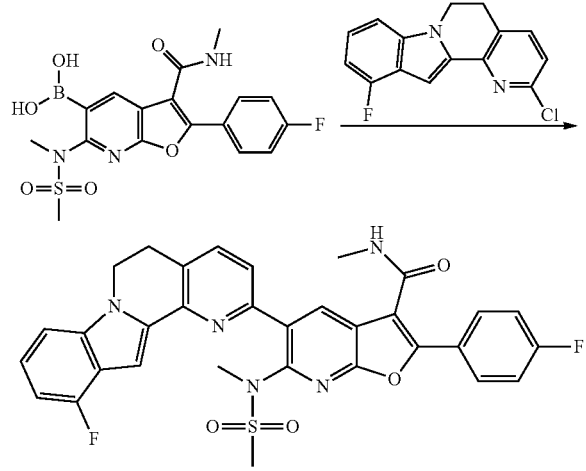

To a degassed solution of (2-(4-fluorophenyl)-3-(methylcarbamoyl)-6-(N-methylmethylsulfonamido)furo[2,3-b]pyridin-5-yl)boronic acid (100 mg, 0.24 mmol), 2-chloro-11-fluoro-5,6-dihydroindolo[1,2-h][1,7]naphthyridine (60 mg, 0.21 mmol) and K₂CO₃ (98 mg, 0.72 mmol) in 1,4-dioxane (3 mL) and H₂O (5 drops) was added Pd₂(dba)₃ (10 mg) and X-Phos (10 mg) under nitrogen atmosphere. The reaction mixture was stirred at 100° C. for 2 h, concentrated in vacuo to remove 1,4-dioxane. The residue was diluted with H₂O and extracted with DCM. The combined organic layers were washed with brine (20 mL), dried over Na₂SO₄, filtered, concentrated and purified to give the desired product (80 mg, yield: 55%) through the prep-HPLC. ¹H-NMR (CDCl₃, 400 MHz) δ 8.60 (s, 1H), 8.00~8.04 (m, 2H), 7.76 (d, J=8.0 Hz, 1H), 7.67 (d, J=8.0 Hz, 1H), 7.35 (s, 1H), 7.21 (t, J=8.8 Hz, 2H), 7.14~7.16 (m, 2H), 6.75~6.80 (m, 1H), 5.97 (br s, 1H), 4.33 (t, J=6.4 Hz, 2H), 3.25~3.32 (m, 5H), 3.18 (s, 3H), 3.00 (d, J=4.8 Hz, 3H). MS (M+H)⁺: 614.

Example 46

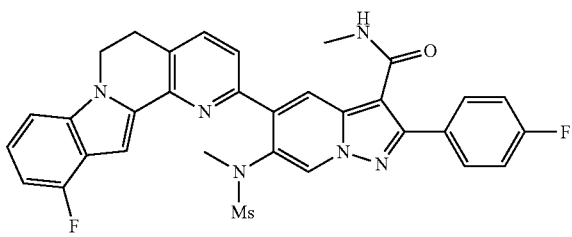 [SMILES: CNC(=O)c1c(-c2ccc(F)cc2)nn2cc(N(C)S(C)(=O)=O)c(-c3ccc4c(n3)-c3cc5c(F)cccc5n3CC4)cc12]

Step 1—Synthesis of 4-(benzyloxy)-3-nitropyridine

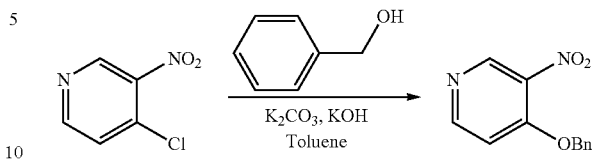

4-chloro-3-nitropyridine (30 g, 0.19 mol) was slowly added to a suspension of phenylmethanol (30 mL, 0.29 mol), K₂CO₃ (26.2 g, 0.19 mol and KOH (42.5 g, 0.76 mmol) in toluene (2 L) at 0° C. A catalytic amount of tris[2-(2-methoxyethoxy)ethyl]amine was added to the reaction mixture, which was then stirred at room temperature for 2 hours. After filtration, the resulting filtrate was concentrated to give the crude product, which was crystallized from DCM/PE (1:5) to afford 4-(benzyloxy)-3-nitropyridine (27.3 g, yield: 62.7%). ¹H-NMR (CDCl₃, 400 MHz) δ 9.00 (s, 1H), 8.56 (d, J=6.0 Hz, 1H), 7.34~7.43 (m, 5H), 7.03 (d, J=6.0 Hz, 1H), 5.29 (s, 2H). MS (M+H)⁺: 231.

Step 2—Synthesis of 4-(benzyloxy)pyridin-3-amine

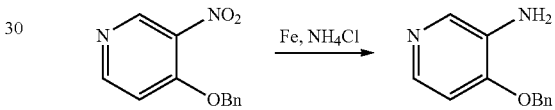

To a solution of 4-(benzyloxy)-3-nitropyridine (42.0 g, 0.18 mol), Fe (30.6 g, 0.55 mol) and NH₄Cl (48.8 g, 0.91 mol) in MeOH:THF:H₂O=(2:2:1, 750 mL) was stirred at reflux for 3 h. After being filtered and concentrated in vacuum, the residue was purified by column chromatography (DCM:MeOH=10:1) to give to give the pure 4-(benzyloxy)pyridin-3-amine (29.5 g, yield: 80.7%). ¹H-NMR (CDCl₃, 400 MHz) δ 8.25 (s, 1H), 7.88 (s, 1H), 7.20~7.65 (m, 5H), 6.89 (s, 1H), 5.18 (s, 2H). MS (M+H)⁺: 201.

Step 3—Synthesis of N-(4-(benzyloxy)pyridin-3-yl)methanesulfonamide

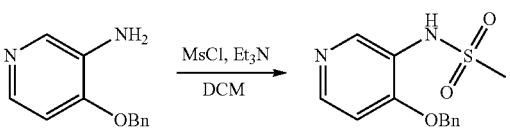

To a solution of 4-(benzyloxy)pyridin-3-amine (40 g, 0.2 mol) and Et₃N (60.6 g, 0.6 mol) in DCM (600 mL), MsCl (45.8 g, 0.4 mol) was added dropwise at 0° C. The mixture was allowed to warm up to room temperature and stirred overnight. The reaction mixture was quenched with NaHCO₃ and extracted with DCM. The organic phase was washed with brine, dried over Na₂SO₄, and concentrated. The residue was dissolved in THF:H₂O=5:1 (500 mL) and LiOH.H₂O (16.8 g, 0.4 mmol) was added. The mixture was stirred for 4 hours at room temperature. EtOAc (300 mL) was added, and the organic phase washed with NaHCO₃ (sat., a.q.), brine, dried over Na₂SO₄, filtrated and concentrated to give pure N-(4-

(benzyloxy)pyridin-3-yl)methanesulfonamide (30.0 g, yield: 54.0%). ¹H-NMR (CDCl₃, 400 MHz) δ 8.67 (s, 1H), 8.34 (d, J=5.6 Hz, 1H), 7.35~7.42 (m, 5H), 6.91 (d, J=5.6 Hz, 1H), 6.61 (br, 1H), 5.15 (s, 2H), 2.96 (s, 3H). MS (M+H)⁺: 279.

Step 4—Synthesis of N-(4-(benzyloxy)pyridin-3-yl)-N-methylmethanesulfonamide

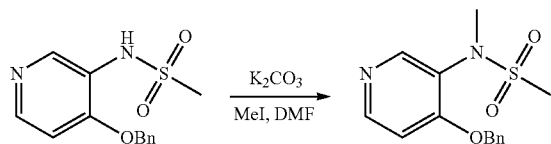

To a suspension of N-(4-(benzyloxy)pyridin-3-yl)methanesulfonamide (30 g, 0.11 mol) and K₂CO₃ (14.9 g, 0.11 mol) in DMF (300 mL) was added dropwise CH₃I (15.3 g, 0.11 mol) at 0° C. under N₂, and then the mixture was stirred for 1 hour at this temperature. H₂O was added to the mixture and extracted with dichloromethane. The combined organic layer was washed with H₂O, brine, dried over Na₂SO₄, filtrated and concentrated in vacuo to give N-(4-(benzyloxy)pyridin-3-yl)-N-methylmethanesulfonamide (15 g, yield: 50%), which was used for the next step without further purification. ¹H-NMR (CDCl₃, 400 MHz) δ 8.46 (s, 1H), 8.41 (d, J=6.0 Hz, 1H), 7.37~7.39 (m, 5H), 6.94 (d, J=6.0 Hz, 1H), 5.15 (s, 2H), 3.22 (s, 3H), 2.79 (s, 3H). MS (M+H)⁺: 293.

Step 5—Synthesis of methyl 5-(benzyloxy)-2-(4-fluorophenyl)-6-(N-methylmethylsulfonamido)pyrazolo[1,5-a]pyridine-3-carboxylate

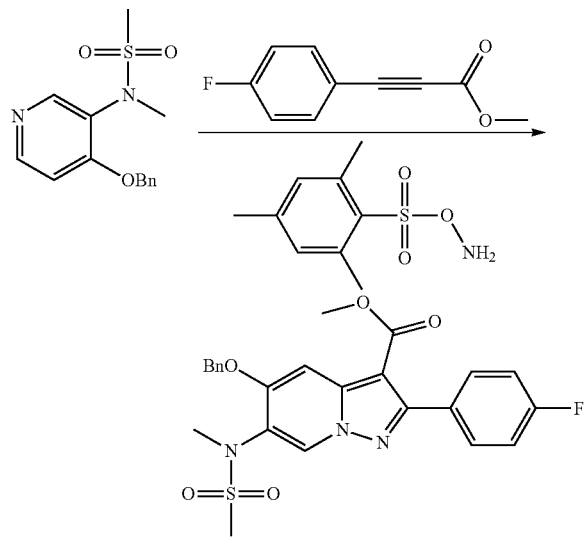

To a solution of N-(4-(benzyloxy)pyridin-3-yl)methanesulfonamide (9.0 g, 30.0 mmol) in DCM (100 mL) was added (O-(mesitylsulfonyl)hydroxylamine) (20 g, 92 mmol) in DCM (20 mL) dropwise quickly at 0° C. under N₂, and stirred for 2 h at room temperature. After concentrated and the residue was dissolved in MeOH, and re-concentrated again. The residue was dissolved in DMF (20 mL), and then added slowly dropwise to a mixture of methyl 3-(4-fluorophenyl) propiolate (6 g, 34 mmol) and K₂CO₃ (21 g, 154 mmol) in DMF (100 mL) at 0° C. under N₂. The mixture was stirred overnight at room temperature. The reaction mixture was then concentrated in vacuo and the resulting residue was suspended in H₂O and extracted with DCM. The organic layer was washed with H₂O, brine and concentrated in vacuo. The residue obtained was purified using flash column chromatography on silica gel (eluted with PE/EtOAc from 5/1 to 3/1) to give methyl 5-(benzyloxy)-2-(4-fluorophenyl)-6-(N-methylmethylsulfonamido)pyrazolo[1,5-a]pyridine-3-carboxylate (3.5 g, yield: 24%). ¹H-NMR (CDCl₃, 400 MHz) δ 8.54 (s, 1H), 7.70~7.74 (m, 2H), 7.68 (s, 1H), 7.42~7.44 (m, 5H), 7.13 (t, J=8.8 Hz, 2H), 5.24 (s, 2H), 3.80 (s, 3H), 3.29 (s, 3H), 2.81 (s, 3H). MS (M+H)⁺: 484.

Step 6—Synthesis of 5-(benzyloxy)-2-(4-fluorophenyl)-6-(N-methylmethylsulfonamido) pyrazolo[1,5-a]pyridine-3-carboxylic acid

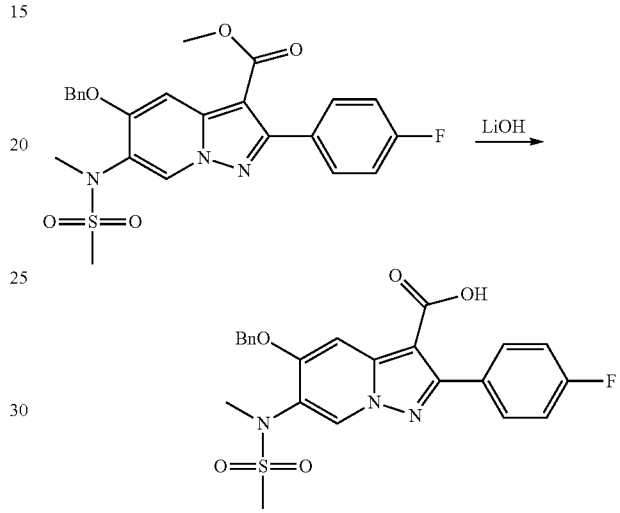

To a solution of methyl 5-(benzyloxy)-2-(4-fluorophenyl)-6-(N-methylmethylsulfonamido)pyrazolo[1,5-a]pyridine-3-carboxylate (3 g, 6.2 mmol) in dioxane/H₂O (1/1, 60 mL) was added LiOH.H₂O (781 mg, 19 mmol), and the mixture was heated to reflux for 3 hours, and concentrated in vacuo. The residue obtained was dissolved in H₂O, 1 N HCl was added until pH reached 3, and the resulting precipitate was collected by filtration, washed with water, dried to afford 5-(benzyloxy)-2-(4-fluorophenyl)-6-(N-methylmethylsulfonamido) pyrazolo[1,5-a]pyridine-3-carboxylic acid (2.8 g, yield: 96%). ¹H-NMR (DMSO-d₆, 400 MHz) δ 12.4 (s, 1H), 8.97 (s, 1H), 7.74~7.77 (m, 2H), 7.59 (s, 1H), 7.54 (d, J=7.2 Hz, 2H), 7.29~7.43 (m, 3H), 7.26 (t, J=8.8 Hz, 2H), 5.32 (s, 2H), 3.54 (s, 3H), 3.20 (s, 3H), 3.00 (s, 3H). MS (M+H)⁺: 470.

Step 7—Synthesis of 5-(benzyloxy)-2-(4-fluorophenyl)-N-methyl-6-(N-methylmethylsulfonamido) pyrazolo[1,5-a]pyridine-3-carboxamide

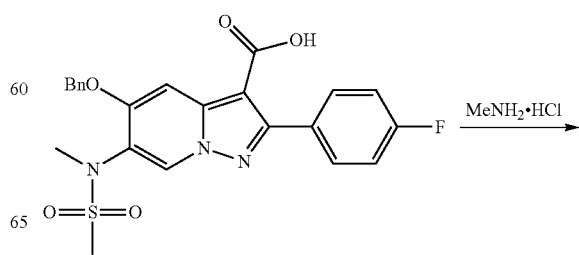

-continued

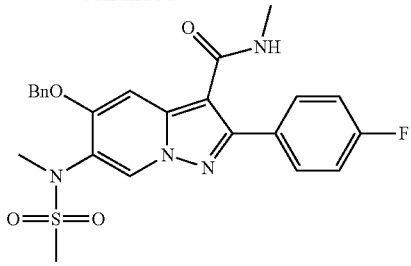

5-(benzyloxy)-2-(4-fluorophenyl)-6-(N-methylmethyl-sulfonamido)pyrazolo[1,5-a]pyridine-3-carboxylic acid (3 g, 6.4 mmol), HOBT (1.3 g, 9.6 mmol) and EDCI (2.5 g, 12.8 mmol) in DMF (50 mL) was allowed to stir at room temperature. After 30 minutes, CH$_3$NH$_2$.HCl (857 mg, 12.8 mmol) and Et$_3$N (1.3 g, 12.8 mmol) were added to the mixture, and the mixture was allowed to stir overnight at room temperature. After the solvent was removed, H$_2$O and NaHCO$_3$ (aq.) were added and the mixture was stirred at room temperature for 1 hour. After filtration, the cake was washed with H$_2$O and dried to give pure 5-(benzyloxy)-2-(4-fluorophenyl)-N-methyl-6-(N-methylmethylsulfonamido)pyrazolo[1,5-a]pyridine-3-carboxamide (3 g, yield: 97%). $^1$H-NMR (CDCl$_3$, 400 MHz) δ 8.43 (s, 1H), 7.86 (s, 1H), 7.56~7.59 (m, 2H), 7.35~7.44 (m, 5H), 7.16 (t, J=8.8 Hz, 2H), 5.41 (br s, 1H), 5.15 (s, 2H), 3.22 (s, 3H), 2.77 (d, J=4.8 Hz, 3H), 2.71 (s, 3H). MS (M+H)$^+$: 483.

Step 8—Synthesis of 2-(4-fluorophenyl)-5-hydroxy-N-methyl-6-(N-methylmethylsulfonamido) pyrazolo[1,5-a]pyridine-3-carboxamide

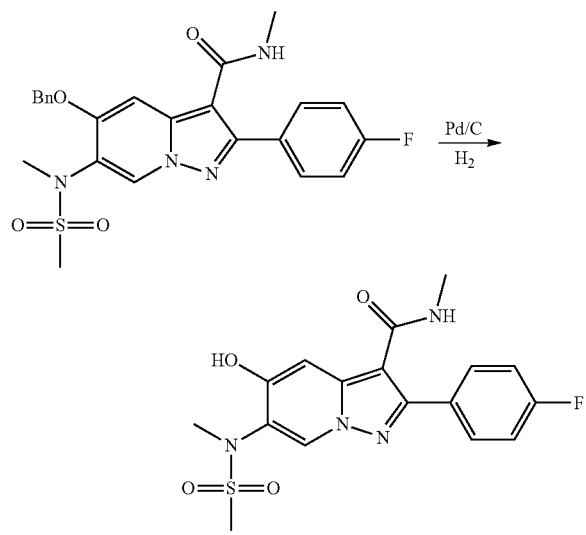

A degassed solution of 5-(benzyloxy)-2-(4-fluorophenyl)-N-methyl-6-(N-methylmethylsulfonamido)pyrazolo[1,5-a]pyridine-3-carboxamide (3.0 g, 6.2 mmol) in THF (50 mL) was charged with 10% palladium on carbon (0.3 g). The reaction mixture was hydrogenated at room temperature under H$_2$ balloon for 4 hours. The reaction mixture was filtered, and washed with DMF twice. The filtrate concentrated in vacuo and dried to afford pure 2-(4-fluorophenyl)-5-hydroxy-N-methyl-6-(N-methylmethylsulfonamido) pyrazolo[1,5-a]pyridine-3-carboxamide (2.3 g, yield: 94%). MS (M+H)$^+$: 393.

Step 9—Synthesis of 2-(4-fluorophenyl)-3-(methylcarbamoyl)-6-(N-methylmethylsulfonamido) pyrazolo[1,5-a]pyridin-5-yl trifluoromethanesulfonate

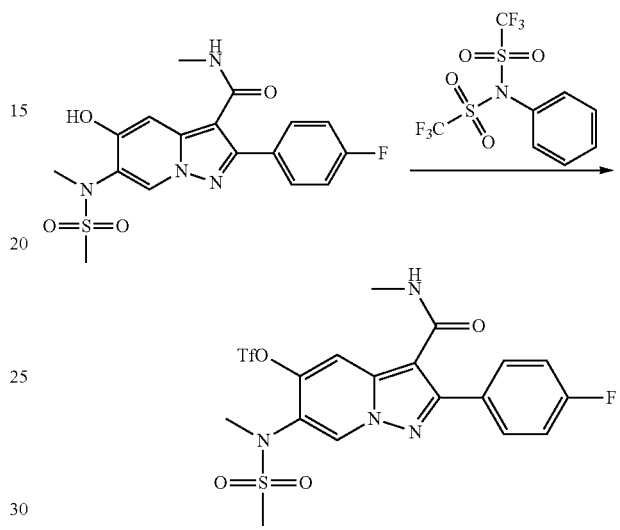

To a solution of 2-(4-fluorophenyl)-5-hydroxy-N-methyl-6-(N-methylmethylsulfonamido)pyrazolo[1,5-a]pyridine-3-carboxamide (2.3 g, 5.8 mmol) and 1,1,1-trifluoro-N-phenyl-N-(trifluoromethylsulfonyl)methanesulfonamide (3.1 g, 8.8 mmol) in DCM (70 mL) was added dropwise Et$_3$N (1.2 g, 11.7 mmol) under N$_2$, and the mixture was stirred overnight at room temperature. After dilution with H$_2$O and extraction with DCM, the organic phase was washed with brine, dried over Na$_2$SO$_4$, and concentrated. The residue obtained was purified using flash column chromatography on silica gel (eluted with PE/EtOAc from 10/1 to 5/1) to give 2-(4-fluorophenyl)-3-(methylcarbamoyl)-6-(N-methylmethylsulfonamido)pyrazolo[1,5-a]pyridin-5-yl trifluoromethanesulfonate (1.5 g, yield: 50%). $^1$H-NMR (CDCl$_3$, 400 MHz) δ 8.65 (s, 1H), 8.35 (s, 1H), 7.61~7.65 (m, 2H), 7.21~7.26 (m, 2H), 5.55 (br s, 1H), 3.34 (s, 3H), 3.14 (s, 3H), 2.83 (d, J=4.8 Hz, 3H). MS (M+H)$^+$: 525.

Step 10—Synthesis of 2-(4-fluorophenyl)-N-methyl-6-(N-methylmethylsulfonamido)-5-(4,4,5,5-tetramethyl-1,3,2-dioxaborolan-2-yl)pyrazolo[1,5-a]pyridine-3-carboxamide

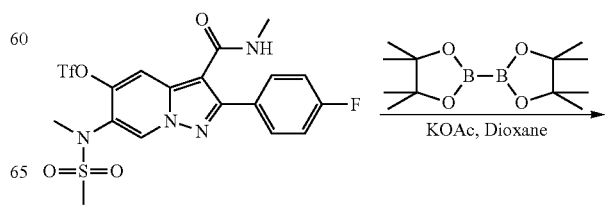

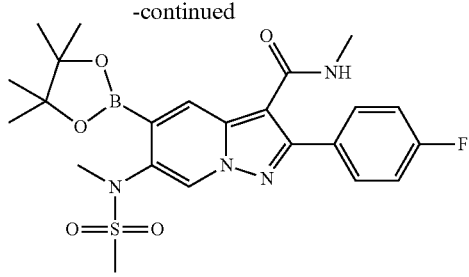

To a N₂ degassed solution of 2-(4-fluorophenyl)-3-(methylcarbamoyl)-6-(N-methylmethylsulfonamido)pyrazolo[1,5-a]pyridin-5-yltrifluoromethanesulfonate (300 mg, 0.6 mmol), KOAc (168 mg, 1.8 mmol) and bis(pinacolato)diboron (726 mg, 3 mmol) in dioxane (10 mL) was added Pd(dppf)Cl₂ under N₂, and the mixture was stirred at room temperature for 1 hour, and then put it into 120° C. oil-batch and stirred for 2 hours. After the solvent was removed, the residue was purified by column chromatography (PE:EA=10:1 to 2:1) to give (PE:EA=5:1, DCM:EA=3:1) to give the product of 2-(4-fluorophenyl)-N-methyl-6-(N-methylmethylsulfonamido)-5-(4,4,5,5-tetramethyl-1,3,2-dioxaborolan-2-yl)pyrazolo[1,5-a]pyridine-3-carboxamide (100 mg, yield: 30%). ¹H-NMR (CDCl₃, 400 MHz) δ 8.70 (s, 1H), 8.48 (s, 1H), 7.60~7.63 (m, 2H), 7.12~7.16 (m, 2H), 5.51 (br s, 1H), 3.72 (s, 3H), 2.93 (s, 3H), 2.81 (d, J=4.8 Hz, 3H), 1.29 (s, 12H). MS (M+H)⁺: 503.

Step 11—Synthesis of 5-(11-fluoro-5,6-dihydroindolo[1,2-h][1,7]naphthyridin-2-yl)-2-(4-fluorophenyl)-N-methyl-6-(N-methylmethylsulfonamido)pyrazolo[1,5-a]pyridine-3-carboxamide by prep-HPLC to give the desired product (50 mg, yield: 44%). ¹H-NMR (CDCl₃, 400 MHz) δ 8.67 (s, 1H), 8.51 (s, 1H), 7.70~7.73 (m, 3H), 7.52 (d, J=8.0 Hz, 1H), 7.27 (s, 1H), 7.23 (s, 1H), 7.14~7.20 (m, 3H), 6.80 (t, J=8.0 Hz, 1H), 5.56 (br s, 1H), 4.36 (t, J=6.4 Hz, 2H), 3.51 (s, 3H), 3.34 (t, J=6.4 Hz, 2H), 2.85 (d, J=4.8 Hz, 3H), 2.63 (s, 3H). MS (M+H)⁺: 613.

Example 47

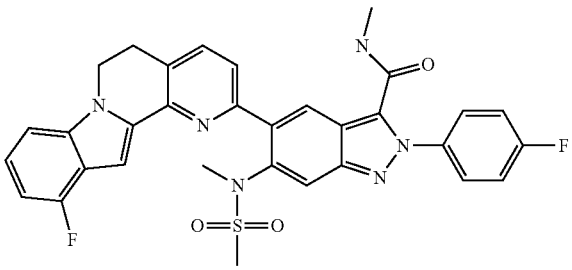 [SMILES: CNC(=O)c1c2cc(-c3ccc4c(n3)-c3cc5c(F)cccc5n3CC4)c(N(C)S(C)(=O)=O)cc2nn1-c1ccc(F)cc1]

Step 1—Synthesis of 5-bromo-2-nitrobenzaldehyde

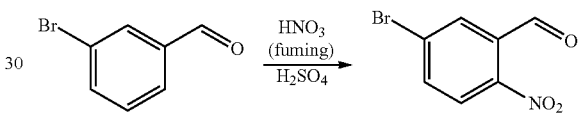

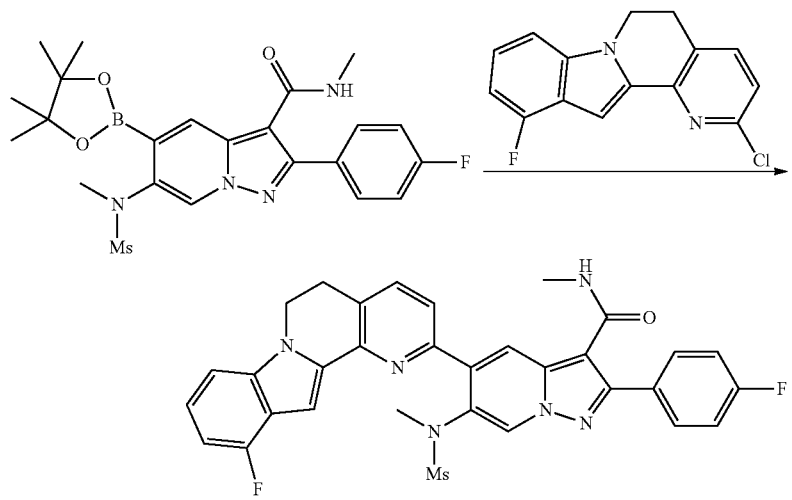

To a solution of 2-(4-fluorophenyl)-N-methyl-6-(N-methylmethylsulfonamido)-5-(4,4,5,5-tetramethyl-1,3,2-dioxaborolan-2-yl)pyrazolo[1,5-a]pyridine-3-carboxamide (110 mg, 0.22 mmol), 2-chloro-11-fluoro-5,6-dihydroindolo[1,2-h][1,7]naphthyridine (50 mg, 0.18 mmol) and K₂CO₃ (50 mg, 0.366 mmol) in 1,4-dioxane (2 mL) were added X-Phos (10 mg) and Pd₂(dba)₃ (10 mg) under N₂. The reaction mixture was stirred at 100° C. for 5 hours and concentrated in vacuo to remove 1,4-dioxane. The reaction mixture was extracted with EtOAc, washed with brine, dried over Na₂SO₄, filtered and evaporated concentrated in vacuo. The residue was purified Fuming nitric acid (200 mL) was added to sulphuric acid (400 mL) at 0° C. and then 3-bromobenzaldehyde (100 g, 0.54 mol) was added dropwise in 15 minutes. After stirring for 10 minutes at the same temperature, the reaction mixture was poured into ice water and filtered to afford the mixture of products which was purified by flash column chromatography eluting with PE/EtOAc (100/1 to 20/1) to give 5-bromo-2-nitrobenzaldehyde as white solid (60 g, 48%). ¹H-NMR (CDCl₃, 400 MHz) δ 10.41 (s, 1H), 8.02~8.06 (m, 2H), 7.88 (s, 1H). MS (M+H)⁺: 230/232.

Step 2—Synthesis of 5-bromo-2,4-dinitrobenzaldehyde

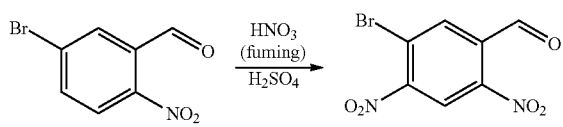

To ice cold sulphuric acid (360 mL) was added fuming nitric acid (180 mL). 5-bromo-2-nitrobenzaldehyde (60 g, 0.26 mol) was added to the solution within 15 min. The reaction mixture was stirred for 10 minutes at the same temperature then at RT for 30 min, at 45° C. for 2 h and finally at 50° C. for 3 h, at which time TLC showed complete reaction. The reaction mixture was poured into ice water and extracted with chloroform to give a mixture of products which was separated by flash column chromatography eluting with PE/EtOAc (20/1 to 3/1). The desired 5-bromo-2,4-dinitrobenzaldehyde was isolated as white solid (6.5 g, 9%). $^1$H-NMR (CDCl$_3$, 400 MHz) δ 10.48 (s, 1H), 8.61 (s, 1H), 8.30 (s, 1H). MS (M+H)$^+$: 275/277.

Step 3—Synthesis of 5-bromo-3-cyano-2-(4-fluorophenyl)-6-nitro-2H-indazole 1-oxide

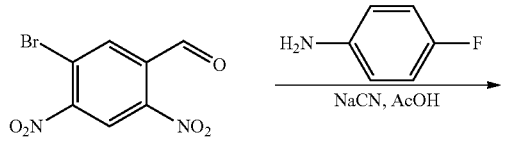

To a stirred suspension of 5-bromo-2,4-dinitrobenzaldehyde (6.5 g, 0.024 mol) in acetic acid (120 mL) was added 4-fluoroaniline (9.28 g, 0.054 mol) and the reaction mixture was heated to 60° C. to get a clear solution. To this was added sodium cyanide portionwise (6.0 g, 0.123 mol) and the reaction mixture was stirred at 60° C. for 5 min. Acetic anhydride (1.9 mL, 0.020 mol) was added and the reaction mixture was stirred for 5 min at the same temperature. Sodium cyanide (6.0 g, 0.123 mol) was then added at the same temperature at which time the product precipitated out. After stirring for 30 min, the mixture was cooled to RT, diluted with water (50 mL), filtered and washed with ethanol to afford crude product, which was purified by flash column chromatography eluting with PE/EtOAc (100/1) to give pure 5-bromo-3-cyano-2-(4-fluorophenyl)-6-nitro-2H-indazole 1-oxide (5.0 g, 56%). $^1$H-NMR (CDCl$_3$, 400 MHz) δ 8.40 (s, 1H), 8.15 (s, 1H), 7.67~7.70 (m, 2H), 7.38~7.42 (m, 2H). MS (M+H)$^+$: 377/379.

Step 4—Synthesis of 5-bromo-2-(4-fluorophenyl)-6-nitro-2H-indazole-3-carbonitrile

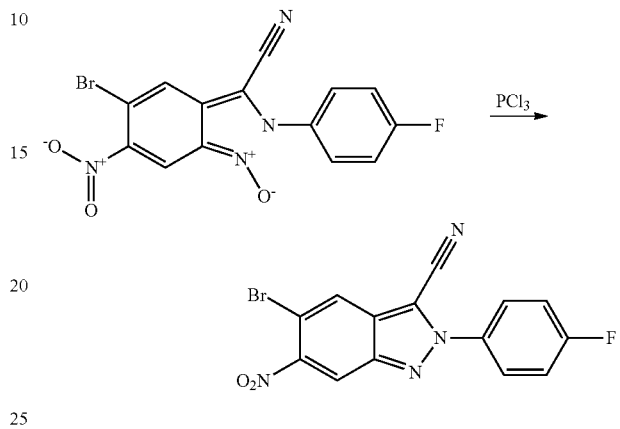

To a stirred solution of 5-bromo-3-cyano-2-(4-fluorophenyl)-6-nitro-2H-indazole 1-oxide (5.0 g, 0.013 mol) in chloroform (50 mL) was added phosphorus trichloride (5.0 mL, 0.057 mol) dropwise and the reaction mixture was heated to 60° C. for 1 h. Then the reaction mixture was poured into ice water and extracted into DCM (2×80 mL). The organic layer was concentrated, and ethanol was added to the residue. After filtration, 5-bromo-2-(4-fluorophenyl)-6-nitro-2H-indazole-3-carbonitrile was collected as solid (4.3 g, 91%). $^1$H-NMR (CDCl$_3$, 400 MHz) δ 8.38 (s, 1H), 8.25 (s, 1H), 7.89~7.91 (m, 2H), 7.33~7.37 (m, 2H). MS (M+H)$^+$: 361/363.

Step 5—Synthesis of 6-amino-5-bromo-2-(4-fluorophenyl)-2H-indazole-3-carbonitrile

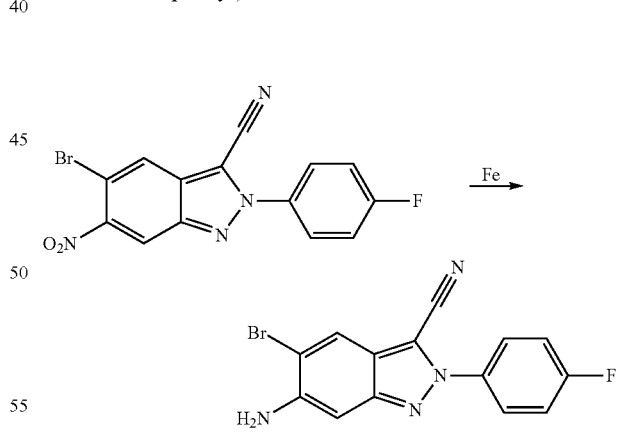

To a suspension of 5-bromo-2-(4-fluorophenyl)-6-nitro-2H-indazole-3-carbonitrile (500 mg, 139 mmol) in a mixture of methanol (50 mL), THF (5 mL) and water (2.5 mL) was added ammonium chloride (370 mg, 6.91 mmol) followed by iron powder (386 mg, 6.91 mmol). The mixture was heated to 80° C. and stirred vigorously for 90 min. The resulting suspension was filtered through celite and washed with EtOAc. The filtrate was concentrated, and the residue was suspended in water and extracted with EtOAc. The organic layer was contracted to give 6-amino-5-bromo-2-(4-fluorophenyl)-2H- indazole-3-carbonitrile (310 mg, 68%) as a yellow solid. $^1$H-NMR (CDCl$_3$, 400 MHz) δ 7.99 (s, 1H), 7.80~7.82 (m, 2H), 7.23~7.57 (m, 2H), 7.03 (s, 1H), 4.40 (s, 2H). MS (M+H)$^+$: 331/333.

Step 6—Synthesis of 6-amino-5-bromo-2-(4-fluorophenyl)-2H-indazole-3-carboxylic acid

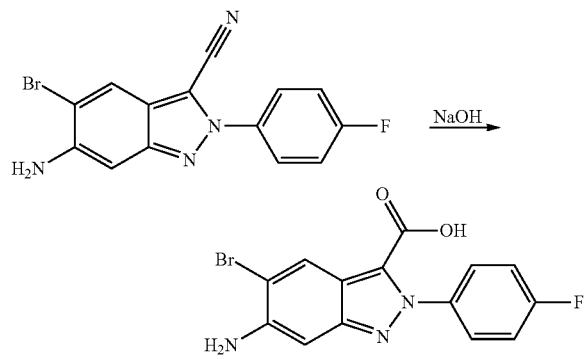

A suspension of 6-amino-5-bromo-2-(4-fluorophenyl)-2H-indazole-3-carbonitrile (50 mg, 0.14 mmol) in 10% NaOH (5 mL) was heated at 100° C. for 48 h. The reaction mixture was cooled to RT and poured into water (10 mL). After pH was adjusted to 4 with 1 N HCl, the mixture was extracted with EtOAc. The combined organic phases were washed with brine, dried over Na$_2$SO$_4$, filtered and evaporated to get 6-amino-5-bromo-2-(4-fluorophenyl)-2H-indazole-3-carboxylic acid (45 mg, yield: 85%). $^1$H-NMR (DMSO-d$_6$, 400 MHz) δ 8.20 (s, 1H), 7.77~7.82 (m, 2H), 7.45~7.52 (m, 2H), 7.03 (s, 1H), 6.61 (s, 1H), 5.60 (s, 2H). MS (M+H)$^+$: 350/352.

Step 7—Synthesis of 6-amino-5-bromo-2-(4-fluorophenyl)-N-methyl-2H-indazole-3-carboxamide

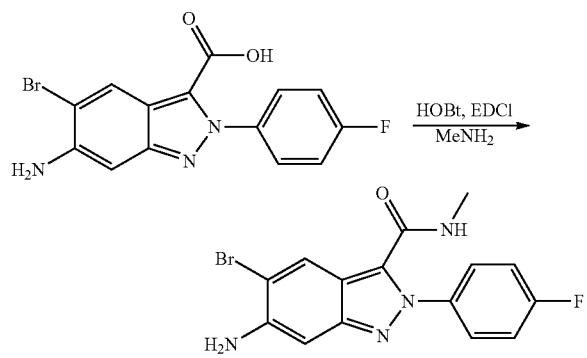

To a solution of 6-amino-5-bromo-2-(4-fluorophenyl)-2H-indazole-3-carboxylic acid (1.0 g, 2.8 mmol) in dry DMF (500 mL) were added EDCI (1.1 g, 6.2 mmol) and HOBT (0.5 g, 4.3 mmol). The reaction mixture was stirred at room temperature for 1 h, and then Et$_3$N (5 mL) and MeNH$_2$.HCl (0.9 g, 14.3 mmol) were added to the reaction mixture. After stirring for another 2 hours, the reaction mixture was concentrated in vacuum and 300 mL Na$_2$CO$_3$ (a.q.) was added to the mixture. The resulting solid was filtered to give the crude product, which was purified by column chromatography (PE: EA=3:1) to give 6-amino-5-bromo-2-(4-fluorophenyl)-N-methyl-2H-indazole-3-carboxamide (0.8 g, yield: 74%). $^1$H-NMR (CDCl$_3$, 400 MHz) δ 8.10 (s, 1H), 7.55~7.58 (m, 2H), 7.20~7.26 (m, 2H), 6.98 (s, 1H), 5.75 (s, 1H), 4.32 (s, 2H), 2.98 (d, J=4.8 Hz, 3H). MS (M+H)$^+$: 363/365.

Step 8—Synthesis of 5-bromo-2-(4-fluorophenyl)-N-methyl-6-(methylsulfonamido)-2H-indazole-3-carboxamide

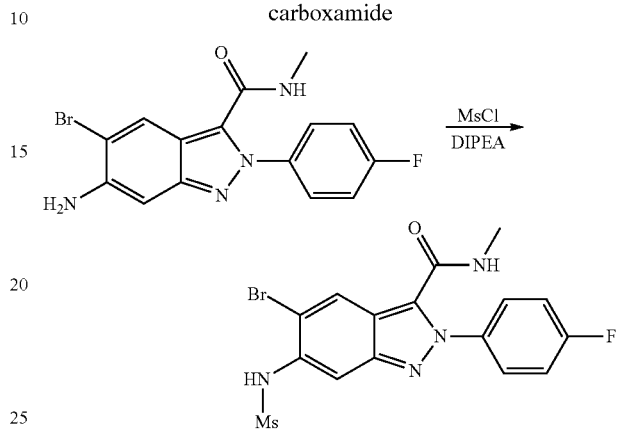

To a degassed solution of 6-amino-5-bromo-2-(4-fluorophenyl)-N-methyl-2H-indazole-3-carboxamide (0.75 g, 2.1 mmol) in DCM/Pyridine (10 mL/3 mL) was added MsCl (1.2 g, 10.5 mmol) under N$_2$ at 0° C. for 30 min. The reaction was stirred at 25° C. for 8 hours. The reaction mixture was diluted with water, extracted with EtOAc and washed with brine, and then dried over Na$_2$SO$_4$. After concentration, the residue was purified by column chromatography (PE:EA=2:1) to give crude 5-bromo-2-(4-fluorophenyl)-N-methyl-6-(methylsulfonamido)-2H-indazole-3-carboxamide (0.65 g, yield: 78%). $^1$H-NMR (CDCl$_3$, 400 MHz) δ 8.30 (s, 1H), 8.03 (s, 1H), 7.56~7.60 (m, 2H), 7.20~7.25 (m, 2H), 6.97 (s, 1H), 5.73 (s, 1H), 3.08 (s, 3H), 2.99 (d, J=4.8 Hz, 3H). MS (M+H)$^+$: 441/443.

Step 9—Synthesis of 5-bromo-2-(4-fluorophenyl)-N-methyl-6-(N-methylmethylsulfonamido)-2H-indazole-3-carboxamide

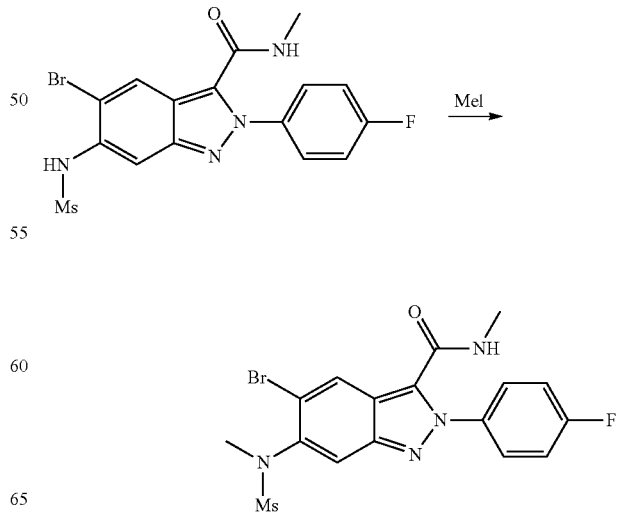

To a suspension of 5-bromo-2-(4-fluorophenyl)-N-methyl-6-(methylsulfonamido)-2H-indazole-3-carboxamide (0.5 g, 1.1 mmol) and K$_2$CO$_3$ (0.5 g, 3.4 mmol) in DMF (10 mL) was added dropwise CH$_3$I (0.8 g, 5.6 mmol) at 0° C. under N$_2$, and then the mixture was stirred at 80° C. for 2 hours. After concentration under vacuum, the residue was suspended in H$_2$O and extracted with DCM. The combined organic layer was washed with H$_2$O, brine, dried over Na$_2$SO$_4$, filtrated and concentrated to give 5-bromo-2-(4-fluorophenyl)-N-methyl-6-(N-methylmethylsulfonamido)-2H-indazole-3-carboxamide (0.48 g, yield: 93%). $^1$H-NMR (CDCl$_3$, 400 MHz) δ 8.21 (s, 1H), 8.01 (s, 1H), 7.56~7.60 (m, 2H), 7.21~7.27 (m, 2H), 6.97 (s, 1H), 3.228 (s, 3H), 3.07 (d, J=4.8 Hz, 3H), 2.77 (s, 3H). MS (M+H)$^+$: 455/457.

Step 10—Synthesis of 2-(4-fluorophenyl)-N-methyl-6-(N-methylmethylsulfonamido)-5-(4,4,5,5-tetramethyl-1,3,2-dioxaborolan-2-yl)-2H-indazole-3-carboxamide

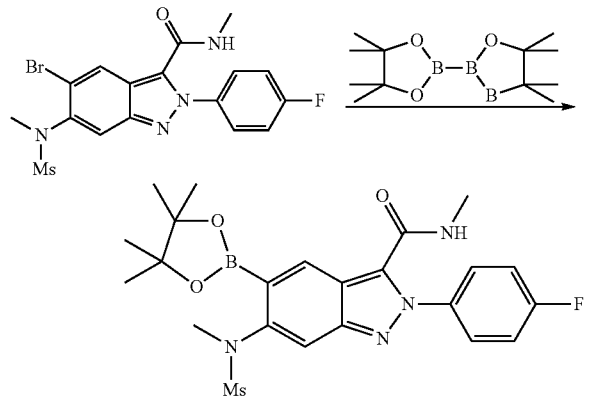

To a degassed solution of 5-bromo-2-(4-fluorophenyl)-N-methyl-6-(N-methylmethylsulfonamido)-2H-indazole-3-carboxamide (0.25 g, 0.55 mmol), KOAc (0.16 g, 1.65 mmol) and bis(pinacolato)diboron (0.71 g, 2.75 mmol) in 1,4-dioxane (5 mL), Pd(dppf)Cl$_2$ (0.05 mg) was added. The reaction mixture was stirred at 100° C. for 6 hours, and then filtered through a celite pad. The filtrate was concentrated in vacuo, and the residue was purified by column chromatography (PE: EA=1:1) to give 2-(4-fluorophenyl)-N-methyl-6-(N-methylmethylsulfonamido)-5-(4,4,5,5-tetramethyl-1,3,2-dioxaborolan-2-yl)-2H-indazole-3-carboxamide (0.15 mg, yield: 50%). $^1$H-NMR (CDCl$_3$, 400 MHz) δ 8.14 (s, 1H), 7.53~7.56 (m, 3H), 7.13~7.17 (m, 2H), 6.37 (s, 1H), 3.26 (s, 3H), 3.16 (d, J=4.8 Hz, 3H), 2.93 (s, 3H), 1.32 (s, 12H). MS (M+H)$^+$: 503.

Step 11—Synthesis of 5-(11-fluoro-5,6-dihydroindolo[1,2-h][1,7]naphthyridin-2-yl)-2-(4-fluorophenyl)-N-methyl-6-(N-methylmethylsulfonamido)-2H-indazole-3-carboxamide

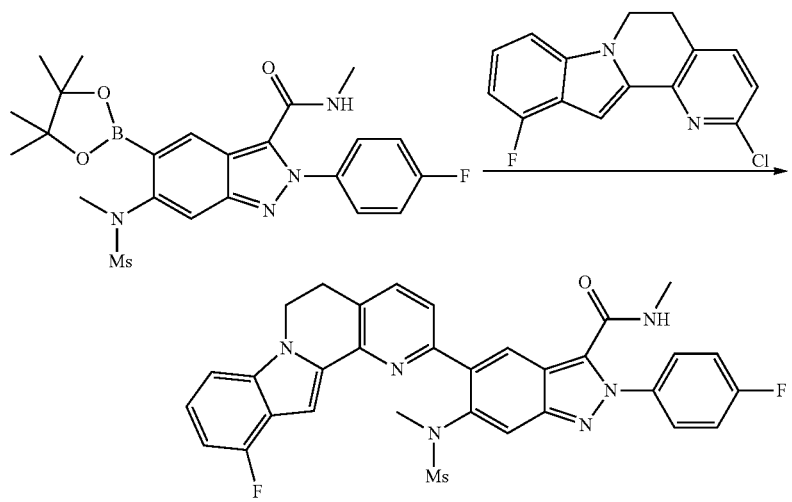

To a degassed solution of 2-(4-fluorophenyl)-N-methyl-6-(N-methylmethylsulfonamido)-5-(4,4,5,5-tetramethyl-1,3,2-dioxaborolan-2-yl)-2H-indazole-3-carboxamide (70 mg, 0.14 mmol), 2-chloro-11-fluoro-5,6-dihydroindolo[1,2-h][1,7]naphthyridine (46 mg, 0.17 mmol) and K$_3$PO$_4$.3H$_2$O (112 mg, 0.42 mmol) in 1,4-dioxane (5 mL) was added Pd$_2$(dba)$_3$ (13 mg, 0.014 mmol) and X-Phos (14 mg, 0.028 mmol) under N$_2$. The reaction mixture was heated to 100° C. and stirred for 3 hours, and then filtered through a celite pad. The filtrate was concentrated in vacuo, and the residue was purified by prep-HPLC to give the desired product (20 mg, yield: 24%). $^1$H-NMR (CDCl$_3$, 400 MHz) δ 8.03 (s, 1H), 7.83 (s, 1H), 7.55~7.60 (m, 1H), 7.52~7.54 (m, 2H), 7.45 (s, 1H), 7.09~7.19 (m, 5H), 6.73 (s, 1H), 6.30 (s, 1H), 6.20 (s, 1H), 4.28 (t, J=6.0 Hz, 2H), 3.32 (s, 3H), 3.25 (t, J=6.0 Hz, 2H), 2.92 (d, J=4.8 Hz, 3H), 2.76 (s, 3H). MS (M+H)$^+$: 613.

Example 48

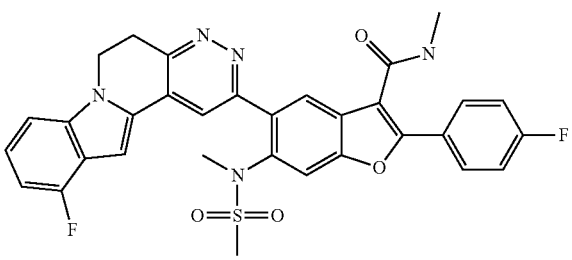 [SMILES: CNC(=O)c1c(-c2ccc(F)cc2)oc2cc(N(C)S(C)(=O)=O)c(-c3cc4c(nn3)CCn3c-4cc4c(F)cccc43)cc12]

Step 1—Synthesis of 4-bromo-1,2-dihydropyridazine-3,6-dione

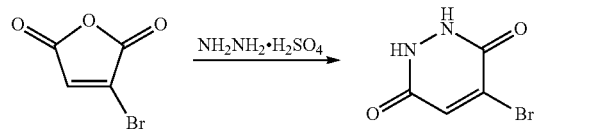

To a solution of NH$_2$NH$_2$.H$_2$SO$_4$ (362 mg, 2.8 mmol) in H$_2$O (5 mL) was added dropwise 3-bromofuran-2,5-dione (500 mg, 2.8 mmol), and the mixture was stirred at 90° C. for 4 hours. After the reaction, the mixture was filtered to get 4-bromo-1,2-dihydropyridazine-3,6-dione (300 mg, yield: 56%). $^1$H-NMR (DMSO-d$_6$, 400 MHz) δ 12.47 (s, 1H), 11.17 (s, $^1$H), 7.62 (s, 1H). MS (M+H)$^+$:191/193.

Step 2—Synthesis of 4-(4-fluoro-1H-indol-2-yl)-1,2-dihydropyridazine-3,6-dione

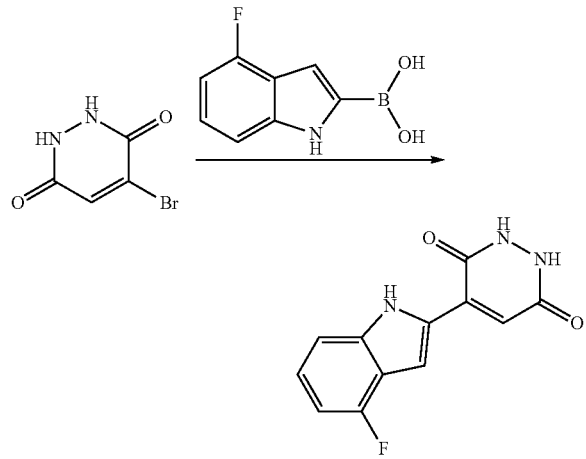

To a degassed solution of 4-bromo-1,2-dihydropyridazine-3,6-dione (100 mg, 0.5 mmol), (4-fluoro-1H-indol-2-yl)boronic acid (131 mg, 0.7 mmol) and K$_3$PO$_4$ (279 mg, 1.1 mmol) in DMF (2 mL) and H$_2$O (0.2 mL) was added Pd(dppf)Cl$_2$ (5 mg) under N$_2$. The mixture was stirred at 80° C. for 12 h. After the solvent was removed, the residue was purified by prep-TLC (DCM:EtOAc=10:1) to give the product of 4-(4-fluoro-1H-indol-2-yl)-1,2-dihydropyridazine-3,6-dione (50 mg, yield: 39%). $^1$H-NMR (DMSO-d$_6$, 400 MHz) δ 11.95 (br. s, 1H), 7.47~7.68 (m, 3H), 7.35 (d, J=8.0 Hz, 1H), 7.11~7.19 (m, 1H), 6.81 (dd, J=8.0, 10.4 Hz, 1H). MS (M+H)$^+$: 246.

Step 3—Synthesis of 2-(3,6-dichloropyridazin-4-yl)-4-fluoro-1H-indole

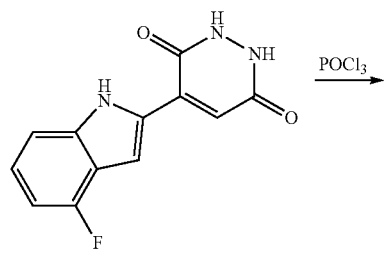

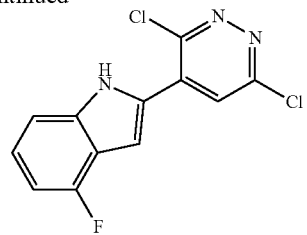

A solution of 4-(4-fluoro-1H-indol-2-yl)-1,2-dihydropyridazine-3,6-dione (60 mg, 0.24 mmol) in POCl$_3$ (5 mL) was stirred at 100° C. for 3 hours. After the reaction, it was concentrated and the residue was purified by column chromatography (PE:EA=5:1) to get the product of 2-(3,6-dichloropyridazin-4-yl)-4-fluoro-1H-indole (30 mg, yield: 43%). $^1$H-NMR (CDCl$_3$, 400 MHz) δ 7.85 (s, 1H), 7.50 (s, 1H), 7.12~7.21 (m, 2H), 6.70~6.77 (m, 1H). MS (M+H)$^+$: 282/284.

Step 4—Synthesis of 2-(6-chloro-3-vinylpyridazin-4-yl)-4-fluoro-1H-indole

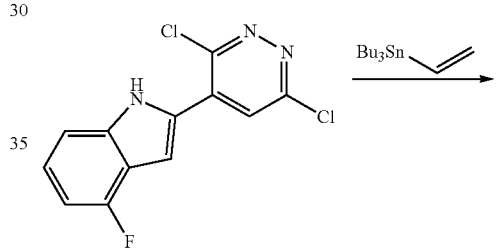

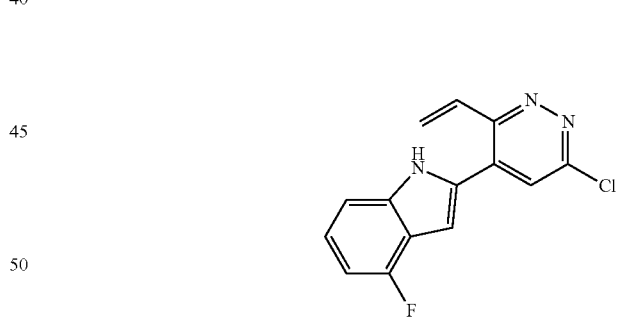

To a degassed solution of 2-(3,6-dichloropyridazin-4-yl)-4-fluoro-1H-indole (500 mg, 1.7 mmol), tributyl(vinyl)stannane (560 mg, 1.7 mmol) and LiCl (375 mg, 8.9 mmol) in DMF (5 mL) was added Pd(PPh$_3$)$_2$Cl$_2$ (30 mg) under N$_2$, and the mixture was stirred at 80° C. for 12 h. After the solvent was removed, the residue was purified by prep-TLC (PE:EtOAc=2:1) to give the product of 2-(6-chloro-3-vinylpyridazin-4-yl)-4-fluoro-1H-indole (140 mg, yield: 29%). $^1$H-NMR (CDCl$_3$, 400 MHz) δ 8.71 (s, 1H), 7.61 (s, 1H), 7.16

(dd, J=10.8, 16.8 Hz, 2H), 7.03 (s, 1H), 6.87 (d, J=6.8 Hz, 2H), 6.68 (s, 1H), 5.79 (s, 1H). MS (M+H)$^+$: 274/276.

Step 5—Synthesis of 2-(6-chloro-3-(2-chloroethyl) pyridazin-4-yl)-4-fluoro-1H-indole

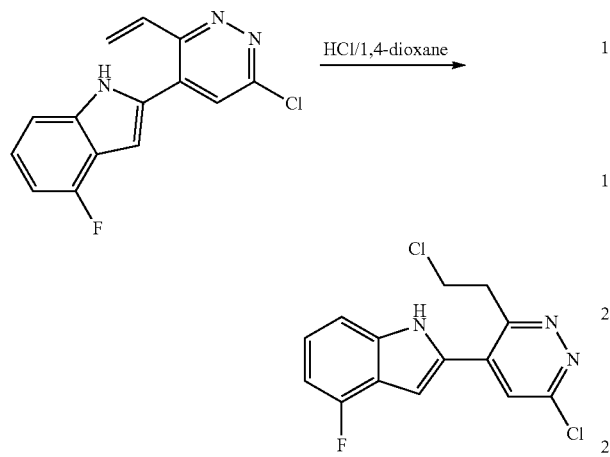

A solution of 2-(6-chloro-3-vinylpyridazin-4-yl)-4-fluoro-1H-indole (80 mg, 0.29 mmol) in HCl-dioxane (5 mL) was stirred at 50° C. After 15 minutes, NaHCO$_3$ (a.q) was added. The mixture was extracted with DCM. The organic phase was dried over Na$_2$SO$_4$. After being concentrated in vacuo, the residue was purified by prep-TLC (DCM) to give the product of 2-(6-chloro-3-(2-chloroethyl)pyridazin-4-yl)-4-fluoro-1H-indole (60 mg, yield: 66%). $^1$H-NMR (CDCl$_3$, 400 MHz) δ 9.04 (s, 1H), 7.63 (s, 1H), 7.28~7.31 (m, 1H), 7.22~7.26 (m, 1H), 6.99 (d, J=1.6 Hz, 1H), 6.84~6.93 (m, 1H), 4.24 (t, J=6.4 Hz, 2H), 3.66 (t, J=6.5 Hz, 2H). MS (M+H)$^+$: 310/312.

Step 6—Synthesis of 2-chloro-11-fluoro-5,6-dihydropyridazino[4',3':3,4]pyrido[1,2-a]indole

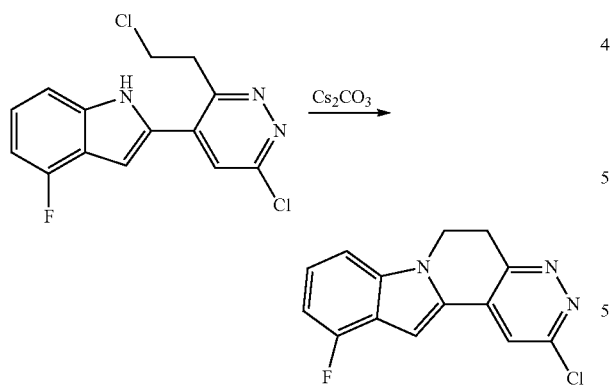

To a suspension of 2-(6-chloro-3-(2-chloroethyl)pyridazin-4-yl)-4-fluoro-1H-indole (60 mg, 0.17 mmol) in DMF (1 mL) was added Cs$_2$CO$_3$ (124 mg, 0.34 mmol), and then the mixture was stirred for 20 minutes at 60° C. After being concentrated in vacuo, the resulting residue was suspended in H$_2$O and extracted with DCM. The combined organic layer was washed with H$_2$O and dried over Na$_2$SO$_4$. After concentration, the residue was purified by prep-TLC (DCM) to give the product of 2-chloro-11-fluoro-5,6-dihydropyridazino[4',3':3,4]pyrido[1,2-a]indole (40 mg, yield: 75%). $^1$H-NMR (CDCl$_3$, 400 MHz) δ 8.40 (s, 1H), 7.63 (s, 1H), 7.47 (d, J=8.22 Hz, 1H), 7.24~7.33 (m, 1H), 6.87~6.97 (m, 1H), 4.52 (t, J=6.4 Hz, 2H), 3.53 (t, J=6.4 Hz, 2H). MS (M+H)$^+$: 274/276.

Step 7—Synthesis of 5-(11-fluoro-5,6-dihydropyridazino[4',3': 3,4]pyrido[1,2-a]indol-2-yl)-2-(4-fluorophenyl)-N-methyl-6-(N-methylmethylsulfonamido)benzofuran-3-carboxamide

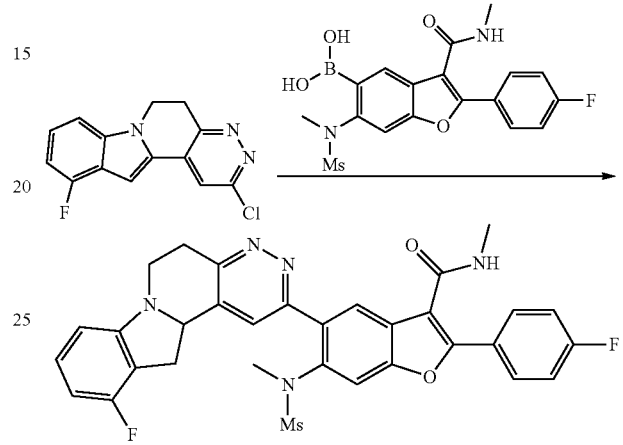

To a degassed solution of 2-chloro-11-fluoro-5,6-dihydropyridazino[4',3':3,4]pyrido[1,2-a]indole (100 mg, 0.37 mmol), (2-(4-fluorophenyl)-3-(methylcarbamoyl)-6-(N-methylmethylsulfonamido)benzofuran-5-yl)boronic acid (169 mg, 0.4 mmol) and K$_3$PO$_4$ (155 mg, 0.73 mmol) in DMF (3 mL) was added Pd(dtbpf)Cl$_2$ (5 mg) under N$_2$. Then the mixture was stirred at 100° C. for 3 hours. The reaction mixture was cooled to RT and filtered. The filtrate was washed with H$_2$O and dried over Na$_2$SO$_4$. After being concentrated, the residue was purified by prep-HPLC to give the product of 5-(11-fluoro-5,6-dihydropyridazino[4',3':3,4]pyrido[1,2-a]indol-2-yl)-2-(4-fluorophenyl)-N-methyl-6-(N-methylmethylsulfonamido)benzofuran-3-carboxamide (30 mg, yield: 13%). $^1$H-NMR (CDCl$_3$, 400 MHz) δ 8.11 (d, J=9.0 Hz, 2H), 8.00 (dd, J=5.6, 8.8 Hz, 2H), 7.66 (s, 1H), 7.25 (s, 1H), 7.15~7.23 (m, 4H), 6.81 (dd, J=7.6, 9.6 Hz, 1H), 6.17 (d, J=4.0 Hz, 1H), 4.47 (t, J=6.4 Hz, 2H), 3.67 (t, J=6.4 Hz, 2H), 3.21 (s, 3H), 3.00 (d, J=4.8 Hz, 3H), 2.97 (s, 3H). MS (M+H)$^+$: 614.

Examples 49-51

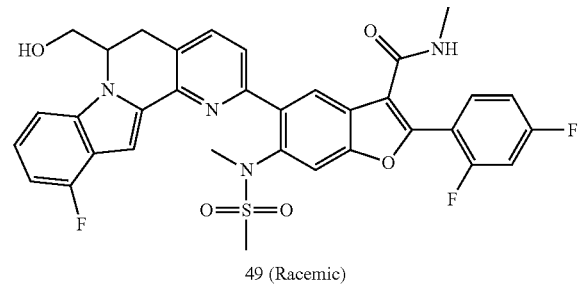

49 (Racemic)

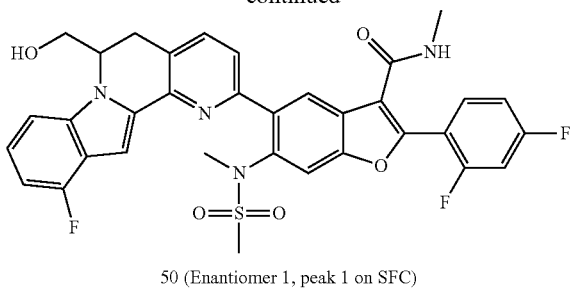

50 (Enantiomer 1, peak 1 on SFC)

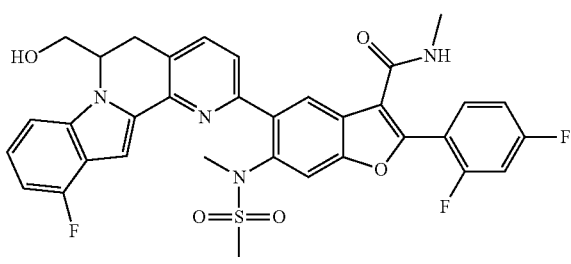

51 (Enantiomer 2, peak 2 on SFC)

Step 1—Synthesis of 2-(3-allyl-6-chloropyridin-2-yl)-4-fluoro-1H-indole

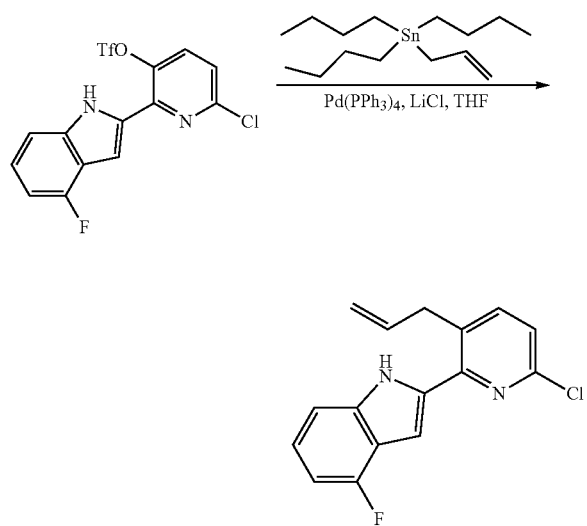

To a mixture of 6-chloro-2-(4-fluoro-1H-indol-2-yl)pyridin-3-yl trifluoromethanesulfonate (2 g, 5.1 mmol), allyltributylstannane (2 g, 6.1 mmol) and anhydrous LiCl (256 mg, 6.1 mmol) in THF (30 mL), Pd(PPh$_3$)$_4$ (588 mg, 0.51 mmol) was added under N$_2$ protection. The reaction mixture was stirred at 60° C. overnight. After it was concentrated in vacuo, the residue was purified by column chromatography (PE:EA=400:1~100:1) to give the product of 2-(3-allyl-6-chloropyridin-2-yl)-4-fluoro-1H-indole (1 g, yield: 68%). $^1$H-NMR (CDCl$_3$, 400 MHz) δ 9.72 (s, 1H), 7.57 (d, J=8.0 Hz, 1H), 7.12~7.24 (m, 3H), 7.02 (s, 1H), 6.77 (t, J=8.0 Hz, 1H), 6.04~6.12 (m, 1H), 5.25 (d, J=10.0 Hz, 1H), 5.13 (d, J=17.2 Hz, 1H), 3.74 (d, J=6.0 Hz, 2H). MS (M+H)$^+$: 287/289.

Step 2—Synthesis of 3-(6-chloro-2-(4-fluoro-1H-indol-2-yl)pyridin-3-yl)propane-1,2-diol

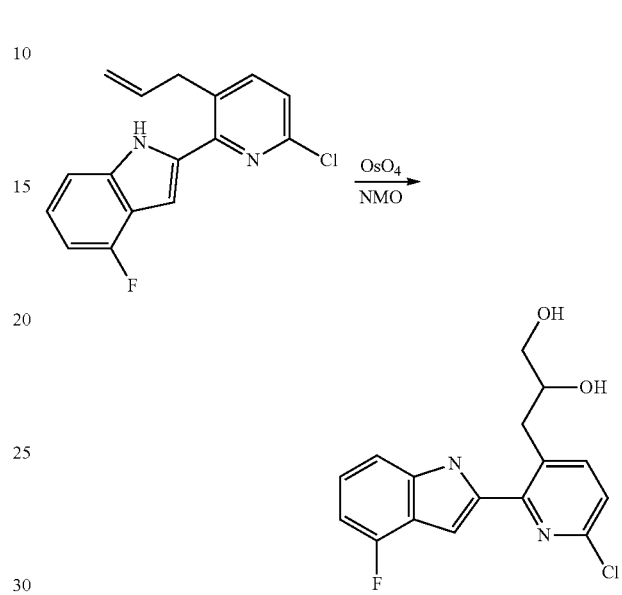

A mixture of 2-(3-allyl-6-chloropyridin-2-yl)-4-fluoro-1H-indole (100 mg, 0.35 mmol) and NMO (124 mg, 1.05 mmol) in THF (5 mL) and H$_2$O (2.5 mL) was stirred at 0° C. Then OsO$_4$ (20 mg) was added, and the mixture was stirred at RT overnight. After cooling to 0° C., a.q. Na$_2$S$_2$O$_3$ was added and extracted with CH$_2$Cl$_2$. Then the organic layer was washed with water, brine, dried over Na$_2$SO$_4$ and concentrated on a rotary evaporator. The residue was purified by column chromatography (PE:EA=2:1~1:1) to give the product of 3-(6-chloro-2-(4-fluoro-1H-indol-2-yl)pyridin-3-yl)propane-1,2-diol (100 mg, yield: 89%). $^1$H-NMR (CDCl$_3$, 400 MHz) δ 9.88 (s, 1H), 7.65 (d, J=8.4 Hz, 1H), 7.12~7.18 (m, 3H), 7.02 (s, 1H), 6.76 (t, J=8.0 Hz, 1H), 4.12~4.16 (m, 1H), 3.81~3.85 (m, 1H), 3.64~3.67 (m, 1H), 3.07~3.15 (m, 2H). MS (M+H)$^+$: 321/323.

Step 3—Synthesis of 3-(6-chloro-2-(4-fluoro-1H-indol-2-yl)pyridin-3-yl)-2-hydroxypropyl methanesulfonate

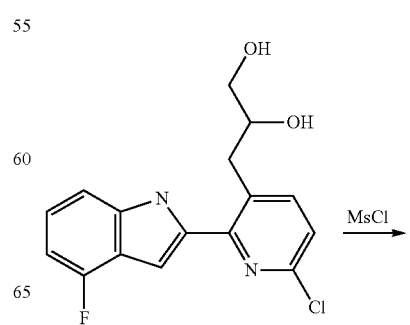

-continued

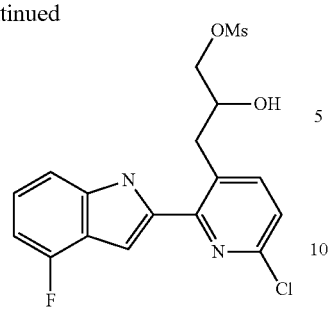

A mixture of 3-(6-chloro-2-(4-fluoro-1H-indol-2-yl)pyridin-3-yl)propane-1,2-diol (100 mg, 0.31 mmol) and TEA (94 mg, 0.93 mmol) in THF (6 mL) was stirred under $N_2$ at 0° C., MsCl (36 mg, 0.31 mmol) was added dropwise. The reaction was stirred at 0° C. for 1 h and RT overnight. Water was added and after extraction with EA, the organic layer was washed with water, brine, dried over $Na_2SO_4$ and concentrated on a rotary evaporator. The residue was purified by column chromatography (PE:EA=2:1~1:1) to give the product of 3-(6-chloro-2-(4-fluoro-1H-indol-2-yl)pyridin-3-yl)-2-hydroxypropyl methanesulfonate (60 mg, yield: 48%). $^1$H-NMR (MeOD, 400 MHz) δ 7.80 (d, J=7.6 Hz, 1H), 7.26~7.32 (m, 2H), 7.09~7.11 (m, 1H), 7.04 (s, 1H), 6.70 (t, J=7.6 Hz, 1H), 4.20~4.29 (m, 3H), 3.09~3.13 (m, 5H). MS (M+H)$^+$: 399/401.

Step 4—Synthesis of (2-chloro-11-fluoro-5,6-dihydroindolo[1,2-h][1,7]naphthyridin-6-yl) methanol -continued

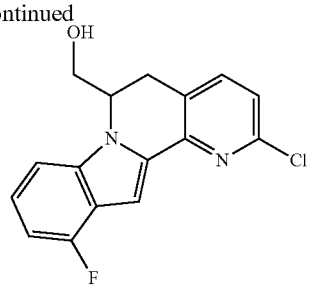

A solution of 3-(6-chloro-2-(4-fluoro-1H-indol-2-yl)pyridin-3-yl)-2-hydroxypropyl methanesulfonate (100 mg, 0.25 mmol) in DMF (5 mL) was stirred under $N_2$ at 0° C. After NaH (30 mg, 60% in mineral oil, 0.75 mmol) was added, the mixture was stirred at 0° C. for 0.5 h and RT for 2 h. After cooling to 0° C., water was added and the mixture extracted with EtOAc. Then the organic layer was washed with water, brine, dried over $Na_2SO_4$ and concentrated on a rotary evaporator. The residue was purified by column chromatography (PE:EA=2:1~1:1) to give the product of (2-chloro-11-fluoro-5,6-dihydroindolo[1,2-h][1,7]naphthyridin-6-yl)methanol (70 mg, yield: 92%). $^1$H-NMR (CDCl$_3$, 400 MHz) δ 7.50 (d, J=7.6 Hz, 1H), 7.37 (s, 1H), 7.13~7.19 (m, 3H), 6.78 (t, J=7.6 Hz, 1H), 4.79~4.84 (m, 1H), 3.69~3.73 (m, 1H), 3.60~3.62 (m, 1H), 3.38~3.42 (m, 1H), 3.24 (d, J=16.4 Hz, 1H). MS (M+H)$^+$: 303/305.

Step 5—Synthesis of 2-(2,4-difluorophenyl)-5-(11-fluoro-6-(hydroxymethyl)-5,6-dihydroindolo[1,2-h][1,7]naphthyridin-2-yl)-N-methyl-6-(N-methylmethylsulfonamido)benzofuran-3-carboxamide, (R or S)-2-(2,4-difluorophenyl)-5-(1.1-fluoro-6-(hydroxymethyl)-5,6-dihydroindolo[1,2-h][1,7]naphthyridin-2-yl)-N-methyl-6-(N-methylmethylsulfonamido)benzofuran-3-carboxamide and (S or R)-2-(2,4-difluorophenyl)-5-(11-fluoro-6-(hydroxymethyl)-5,6-dihydroindolo[1,2-h][1,7]naphthyridin-2-yl)-N-methyl-6-(N-methylmethylsulfonamido)benzofuran-3-carboxamide (Compound 48, Compound 49 and Compound 50)

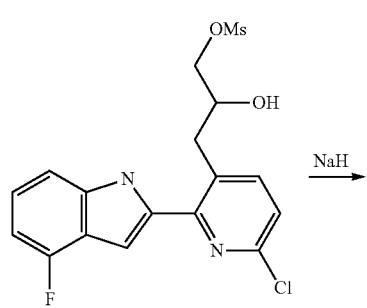

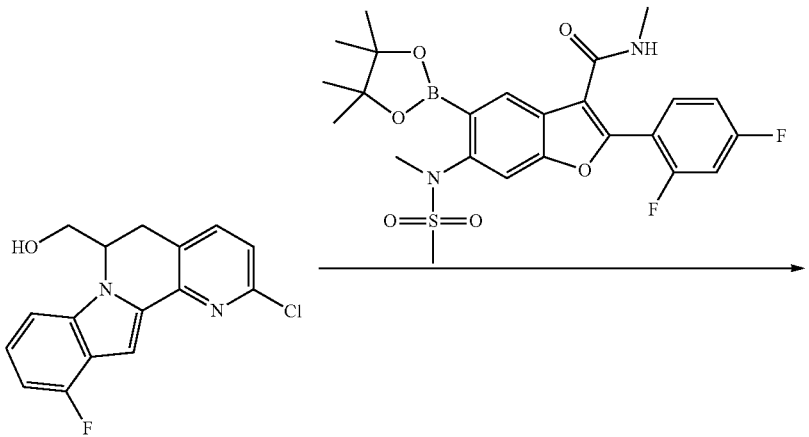

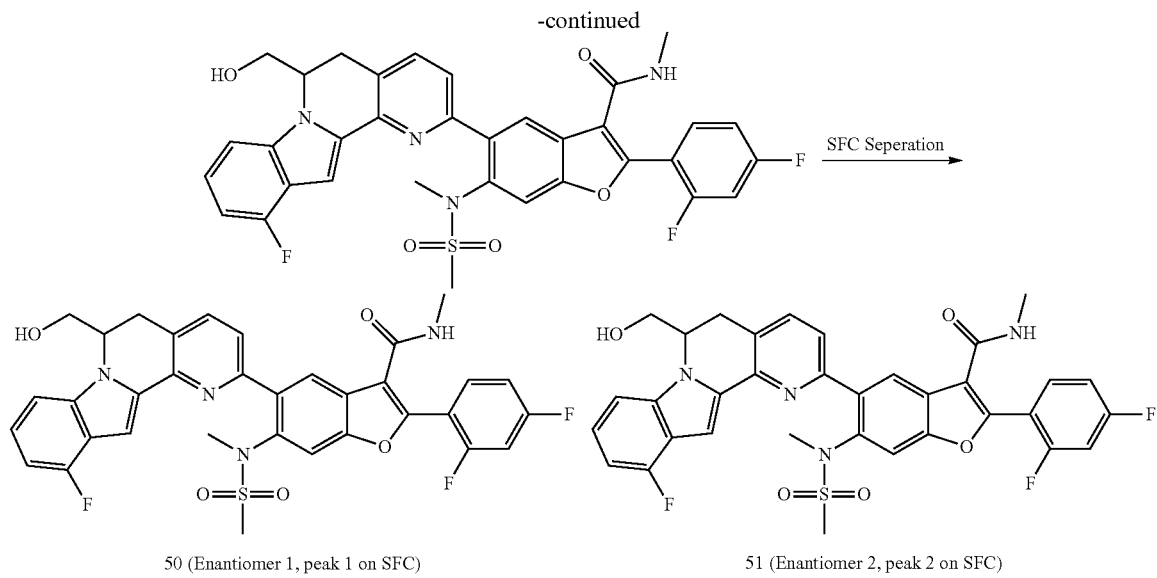

50 (Enantiomer 1, peak 1 on SFC)  51 (Enantiomer 2, peak 2 on SFC)

To a solution of (2-chloro-11-fluoro-5,6-dihydroindolo[1,2-h][1,7]naphthyridin-6-yl)methanol (200 mg, 0.66 mmol), 2-(2,4-difluorophenyl)-N-methyl-6-(N-methylmethyl sulfonamido)-5-(4,4,5,5-tetramethyl-1,3,2-dioxaborolan-2-yl)benzofuran-3-carboxamide (346 mg, 0.66 mmol), $K_3PO_4$ (420 mg, 1.98 mmol), $Pd_2(dba)_3$ (63 mg) and X-Phos (63 mg) in dioxane/$H_2O$ (9 mL/2 mL) was stirred at 100° C. for 3 h. After the reaction, the mixture was filtered to remove the solid and then the mixture was diluted with water and extracted with EA. The organic layer was washed with brine, dried over aq. $Na_2SO_4$ and concentrated. The residue was purified by column chromatography (PE:EA=1:1) to give 2-(2,4-difluorophenyl)-5-(11-fluoro-6-(hydroxymethyl)-5,6-dihydroindolo[1,2-h][1,7]naphthyridin-2-yl)-N-methyl-6-(N-methylmethylsulfonamido)benzofuran-3-carboxamide (Compound 49, 350 mg, yield: 87%). $^1$H-NMR (CDCl3, 400 MHz) δ 8.09 (s, 1H), 7.63~7.73 (m, 3H), 7.43 (d, J=8.0 Hz, 1H), 7.1~57.25 (m, 3H), 6.90~7.03 (m, 2H), 6.78 (d, J=8.0 Hz, 1H), 5.79~5.81 (m, 1H), 4.85~4.87 (m, 1H), 3.51~3.76 (m, 3H), 3.38 (s, 3H), 3.28~3.32 (m, 1H), 2.92 (d, J=5.2 Hz, 3H), 2.64 (s, 3H). MS (M+H)$^+$: 661.

2-(2,4-difluorophenyl)-5-(11-fluoro-6-(hydroxymethyl)-5,6-dihydroindolo[1,2-h][1,7]naphthyridin-2-yl)-N-methyl-6-(N-methylmethylsulfonamido)benzofuran-3-carboxamide was separated by SFC to afford two single enantiomers.

Compound 50 (enantiomer 1, peak 1 on SFC, AD-H__3UM_4_5_40_4ML_3 MIN, HPLC_RT=2.193 min HPLC_RT=2.193 min) (120 mg). $^1$H-NMR (CDCl$_3$, 400 MHz) δ 8.09 (s, 1H), 7.63~7.73 (m, 3H), 7.43 (d, J=8.0 Hz, 1H), 7.15~7.25 (m, 3H), 6.90~7.03 (m, 2H), 6.78 (d, J=8.0 Hz, 1H), 5.79~5.81 (m, 1H), 4.85~4.87 (m, 1H), 3.51~3.76 (m, 3H), 3.38 (s, 3H), 3.2~83.32 (m, 1H), 2.92 (d, J=5.2 Hz, 3H), 2.64 (s, 3H). MS (M+H)$^+$: 661.

Compound 51 (enantiomer 2, peak 2 on SFC, AD-H__3UM_4_5_40_4ML_3 MIN, HPLC_RT=2.193 min HPLC_RT=2.555 min) (120 mg). $^1$H-NMR (CDCl3, 400 MHz) δ 8.09 (s, 1H), 7.63~7.73 (m, 3H), 7.43 (d, J=8.0 Hz, 1H), 7.15~7.25 (m, 3H), 6.90~7.03 (m, 2H), 6.78 (d, J=8.0 Hz, 1H), 5.79~5.81 (m, 1H), 4.85~4.87 (m, 1H), 3.51~3.76 (m, 3H), 3.38 (s, 3H), 3.2~83.32 (m, 1H), 2.92 (d, J=5.2 Hz, 3H), 2.64 (s, 3H). MS (M+H)$^+$: 661.

Examples 52-54

Examples 52-54, depicted in the table below, were prepared in accordance with the method described for Examples 49-51.

| Example | Structure | MS (M + H)$^+$ |
|---|---|---|
| 52 | racemic | 643 |

-continued
| Example | Structure | MS (M + H)+ |
|---|---|---|
| 53 | enantiomer 1 | 643 |
| 54 | enantiomer 2 | 643 |
| 55 | 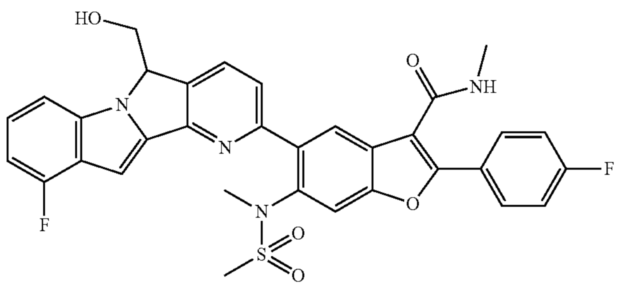 [SMILES: CNC(=O)c1c(-c2ccc(F)cc2)oc2cc(N(C)S(C)(=O)=O)c(-c3ccc4c(n3)-c3cc5c(F)cccc5n3C4CO)cc12] | 629 |
Examples 56-57
56 (Enantiomer 1, peak 1 on SFC)
57 (Enantiomer 2, peak 2 on SFC)
Step 1—Synthesis of (2-chloro-11-fluoro-5,6-dihydroindolo[1,2-h][1,7]naphthyridin-6-yl)methyl methanesulfonate
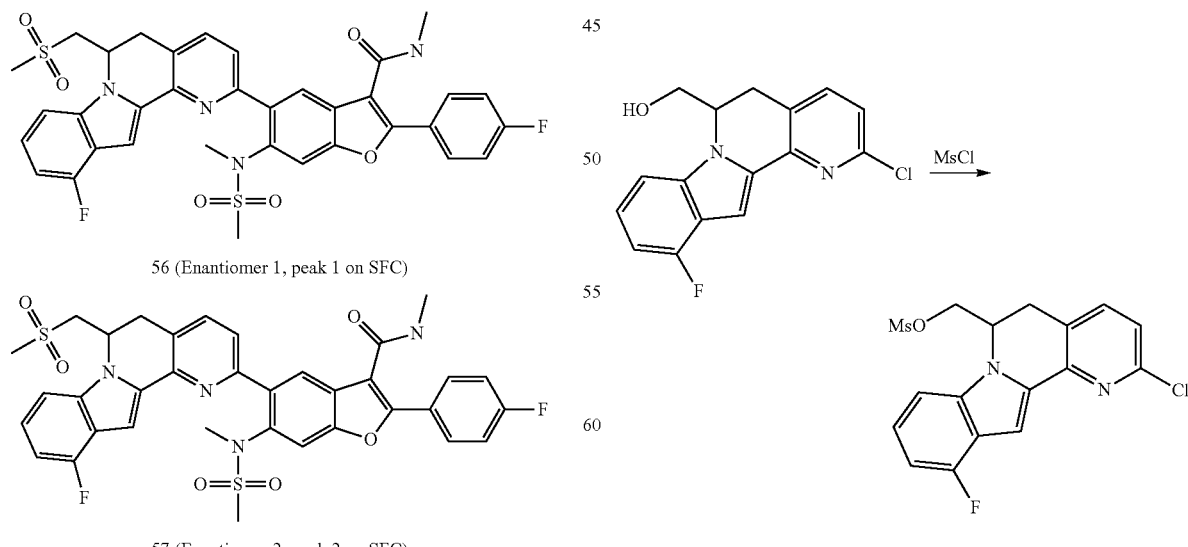
A mixture of (2-chloro-11-fluoro-5,6-dihydroindolo[1,2-h][1,7]naphthyridin-6-yl)methanol (200 mg, 0.66 mmol) and TEA (200 mg, 1.98 mmol) in THF (8 mL) was stirred at 0° C. and MsCl (114 mg, 0.99 mmol) was added dropwise. The reaction was stirred at RT for 8 h. The reaction was washed with 1N HCl and extracted with DCM, dried with $Na_2SO_4$ and concentrated to give (2-chloro-11-fluoro-5,6-dihydroindolo[1,2-h][1,7]naphthyridin-6-yl)methyl methanesulfonate (200 mg, yield: 80%). $^1$H-NMR ($CDCl_3$, 400 MHz) δ 7.54 (d, J=8.0 Hz, 1H), 7.41 (s, 1H), 7.11~7.20 (m, 3H), 6.79~6.83 (m, 1H), 5.03~5.08 (m, 1H), 4.06~4.21 (m, 2H), 3.46~3.52 (m, 1H), 3.24~3.28 (m, 1H), 2.69 (s, 3H). MS $(M+H)^+$: 381/383.

Step 2—Synthesis of (2-chloro-11-fluoro-5,6-dihydroindolo[1,2-h][1,7]naphthyridin-6-yl)methyl methanesulfonate

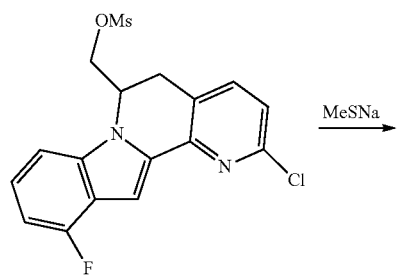

To a degassed solution of (2-chloro-11-fluoro-5,6-dihydroindolo[1,2-h][1,7]naphthyridin-6-yl)methyl methanesulfonate (600 mg, 1.6 mmol) in DMF (6 mL) was added $CH_3SNa$ (100 mg, 1.6 mmol) at 0° C., and the mixture was stirred at 0° C. for 3 h. Then the mixture was diluted with water (10 mL) and extracted with EtOAc (10 mL*3). The combined organic layer was washed with brine (30 mL), dried over $Na_2SO_4$ and concentrated. The residue was purified by column chromatography (PE:EA=5:1) to afford the desired product of 2-chloro-11-fluoro-6-((methylthio)methyl)-5,6-dihydroindolo[1,2-h][1,7]naphthyridine (350 mg, yield: 66.8%). $^1$H-NMR ($CDCl_3$, 400 MHz) δ 7.61 (d, J=7.6 Hz, 1H), 7.45 (s, 1H), 7.18~7.26 (m, 3H), 6.87 (dd, J=8.0, 9.6 Hz, 1H), 4.84~4.92 (m, 1H), 3.42~3.55 (m, 2H), 2.65~2.72 (m, 1H), 2.52~2.60 (m, 1H), 2.15 (s, 3H). MS $(M+H)^+$: 333/335.

Step 3—Synthesis of 2-chloro-11-fluoro-6-((methylsulfonyl)methyl)-5,6-dihydroindolo[1,2-h][1,7]naphthyridine

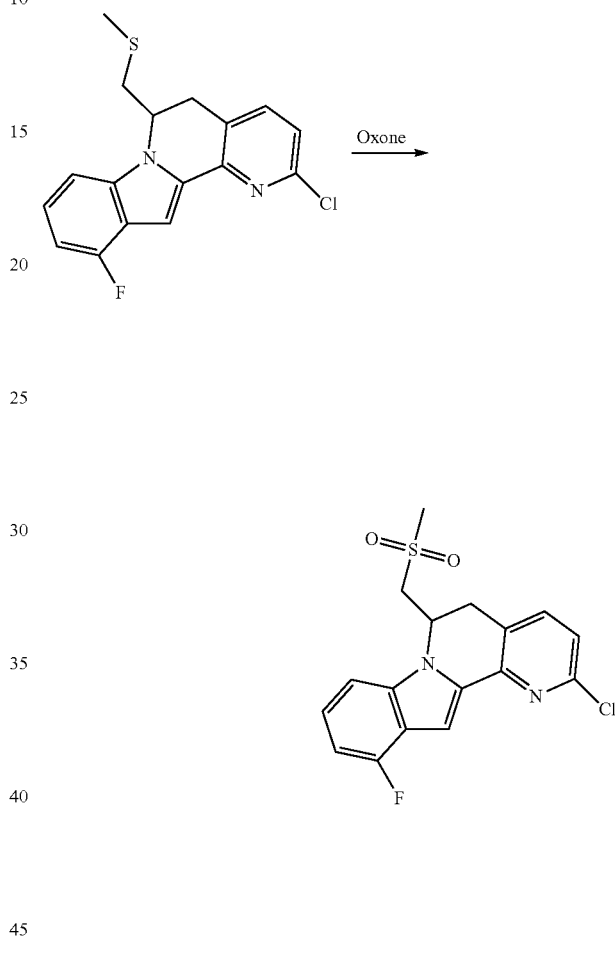

To a degassed solution of 2-chloro-11-fluoro-6-((methylthio)methyl)-5,6-dihydroindolo[1,2-h][1,7]naphthyridine (100 mg, 0.3 mmol) in MeOH (2 mL) was added a solution of Oxone (185 mg, 0.3 mmol) in $H_2O$ (2 mL) at 0° C., and the mixture was stirred at 25° C. for 24 h. Then the mixture was diluted with water (5 mL) and extracted with EtOAc (5 mL×3). The combined organic layer was washed with brine (10 mL), dried over $Na_2SO_4$ and concentrated. The residue was purified by column chromatography (DCM:EA=10:1) to afford the desired product of 2-chloro-11-fluoro-6-((methylsulfonyl)methyl)-5,6-dihydroindolo[1,2-h][1,7]naphthyridine (70 mg, yield: 64%). $^1$H-NMR ($CDCl_3$, 400 MHz) δ 7.62 (d, J=7.6 Hz, 1H), 7.43 (s, 1H), 7.22~7.29 (m, 3H), 6.83~6.89 (m, 1H), 5.45~5.51 (m, 1H), 3.51~3.62 (m, 2H), 3.14~3.21 (m, 1H), 2.97~3.05 (m, 1H), 2.84 (s, 3H). MS $(M+H)^+$: 365/367.

Step 4—Synthesis of (R or S)-5-(11-fluoro-6-((methylsulfonyl)methyl)-5,6-dihydroindolo[1,2-h][1,7]naphthyridin-2-yl)-2-(4-fluorophenyl)-N-methyl-6-(N-methylmethylsulfonamido)benzofuran-3-carboxamide and (S or R)-5-(11-fluoro-6-((methylsulfonyl)methyl)-5,6-dihydroindolo[1,2-h][1,7]naphthyridin-2-yl)-2-(4-fluorophenyl)-N-methyl-6-(N-methylmethylsulfonamido)benzofuran-3-carboxamide

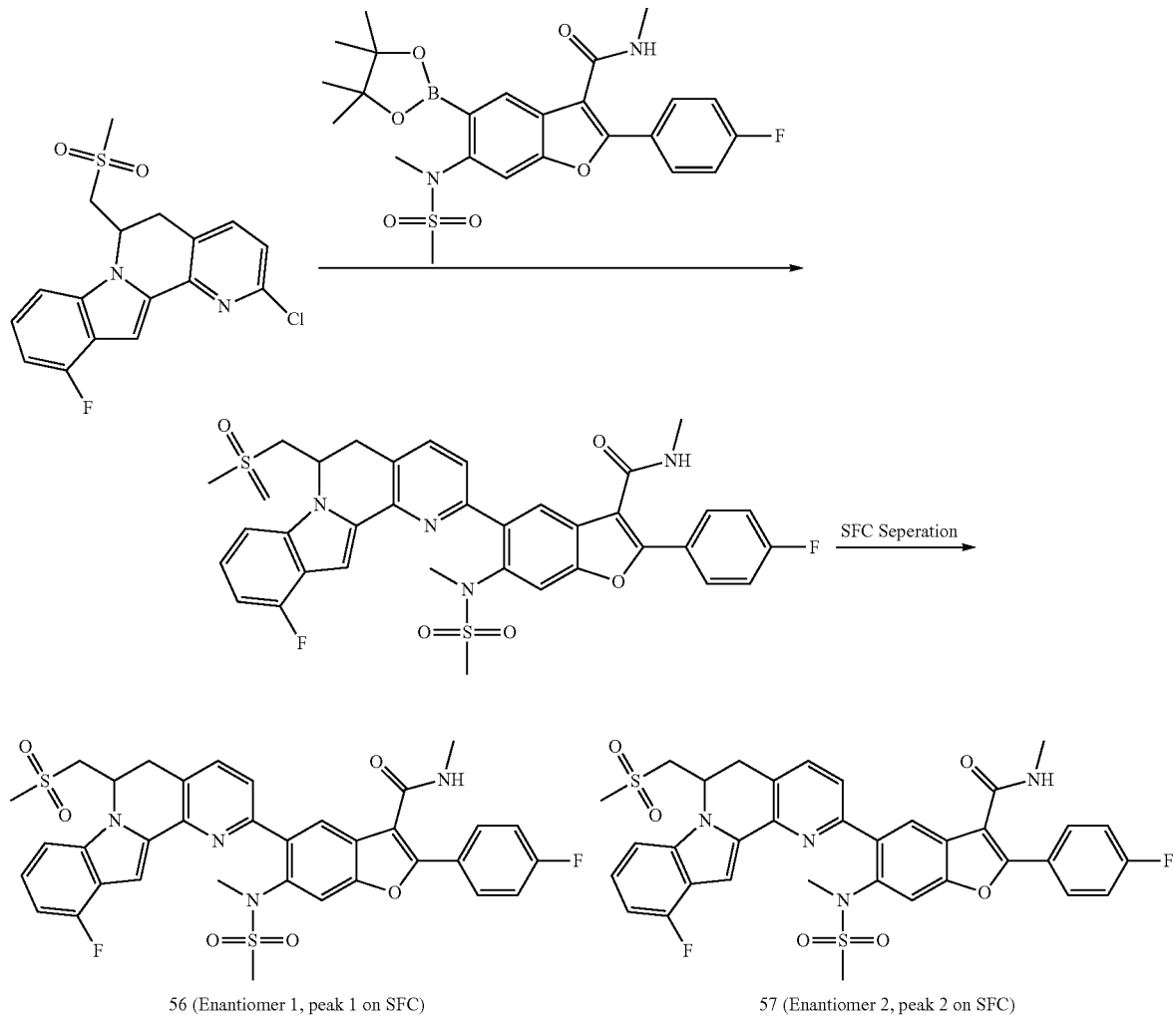

56 (Enantiomer 1, peak 1 on SFC) 57 (Enantiomer 2, peak 2 on SFC)

To a degassed solution of 2-chloro-11-fluoro-6-((methylsulfonyl)methyl)-5,6-dihydroindolo[1,2-h][1,7]naphthyridine (220 mg, 0.6 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (333 mg, 0.66 mmol) and Na$_2$CO$_3$ (128 mg, 1.2 mmol) in dioxane/water (5 mL/1 ml) was added Pd(dtbpf)Cl$_2$ (22 mg) under N$_2$. The mixture was stirred at 100° C. for 3 h. After the solvent was removed, the residue was purified by prep-TLC (DCM:EtOAc=3:1) and SFC to give two single enantiomers.

Compound 56 (enantiomer 1, peak 1 on SFC, AD-H_3UM_5_40_4ML_8 MIN, HPLC_RT=3.116 min) (100 mg, yield: 23.5%). $^1$H-NMR (CDCl$_3$, 400 MHz) δ 8.06 (s, 1H), 7.97 (dd, J=5.6, 8.0 Hz, 2H), 7.77 (d, J=7.6 Hz, 1H), 7.66 (s, 1H), 7.52 (d, J=7.6 Hz, 1H), 7.3~17.35 (m, 2H), 7.19~7.25 (m, 3H), 6.85 (t, J=8.8 Hz, 1H), 5.89 (d, J=4.4 Hz, 1H), 5.52 (br. s, 1H), 3.60~3.68 (m, 2H), 3.42 (s, 3H), 3.26 (dd, J=9.6, 13.6 Hz, 1H), 3.08 (d, J=13.6 Hz, 1H), 3.00 (d, J=4.8 Hz, 3H), 2.83 (s, 3H), 2.77 (s, 3H). MS (M+H)$^+$: 705.

Compound 57 (enantiomer 2, peak 2 on SFC, AD-H_3UM_5_40_4ML_8 MIN, HPLC_RT=4.637 min) (100 mg, yield: 23.5%). $^1$H-NMR (CDCl$_3$, 400 MHz) δ 8.06 (s, 1H), 7.97 (dd, J=5.6, 8.0 Hz, 2H), 7.77 (d, J=7.6 Hz, 1H), 7.66 (s, 1H), 7.52 (d, J=7.6 Hz, 1H), 7.31~7.35 (m, 2H), 7.19~7.25 (m, 3H), 6.85 (t, J=8.8 Hz, 1H), 5.89 (d, J=4.4 Hz, 1H), 5.52 (br. s, 1H), 3.60~3.68 (m, 2H), 3.42 (s, 3H), 3.26 (dd, J=9.6, 13.6 Hz, 1H), 3.08 (d, J=13.6 Hz, 1H), 3.00 (d, J=4.8 Hz, 3H), 2.83 (s, 3H), 2.77 (s, 3H). MS (M+H)$^+$: 705.

Examples 58-59

Compounds 58 and 59, depicted in the table below, were prepared in accordance with the method described for Examples 56-57.

| Compound ID | Structure | NMR | MS (M + H)+ |
|---|---|---|---|
| 58 | 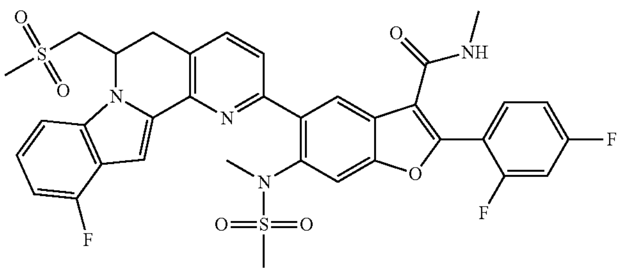 [SMILES: CNC(=O)c1c(-c2ccc(F)cc2F)oc2cc(N(C)S(C)(=O)=O)c(-c3ccc4c(n3)-c3cc5c(F)cccc5n3C(CS(C)(=O)=O)C4)cc12] | $^1$H-NMR (CDCl$_3$, 400 MHz) δ 8.14 (s, 1H), 7.78 (d, J = 7.6 Hz, 2H), 7.68 (s, 1H), 7.52 (d, J = 7.6 Hz, 1H), 7.31~7.35 (m, 2H), 7.21~7.25 (m, 1H), 7.09 (t, J = 7.6 Hz, 1H), 7.02 (t, J = 8.8 Hz, 1H), 6.85 (t, J = 1H), 5.75 (br s, 1H), 5.52 (br s, 1H), 3.62~3.69 (m, 2H), 3.42 (s, 3H), 3.23~3.29 (m, 1H), 3.08 (d, J = 12.4 Hz, 1H), 2.97 (d, J = 4.8 Hz, 3H), 2.84 (s, 3H), 2.77 (s, 3H). | 723 |
| 59 | 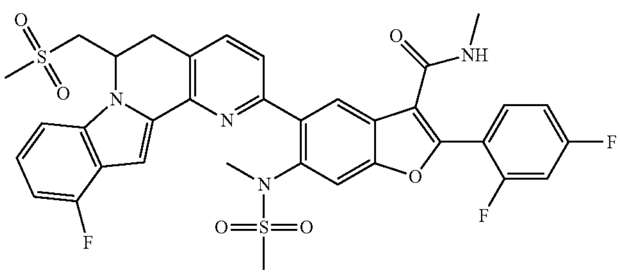 [SMILES: CNC(=O)c1c(-c2ccc(F)cc2F)oc2cc(N(C)S(C)(=O)=O)c(-c3ccc4c(n3)-c3cc5c(F)cccc5n3C(CS(C)(=O)=O)C4)cc12] | $^1$H-NMR (CDCl$_3$, 400 MHz) δ 8.14 (s, 1H), 7.78 (d, J = 7.6 Hz, 2H), 7.68 (s, 1H), 7.52 (d, J = 7.6 Hz, 1H), 7.31~7.35 (m, 2H), 7.21~7.25 (m, 1H), 7.09 (t, J = 7.6 Hz, 1H), 7.02 (t, J = 8.8 Hz, 1H), 6.85 (t, J = 8.8 Hz, 1H), 5.75 (br s, 1H), 5.52 (br s, 1H), 3.62~3.69 (m, 2H), 3.42 (s, 3H), 3.23~3.29 (m, 1H), 3.08 (d, J = 12.4 Hz, 1H), 2.97 (d, J = 4.8 Hz, 3H), 2.84 (s, 3H), 2.77 (s, 3H). | 723 |

Examples 60-61

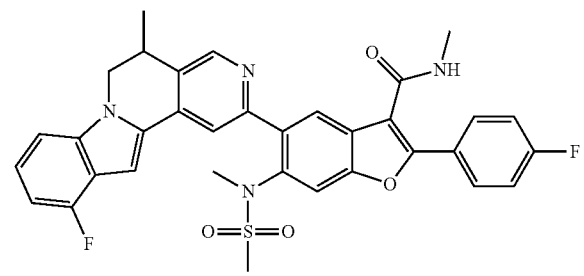

60 (Enantiomer 1, peak 1 on SFC)

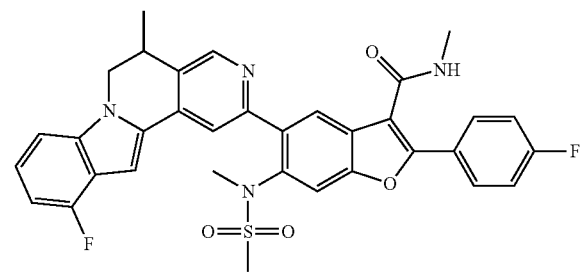

61 (Enantiomer 2, peak 2 on SFC)

Step 1—Synthesis of 2-(2-chloro-5-(prop-1-en-2-yl)pyridin-4-yl)-4-fluoro-1H-indole

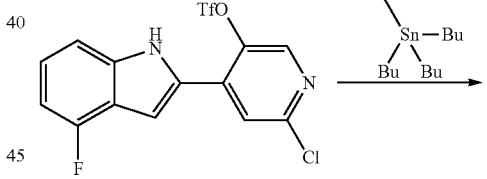

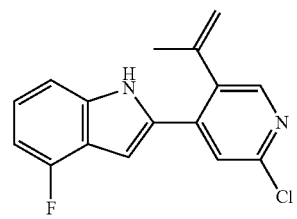

To a suspension of 6-chloro-4-(4-fluoro-1H-indol-2-yl)pyridin-3-yl trifluoromethanesulfonate (100 mg, 0.25 mmol) and tributyl(prop-1-en-2-yl)stannane (100 mg, 0.28 mmol) in DMF (2 mL) was added Pd(PPh$_3$)$_4$ (10 mg, 0.02 mmol) at 100° C. under N$_2$, and the mixture was stirred for 5 hours. After concentrated in vacuum, the residue was suspended in H$_2$O and extracted with EA. The combined organic layer was washed with H$_2$O, brine, dried over Na$_2$SO$_4$, filtrated and concentrated to give 2-(2-chloro-5-(prop-1-en-2-yl)pyridin-4-yl)-4-fluoro-1H-indole (50 mg, yield: 70%). $^1$H-NMR (CDCl$_3$, 400 MHz) δ 8.96 (s, 1H), 8.14 (s, 1H), 7.47 (s, 1H), 7.08~7.13 (m, 2H), 6.95 (s, 1H), 6.72~6.76 (m, 1H), 5.39 (s, 1H), 5.23 (s, 1H), 1.77 (s, 3H). MS (M+H)+: 287/289.

Step 2—Synthesis of 2-(6-chloro-4-(4-fluoro-1H-indol-2-yl)pyridin-3-yl)propan-1-ol

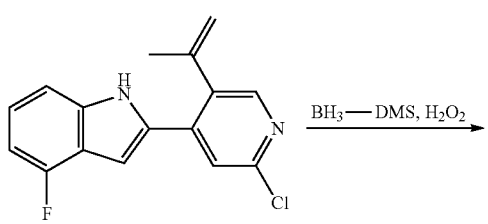

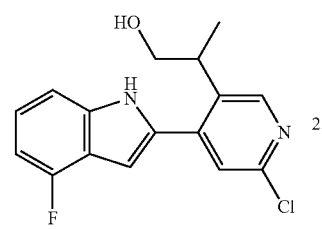

To a degassed solution of 2-(2-chloro-5-(prop-1-en-2-yl)pyridin-4-yl)-4-fluoro-1H-indole (50 mg, 0.17 mmol) was added BH$_3$-DMS (0.5 mL) under N$_2$ protection at 0° C., and the mixture was stirred for 1 hour. Then NaBO$_3$.4H$_2$O (60 mg, 0.34 mmol) and H$_2$O$_2$ (0.2 mL) was added under N$_2$ protection at 0° C. for 0.5 hours, and the reaction mixture was stirred at RT for 2 hours. After diluted with H$_2$O and extracted with EtOAc, the combined organic layer was washed with H$_2$O, brine, dried over Na$_2$SO$_4$, and the residue was purified by prep-HPLC to give 2-(6-chloro-4-(4-fluoro-1H-indol-2-yl)pyridin-3-yl)propan-1-ol (20 mg, yield: 36%). $^1$H-NMR (CDCl$_3$, 400 MHz) δ 10.86 (s, 1H), 8.17 (s, 1H), 7.33 (s, 1H), 7.18 (s, 1H), 7.06~7.10 (m, 1H), 6.71~7.76 (m, 2H), 4.10 (s, 1H), 3.95 (s, 1H), 3.75 (t, J=12.0 Hz 1H), 3.42~3.51 (m, 1H), 1.14 (d, J=8.0 Hz, 3H). MS (M+H)+: 305/307.

Step 3—Synthesis of 2-chloro-11-fluoro-5-methyl-5,6-dihydroindolo[2,1-a][2,6]naphthyridine

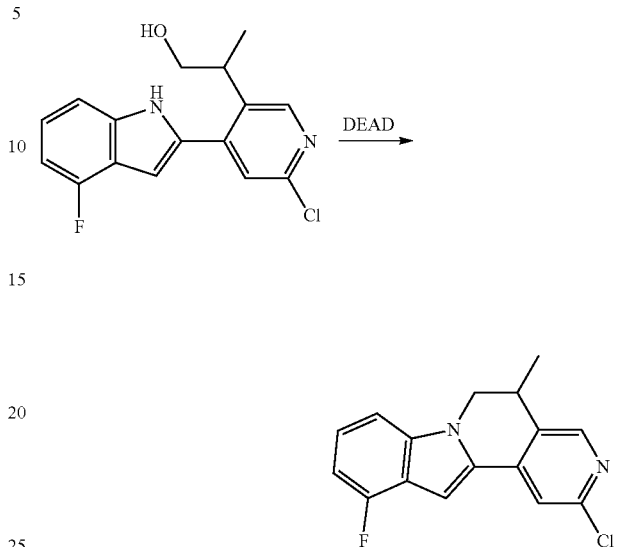

To a suspension of 2-(6-chloro-4-(4-fluoro-1H-indol-2-yl)pyridin-3-yl)propan-1-ol (60 mg, 0.21 mmol) and DEAD (111 mg, 0.63 mmol) in THF (4 mL) was added PPh$_3$ (156 mg, 0.63 mmol) at 0° C. under N$_2$, and the mixture was stirred for 12 hours. Then the mixture was diluted with H$_2$O and extracted with EA. The combined organic layer was washed with H$_2$O, brine, dried over Na$_2$SO$_4$, filtrated and concentrated to give 2-chloro-11-fluoro-5-methyl-5,6-dihydroindolo[2,1-a][2,6]naphthyridine (30 mg, yield: 56%). $^1$H-NMR (CDCl$_3$, 400 MHz) δ 8.26 (s, 1H), 7.54 (s, 1H), 7.05~7.15 (m, 3H), 6.73~6.77 (m, 1H), 4.16~4.20 (m, 1H), 4.00~4.04 (m, 1H), 3.31~3.35 (m, 1H), 1.30 (d, J=8.0 Hz, 3H). MS (M+H)+: 287/289.

Step 4—Synthesis of (R or S)-5-(11-fluoro-5-methyl-5,6-dihydroindolo[2,1-a][2,6]naphthyridin-2-yl)-2-(4-fluorophenyl)-N-methyl-6-(N-methylmethylsulfonamido)benzofuran-3-carboxamide and (S or R)-5-(11-fluoro-5-methyl-5,6-dihydroindolo[2,1-a][2,6]naphthyridin-2-yl)-2-(4-fluorophenyl)-N-methyl-6-(N-methylmethylsulfonamido)benzofuran-3-carboxamide

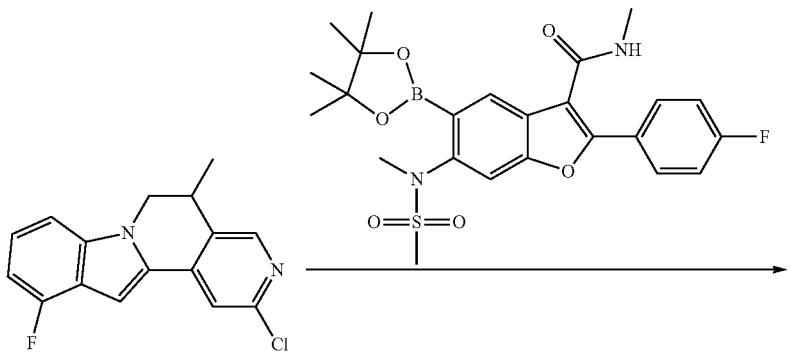

-continued

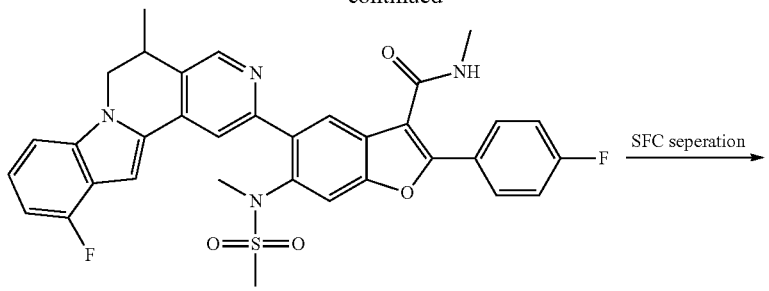

SFC seperation →

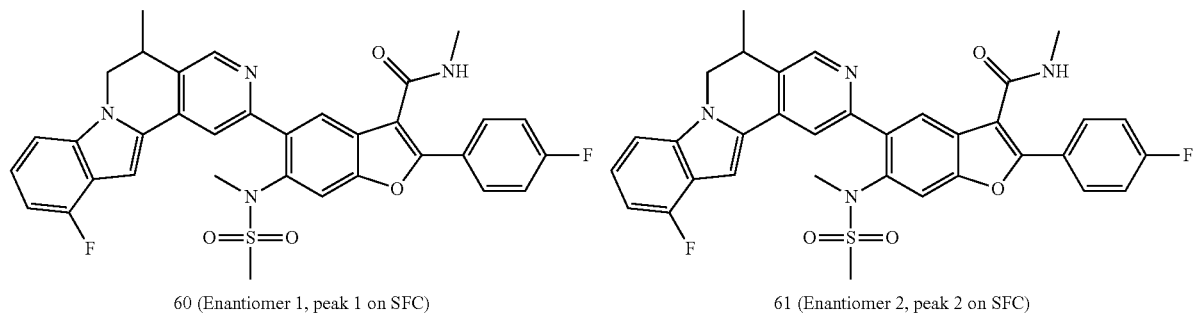

60 (Enantiomer 1, peak 1 on SFC)    61 (Enantiomer 2, peak 2 on SFC)

To a stirring mixture of 2-chloro-11-fluoro-5-methyl-5,6-dihydroindolo[2,1-a][2,6]naphthyridine (100 mg, 0.34 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (191 mg, 0.38 mmol) and $K_3PO_4 \cdot 3H_2O$ (79 mg, 1.00 mmol) in Dioxane/$H_2O$ (2 mL/0.2 mL) was added X-Phos (20 mg) and $Pd_2(dba)_3$ (20 mg) under $N_2$ protection. The mixture was stirred at a pre-heated oil-bath at 100° C. for 2 h. The reaction mixture was concentrated in vacuo and it was extracted with EtOAc. It was washed with $H_2O$, brine and dried over $Na_2SO_4$. After concentration, the residue was purified by prep-HPLC and SFC to give two single enantiomers.

Compound 60 (enantiomer 1, peak 1 on SFC, AD-H__3UM__5__60__3ML__5MIN, HPLC_RT=0.810 min) (40 mg, yield: 19.8%). $^1$H-NMR (CDCl$_3$, 400 MHz) δ 8.65 (s, 1H), 7.98~8.05 (m, 4H), 7.69 (s, 1H), 7.16~7.23 (m, 5H), 6.80~6.84 (m, 1H), 6.09 (s, 1H), 4.31~4.35 (m, 1H), 4.12~4.16 (m, 1H), 3.47~3.52 (m, 1H), 3.24 (s, 3H), 3.01 (d, J=4.8 Hz, 3H), 2.88 (s, 3H), 1.30 (d, J=8.0 Hz, 3H). MS (M+H)$^+$: 627.

Compound 61 (enantiomer 2, peak 2 on SFC, AD-H__3UM__5__60__3ML__5MIN, HPLC_RT=2.422 min) (40 mg, yield: 19.8%). $^1$H-NMR (CDCl$_3$, 400 MHz) δ 8.56 (s, 1H), 7.90~8.95 (m, 4H), 7.59 (s, 1H), 7.16~7.23 (m, 5H), 6.80~6.84 (m, 1H), 6.09 (s, 1H), 4.22~4.26 (m, 1H), 4.04~4.07 (m, 1H), 3.39~3.41 (m, 1H), 3.16 (s, 3H), 2.93 (d, J=4.8 Hz, 3H), 2.80 (s, 3H), 1.37 (d, J=8.0 Hz, 3H). MS (M+H)$^+$: 627.

Example 62

Example 62, depicted in the table below, were prepared in accordance with the method described for Examples 60-61.

| Example | Structure | NMR | MS (M + H)$^+$ |
|---|---|---|---|
| 62 | racemic | $^1$H-NMR (CDCl$_3$, 400 MHz) δ 7.95~8.00 (m, 3H), 7.71 (d, J = 8.0 Hz, 1H), 7.67 (s, 1H), 7.50 (d, J = 8.0 Hz, 1H), 7.29 (s, 1H), 7.17~7.22 (m, 4H), 6.80~6.83 (m, 1H), 6.06 (s, 1H), 4.33~4.37 (m, 1H), 4.07~4.11 (m, 1H), 3.46~3.49 (m, 1H), 3.44 (s, 3H), 2.98 (d, J = 4.8 Hz, 3H), 2.66 (s, 3H), 1.45 (d, J = 8.0 Hz, 3H). | 627 |

Example 63

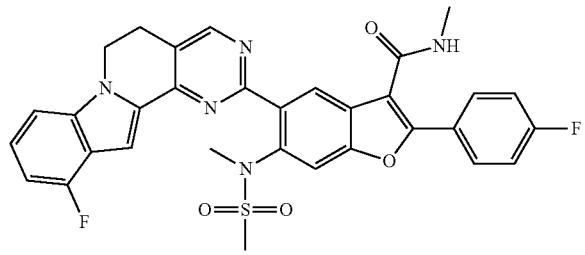 [SMILES: CNC(=O)c1c(-c2ccc(F)cc2)oc2cc(N(C)S(C)(=O)=O)c(-c3ncc4c(n3)-c3cc5c(F)cccc5n3CC4)cc12]

Step 1—Synthesis of 2-chloro-4-(4-fluoro-1H-indol-2-yl)pyrimidin-5-yl trifluoromethanesulfonate

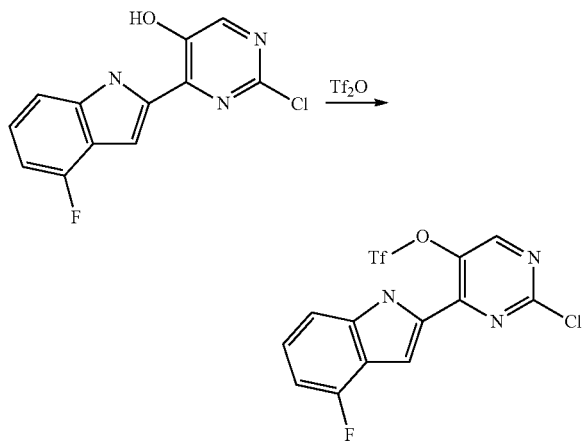

DIPEA (1.5 g, 11.61 mmol) was added to a suspension of 2-chloro-4-(4-fluoro-1H-indol-2-yl)pyrimidin-5-ol (1.0 g, 3.79 mmol) in anhydrous DCM (20 mL) under $N_2$. The reaction mixture was cooled to 0° C., and then trifluoromethanesulfonic anhydride (2.2 g, 7.80 mmol) was added dropwise. After stirring at 0° C. for 30 minutes, the mixture was diluted with water and extracted with $CH_2Cl_2$. The organic layers were washed with brine, dried over $Na_2SO_4$, and concentrated. The residue was purified by column chromatography (PE:EA=10:1) to give the product of 2-chloro-4-(4-fluoro-1H-indol-2-yl)pyrimidin-5-yl trifluoromethanesulfonate (1.0 g, yield: 66.7%). $^1$H-NMR (DMSO-$d_6$, 400 MHz) δ 12.47 (s, 1H), 9.09 (s, 1H), 7.41~7.46 (m, 2H), 7.28~7.34 (m, 1H), 6.89~6.94 (m, 1H). MS (M+H)$^+$: 396/398.

Step 2—Synthesis of 2-(2-chloro-5-vinylpyrimidin-4-yl)-4-fluoro-1H-indole

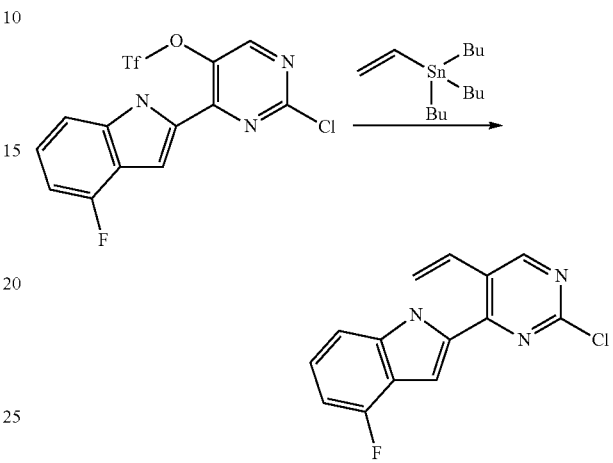

To a mixture of 2-chloro-4-(4-fluoro-1H-indol-2-yl)pyrimidin-5-yl trifluoromethanesulfonate (500 mg, 1.26 mmol), tributyl(vinyl)stannane (400 mg, 1.26 mmol) and anhydrous LiCl (150 mg, 3.54 mmol) in DMF (5 mL), Pd(PPh$_3$)$_2$Cl$_2$ (50 mg, 0.07 mmol) was added under $N_2$ protection. The reaction mixture was stirred at 60° C. for 1 h. Then it was concentrated in vacuo, and the residue was purified by column chromatography (PE:EA=10:1) to give the product of 2-(2-chloro-5-vinylpyrimidin-4-yl)-4-fluoro-1H-indole (250 g, yield: 72.3%). $^1$H-NMR (DMSO-$d_6$, 400 MHz) δ 12.21 (br s, 1H), 8.85 (s, 1H), 7.41 (d, J=7.6 Hz, 1H), 7.21~7.27 (m, 1H), 7.08~7.20 (m, 2H), 6.87 (dd, J=10.4, 7.6 Hz, 1H), 6.01 (dd, J=17.6, 1.2 Hz, 1H), 5.72 (dd, J=11.2, 1.2 Hz, 1H). MS (M+H)$^+$: 274/276.

Step 3—Synthesis of 5-(4-(4-fluoro-1H-indol-2-yl)-5-vinylpyrimidin-2-yl)-2-(4-fluorophenyl)-N-methyl-6-(N-methylmethylsulfonamido)benzofuran-3-carboxamide

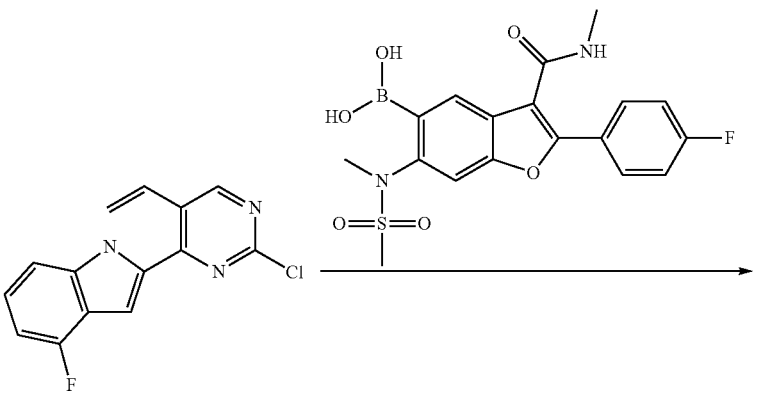

-continued

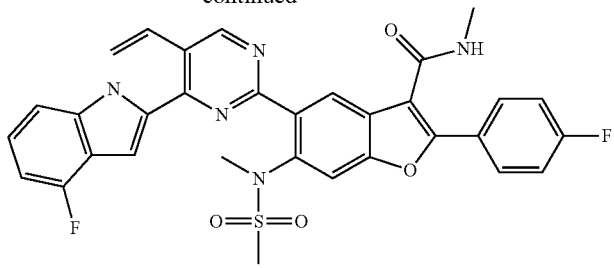

To a degassed solution of 2-(2-chloro-5-vinylpyrimidin-4-yl)-4-fluoro-1H-indole (100 mg, 0.36 mmol) and (2-(4-fluorophenyl)-3-(methylcarbamoyl)-6-(N-methylmethyl sulfonamido)benzofuran-5-yl)boronic acid (150 mg, 0.36 mmol) in 1,4-dioxane (5 mL), $Pd_2(dba)_3$ (20 mg), X-Phos (20 mg) and $K_3PO_4$ (200 mg, 0.56 mmol) were added under $N_2$. The mixture was heated to 80° C. for 2 hours. The reaction mixture was cooled to RT, filtered and washed with EtOAc. The filtrate was washed with $H_2O$, brine, and dried over $Na_2SO_4$. After concentration, the residue was purified by column chromatography (DCM:MeOH 40:1) to give the product of 5-(4-(4-fluoro-1H-indol-2-yl)-5-vinylpyrimidin-2-yl)-2-(4-fluorophenyl)-N-methyl-6-(N-methylmethylsulfonamido)benzofuran-3-carboxamide (150 mg, yield: 68.4%). $^1$H-NMR ($CDCl_3$, 400 MHz) δ 10.76 (br s, 1H), 8.88 (s, 1H), 8.63 (s, 1H), 7.98~8.05 (m, 2H), 7.64 (s, 1H), 7.59 (s, 1H), 7.15~7.25 (m, 6H), 6.74~6.84 (m, 1H), 5.91 (d, J=18.0 Hz, 1H), 5.69 (d, J=11.2 Hz, 1H), 3.39 (s, 3H), 3.03 (d, J=4.8 Hz, 3H), 2.87 (s, 3H). MS $(M+H)^+$: 614

Step 4—Synthesis of 5-(11-fluoro-5,6-dihydropyrimido[4',5':3,4]pyrido[1,2-a]indol-2-yl)-2-(4-fluorophenyl)-N-methyl-6-(N-methylmethylsulfonamido)benzofuran-3-carboxamide

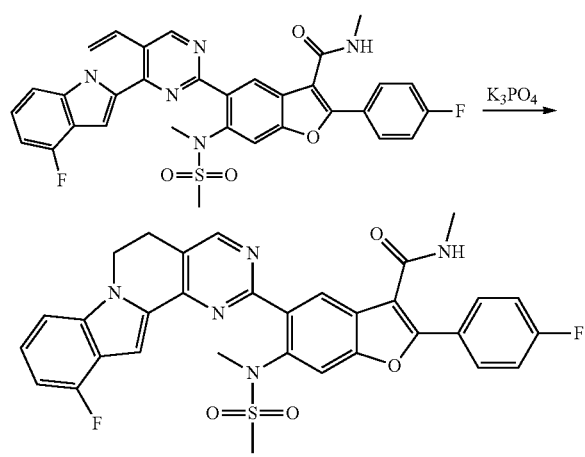

To a solution of 5-(4-(4-fluoro-1H-indol-2-yl)-5-vinylpyrimidin-2-yl)-2-(4-fluorophenyl)-N-methyl-6-(N-methylmethylsulfonamido)benzofuran-3-carboxamide (50 mg, 0.08 mmol) in DMAc (1 mL), $K_3PO_4$ (100 mg, 0.37 mmol) was added under $N_2$ protection. The reaction mixture was stirred at 90° C. overnight. Then the mixture was diluted with water and extracted with EtOAc. The organic layers were washed with brine, dried over $Na_2SO_4$, and concentrated. The residue was purified by prep-HPLC to give the product of 5-(11-fluoro-5,6-dihydropyrimido[4',5':3,4]pyrido[1,2-a]indol-2-yl)-2-(4-fluorophenyl)-N-methyl-6-(N-methylmethylsulfonamido)benzofuran-3-carboxamide (10 mg, yield: 20.0%). $^1$H-NMR ($CDCl_3$, 400 MHz) δ 8.75 (s, 1H), 8.36 (s, 1H), 8.00~8.10 (m, 2H), 7.75 (s, 1H), 7.53 (s, 1H), 7.15~7.25 (m, 4H), 6.84 (t, J=8.8 Hz, 1H), 6.01 (br s, 1H), 4.41 (t, J=6.4 Hz, 2H), 3.50 (s, 3H), 3.34 (t, J=6.4 Hz, 2H), 3.05 (d, J=4.8 Hz, 3H), 2.83 (s, 3H). MS $(M+H)^+$: 614

Example 64

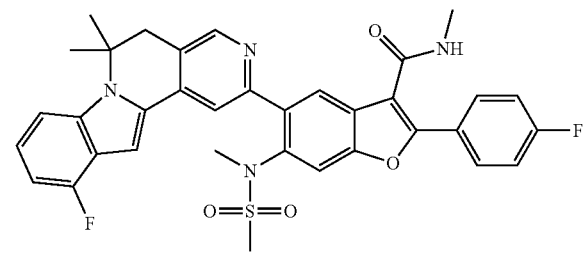 [SMILES: CNC(=O)c1c(-c2ccc(F)cc2)oc2cc(N(C)S(C)(=O)=O)c(-c3cc4c(cn3)CC(C)(C)n3c-4cc4c(F)cccc43)cc12]

Step 1—Synthesis of 1-(6-chloro-4-(4-fluoro-1H-indol-2-yl)pyridin-3-yl)ethane-1,2-diol

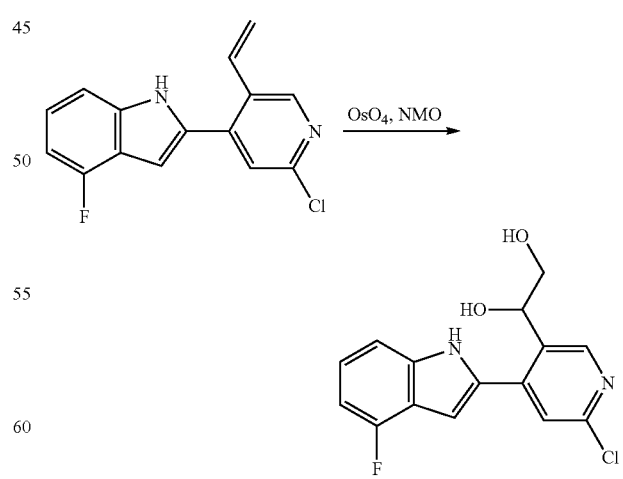

To a solution of 2-(2-chloro-5-vinylpyridin-4-yl)-4-fluoro-1H-indole (2 g, 7.35 mmol) in THF—$H_2O$ (26 mL-13 mL), NMO (2.15 g, 18.38 mmol) and $OsO_4$ (56 mg, 0.22 mmol) were added. The reaction mixture was stirred at room temperature for 2 hours. Then Na$_2$SO$_3$ and water were added. The mixture was stirred at room temperature for 20 min and filtered. The filtrate was extracted with EA. The organic layer was washed with brine, dried over Na$_2$SO$_4$ and concentrated. The residue was purified by column chromatography (DCM:MeOH=10:1) to give 1-(6-chloro-4-(4-fluoro-1H-indol-2-yl)pyridin-3-yl)ethane-1,2-diol (1.9 g, yield: 84.4%). $^1$H-NMR (Methanol-d$_4$, 400 MHz) 8.61 (s, 1H), 7.63 (s, 1H), 7.24 (d, J=8.0 Hz, 1H), 7.08~7.19 (m, 1H), 6.90 (s, 1H), 6.75 (dd, J=7.6, 10.0 Hz, 1H), 5.19 (t, J=6.0 Hz, 1H), 3.75~3.82 (m, 1H), 3.67~3.74 (m, 1H). MS (M+H)$^+$: 307/309.

Step 2—Synthesis of 6-chloro-4-(4-fluoro-1H-indol-2-yl)nicotinaldehyde

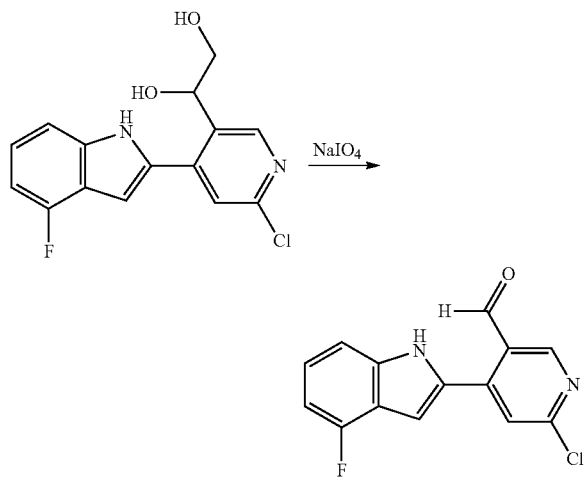

To a solution of 1-(6-chloro-4-(4-fluoro-1H-indol-2-yl)pyridin-3-yl)ethane-1,2-diol (1.9 g, 6.21 mmol) in THF—H$_2$O (26 mL-13 mL), NaIO$_4$ (1.94 g, 9.31 mmol) was added, the reaction mixture was stirred at room temperature for 2 hours. Then Na$_2$SO$_3$ and water were added and the mixture was stirred at room temperature for 30 min. The mixture was extracted with EA. The organic layer was washed with brine, dried over Na$_2$SO$_4$ and concentrated. The residue was purified by column chromatography (DCM:MeOH=20:1) to afford the desired product of 6-chloro-4-(4-fluoro-1H-indol-2-yl)nicotinaldehyde (1.4 g, yield: 82.4%). $^1$H-NMR (Methanol-d$_4$, 400 MHz) δ 8.48 (s, 1H), 7.79 (s, 1H), 7.40 (d, J=8.4 Hz, 1H), 7.17~7.25 (m, 1H), 6.95 (s, 1H), 6.79 (dd, J=8.0, 10.0 Hz, 1H), 6.70 (s, 1H). MS (M+H)$^+$: 275/277.

Step 3—Synthesis of 2-(2-chloro-5-(2-methylprop-1-en-1-yl)pyridin-4-yl)-4-fluoro-1H-indole

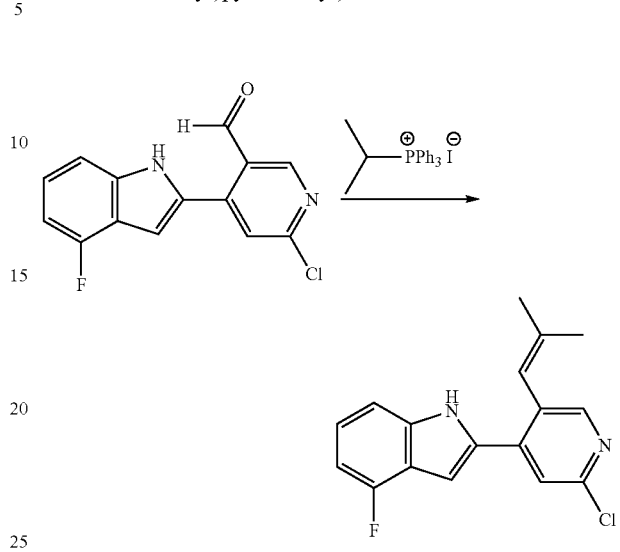

n-BuLi (3.15 mL, 7.88 mmol, 2.5 M in hexane) was added dropwise to a mixture of isopropyltriphenylphosphonium iodide (3.55 g, 8.21 mmol) in THF (30 mL) at −78° C. under N$_2$ atmosphere. The mixture was stirred at −78° C. for 1 hour. Then a solution of 6-chloro-4-(4-fluoro-1H-indol-2-yl)nicotinaldehyde (900 mg, 3.28 mmol) in THF (10 mL) was added dropwise to the mixture at −78° C. The mixture was stirred at room temperature overnight. The mixture was then diluted with water (100 mL) and extracted with EA (50 mL*3). The organic layer was washed with brine (50 mL), dried over Na$_2$SO$_4$ and concentrated. The residue was purified by column chromatography (PE:EA=4:1) to give the product of 2-(2-chloro-5-(2-methylprop-1-en-1-yl)pyridin-4-yl)-4-fluoro-1H-indole (500 mg, yield: 50.6%). $^1$H-NMR (CDCl$_3$, 400 MHz) δ 8.66 (br s, 1H), 8.17 (s, 1H), 7.51 (s, 1H), 7.12 (br s, 2H), 6.96 (d, J=1.6 Hz, 1H), 6.70~6.81 (m, 1H), 6.22 (br s, 1H), 1.97 (s, 3H), 1.68~1.70 (m, 1H), 1.74 (s, 3H). MS (M+H)$^+$: 301/303.

Step 4—Synthesis of 5-(4-(4-fluoro-1H-indol-2-yl)-5-(2-methylprop-1-en-1-yl)pyridin-2-yl)-2-(4-fluorophenyl)-N-methyl-6-(N-methylmethylsulfonamido)benzofuran-3-carboxamide

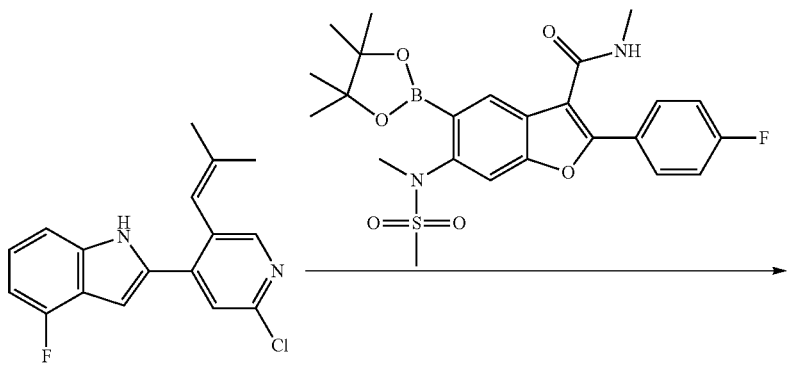

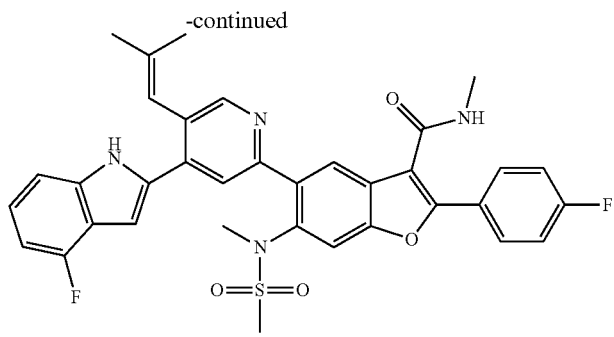

To a degassed solution of 2-(2-chloro-5-(2-methylprop-1-en-1-yl)pyridin-4-yl)-4-fluoro-1H-indole (230 mg, 0.767 mmol) and 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (322 mg, 0.767 mmol) in 1,4-dioxane/H$_2$O (4 mL/1 mL), Pd$_2$(dba)$_3$ (30 mg, 0.038 mmol), X-Phos (36 mg, 0.076 mmol) and K$_3$PO$_4$ (612 mg, 2.301 mmol) were added under N$_2$ atmosphere. The mixture was stirred at 90° C. for 3 hours under N$_2$ atmosphere. The reaction mixture was then diluted with water (100 mL) and extracted with EA (50 mL×3). The organic layer was washed with brine (10 mL), dried over Na$_2$SO$_4$. After concentrated, the residue was purified by column chromatography (PE:EA=2:1) to give the product of 5-(4-(4-fluoro-1H-indol-2-yl)-5-(2-methylprop-1-en-1-yl)pyridin-2-yl)-2-(4-fluorophenyl)-N-methyl-6-(N-methylmethylsulfonamido)benzofuran-3-carboxamide (400 mg, yield: 81.5%). $^1$H-NMR (CDCl$_3$, 400 MHz) δ 9.67 (br s, 1H), 8.61 (s, 1H), 8.20 (s, 1H), 8.09 (s, 1H), 8.00~8.06 (m, 2H), 7.54 (s, 1H), 7.11~7.24 (m, 4H), 6.99 (s, 1H), 6.75~6.83 (m, 1H), 6.39 (br s, 1H), 6.01 (br s, 1H), 3.22 (s, 3H), 2.99~3.06 (m, 6H), 2.07 (s, 3H), 1.93 (s, 3H). MS (M+H)$^+$: 641.

Step 5—Synthesis of 5-(11-fluoro-6,6-dimethyl-5,6-dihydroindolo[2,1-a][2,6]naphthyridin-2-yl)-2-(4-fluorophenyl)-N-methyl-6-(N-methylmethylsulfonamido)benzofuran-3-carboxamide

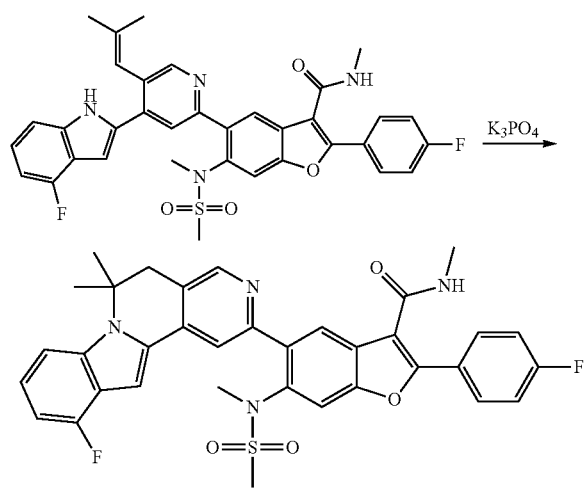

A mixture of 5-(4-(4-fluoro-1H-indol-2-yl)-5-(2-methylprop-1-en-1-yl)pyridin-2-yl)-2-(4-fluorophenyl)- N-methyl-6-(N-methylmethylsulfonamido)benzofuran-3-carboxamide (100 mg, 0.156 mmol) and K$_3$PO$_4$ (166 mg, 0.781 mmol) in DMAc (0.8 mL) was stirred at 100° C. overnight. The mixture was then diluted with water (40 mL) and extracted with EA (20 mL*3). The organic layer was washed with brine (30 mL*3), dried over Na$_2$SO$_4$ and concentrated. The residue was purified by prep-TLC (DCM:EA=1:1) to afford the product of 5-(11-fluoro-6,6-dimethyl-5,6-dihydroindolo[2,1-a][2,6]naphthyridin-2-yl)-2-(4-fluorophenyl)-N-methyl-6-(N-methylmethylsulfonamido)benzofuran-3-carboxamide (40 mg, yield: 40.0%). $^1$H-NMR (CDCl$_3$, 400 MHz) δ 8.49 (s, 1H), 7.86~8.00 (m, 4H), 7.61 (s, 1H), 7.45 (d, J=8.0 Hz, 1H), 7.00~7.18 (m, 4H), 6.72 (t, J=8.4 Hz, 1H), 6.01 (br s, 1H), 3.16 (s, 3H), 3.08 (br s, 2H), 2.93 (d, J=4.4 Hz, 3H), 2.77 (s, 3H), 1.69 (br s, 6H). MS (M+H)$^+$: 641.

Example 65

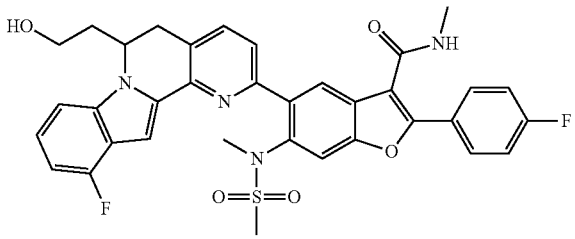 [SMILES: CNC(=O)c1c(-c2ccc(F)cc2)oc2cc(N(C)S(C)(=O)=O)c(-c3ccc4c(n3)-c3cc5c(F)cccc5n3C(CCO)C4)cc12]

Step 1—Synthesis of 4-(tributylstannyl)but-3-en-1-ol

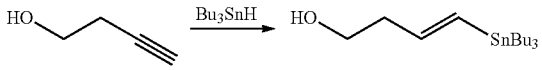

A stirred mixture of but-3-yn-1-ol (7.00 g, 99.87 mmol) and AIBN (0.50 g, 2.81 mmol), contained in large round-bottomed flask equipped with a reflux condenser, was degassed with N$_2$ at 25° C. and treated with Bu$_3$SnH (40.4 mL, 150 mmol). The mixture was slowly heated to 90° C. and stirred at 100° C. for 16 hours. The solution was cooled and the crude product was subjected to chromatography on Al$_2$O$_3$ gel with a 1-10% gradient of EtOAc in PE. The mixture of E-isomer and Z-isomer were obtained as colorless oil (15 g, 40.9%).

Step 2—Synthesis of 4-(6-chloro-2-(4-fluoro-1H-indol-2-yl)pyridin-3-yl)but-3-en-1-ol

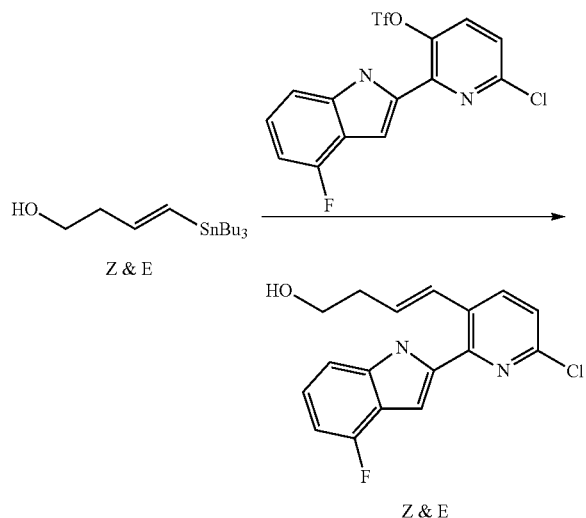

To a N₂ degassed solution of 4-(tributylstannyl)but-3-en-1-ol (1.2 g, 3.32 mmol), 6-chloro-2-(4-fluoro-1H-indol-2-yl)pyridin-3-yltrifluoromethanesulfonate (1.19 g, 3.02 mmol) and LiCl (128 mg, 3.02 mmol) in THF (10 mL) was added Pd(PPh₃)₄ (100 mg) under N₂. The reaction mixture was stirred at 60° C. for 15 hours. To the mixture, H₂O was added and the mixture was extracted with EtOAc. The combined organic phase was washed with brine, dried over Na₂SO₄. The crude product was purified by column (PE:EA=10:1 to 4:1) to give the mixture of (Z and E)-4-(6-chloro-2-(4-fluoro-1H-indol-2-yl)pyridin-3-yl)but-3-en-1-ol (530 mg, yield: 50%).

Step 3—Synthesis of (E)-5-(6-(4-fluoro-1H-indol-2-yl)-5-(4-hydroxybut-1-en-1-yl)pyridin-2-yl)-2-(4-fluorophenyl)-N-methyl-6-(N-methylmethylsulfonamido)benzofuran-3-carboxamide A solution of 4-(6-chloro-2-(4-fluoro-1H-indol-2-yl)pyridin-3-yl)but-3-en-1-ol (500 mg, 1.58 mmol), (2-(4-fluorophenyl)-3-(methylcarbamoyl)-6-(N-methylmethyl sulfonamido)benzofuran-5-yl)boronic acid (800 mg, 1.89 mmol) and Na₂CO₃ (340 mg, 3.15 mmol) in dioxane/DMF/H₂O (5 mL/1 mL/0.2 mL) was added Pd₂(dba)₃ (10 mg) and X-Phos (10 mg) under N₂. It was put into a pre-heated oil-bath at 110° C. for 8 hours. The mixture was concentrated and it was extracted with EtOAc. The combined organic phase was washed with brine, and dried over Na₂SO₄. The crude product was purified by column (PE:EA=1:1) to give the pure product of (Z and E)-5-(6-(4-fluoro-1H-indol-2-yl)-5-(4-hydroxybut-1-en-1-yl)pyridin-2-yl)-2-(4-fluorophenyl)-N-methyl-6-(N-methylmethylsulfonamido)benzofuran-3-carboxamide (570 mg, yield: 52%).

Step 4—Synthesis of 5-(11-fluoro-6-(2-hydroxyethyl)-5,6-dihydroindolo[1,2-h][1,7]naphthyridin-2-yl)-2-(4-fluorophenyl)-N-methyl-6-(N-methylmethylsulfonamido)benzofuran-3-carboxamide

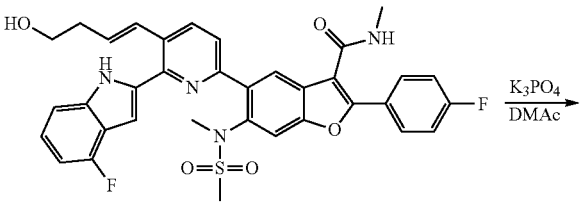

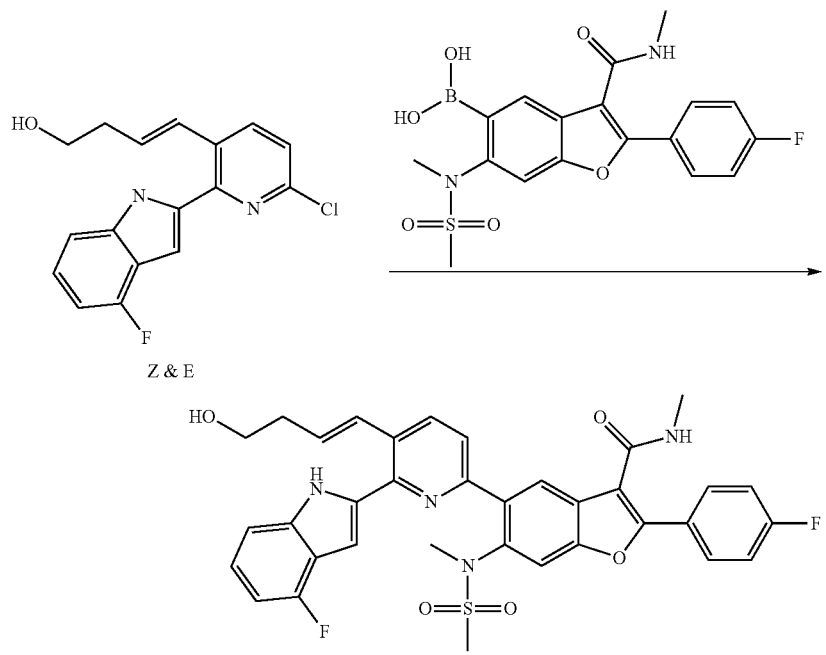 [SMILES: OCC/C=C/c1ccc(Cl)nc1-c1cc2c(F)cccc2[nH]1 ; CNC(=O)c1c(-c2ccc(F)cc2)oc2cc(N(C)S(C)(=O)=O)c(B(O)O)cc12 ; CNC(=O)c1c(-c2ccc(F)cc2)oc2cc(N(C)S(C)(=O)=O)c(-c3ccc(/C=C/CCO)c(-c4cc5c(F)cccc5[nH]4)n3)cc12]

139

-continued

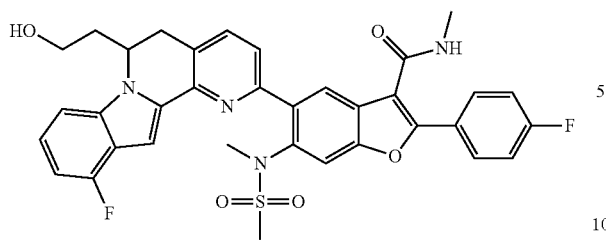

A solution of (Z and E)-5-(6-(4-fluoro-1H-indol-2-yl)-5-(4-hydroxybut-1-en-1-yl)pyridin-2-yl)-2-(4-fluorophenyl)-N-methyl-6-(N-methylmethylsulfonamido)benzofuran-3-carboxamide (300 mg, 0.457 mmol) in DMAc (9 mL) was added K₃PO₄.3H₂O (606 mg, 2.28 mmol) under N₂. It was put into a pre-heated oil-bath at 110° C. for 3 hours. The mixture was diluted with H₂O and it was extracted with EtOAc (500 mL×5). The combined organic phase was washed with brine, and dried over Na₂SO₄. The crude product was purified with Prep-HPLC to give the pure product of 5-(11-fluoro-6-(2-hydroxyethyl)-5,6-dihydroindolo[1,2-h][1,7]naphthyridin-2-yl)-2-(4-fluorophenyl)-N-methyl-6-(N-methylmethylsulfonamido)benzofuran-3-carboxamide (100 mg, yield: 30%). $^1$H-NMR (CDCl₃, 400 MHz) δ 7.97 (s, 1H), 7.88~7.92 (m, 2H), 7.63 (s, 1H), 7.60 (s, 1H), 7.40 (d, J=8.0 Hz, 1H), 7.09~7.22 (m, 5H), 6.72 (t, J=8.4 Hz, 1H), 5.83 (s, 1H), 5.02 (d, J=6.4 Hz, 1H), 3.43~3.55 (m, 4H), 3.35 (s, 3H), 3.10 (d, J=24.0 Hz, 1H), 2.94 (d, J=4.4 Hz, 3H), 2.61 (s, 3H), 1.78 (d, J=5.2 Hz, 2H). MS (M+H)⁺: 657.

Example 66

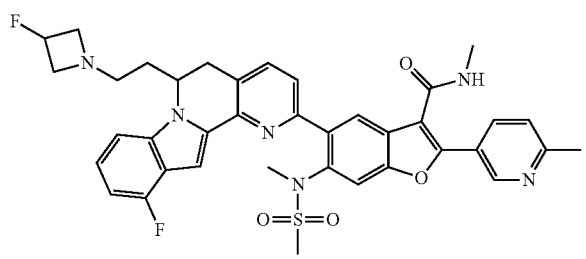 [SMILES: CNC(=O)c1c(-c2ccc(C)nc2)oc2cc(N(C)S(C)(=O)=O)c(-c3ccc4c(n3)-c3cc5c(F)cccc5n3C(CCN3CC(F)C3)C4)cc12]

Step 1—Synthesis of 2-(2-chloro-11-fluoro-5,6-dihydroindolo[1,2-h][1,7]naphthyridin-6-yl)acetonitrile

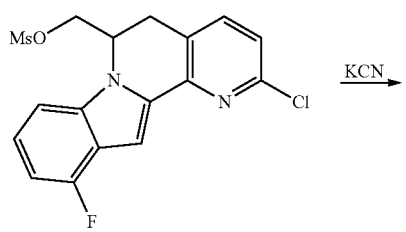

140

-continued

[structure]

A mixture of (2-chloro-11-fluoro-5,6-dihydroindolo[1,2-h][1,7]naphthyridin-6-yl)methyl methanesulfonate (1 g, 2.52 mmol) and KCN (491 mg, 7.55 mmol) in DMF (15 mL) was stirred at 80° C. for 15 hours. The mixture was diluted with water (30 mL) and extracted with EA (20 mL×3). The organic layer was washed with brine (30 mL), dried over Na₂SO₄ and concentrated. The residue was purified by column (PE:EA=1:1) to afford the desired product of 2-(2-chloro-11-fluoro-5,6-dihydroindolo[1,2-h][1,7]naphthyridin-6-yl)acetonitrile (600 mg, yield: 73%). $^1$H-NMR (CDCl₃, 400 MHz) δ 7.49 (d, J=8.0 Hz, 1H), 7.35 (s, 1H), 7.18 (d, J=8.0 Hz 2H), 7.09 (d, J=8.4 Hz, 1H), 6.77~6.79 (m, 1H), 5.00~5.06 (m, 1H), 3.48~3.54 (m, 1H), 3.27 (d, J=16.4 Hz, 1H), 2.54~2.59 (m, 1H), 2.37~2.44 (m, 1H). MS (M+H)⁺: 312/314.

Step 2—Synthesis of 2-(2-chloro-11-fluoro-5,6-dihydroindolo[1,2-h][1,7]naphthyridin-6-yl)acetaldehyde

[structure with DIBAL-H arrow]

A solution of 2-(2-chloro-11-fluoro-5,6-dihydroindolo[1,2-h][1,7]naphthyridin-6-yl)acetonitrile (300 mg, 0.78 mmol) in DCM (6 mL) was stirred at −78° C. for 10 minutes. Then DIBAL-H (1 ml, 1 mmol) was added slowly to the reaction mixture at −78° C. Then the mixture was heated at −78° C. for 2 hours. The mixture was diluted with water (30 mL) and extracted with EA (20 mL×3). The organic layer was washed with brine (30 mL), dried over Na₂SO₄ and concentrated. The residue was purified by column (PE:EA=3:1) to afford the desired product of 2-(2-chloro-11-fluoro-5,6-dihydroindolo[1,2-h][1,7]naphthyridin-6-yl)acetaldehyde (200 mg, yield: 66%). $^1$H-NMR (CDCl₃, 400 MHz) δ 9.63 (s, 1H), 7.44 (d, J=7.8 Hz, 1H), 7.34 (d, J=9.8 Hz, 1H), 7.11~7.13 (m, 2H), 7.04 (d, J=8.4 Hz, 1H), 6.75 (t, J=8.0 Hz, 1H), 3.42 (s, 1H), 3.03 (d, J=8.4 Hz, 1H), 2.61~2.70 (m, 2H). MS (M+H)+: 315/317.

Step 3—Synthesis of 2-chloro-11-fluoro-6-(2-(3-fluoroazetidin-1-yl)ethyl)-5,6-dihydroindolo[1,2-h][1,7]naphthyridine

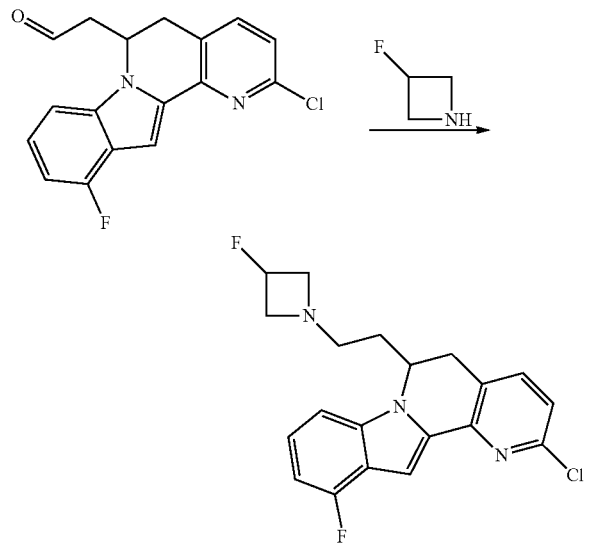

A mixture of 2-(2-chloro-11-fluoro-5,6-dihydroindolo[1,2-h][1,7]naphthyridin-6-yl)acetaldehyde (200 mg, 0.617 mmol) and 3-fluoroazetidine (95 mg, 1.23 mmol) in DCM (4 mL) was stirred at room temperature for 30 minutes under $N_2$. Then Na(OAc)$_3$BH (50 mg) was added to the mixture, and the mixture was stirred at room temperature for 1 hour. After dilution with water (30 mL) and extraction with EA (20 mL×3), the organic layer was washed with brine (30 mL*3), dried over $Na_2SO_4$ and concentrated. The residue was purified by column chromatography (PE:EA=1:1) to afford the desired product of 2-chloro-11-fluoro-6-(2-(3-fluoroazetidin-1-yl)ethyl)-5,6-dihydroindolo[1,2-h][1,7]naphthyridine (100 mg, yield: 43%). $^1$H-NMR (CDCl$_3$, 400 MHz) δ 7.44 (d, J=8.0 Hz, 1H), 7.3 (s, 1H), 7.16 (d, J=8.0 Hz, 1H), 7.10 (t, J=4.8 Hz, J=2.7 Hz, 2H), 6.69~6.74 (m, 1H), 5.11~5.14 (m, 0.5H), 4.97~4.50 (m, 0.5H), 4.87 (t, J=4.8 Hz, 1H), 3.57 (d, J=6.8 Hz, 1H), 3.33~3.39 (m, 1H), 2.95~3.06 (m, 2H), 2.2~72.38 (m, 1H). MS (M+H)+: 374/376.

Step 4—Synthesis of 5-(11-fluoro-6-(2-(3-fluoroazetidin-1-yl)ethyl)-5,6-dihydroindolo[1,2-][1,7]naphthyridin-2-yl)-N-methyl-6-(N-methylmethylsulfonamido)-2-(6-methylpyridin-3-yl)benzofuran-3-carboxamide

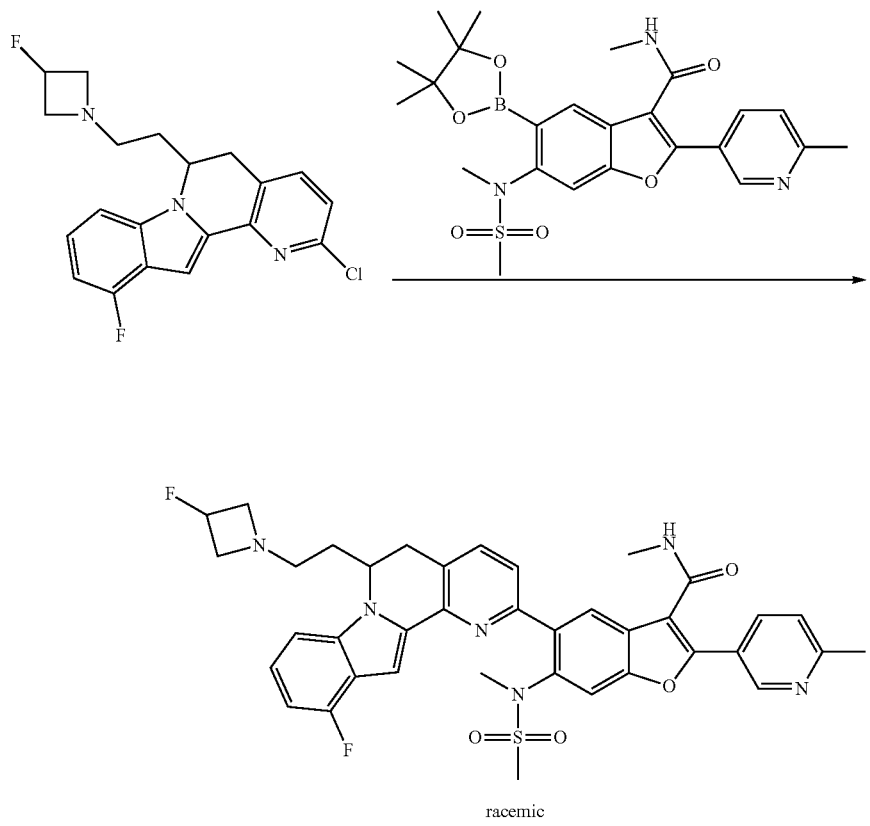

A mixture of 2-chloro-11-fluoro-6-(2-(3-fluoroazetidin-1-yl)ethyl)-5,6-dihydroindolo[1,2-h][1,7]naphthyridine (100 mg, 0.269 mmol), N-methyl-6-(N-methylmethylsulfonamido)-2-(6-methylpyridin-3-yl)-5-(4,4,5,5-tetramethyl-1,3,2-dioxaborolan-2-yl)benzofuran-3-carboxamide (150 mg, 0.295 mmol), $K_2CO_3$ (75 mg, 0.537 mmol), $Pd_2(dba)_3$ (15 mg, 0.027 mmol) and X-Phos (10 mg, 0.054 mmol) in dioxane/$H_2O$ (4 mL/10 d) was stirred at 110° C. for 4 hours under $N_2$ atmosphere. The mixture was then filtered through Celite and concentrated. The residue was purified by column chromatography (PE:EA=2:1) to afford the desired product of 5-(11-fluoro-6-(2-(3-fluoroazetidin-1-yl)ethyl)-5,6-dihydroindolo[1,2-h][1,7]naphthyridin-2-yl)-N-methyl-6-(N-methylmethylsulfonamido)-2-(6-methylpyridin-3-yl)benzofuran-3-carboxamide (85 mg, yield: 44.9%). $^1$H-NMR (CDCl$_3$, 400 MHz) δ 8.97 (s, 1H), 8.17 (t, J=6.0, 2.0 Hz, 1H), 8.00 (s, 1H), 7.61 (t, J=8.0 Hz, 2H), 7.39 (d, J=8.0 Hz, 1H), 7.24 (d, J=6.8 Hz, 2H), 7.12 (s, 2H), 6.73~6.77 (m, 1H), 5.97 (d, J=4.8 Hz, 1H), 4.97~5.14 (m, 1H), 4.95 (d, J=6.0 Hz, 1H), 3.49~3.56 (m, 4H), 3.33 (s, 3H), 3.00~3.06 (m, 3H), 2.95 (d, J=4.8 Hz, 3H), 2.62 (s, 3H), 2.58 (s, 3H), 2.33~2.36 (m, 1H), 1.59~1.56 (m, 2H). MS (M+H)$^+$: 711.

Examples 67-71

Examples 67 to 71, depicted in the table below, were prepared in accordance with the method described in Example 66.

| Example | Structure | NMR | MS (M + H)$^+$ |
|---|---|---|---|
| 67 | enantiomer 1 | Same as compound 66 | 711 |
| 68 | enantiomer 2 | Same as compound 66 | 711 |
| 69 | 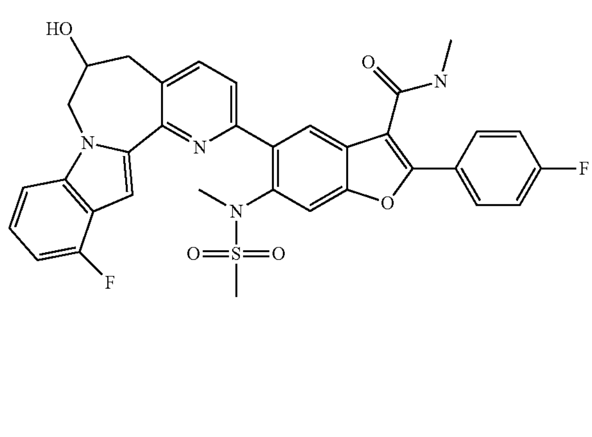 [SMILES: CNC(=O)c1c(-c2ccc(F)cc2)oc2cc(N(C)S(C)(=O)=O)c(-c3ccc4c(n3)-c3cc5c(F)cccc5n3CC(O)C4)cc12] | $^1$H-NMR (CDCl$_3$, 400 MHz) δ 8.02 (s, 1H), 7.96 (dd, J =5.6, 8.4 Hz, 2H), 7.63~7.69 (m, 2H), 7.53 (d, J = 7.6 Hz, 1H), 7.14~7.23 (m, 4H), 7.08 (s, 1H), 6.74~6.82 (m, 1H), 6.07~6.08 (m, 1H), 4.62~4.65 (m, 1H), 4.08~4.17 (m, 2H), 3.31 (s, 3H), 3.06 (dd, J = 6.0, 13.6 Hz, 1H), 2.97 (d, J = 4.8 Hz, 3H), 2.78 (s, 3H), 2.70 (dd, J = 6.8, 13.6 Hz, 1H). | 643 |

| Example | Structure | NMR | MS (M + H)+ |
|---|---|---|---|
| 70 | 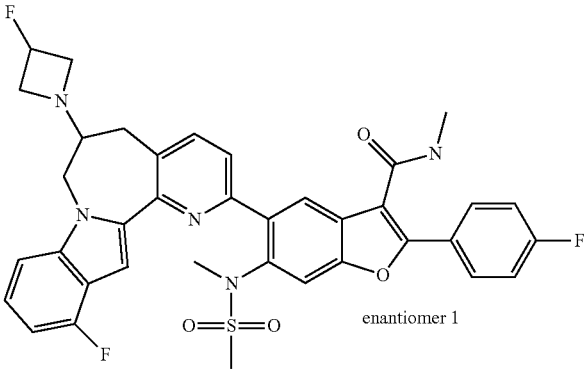 [SMILES: CNC(=O)c1c(-c2ccc(F)cc2)oc2cc(N(C)S(C)(=O)=O)c(-c3ccc4c(n3)-c3cc5c(F)cccc5n3CC(N3CC(F)C3)C4)cc12] enantiomer 1 | ¹H-NMR (CDCl₃, 400 MHz) δ 8.98 (s, 1H), 8.18 (d, J = 8.4 Hz, 1H), 7.95 (s, 1H), 7.63 (d, J = 9.6 Hz, 2H), 7.50 (d, J = 7.6 Hz, 1H), 7.23 (d, J = 8.0 Hz, 1H), 7.12~7.14 (m, 1H), 7.05 (d, J = 8.0 Hz, 1H), 7.00 (s, 1H), 6.73 (t, J = 10.0 Hz, 1H), 6.12 (br d, J = 4.8 Hz, 1H), 5.20 (d, J = 5.2 Hz, 0.5H), 5.06 (t, J = 5.2 Hz, 0.5H), 3.46~3.89 (m, 2H), 3.70 (s, 3H), 3.56 (s, 3H), 3.25~3.68 (m, 5H), 2.94 (d, J = 4.4 Hz, 3H), 2.44~2.62 (m, 5H). | 697 |
| 71 | 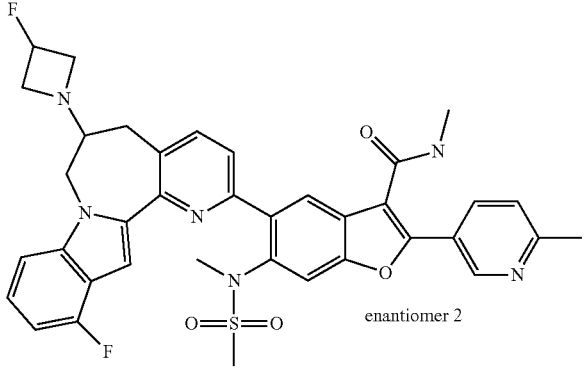 [SMILES: CNC(=O)c1c(-c2ccc(C)nc2)oc2cc(N(C)S(C)(=O)=O)c(-c3ccc4c(n3)-c3cc5c(F)cccc5n3CC(N3CC(F)C3)C4)cc12] enantiomer 2 | Same as compound 71 | 697 |

Example 72

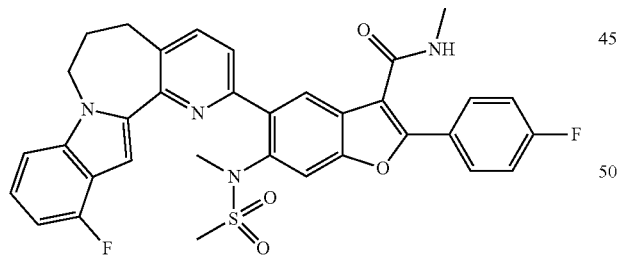

Step 1—Synthesis of (E)-ethyl 3-(2,6-dichloropyridin-3-yl)acrylate

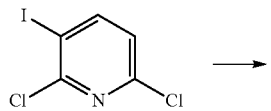 →

-continued

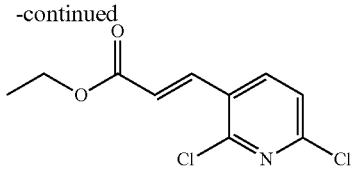

To a solution of 2,6-dichloro-3-iodopyridine (3.0 g, 10.95 mmol), (E)-ethyl 3-(4,4,5,5-tetramethyl-1,3,2-dioxaborolan-2-yl)acrylate (2.476 g, 10.95 mmol), and Dichloro[1,1'-bis(di-tert-butylphosphino)ferrocene]palladium (II) (0.357 g, 0.548 mmol) in THF (81 mL) was added 1M (aq) K₂CO₃ (54.8 mL, 54.8 mmol). A steady stream of N₂ was bubbled through the resultant mixture for 5 minutes. Stirring was continued at ambient temperature for 2 h then the mixture was diluted with EtOAc and the organic layer washed successively with water (1×) and brine (1×). The organic layer was dried over MgSO₄, filtered, and concentrated in vacuo. The residue was purified by silica gel column chromatography using a gradient of 0-30% EtOAc/Hexanes as eluent to give the title compound as a tan solid. ¹H NMR δ (ppm) (CHCl₃-d): 7.95 (1H, d, J=16 Hz), 7.90 (1H, d, J=8.1 Hz), 7.35 (1H, d, J=8.1 Hz), 6.47 (1H, d, J=16 Hz), 4.32 (2H, q, J=7.15 Hz), 1.38 (3H, t, J=7.14 Hz). MS (M+H)+: 245.

Step 2—Synthesis of ethyl 3-(2,6-dichloropyridin-3-yl)propanoate

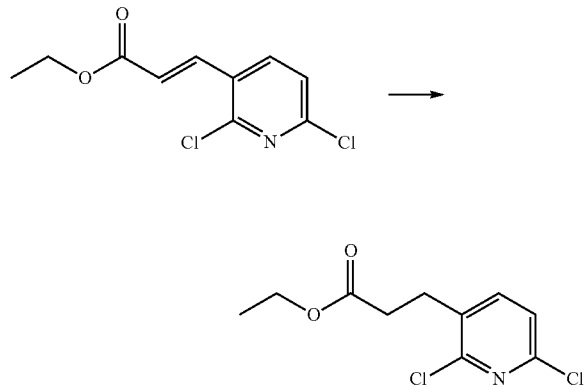

To a solution of (E)-ethyl 3-(2,6-dichloropyridin-3-yl) acrylate (500 mg, 2.032 mmol) in Ethanol (15 mL) was added 10% platinum on carbon (96 mg, 0.049 mmol). The flask was alternately evacuated and filled with hydrogen five times. The solution was stirred under 1 ATM (balloon) of hydrogen for 1 h, then filtered through celite, while washing well with MeOH and EtOAc. The filtrate was concentrated in vacuo to provide the title compound which was used without further purification. $^1$H NMR δ (ppm) (CHCl$_3$-d): 7.62 (1H, d, J=7.92 Hz), 7.24 (1H, d, J=7.8), 4.15 (2H, q, J=7.15 Hz), 3.05 (2H, t, J=7.35 Hz), 2.69 (2H, t, J=7.35 Hz), 1.31~1.24 (3H, m). MS (M+H)+: 247.

Step 3—Synthesis of ethyl 3-(2,6-dichloropyridin-3-yl)propan-1-ol

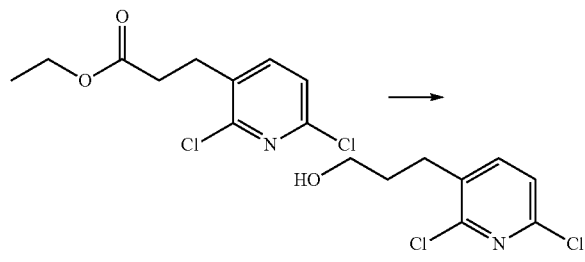

To a solution of ethyl 3-(2,6-dichloropyridin-3-yl)propanoate in THF (12 mL) was added LiBH$_4$ (88 mg, 4.03 mmol). The resultant mixture was stirred at ambient temperature for 2.5 h then was cooled to 0° C. and carefully quenched by addition of saturated NH$_4$Cl(aq) solution. The reaction mixture was diluted with EtOAc and the organic layer washed successively with H$_2$O (1×) and brine (1×). The organic extract was dried over MgSO$_4$, filtered, and concentrated in vacuo. Purification by silica gel column chromatography using a gradient of 0-60% EtOAc/Hexanes as eluent provided the title compound. $^1$H NMR δ (ppm) (CHCl$_3$-d): 7.58 (1H, d, J=7.92 Hz), 7.25 (1H, d, J=7.80), 3.73 (2H, q, J=5.48 Hz), 2.85 (2H, t, J=7.76 Hz), 1.95~1.88 (2H, m), 1.42 (1H, m). MS (M+H)+: 205.

Step 4—Synthesis of 5-(6-chloro-5-(3-hydroxypropyl)pyridin-2-yl)-2-(4-fluorophenyl)-N-methyl-6-(N-methylmethylsulfonamido)benzofuran-3-carboxamide

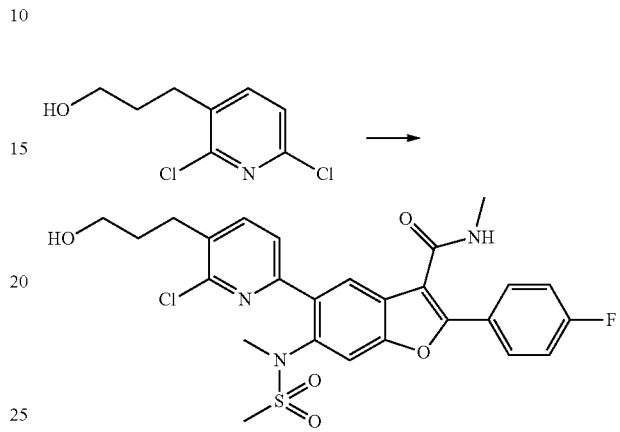

To a mixture of ethyl 3-(2,6-dichloropyridin-3-yl)propan-1-ol (180 mg, 0.873 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (439 mg, 0.873 mmol), XantPhos Biphenyl precatalyst (78 mg, 0.087 mmol), and cesium carbonate (854 mg, 2.62 mmol) was added 1,4-Dioxane (7.3 mL) and water (1.5 mL). A steady stream of N$_2$ was bubbled through the reaction mixture for 5 minutes then the mixture was heated to 70° C. for 4 h. The mixture was cooled to ambient temperature, diluted with EtOAc, and washed successively with H$_2$O (1×) and brine (1×). The organic layer was dried over MgSO$_4$, filtered, and concentrated in vacuo. The residue was purified by silica gel column chromatography using a gradient of 0-100% EtOAc/CH$_2$Cl$_2$ as eluent. Further purification by preparative TLC using 50% EtOAc/CH$_2$Cl$_2$ as eluent provided the title compound. $^1$H NMR δ (ppm) (CHCl$_3$-d): 8.01~7.96 (3H, m), 7.72 (1H, d, J=7.68 Hz), 7.68 (1H, s), 7.56 (1H, d, J=7.70 Hz), 7.23 (2H, t, J=8.6 Hz), 5.95 (1H, br s), 3.78 (2H, q, J=5.76 Hz), 3.24 (3H, s), 3.03 (3H, d, J=4.88 Hz), 2.93 (2H, t, J=7.76 Hz), 2.88 (3H, s), 2.03~1.97 (2H, m). MS (M+H)+: 545.

Step 5—Synthesis of 5-(6-(4-fluoro-1H-indol-2-yl)-5-(3-hydroxypropyl)pyridin-2-yl)-2-(4-fluorophenyl)-N-methyl-6-(N-methylmethylsulfonamido)benzofuran-3-carboxamide

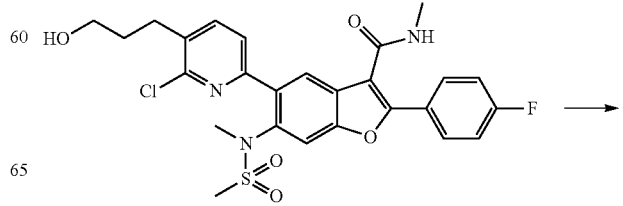

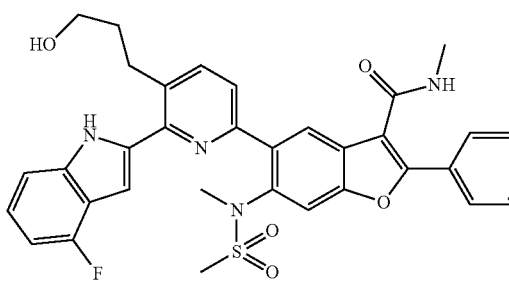

Step 6—Synthesis of 5-(12-fluoro-6,7-dihydro-5H-pyrido[2',3':3,4]azepino[1,2-a]indol-2-yl)-2-(4-fluorophenyl)-N-methyl-6-(N-methylmethylsulfonamido)benzofuran-3-carboxamide

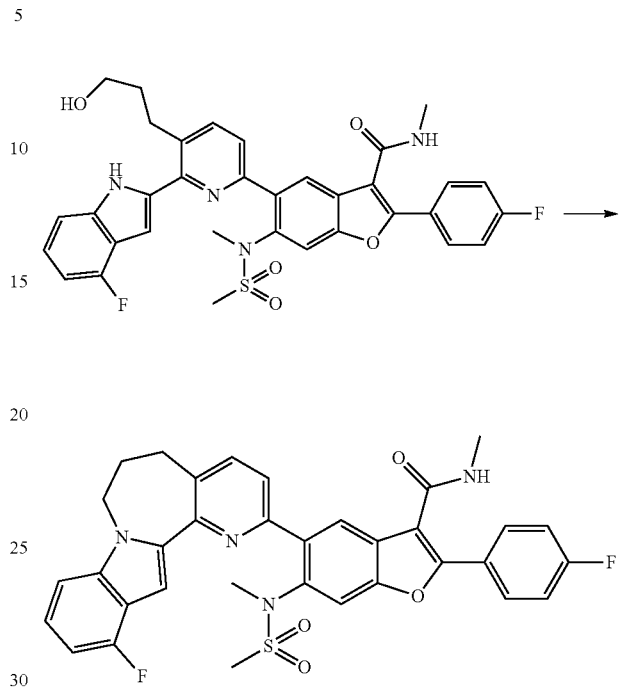

To a mixture of 5-(6-chloro-5-(3-hydroxypropyl)pyridin-2-yl)-2-(4-fluorophenyl)-N-methyl-6-(N-methylmethylsulfonamido)benzofuran-3-carboxamide (180 mg, 0.330 mmol), 4-fluoroindole-2-boronic acid pinacol ester (129 mg, 0.494 mmol), cesium carbonate (215 mg, 0.659 mmol) and dichloro[1,1'-bis(di-tert-butylphosphino)ferrocene]palladium (II) (21.49 mg, 0.033 mmol) was added 1,4-dioxane (3 mL) and H$_2$O (0.3 mL). A steady stream of N$_2$ was bubbled through the reaction mixture for 5 minutes then the mixture was heated to 90° C. for 3 h. The mixture was cooled to ambient temperature, diluted with EtOAc, and washed successively with H$_2$O (1×) and brine (1×). The organic layer was dried over MgSO$_4$, filtered, and concentrated in vacuo. The residue was purified by silica gel column chromatography using a gradient of 0-100% EtOAc/CH$_2$Cl$_2$ as eluent. The residue was triturated with CH$_2$Cl$_2$ to provide the title compound as a white solid. $^1$H NMR δ (ppm) (CHCl$_3$-d): 10.30 (1H, br s), 8.07 (1H, s), 8.00 (2H, dd, J=8.56, 5.31 Hz), 7.78 (1H, d, J=7.88 Hz), 7.69 (1H, s), 7.50 (1H, d, J=7.85 Hz), 7.27~7.23 (3H, m), 7.17~7.13 (2H, m), 6.81~6.78 (1H, m), 5.93~5.87 (1H, m), 3.89 (2H, d, J=5.37 Hz), 3.24 (2H, t, J=7.86 Hz), 3.16 (3H, s), 3.02 (3H, d, J=4.90 Hz), 2.92 (3H, s), 2.13 (2H, t, J=7.43 Hz). MS (M+H)$^+$: 645.

To a solution of 5-(6-(4-fluoro-1H-indol-2-yl)-5-(3-hydroxypropyl)pyridin-2-yl)-2-(4-fluorophenyl)-N-methyl-6-(N-methylmethylsulfonamido)benzofuran-3-carboxamide (153 mg, 0.237 mmol) and triphenylphosphine (62.2 mg, 0.237 mmol) in THF was added diisopropyl azodicarboxylate (0.046 mL, 0.237 mmol). The resultant mixture was stirred at ambient temperature for 10 h then was concentrated in vacuo and the residue purified by silica gel column chromatography using a step gradient of 0-50-100% EtOAc/Hexanes as eluent. $^1$H NMR δ (ppm) (CHCl$_3$-d): 8.07 (1H, s), 8.02 (2H, dd, J=8.61, 5.32 Hz), 7.75 (1H, d, J=7.78 Hz), 7.70 (1H, s), 7.60 (1H, d, J=7.77 Hz), 7.26~7.0 (4H, m), 7.09 (1H, s), 6.85~6.81 (1H, m), 5.98 (1H, br s), 4.23 (2H, t, J=6.66 Hz), 3.35 (3H, s), 3.03 (3H, d, J=4.90 Hz), 2.85 (2H, t, J=7.00 Hz), 2.80 (3H, s), 2.47~2.42 (2H, m), MS (M+H)$^+$: 627.

Example 73

Example 73, depicted in the table below, were prepared in accordance with the method described in Example 72.

| Compound ID | Structure | NMR | MS (M + H)$^+$ |
| --- | --- | --- | --- |
| 73 | ![structure] | $^1$NMR δ (ppm)(CHCl$_3$-d): 8.09 (1H, s), 8.04-8.00 (2H, m), 7.77 (1H, d, J = 7.83 Hz), 7.68 (1H, s), 7.65 (2H, d, J = 7.90 Hz), 7.52 (1H, d, J = 7.34 Hz), 7.34-7.30 (1H, m), 7.25-7.21 (3H, m) 5.96 (1H, br s) 4.27 (2H, t, J = 6.64 Hz), 3.36 (3H, s), 3.04 (3H, d, J = 4.91 Hz), 2.89-2.82 (5H, m), 2.50-2.43 (2H, m). | 634 |

Example 74

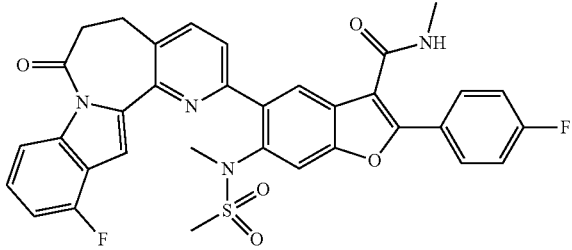 [SMILES: CNC(=O)c1c(-c2ccc(F)cc2)oc2cc(N(C)S(C)(=O)=O)c(-c3ccc4c(n3)-c3cc5c(F)cccc5n3C(=O)CC4)cc12]

Step 1—Synthesis of ethyl 3-(2-chloro-6-(2-(4-fluorophenyl)-3-(methylcarbamoyl)-6-(N-methylmethylsulfonamido)benzofuran-5-yl)pyridin-3-yl)propanoate

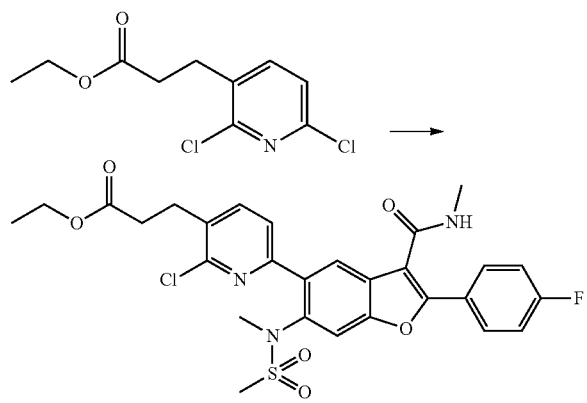

To a mixture of ethyl 3-(2,6-dichloropyridin-3-yl)propanoate (170 mg, 0.685 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (344 mg, 0.685 mmol), XantPhos Biphenyl precatalyst (60.9 mg, 0.069 mmol), and cesium carbonate (670 mg, 2.056 mmol) was added 1,4-dioxane (5.7 mL) and H$_2$O (1.2 mL). A steady stream of N$_2$ was bubbled through the reaction mixture for 5 minutes then the mixture was heated to 70° C. for 16 h. The mixture was cooled to ambient temperature, diluted with EtOAc, and washed successively with H$_2$O (1×) and brine (1×). The organic layer was dried over MgSO$_4$, filtered, and concentrated in vacuo. The residue was purified by silica gel column chromatography using a gradient of 0-100% EtOAc/Hexanes as eluent. $^1$H NMR δ (ppm) (CHCl$_3$-d): 8.01~7.96 (3H, m), 7.75 (1H, t, J=7.74 Hz), 7.69 (1H, s), 7.55 (1H, d, J=7.70 Hz), 7.27~7.21 (2H, m) 5.91 (1H, br s), 4.19 (2H, q, J=7.12 Hz), 3.27~3.20 (3H, m), 3.18~3.12 (2H, m), 3.03 (3H, d, J=4.92 Hz), 2.90~2.80 (3H, m), 2.77 (2H, t, J=7.51 Hz), 1.30 (3H, t, J=7.15 Hz). MS (M+H)$^+$: 588.

Step 2—Synthesis of ethyl 3-(2-(4-fluoro-1H-indol-2-yl)-6-(2-(4-fluorophenyl)-3-(methylcarbamoyl)-6-(N-methylmethylsulfonamido)benzofuran-5-yl)pyridin-3-yl)propanoate

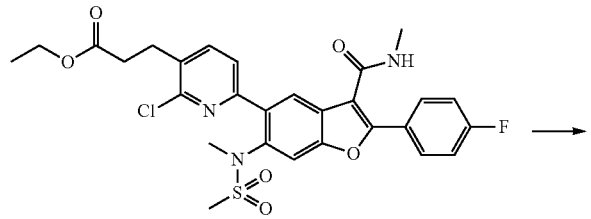

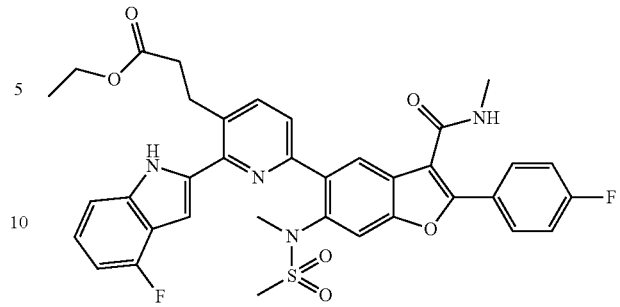

To a mixture of ethyl 3-(2-chloro-6-(2-(4-fluorophenyl)-3-(methylcarbamoyl)-6-(N-methylmethylsulfonamido)benzofuran-5-yl)pyridin-3-yl)propanoate (120 mg, 0.204 mmol), 4-fluoro-2-(4,4,5,5-tetramethyl-1,3,2-dioxaborolan-2-yl)-1H-indole (80 mg, 0.306 mmol), cesium carbonate (133 mg, 0.408 mmol) and dichloro[1,1'-bis(di-t-butylphosphino)ferrocene]palladium (II) (13.3 mg, 0.02 mmol) was added 1,4-dioxane (1.86 mL) and H$_2$O (0.186 mL). A steady stream of N$_2$ was bubbled through the reaction mixture for 5 minutes then the mixture was heated to 90° C. for 9 h. The mixture was cooled to ambient temperature, diluted with EtOAc, and washed successively with H$_2$O (1×) and brine (1×). The organic layer was dried over MgSO$_4$, filtered, and concentrated in vacuo. The residue was purified by silica gel column chromatography using a gradient of 0-100% EtOAc/Hexanes as eluent and further purified by silica gel column chromatography using a step gradient of 0-20-80% EtOAc/CH$_2$Cl$_2$ as eluent. MS (M+H)+: 687.

Step 3—Synthesis of 3-(2-(4-fluoro-1H-indol-2-yl)-6-(2-(4-fluorophenyl)-3-(methylcarbamoyl)-6-(N-methylmethylsulfonamido)benzofuran-5-yl)pyridin-3-yl)propanoic acid

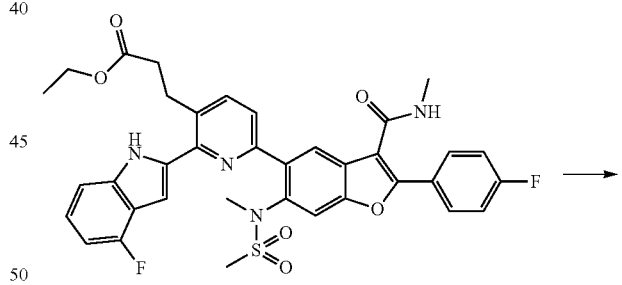

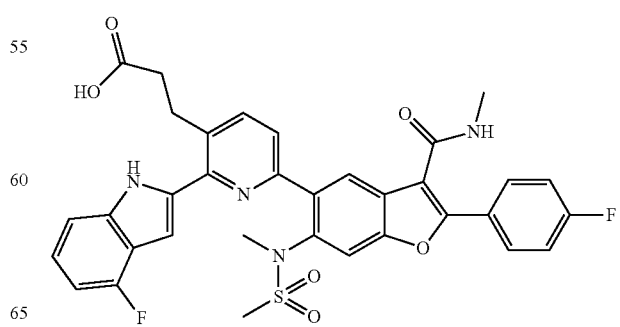

A mixture of ethyl 3-(2-(4-fluoro-1H-indol-2-yl)-6-(2-(4-fluorophenyl)-3-(methylcarbamoyl)-6-(N-methylmethylsulfonamido)benzofuran-5-yl)pyridin-3-yl)propanoate (91 mg, 0.133 mmol) and lithium hydroxide monohydrate (27.8 mg, 0.663 mmol) were suspended in THF (0.53 mL), MeOH (0.27 mL), and H₂O (0.2 mL). The resultant mixture was stirred at ambient temperature overnight then cooled in an ice bath and acidified to pH 2 with 1 N HCl. The mixture was then diluted with EtOAc and H₂O, separated into layers and the aqueous layer extracted with EtOAc (2×). The combined organic layers were washed with brine (4×) until last brine wash was pH 7 then were dried over MgSO₄, filtered, and concentrated in vacuo. The resulting product was azeotroped from CH₃CN (4×) and used as a tan solid without further purification. MS (M+H)⁺: 659.

ant mixture was stirred for 1 h at ambient temperature then was diluted with EtOAc and washed successively with H₂O (3×) and brine (1×). The organic layer was dried over MgSO₄, filtered, concentrated in vacuo, and the residue purified by silica gel column chromatography using a gradient of 0-30% EtOAc/CH₂Cl₂ as eluent. ¹H NMR δ (ppm) (CHCl₃-d): 8.38 (1H, d, J=8.46 Hz), 8.12 (1H, s), 8.02 (2H, dd, J=8.55, 5.32 Hz), 7.69 (3H, d, J=9.74 Hz), 7.60 (1H, d, J=7.80 Hz), 7.36 (1H, td, J=8.24, 5.56 Hz), 7.25 (2H, t, J=8.60 Hz), 7.02 (1H, t, J=8.68 Hz), 5.95 (1H, br s), 3.35 (3H, s), 3.27~3.22 (2H, m), 3.20~3.15 (2H, m), 3.05 (3H, d, J=4.90 Hz), 2.85 (3H, s). MS (M+H)⁺: 641.

Example 75

Example 75, depicted in the table below, were prepared in accordance with the method described in Example 74.

| Example | Structure | NMR | MS (M + H)⁺ |
|---|---|---|---|
| 75 | 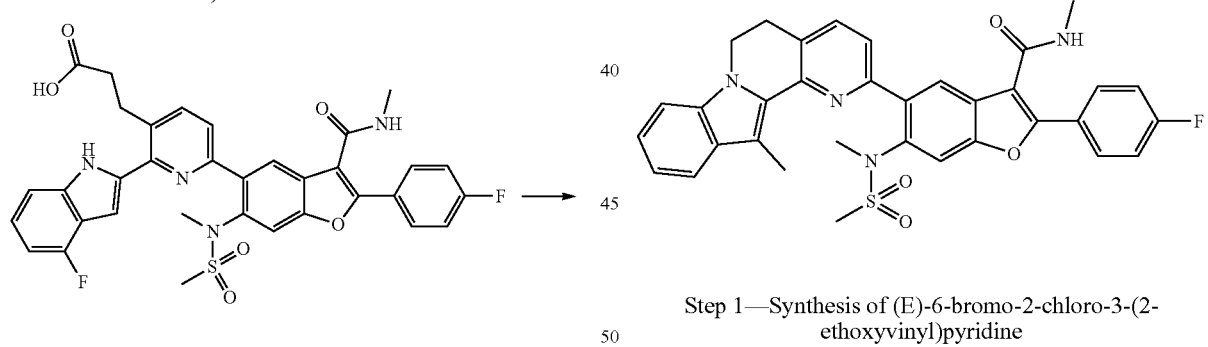 | ¹H NMR δ (ppm)(CHCl₃-d): 8.82 (1 H, d, J = 8.52 Hz), 8.12 (1 H, s), 8.05-7.99 (2 H, m), 7.82 (1 H, s), 7.72 (1 H, d, J = 7.87 Hz), 7.68-7.62 (3 H, m), 7.47 (1 H, t, J = 8.02 Hz), 7.24 (2 H, t, J = 8.65 Hz), 6.00 (1 H, br s), 3.40 (3 H, s), 3.31-3.25 (2 H, m), 3.23-3.17 (2 H, m), 3.05 (3 H, dd, J = 9.71, 4.93 Hz), 2.90-2.88 (3 H, m). | 648 |

Step 4—Synthesis of 5-(12-fluoro-7-oxo-6,7-dihydro-5H-pyrido[2',3':3,4]azepino[1,2-a]indol-2-yl)-2-(4-fluorophenyl)-N-methyl-6-(N-methylmethylsulfonamido)benzofuran-3-carboxamide

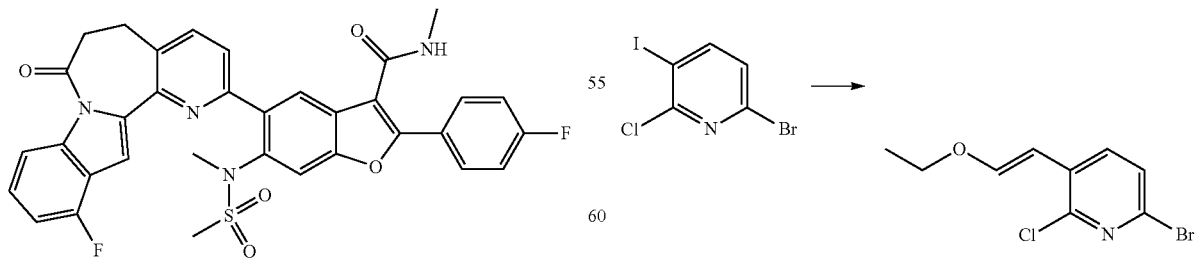

To a mixture of 3-(2-(4-fluoro-1H-indol-2-yl)-6-(2-(4-fluorophenyl)-3-(methylcarbamoyl)-6-(N-methylmethylsulfonamido)benzofuran-5-yl)pyridin-3-yl)propanoic acid (88 mg, 0.133 mmol) and HATU (126 mg, 0.333 mmol) in DMF (6650 μl) was added DIEA (116 μl, 0.665 mmol). The result- Example 76

Step 1—Synthesis of (E)-6-bromo-2-chloro-3-(2-ethoxyvinyl)pyridine

To a mixture of 6-bromo-2-chloro-3-iodopyridine (8.0 g, 25.1 mmol), (E)-2-(2-ethoxyvinyl)-4,4,5,5-tetramethyl-1,3,2-dioxaborolane (4.98 g, 25.1 mmol), cesium carbonate (16.38 g, 50.3 mmol), and [1,1'-bis(diphenylphosphino)ferrocene]dichloropalladium(II) (2.052, 2.51 mmol) was added 1,4-dioxane (100 mL) and H₂O (10 mL). A steady stream of N₂ was bubbled through the reaction mixture for 15 minutes then the mixture was heated to 73° C. for 20 h. The mixture was cooled to ambient temperature, diluted with EtOAc, and washed successively with H₂O (2×) and brine (1×). The organic layer was dried over MgSO₄, filtered, and concentrated in vacuo. The residue was purified by silica gel column chromatography using a step gradient of 0-10-60% EtOAc/Hexanes as eluent. MS (M+H): 261.

Step 2—Synthesis of (E)-5-(6-chloro-5-(2-ethoxyvinyl)pyridin-2-yl)-2-(4-fluorophenyl)-N-methyl-6-(N-methylmethylsulfonamido)benzofuran-3-carboxamide

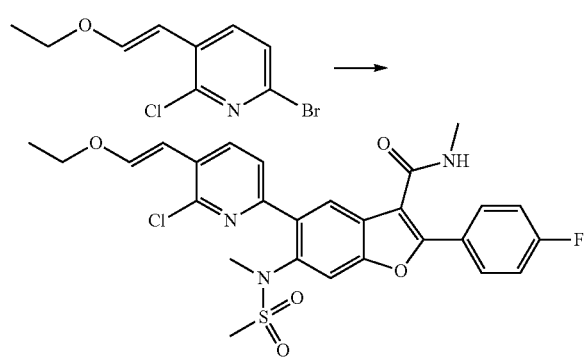

To a mixture of (E)-6-bromo-2-chloro-3-(2-ethoxyvinyl)pyridine (3.37 g, 12.84 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (6.45 g, 12.84 mmol), cesium carbonate (10.46 g, 32.1 mmol), and 1,1' Bis(diphenylphosphino)ferrocene-palladium(II)dichloride dichloromethane complex (0.524 g, 0.642 mmol) was added 1,4-Dioxane (83 mL) followed by H₂O (8.34 mL). A steady stream of N₂ was bubbled through the reaction mixture for 7 minutes then the mixture was heated to 60° C. for 16 h. The mixture was cooled to ambient temperature, diluted with EtOAc, and washed successively with H₂O (1×) and brine (1×). The organic layer was dried over MgSO₄, filtered, and concentrated in vacuo. The solid residue was triturated with EtOAc and further purified by silica gel column chromatography using a gradient of 0-30% EtOAc/CH₂Cl₂ as eluent. Further purification by silica gel column chromatography with a gradient of 0-100% EtOAc/Hexanes as eluent provided the title compound as a tan solid. ¹H NMR δ (ppm) (CHCl₃-d): 8.03~7.97 (3H, m), 7.79 (1H, d, J=7.96 Hz), 7.69 (1H, s), 7.52 (1H, d, J=7.50 Hz), 7.28~7.00 (2H, m), 7.11 (1H, d, J=13.00 Hz), 6.12 (1H, d, J=13.00 Hz), 5.91 (1H, br s), 4.04 (2H, q, J=7.04 Hz), 3.24 (3H, s), 3.03 (3H, d, J=4.87 Hz), 2.89 (3H, s), 1.44 (3H, t, J=7.00). MS (M+H): 557.

Step 3-Synthesis of (E)-tert-butyl 2-(3-(2-ethoxyvinyl)-6-(2-(4-fluorophenyl)-3-(methylcarbamoyl)-6-(N-methylmethylsulfonamido)benzofuran-5-yl)pyridin-2-yl)-3-methyl-1H-indole-1-carboxylate

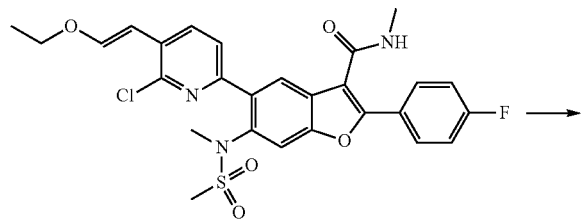

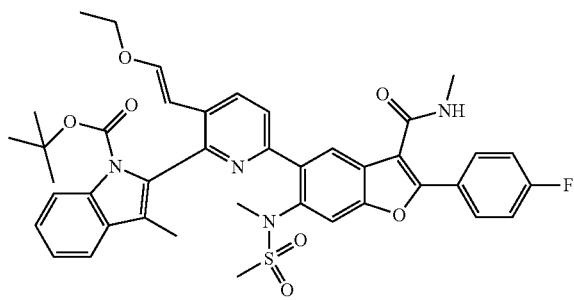

To a mixture of (E)-5-(6-chloro-5-(2-ethoxyvinyl)pyridin-2-yl)-2-(4-fluorophenyl)-N-methyl-6-(N-methylmethylsulfonamido)benzofuran-3-carboxamide (150 mg, 0.269 mmol), tert-butyl 3-methyl-2-(4,4,5,5-tetramethyl-1,3,2-dioxaborolan-2-yl)-1H-indole-1-carboxylate (144 mg, 0.403 mmol), cesium carbonate (175 mg, 0.538 mmol), and 1,1'-bis(di-tert-butylphosphino)ferrocene palladium dichloride (17.5 mg, 0.027 mmol) was added 1,4-dioxane (2.44 mL) and H₂O (0.244 mL). A steady stream of N₂ was bubbled through the reaction mixture for 5 minutes then the mixture was heated to 90° C. for 10 h. The mixture was cooled to ambient temperature, diluted with EtOAc, and washed successively with H₂O (1×) and brine (1×). The organic layer was dried over MgSO₄, filtered, and concentrated in vacuo. The residue was purified by silica gel column chromatography using a gradient of 0-100% EtOAc/Hexanes as eluent. MS (M+H): 753.

Step 4-Synthesis of tert-butyl 2-(6-(2-(4-fluorophenyl)-3-(methylcarbamoyl)-6-(N-methylmethylsulfonamido)benzofuran-5-yl)-3-(2-hydroxyethyl)pyridin-2-yl)-3-methyl-1H-indole-1-carboxylate

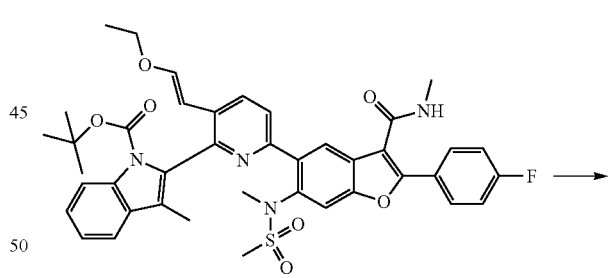

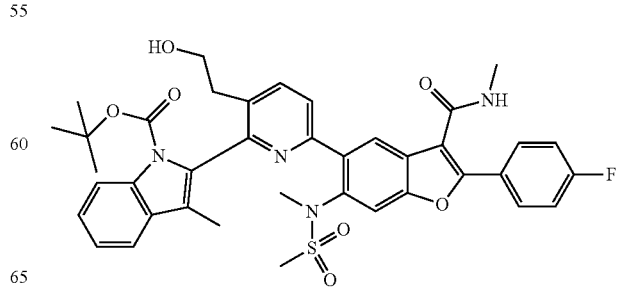

To a solution of (E)-tert-butyl 2-(3-(2-ethoxyvinyl)-6-(2-(4-fluorophenyl)-3-(methylcarbamoyl)-6-(N-methylmethyl-sulfonamido)benzofuran-5-yl)pyridin-2-yl)-3-methyl-1H-indole-1-carboxylate (72 mg, 0.096 mmol) in THF (0.350 mL) at 0° C. was added Mercuric acetate (36.6 mg, 0.115 mmol) in H$_2$O (0.350 mL). After stirring the resultant mixture at 0° C. for 30 min, NaBH$_4$ (14.47 mg, 0.383 mmol) in 0.580 mL of saturated (aq) K$_2$CO$_3$ solution was added and the reaction mixture was warmed to ambient temperature. After 1.5 h at ambient temperature, the reaction mixture was diluted with EtOAc and washed successively with H$_2$O (2×) and brine (1×). The organic layer was dried over MgSO$_4$, filtered, and concentrated in vacuo. The residue was purified by silica gel column chromatography using a gradient of 0-90% EtOAc/CH$_2$Cl$_2$ as eluent. $^1$H NMR δ (ppm) (CHCl$_3$-d): 8.16 (1H, d, J=8.33 Hz), 8.03~7.99 (3H, m), 7.87 (1H, d, J=7.99 Hz), 7.69~7.65 (2H, m), 7.57 (1H, d, J=7.77 Hz), 7.39 (1H, t, J=7.73 Hz), 7.33 (1H, t, J=7.42 Hz), 7.22 (2H, t, J=8.58 Hz), 5.95 (1H, br s), 3.81 (2H, m), 3.19 (3H, s), 3.00 (3H, d, J=4.88 Hz), 2.98~2.83 (2H, m), 2.78 (3H, s), 2.11 (3H, s), 1.45 (6H, s), 1.27 (3H, s). MS (M+H): 727.

Step 5—Synthesis of 2-(4-fluorophenyl)-5-(5-(2-hydroxyethyl)-6-(3-methyl-1H-indol-2-yl)pyridin-2-yl)-N-methyl-6-(N-methylmethylsulfonamido)ben-zofuran-3-carboxamide

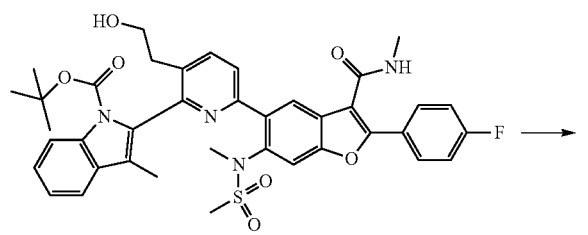

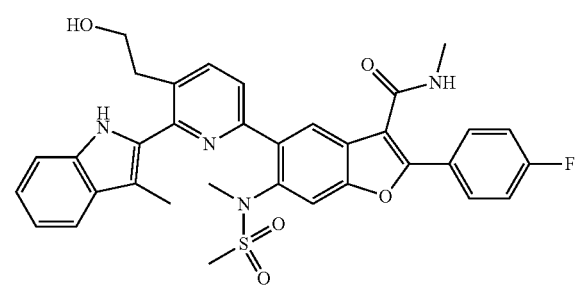

To a solution of tert-butyl 2-(6-(2-(4-fluorophenyl)-3-(me-thylcarbamoyl)-6-(N-methylmethylsulfonamido)benzofu-ran-5-yl)-3-(2-hydroxyethyl)pyridin-2-yl)-3-methyl-1H-in-dole-1-carboxylate (50 mg, 0.069 mmol) in CH$_2$Cl$_2$ (1.5 mL) was added TFA (1.5 mL). The resultant mixture was stirred at ambient temperature for 1.5 h then was concentrated in vacuo, diluted with EtOAc and washed successively with saturated NaHCO$_3$ (aq) solution (1×) and brine (1×). The organic layer was dried over MgSO$_4$, filtered, and concentrated in vacuo to give the title compound, which was used without further purification. MS (M+H): 627.

Step 6—Synthesis of 2-(4-fluorophenyl)-N-methyl-5-(12-methyl-5,6-dihydroindolo[1,2-h][1,7]naphthy-ridin-2-yl)-6-(N-methylmethylsulfonamido)benzofu-ran-3-carboxamide

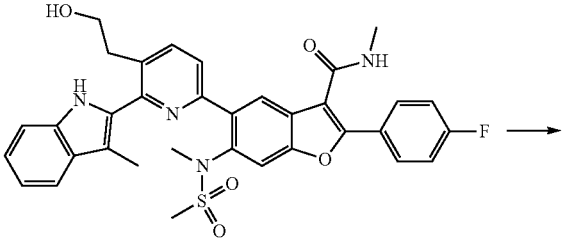

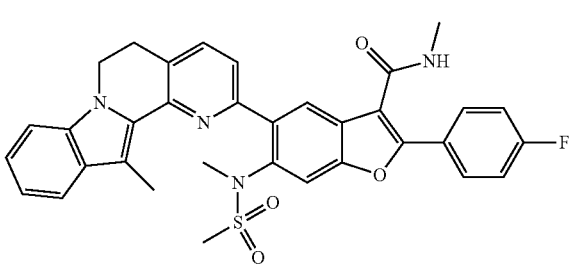

To a mixture of 2-(4-fluorophenyl)-5-(5-(2-hydroxyethyl)-6-(3-methyl-1H-indol-2-yl)pyridin-2-yl)-N-methyl-6-(N-methylmethylsulfonamido)benzofuran-3-carboxamide (43 mg, 0.069 mmol) and triphenylphosphine (90 mg, 0.343 mmol) in THF (4 mL) was diisopropyl azodicarboxylate (0.067 mL, 0.343 mmol). The resultant mixture was stirred at ambient temperature for 16 h, diluted with EtOAc and washed successively with H$_2$O (2×) and brine (1×). The organic layer was dried over MgSO$_4$, filtered, and concentrated in vacuo. The residue was purified by silica gel column chromatography using a step gradient of 0-40-90% EtOAc/Hexanes as eluent. Further purification by silica gel column chromatography with a gradient of 0-10% EtOAc/CH$_2$Cl$_2$ as eluent, followed by lyophilization from CH$_3$CN/H$_2$O provided the title compound. $^1$H NMR δ (ppm) (CHCl$_3$-d): 8.16 (1H, s), 8.07~8.03 (2H, m), 7.70~7.66 (3H, m), 7.47 (1H, d, J=7.77 Hz), 7.37 (1H, d, J=8.24 Hz), 7.32 (1H, D, J=7.1 Hz), 7.26~7.22 (2H, m), 7.16 (1H, t, J=7.40 Hz), 5.95 (1H, br s), 4.34 (2H, t, J=6.37 Hz), 3.32 (3H, s), 3.28 (2H, t, J=6.4 Hz), 3.05 (3H, d, J=4.91 Hz), 2.83 (3H, s), 2.75 (3H, s). MS (M+H): 609.

Examples 77 and 78

Examples 77 and 78, depicted in the table below, were prepared in accordance with the methods described above for Example 76.

| Example | Structure | NMR | MS (M + H)+ |
|---|---|---|---|
| 77 | 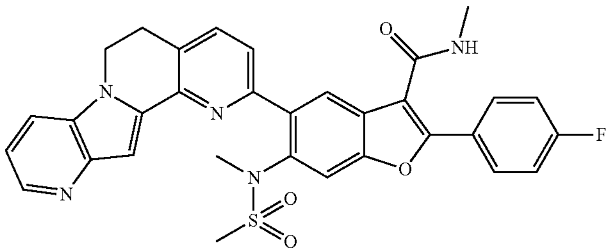 [SMILES: CNC(=O)c1c(-c2ccc(F)cc2)oc2cc(N(C)S(C)(=O)=O)c(-c3ccc4c(n3)-c3cc5ncccc5n3CC4)cc12] | ¹H NMR δ (ppm)(DMSO-d₆): 8.58 (1 H, q, J = 4.63 Hz), 8.37 (1 H, dd, J = 4.55, 1.38 Hz), 8.06-8.01 (3 H, m), 7.99 (1 H, d, J = 8.34 Hz), 7.90 (1 H, d, J = 8.0 Hz), 7.86 (1 H, s), 7.58 (1 H, d, J = 7.88 Hz), 7.42 (2 H, t, J = 8.79 Hz), 7.22-7.18 (1 H, m), 7.16 (1 H, s), 4.42 (2 H, t, J = 6.62 Hz), 3.36-3.31 (5 H, m), 2.94 (3 H, s), 2.83 (3 H, d, J = 4.58 Hz) | 596 |
| 78 | 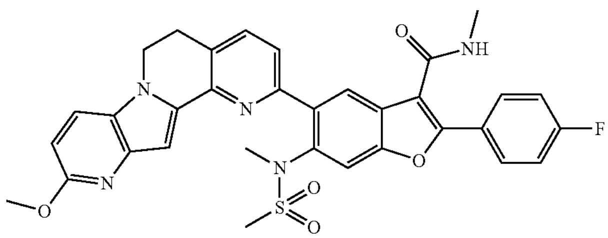 [SMILES: CNC(=O)c1c(-c2ccc(F)cc2)oc2cc(N(C)S(C)(=O)=O)c(-c3ccc4c(n3)-c3cc5nc(OC)ccc5n3CC4)cc12] | ¹H NMR δ (ppm)(DMSO-d₆): 8.58-8.54 (1 H, m), 8.06-8.01 (3 H, m), 7.95 (1 H, d, J = 8.86 Hz), 7.87-7.52 (3 H, m), 7.42 (2 H, t, J = 8.77 Hz), 7.00 (1 H, s), 6.67 (1 H, d, J = 8.82 Hz), 4.37 (2 H, t, J = 6.66 Hz), 3.87 (3 H, s), 3.33-3.29 (5 H, m), 2.92 (3 H, s), 2.83 (3 H, d, J = 4.58 Hz). | 626 |

Example 79

Step 1—Synthesis of 2-(4-fluorophenyl)-N-methyl-5-(12-methylindolo[1,2-h][1,7]naphthyridin-2-yl)-6-(N-methylmethylsulfonamido)benzofuran-3-carboxamide

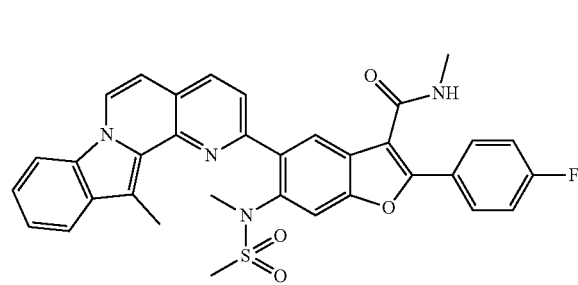 [SMILES: CNC(=O)c1c(-c2ccc(F)cc2)oc2cc(N(C)S(C)(=O)=O)c(-c3ccc4ccn5c6ccccc6c(C)c5c4n3)cc12]

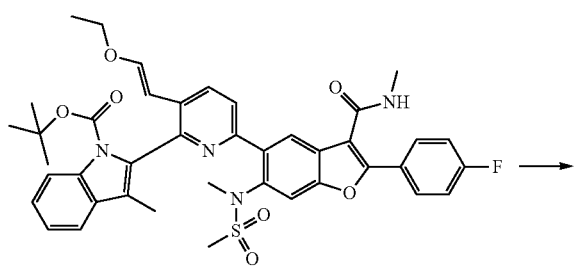

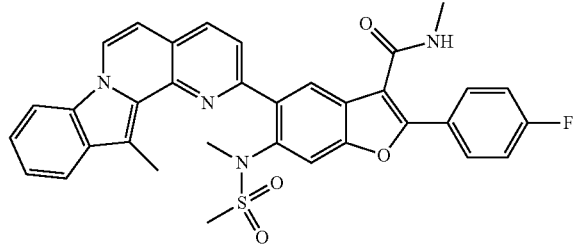

To a solution of (E)-tert-butyl 2-(3-(2-ethoxyvinyl)-6-(2-(4-fluorophenyl)-3-(methylcarbamoyl)-6-(N-methylmethylsulfonamido)benzofuran-5-yl)pyridin-2-yl)-3-methyl-1H-indole-1-carboxylate (60 mg, 0.080 mmol) in 1,4-Dioxane (2 mL) was added 4 M HCl in dioxane (1 mL, 4.00 mmol). The resultant bright orange mixture was stirred at ambient temperature for 45 minutes then was heated at 60° C. for 1.75 h. The mixture was concentrated in vacuo, azeotroping from CH₃CN, and the residue was diluted with saturated NaHCO₃ (aq) solution and extracted into EtOAc. The organic layer was washed with brine (1×), dried over MgSO₄, concentrated in vacuo, and purified by silica gel column chromatography using a gradient of 0-70% EtOAc/Hexanes as eluent. Lyophilization from CH₃CN/H₂O provided the title compound. ¹H NMR δ (ppm) (CHCl₃-d): 8.27 (1H, s), 8.14 (1H, d, J=7.34 Hz), 8.09~8.05 (2H, m), 7.91~7.84 (3H, m), 7.71~7.68 (2H, m), 7.46~7.43 (2H, m), 7.24 (2H, t, J=8.65 Hz), 6.61 (1H, d, J=7.33 Hz), 5.96 (1H, br s), 3.35 (3H, s), 3.06 (6H, m), 2.73 (3H, s). MS (M+H): 607.

Examples 80 and 81

Examples 80 and 81, depicted in the table below, were prepared in accordance with the methods described in Example 79.

| Example | Structure | NMR | MS (M + H)+ |
|---|---|---|---|
| 80 | 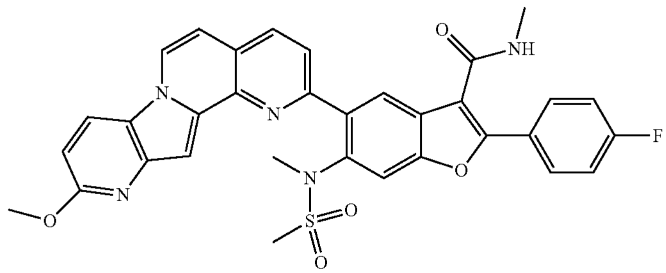 [SMILES: CNC(=O)c1c(-c2ccc(F)cc2)oc2cc(N(C)S(C)(=O)=O)c(-c3ccc4ccn5c6ccc(OC)nc6cc5c4n3)cc12] | $^1$H NMR δ (ppm)(DMSO-$d_6$): 8.77 (1 H, d, J = 7.28 Hz), 8.61-8.57 (2 H, m), 8.26 (1 H, d, J = 8.17 Hz), 8.11 (1 H, s), 8.05 (2 H, dd, J = 8.48, 5.31 Hz), 7.95 (1 H, s), 7.81 (1 H, d, J = 8.18 Hz), 7.43 (2 H, t, J = 8.69 Hz), 7.37 (1 H, s), 7.10 (1 H, d, J = 7.30 Hz), 6.84 (1 H, d, J = 8.90 Hz), 3.96 (3 H, s), 3.40 (3 H, s), 2.90 (3 H, s), 2.84 (3 H, s) | 624 |
| 81 | 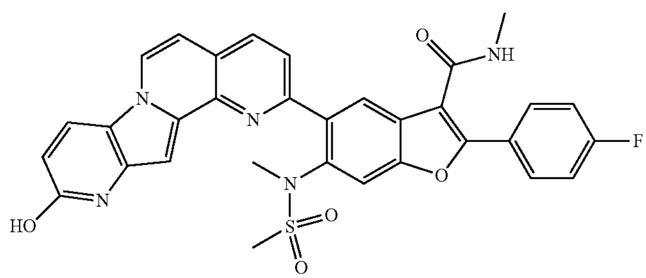 [SMILES: CNC(=O)c1c(-c2ccc(F)cc2)oc2cc(N(C)S(C)(=O)=O)c(-c3ccc4ccn5c6ccc(O)nc6cc5c4n3)cc12] | $^1$H NMR δ (ppm)(DMSO-$d_6$): 11.75 (1 H, br s), 8.66 (1 H, d, J = 7.53 Hz), 8.60 (1 H, d, J = 5.72 Hz), 8.38 (1 H, d, J = 9.72 Hz), 8.25 (1 H, d, J = 8.31 Hz), 8.09-7.96 (3 H, m), 7.79 (1 H, d, J = 8.36 Hz), 7.43 (3 H, t, J = 8.68 Hz), 7.14 (1 H, d, J = 7.33 Hz), 6.96 (1 H, s), 6.24 (1 H, d, J = 9.83 Hz), 2.97-2.91 (3 H, m), 2.87-2.80 (3 H, m) | 610 |

Examples 82 and 82'

82

82'

Step 1—Synthesis of (E)-2,6-dichloro-3-(2-ethoxyvinyl)pyridine

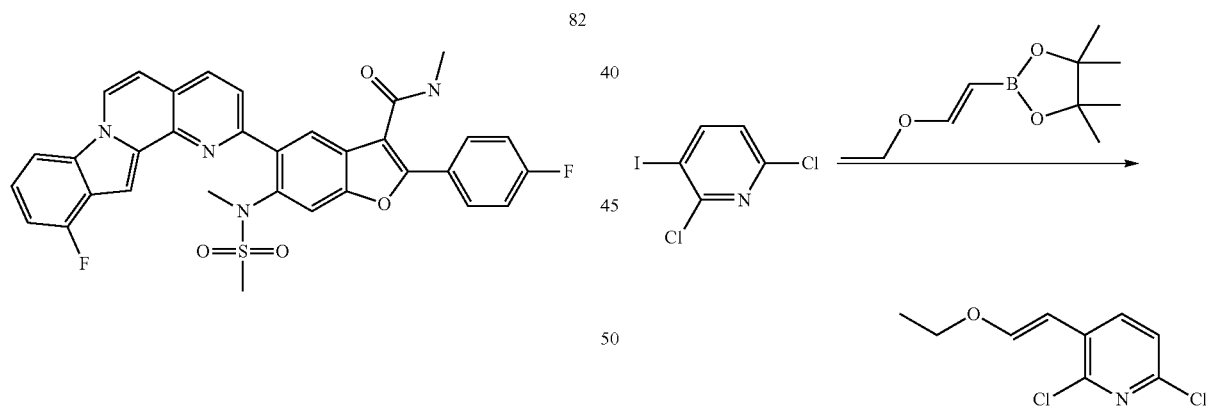

To a degassed solution of 2,6-dichloro-3-iodopyridine (3.0 g, 11 mmol) and (E)-2-(2-ethoxyvinyl)-4,4,5,5-tetramethyl-1,3,2-dioxaborolane (2.2 g, 11 mmol) in 1,4-dioxane (20 mL) and water (1.0 mL) was added $CS_2CO_3$ (7.1 g, 22 mmol) and 1,1'-bis(di-tert-butylphosphino)ferrocene palladium chloride (357 mg, 0.54 mmol) under $N_2$ protection. The resulting mixture was heated to 70° C. and stirred at this temperature overnight. The reaction was cooled, filtered through a pad of the celite and washed with ethyl acetate. The combined filtrate was evaporated in vacuo. The resulting residue was purified using column chromatography (eluted with 0-20% EtOAc/DCM) to provide (E)-2,6-dichloro-3-(2-ethoxyvinyl)pyridine (1.96 mg, yield: 86%). MS (M+H)+: 218.

Step 2—Synthesis of (E)-5-(6-chloro-5-(2-ethoxyvinyl)pyridin-2-yl)-2-(4-fluorophenyl)-N-methyl-6-(N-methylmethylsulfonamido)benzofuran-3-carboxamide

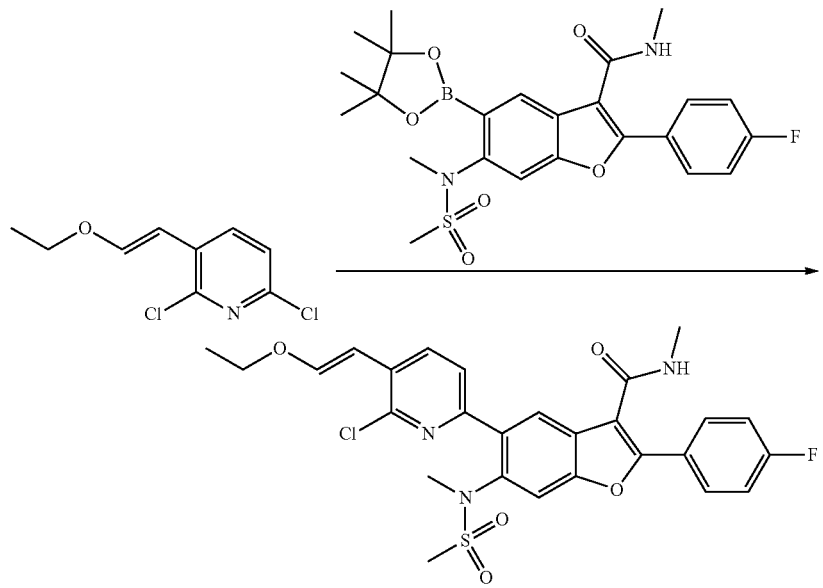

To a degassed solution of (E)-2,6-dichloro-3-(2-ethoxyvinyl)pyridine (500 mg, 2.29 mmol) and 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (1.15 g, 2.29 mmol) in 1,4-dioxane (8 mL) and water (200 μL) was added $CS_2CO_3$ (1.49 g, 4.59 mmol) and 1,1'-bis(di-tert-butylphosphino)ferrocene palladium chloride (120 mg, 0.18 mmol) under $N_2$ protection. The resulting mixture was heated to 90° C. and stirred at this temperature overnight. The reaction was cooled, filtered through a pad of the celite and washed with ethyl acetate. The combined filtrate was evaporated in vacuo. The resulting residue was purified using column chromatography (eluted with 0-30% EtOAc/DCM) to provide (E)-5-(6-chloro-5-(2-ethoxyvinyl)pyridin-2-yl)-2-(4-fluorophenyl)-N-methyl-6-(N-methylmethylsulfonamido)benzofuran-3-carboxamide (200 mg, yield: 16%). MS $(M+H)^+$: 558.

Step 3—Synthesis of (E)-5-(5-(2-ethoxyvinyl)-6-(4-fluoro-1H-indol-2-yl)pyridin-2-yl)-2-(4-fluorophenyl)-N-methyl-6-(N-methylmethylsulfonamido)benzofuran-3-carboxamide

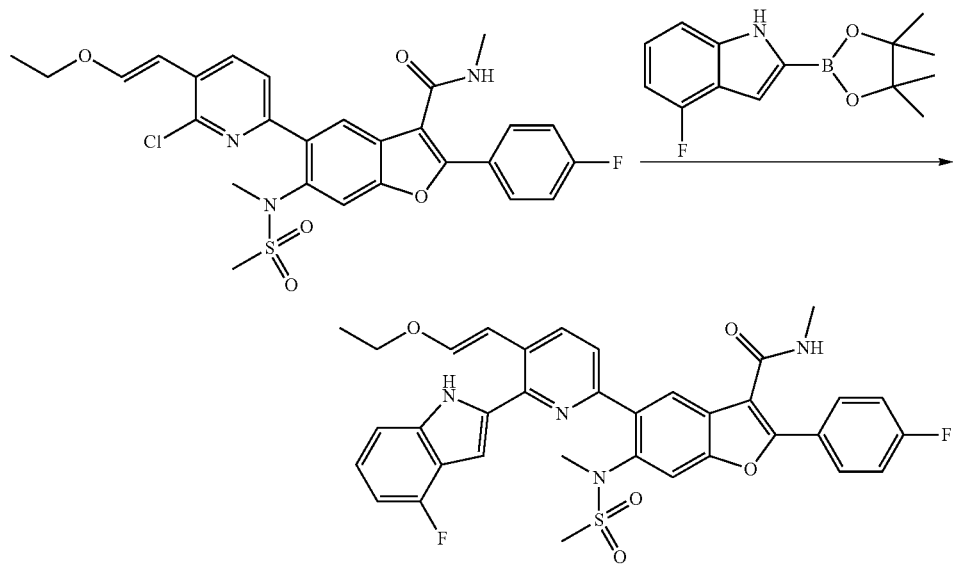

To a degassed solution of (E)-5-(6-chloro-5-(2-ethoxyvinyl)pyridin-2-yl)-2-(4-fluorophenyl)-N-methyl-6-(N-methylmethylsulfonamido)benzofuran-3-carboxamide (200 mg, 0.36 mmol) and 4-fluoro-2-(4,4,5,5-tetramethyl-1,3,2-dioxaborolan-2-yl)-1H-indole (140 mg, 0.54 mmol) in 1,4-dioxane (3 mL) and water (200 μl) was added $CS_2CO_3$ (234 mg, 0.72 mmol) and 1,1'-bis(di-tert-butylphosphino)ferrocene palladium chloride (24 mg, 0.04 mmol) under $N_2$ protection. The resulting mixture was heated to 90° C. and stirred at this temperature for 3 hours. The reaction was cooled, filtered through a pad of the celite and washed with ethyl acetate. The combined filtrate was evaporated in vacuo. Preparative TLC (eluted with 0-30% acetone/hexane) provided (E)-5-(5-(2-ethoxyvinyl)-6-(4-fluoro-1H-indol-2-yl)pyridin-2-yl)-2-(4-fluorophenyl)-N-methyl-6-(N-methylmethylsulfonamido) benzofuran-3-carboxamide (65 mg, yield: 28%) MS $(M+H)^+$: 657.

Step 4—Synthesis of compound 82 and 82'

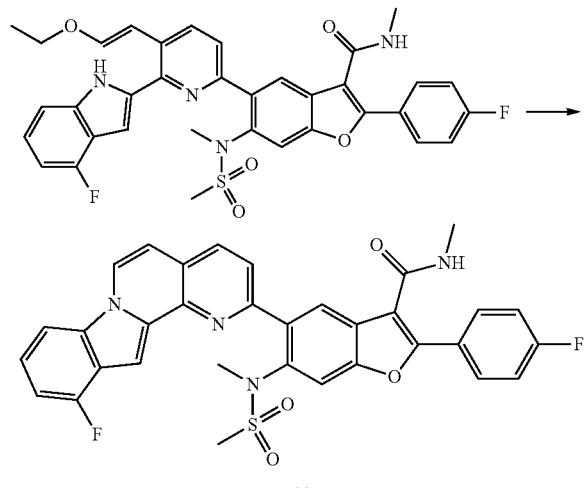

82

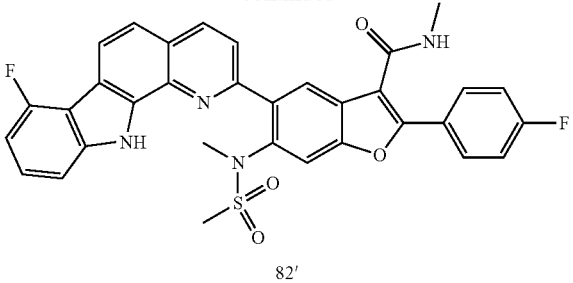

82'

To a solution of (E)-5-(5-(2-ethoxyvinyl)-6-(4-fluoro-1H-indol-2-yl)pyridin-2-yl)-2-(4-fluorophenyl)-N-methyl-6-(N-methylmethylsulfonamido)benzofuran-3-carboxamide (70 mg, 0.11 mmol) in acetonitrile (4 ml) was added NaI (80 mg, 0.53 mmol) and TMSCl (58 mg, 0.53 mmol). The resulting mixture was stirred at RT for 3 hours, then treated with $NaHCO_3$ and extracted with EtOAc. The organic layer was washed with brine, dried ($Na_2SO_4$), filtered and concentrated in vacuo. Preparative TLC gave 5-(11-fluoroindolo[1,2-h][1,7]naphthyridin-2-yl)-2-(4-fluorophenyl)-N-methyl-6-(N-methylmethylsulfonamido)benzofuran-3-carboxamide (compound 82, 22 mg, yield: 34%) and 5-(7-fluoro-11H-pyrido[2,3-a]carbazol-2-yl)-2-(4-fluorophenyl)-N-methyl-6-(N-methylmethylsulfonamido)benzofuran-3-carboxamide (compound 82', 10 mg, yield: 15%).

Examples 83 and 84

Examples 83 and 84, depicted in the table below, were prepared in accordance with the methods described above for Example 82.

| Example | Structure | MS M + H)+ |
|---|---|---|
| 83 | 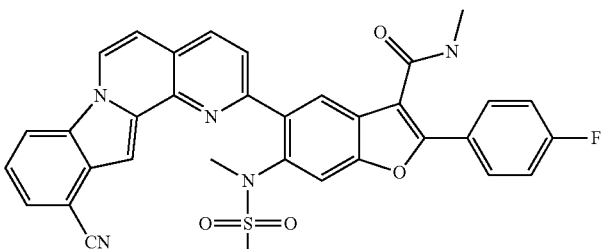 | 617 |
| 84 | 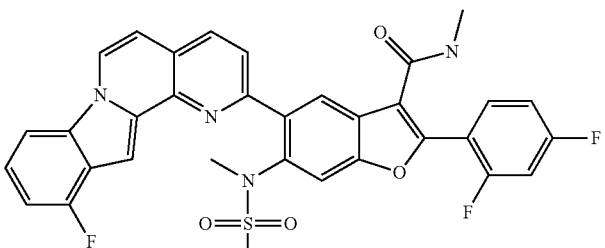 | 628 |

Example 85

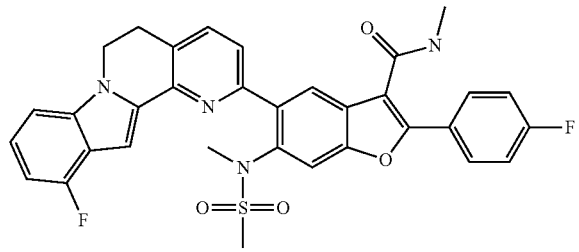 [SMILES: CNC(=O)c1c(-c2ccc(F)cc2)oc2cc(N(C)S(C)(=O)=O)c(-c3ccc4c(n3)-c3cc5c(F)cccc5n3CC4)cc12]

Step 1—Synthesis of 2-(2,6-dichloropyridin-3-yl)acetaldehyde

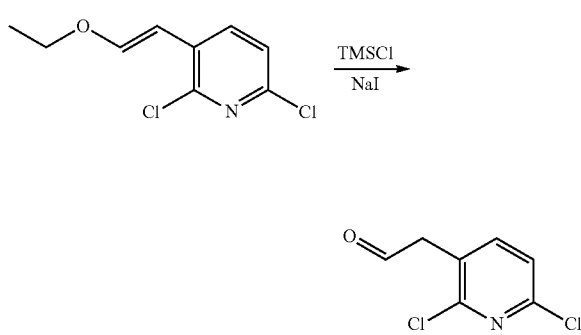

To a solution of (E)-2,6-dichloro-3-(2-ethoxyvinyl)pyridine (890 mg, 4.08 mmol) in acetonitrile (10 ml) was added NaI (1.84 g, 12.2 mmol) and TMSCl (887 mg, 8.16 mmol). The resulting mixture was stirred at RT for 4 hours, then treated with NaHCO$_3$ and extracted with EtOAc. The organic layer was washed with brine, dried (Na$_2$SO$_4$), filtered and concentrated in vacuo to give the yellow oil 2-(2,6-dichloropyridin-3-yl)acetaldehyde (760 mg, yield: 98%). MS (M+H)$^+$: 190.

Step 2—Synthesis of 2-(2,6-dichloropyridin-3-yl)ethanol

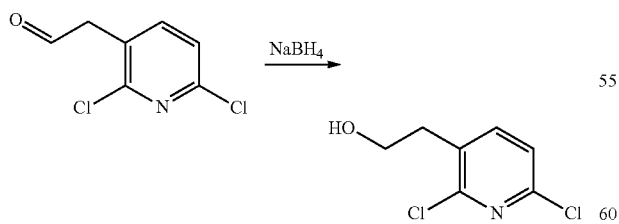

NaBH$_4$ (80 mg, 2.11 mmol) was added to a solution of 2-(2,6-dichloropyridin-3-yl)acetaldehyde (200 mg, 1.05 mmol) in THF (1 ml) and MeOH (1 ml) and stirred at RT for 1 hour. The resulting mixture was treated with NH$_4$Cl and extracted with EtOAc. The organic layer was washed with brine, dried (Na$_2$SO$_4$), filtered and concentrated in vacuo to give the yellow oil 2-(2,6-dichloropyridin-3-yl)ethanol (200 mg, yield: 99%)

Step 3—Synthesis of 2-(6-chloro-2-(4-fluoro-1H-indol-2-yl)pyridin-3-yl)ethanol

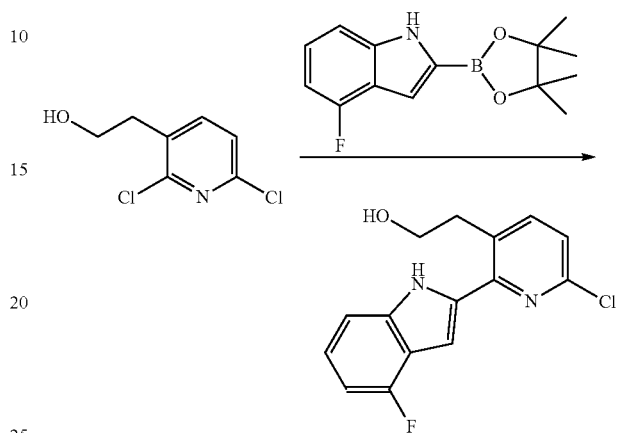

To a degassed solution of 2-(2,6-dichloropyridin-3-yl)ethanol (200 mg, 1.04 mmol) and 4-fluoro-2-(4,4,5,5-tetramethyl-1,3,2-dioxaborolan-2-yl)-1H-indole (272 mg, 1.04 mmol) in 1,4-dioxane (8 mL) and water (200 µl) was added CS$_2$CO$_3$ (679 mg, 2.08 mmol) and 1,1'-bis(di-tert-butylphosphino)ferrocene palladium chloride (68 mg, 0.10 mmol) under N$_2$ protection. The resulting mixture was heated to 90° C. and stirred at this temperature overnight. The reaction was cooled, filtered through a pad of the celite and washed with ethyl acetate. The combined filtrate was evaporated in vacuo. Preparative TLC (eluted with 20% EtOAc/DCM) to provide 2-(6-chloro-2-(4-fluoro-1H-indol-2-yl)pyridin-3-yl)ethanol (60 mg, yield: 19%) MS (M+H)$^+$: 291.

Step 4—Synthesis of 2-chloro-11-fluoro-5,6-dihydroindolo[1,2-h][1,7]naphthyridine

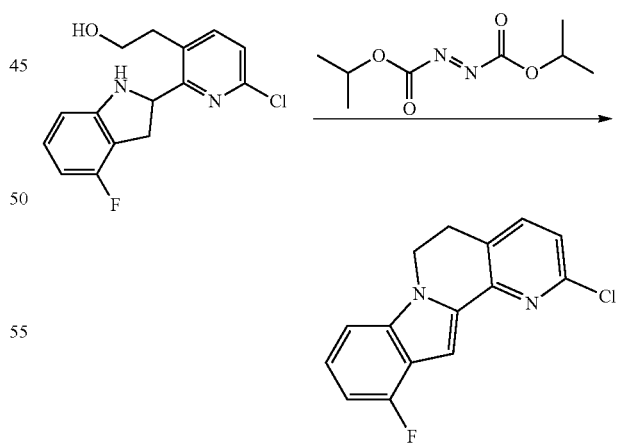

2-(6-chloro-2-(4-fluoro-1H-indol-2-yl)pyridin-3-yl)ethanol (60 mg, 0.21 mmol) was dissolved in THF (4 ml). To the resulting mixture was added diisopropyl azodicarboxylate (42 mg, 0.21 mmol) and PPh$_3$ (54 mg, 0.21 mmol). The resulting mixture was stirred at RT overnight. Preparative TLC gave 2-chloro-11-fluoro-5,6-dihydroindolo[1,2-h][1,7] naphthyridine (50 mg, yield: 89%) MS (M+H)$^+$: 273.

Step 5—Synthesis of 5-(11-fluoro-5,6-dihydroindolo[1,2-h][1,7]naphthyridin-2-yl)-2-(4-fluorophenyl)-N-methyl-6-(N-methylmethylsulfonamido)benzofuran-3-carboxamide

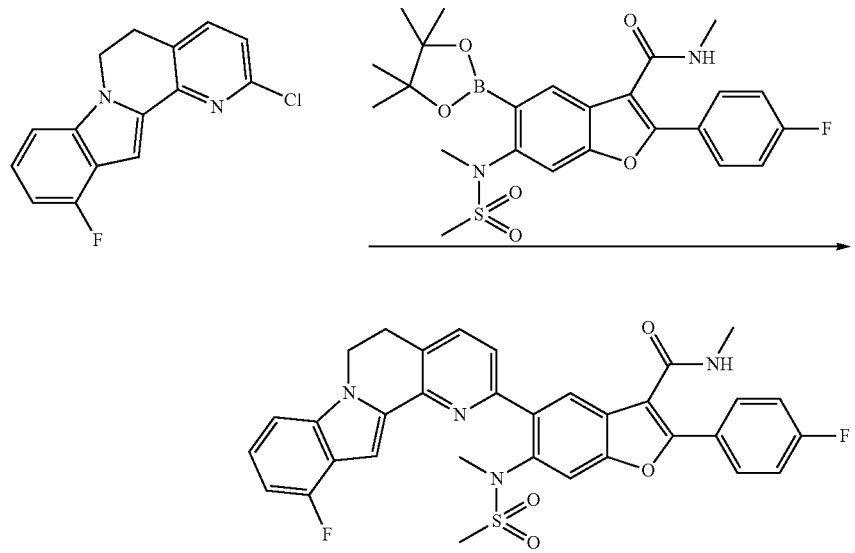 [SMILES: Fc1cccc2c1cc1n2CCc2ccc(Cl)nc2-1 ; CNC(=O)c1c(-c2ccc(F)cc2)oc2cc(N(C)S(C)(=O)=O)c(B3OC(C)(C)C(C)(C)O3)cc12 ; CNC(=O)c1c(-c2ccc(F)cc2)oc2cc(N(C)S(C)(=O)=O)c(-c3ccc4c(n3)-c3cc5c(F)cccc5n3CC4)cc12]

To a degassed solution of 2-chloro-11-fluoro-5,6-dihydroindolo[1,2-h][1,7]naphthyridine (50 mg, 0.18 mmol) and 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (120 mg, 0.24 mmol) in 1,4-dioxane (8 mL) and water (200 μl) was added $Cs_2CO_3$ (119 mg, 0.37 mmol) and 1,1'-bis(di-tert-butylphosphino)ferrocene palladium chloride (20 mg, 0.03 mmol) under $N_2$ protection. The resulting mixture was heated to 90° C. and stirred for 4 hours. The reaction was cooled, filtered through a pad of the celite and washed with ethyl acetate. The combined filtrate was evaporated in vacuo. Preparative TLC (eluted with 30% EtOAc/DCM) provide 5-(11-fluoro-5,6-dihydroindolo[1,2-h][1,7]naphthyridin-2-yl)-2-(4-fluorophenyl)-N-methyl-6-(N-methylmethylsulfonamido)benzofuran-3-carboxamide (90 mg, yield: 80%) MS (M+H)$^+$: 613.

Example 86

Example 86, depicted in the table below, was prepared in accordance with the methods described above for Example 85.

Example 87

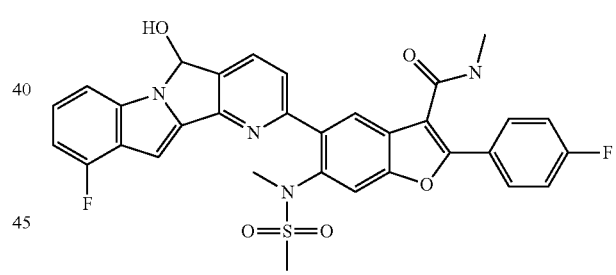

| Compound ID | Structure | MS M + H$^+$ |
|---|---|---|
| 86 | 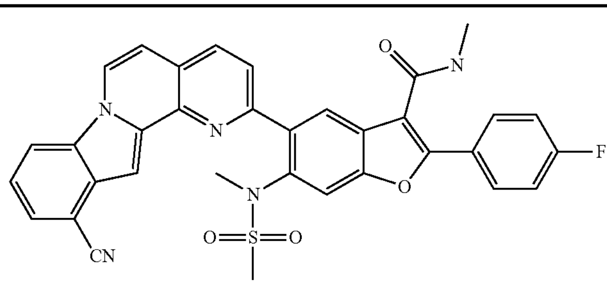 | 619 |

Step 1—Synthesis of 5-(6-chloro-5-formylpyridin-2-yl)-2-(4-fluorophenyl)-N-methyl-6-(N-methylmethylsulfonamido)benzofuran-3-carboxamide

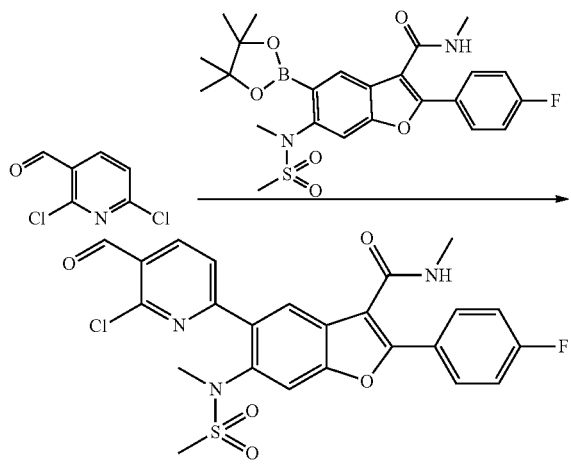

To a degassed solution of 2,6-dichloronicotinaldehyde (315 mg, 1.79 mmol) and 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (600 mg, 1.19 mmol) in 1,4-dioxane (8 mL) and water (300 μL) was added K$_2$CO$_3$ (330 mg, 2.40 mmol) and Pd(dppf)Cl$_2$ (175 mg, 0.24 mmol) under N$_2$ protection. The resulting mixture was heated to 80° C. and stirred at this temperature overnight. The reaction was cooled, filtered through a pad of celite and washed with ethyl acetate. The combined filtrate was evaporated in vacuo. The resulting residue was purified using column chromatography (eluted with 0-30% EtOAc/DCM) to provide 5-(6-chloro-5-formylpyridin-2-yl)-2-(4-fluorophenyl)-N-methyl-6-(N-methylmethylsulfonamido)benzofuran-3-carboxamide (530 mg, yield: 86%) MS (M+H)$^+$: 516.

Step 3—Synthesis of 5-(10-fluoro-5H-pyrido[2',3':3,4]pyrrolo[1,2-a]indol-2-yl)-2-(4-fluorophenyl)-N-methyl-6-(N-methylmethylsulfonamido)benzofuran-3-carboxamide To a degassed solution of 5-(6-chloro-5-formylpyridin-2-yl)-2-(4-fluorophenyl)-N-methyl-6-(N-methylmethylsulfonamido)benzofuran-3-carboxamide (150 mg, 0.29 mmol) and 4-fluoro-2-(4,4,5,5-tetramethyl-1,3,2-dioxaborolan-2-yl)-1H-indole (94 mg, 0.35 mmol) in 1,4-dioxane (3 mL) and water (200 μL) was added CS$_2$CO$_3$ (189 mg, 0.58 mmol) and 1,1'-bis(di-tert-butylphosphino)ferrocene palladium chloride (30 mg, 0.05 mmol) under N$_2$ protection. The resulting mixture was heated to 90° C. and stirred for 3 hours. The reaction was cooled, filtered through a pad of celite and washed with ethyl acetate. The combined filtrate was evaporated in vacuo. Preparative TLC (eluted with (30% ethyl acetate/DCM) to provide 5-(10-fluoro-5-hydroxy-5H-pyrido[2',3':3,4]pyrrolo[1,2-a]indol-2-yl)-2-(4-fluorophenyl)-N-methyl-6-(N-methylmethylsulfonamido)benzofuran-3-carboxamide (40 mg, yield: 22%) MS (M+H)$^+$: 615.

Example 88

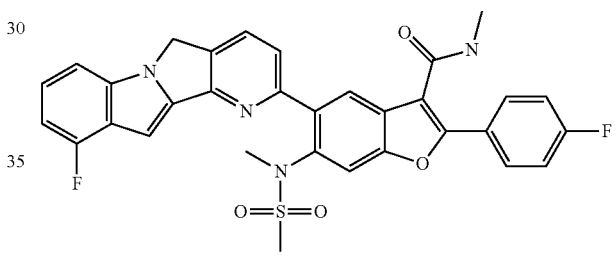

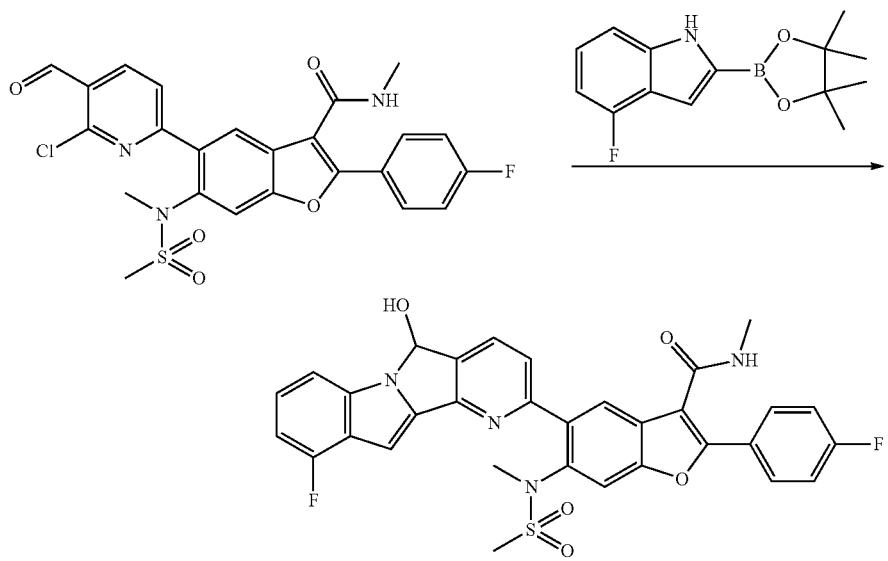

Step 1—Synthesis of 5-(6-chloro-5-(hydroxymethyl)pyridin-2-yl)-2-(4-fluorophenyl)-N-methyl-6-(N-methylmethylsulfonamido)benzofuran-3-carboxamide

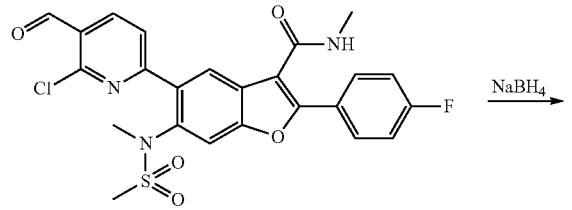

To a solution of 5-(6-chloro-5-formylpyridin-2-yl)-2-(4-fluorophenyl)-N-methyl-6-(N-methylmethylsulfonamido)benzofuran-3-carboxamide (300 mg, 0.58 mmol) in THF (4 ml) and MeOH (1 ml) was added NaBH₄ (66 mg, 1.74 mmol). The resulting mixture was stirred at RT for 3 hours then treated with NH₄Cl and extracted with EtOAc. The organic layer was washed with brine, dried (Na₂SO₄), filtered and concentrated in vacuo to give 5-(6-chloro-5-(hydroxymethyl)pyridin-2-yl)-2-(4-fluorophenyl)-N-methyl-6-(N-methylmethylsulfonamido)benzofuran-3-carboxamide (300 mg, yield: 100%). MS (M+H)⁺: 518.

Step 2—Synthesis of 5-(6-(4-fluoro-1H-indol-2-yl)-5-(hydroxymethyl)pyridin-2-yl)-2-(4-fluorophenyl)-N-methyl-6-(N-methylmethylsulfonamido)benzofuran-3-carboxamide

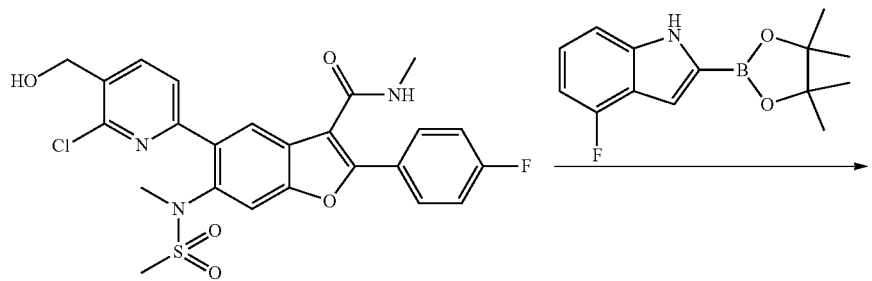

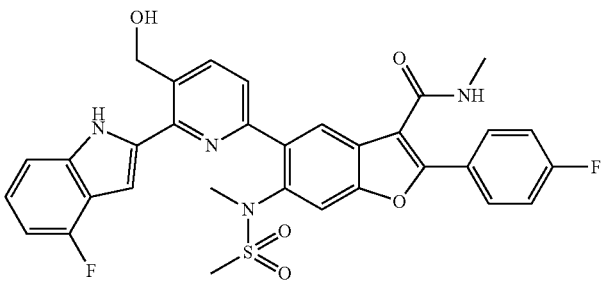

To a degassed solution of 5-(6-chloro-5-(hydroxymethyl)pyridin-2-yl)-2-(4-fluorophenyl)-N-methyl-6-(N-methylmethylsulfonamido)benzofuran-3-carboxamide (300 mg, 0.58 mmol) and 4-fluoro-2-(4,4,5,5-tetramethyl-1,3,2-dioxaborolan-2-yl)-1H-indole (197 mg, 0.75 mmol) in 1,4-dioxane (5 mL) and water (300 μL) was added Cs₂CO₃ (377 mg, 1.16 mmol) and 1,1'-bis(di-tert-butylphosphino)ferrocene palladium chloride (38 mg, 0.06 mmol) under N₂ protection. The resulting mixture was heated to 80° C. and stirred at this temperature overnight. The reaction was cooled, filtered through a pad of celite and washed with ethyl acetate. The combined filtrate was evaporated in vacuo. Preparative TLC (eluted with 0-30% acetone/hexane) to provide 5-(6-(4-fluoro-1H-indol-2-yl)-5-(2-hydroxyethyl)pyridin-2-yl)-2-(4-fluorophenyl)-N-methyl-6-(N-methylmethylsulfonamido)benzofuran-3-carboxamide (280 mg, yield: 78%) MS (M+H)⁺: 617.

Step 3—Synthesis of 5-(10-fluoro-5H-pyrido[2',3':3,4]pyrrolo[1,2-a]indol-2-yl)-2-(4-fluorophenyl)-N-methyl-6-(N-methylmethylsulfonamido)benzofuran-3-carboxamide

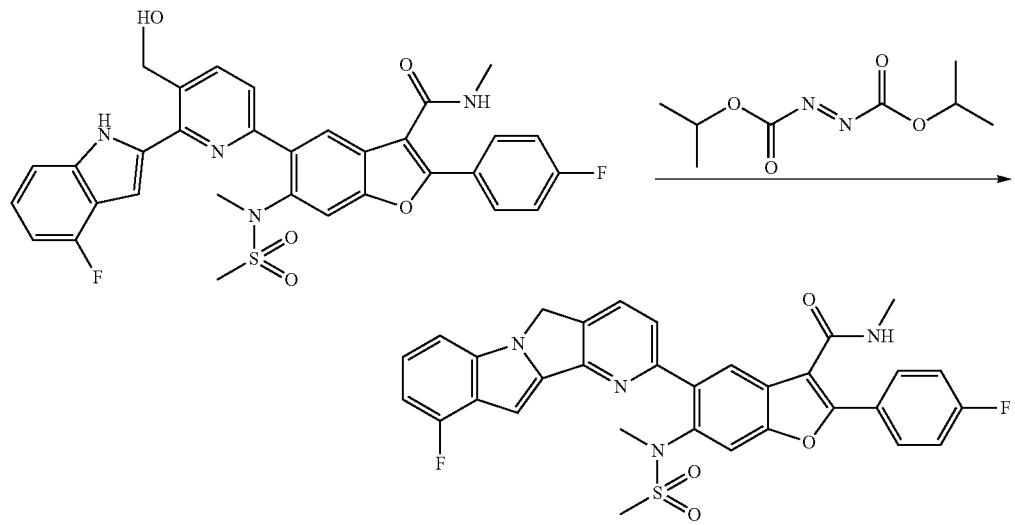

5-(6-(4-fluoro-1H-indol-2-yl)-5-(hydroxymethyl)pyridin-2-yl)-2-(4-fluorophenyl)-N-methyl-6-(N-methylmethylsulfonamido)benzofuran-3-carboxamide (280 mg, 0.45 mmol) was dissolved in THF (8 mL). To the resulting mixture was added diisopropyl azodicarboxylate (184 mg, 0.91 mmol) and PPh$_3$ (238 mg, 0.91 mmol). The resulting mixture was stirred at RT overnight. Preparative TLC gave 5-(10-fluoro-5H-pyrido[2',3':3,4]pyrrolo[1,2-a]indol-2-yl)-2-(4-fluorophenyl)-N-methyl-6-(N-methylmethylsulfonamido)benzofuran-3-carboxamide (230 mg, yield: 85%) MS (M+H)$^+$: 599.

Example 89

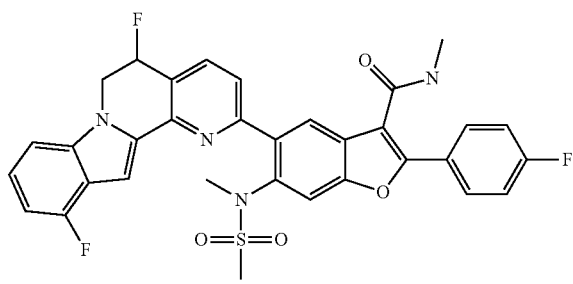 [SMILES: CNC(=O)c1c(-c2ccc(F)cc2)oc2cc(N(C)S(C)(=O)=O)c(-c3ccc4c(n3)-c3cc5c(F)cccc5n3CC4F)cc12]

Step 1—Synthesis of 2-(benzyloxy)-1-(6-bromo-2-chloropyridin-3-yl)ethanol

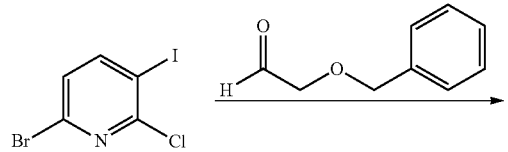

-continued

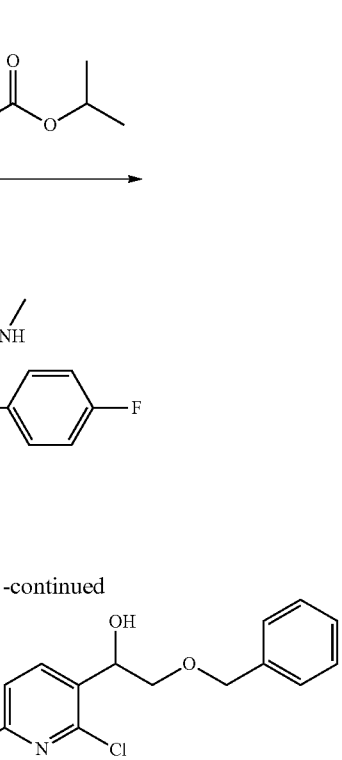

6-Bromo-2-chloro-3-iodopyridine (1.50 g, 4.71 mmol) was dissolved in THF (15 mL) and cooled to −78° C., followed by addition of isopropylmagnesium chloride-lithium chloride complex (3.99 mL, 5.18 mmol). The mixture was stirred at −78° C. for 1 h. 2-(benzyloxy)acetaldehyde (0.849 g, 5.65 mmol) was added and the resulting mixture warmed to 0° C. and stirred for 2 h. The mixture was treated with saturated NH4Cl and extracted with ethyl acetate. The organic layer was washed with brine, dried (Na$_2$SO$_4$), filtered and concentrated in vacuo to gave 2-(benzyloxy)-1-(6-bromo-2-chloropyridin-3-yl)ethanol (1.54 g, yield: 95%). MS (M+H)$^+$: 344.

Step 2—Synthesis of 3-(2-(benzyloxy)-1-fluoroethyl)-6-bromo-2-chloropyridine

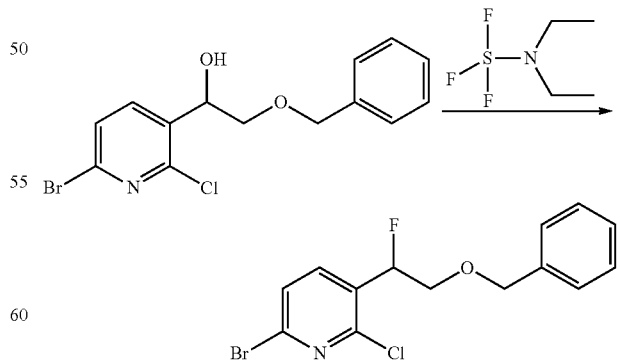

To a solution of 2-(benzyloxy)-1-(6-bromo-2-chloropyridin-3-yl)ethanol (1.54 g, 4.49 mmol) in DCM (10 mL) at 0° C. was added diethylaminosulfur trifluoride (0.594 ml, 4.49 mmol). The resulting mixture was stirred at 0° C. for 30 min, then warmed to RT and stirred for 1 h. The mixture was concentrated in vacuo and the resulting residue purified using column chromatography (eluted with 0-20% ethyl acetate/hexane) to provide 3-(2-(benzyloxy)-1-fluoroethyl)-6-bromo-2-chloropyridine (490 mg, yield: 32%)

Step 3—Synthesis of 5-(5-(2-(benzyloxy)-1-fluoroethyl)-6-chloropyridin-2-yl)-2-(4-fluorophenyl)-N-methyl-6-(N-methylmethylsulfonamido)benzofuran-3-carboxamide

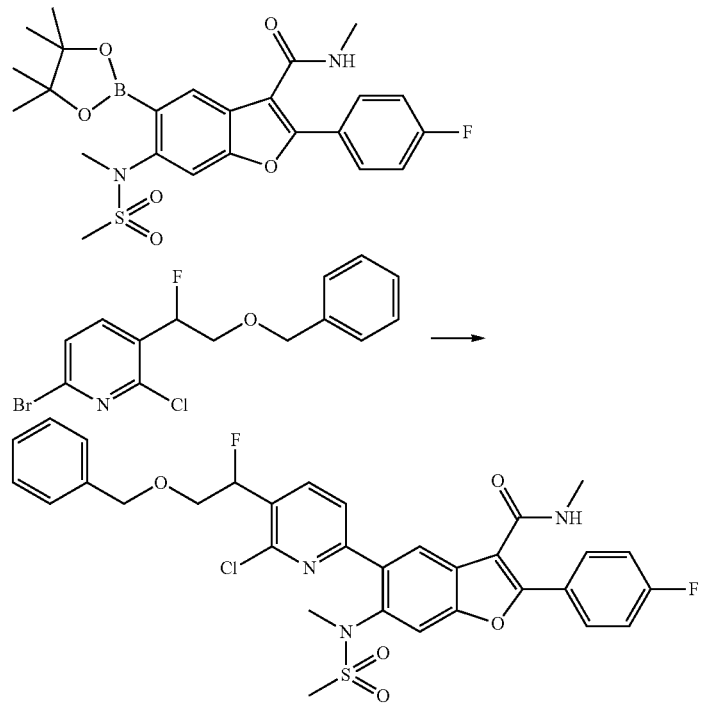

To a degassed solution of 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (714 mg, 1.422 mmol) and 3-(2-(benzyloxy)-1-fluoroethyl)-6-bromo-2-chloropyridine (490 mg, 1.422 mmol) in 1,4-Dioxane (15 ml) and water (2 mL) was added $K_2CO_3$ (393 mg, 2.84 mmol) and Pd(dppf)Cl$_2$ (100 mg, 0.137 mmol) under $N_2$ protection. The resulting mixture was heated to 85° C. and stirred for 6 h. The reaction was cooled, filtered through a pad of celite and washed with ethyl acetate. The combined filtrate was evaporated in vacuo. The resulting residue was purified using column chromatography (eluted with 0-20% ethyl acetate/DCM) to provide 5-(5-(2-(benzyloxy)-1-fluoroethyl)-6-chloropyridin-2-yl)-2-(4-fluorophenyl)-N-methyl-6-(N-methylmethylsulfonamido)benzofuran-3-carboxamide (660 mg, yield: 67%). MS (M+H)$^+$: 641.

Step 4—Synthesis of 5-(5-(2-(benzyloxy)-1-fluoroethyl)-6-chloropyridin-2-yl)-2-(4-fluorophenyl)-N-methyl-6-(N-methylmethylsulfonamido)benzofuran-3-carboxamide

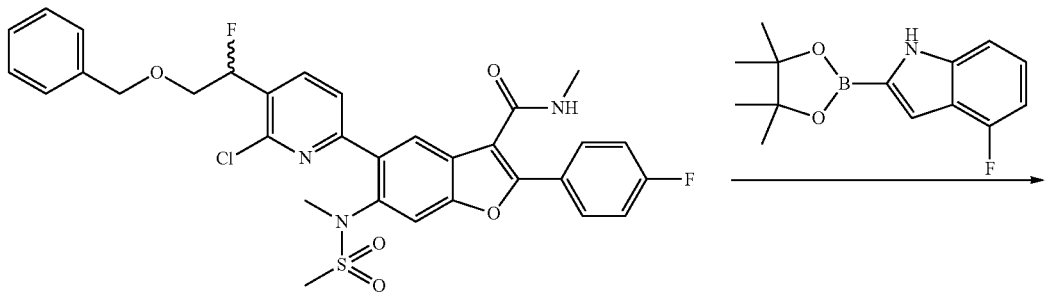

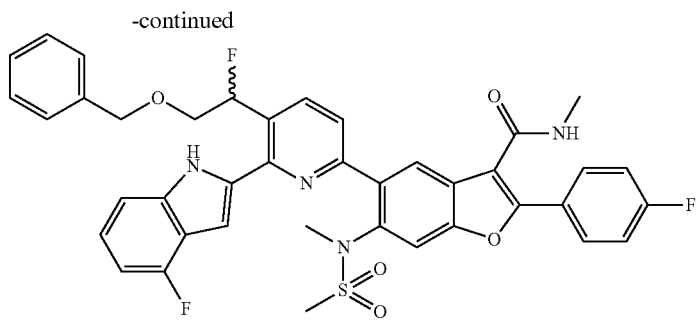

To a degassed solution of 5-(5-(2-(benzyloxy)-1-fluoroethyl)-6-chloropyridin-2-yl)-2-(4-fluorophenyl)-N-methyl-6-(N-methylmethylsulfonamido)benzofuran-3-carboxamide (610 mg, 0.953 mmol) and 4-fluoro-2-(4,4,5,5-tetramethyl-1,3,2-dioxaborolan-2-yl)-1H-indole (373 mg, 1.429 mmol) in 1,4-Dioxane (8 mL) and water (300 μL) was added Cs$_2$CO$_3$ (621 mg, 1.906 mmol) and DTBPF PdCl$_2$ (60 mg, 0.092 mmol) under N$_2$ protection. The resulting mixture was heated to 85° C. and stirred overnight. The reaction was cooled, filtered through a pad of celite and washed with ethyl acetate. The combined filtrate was evaporated in vacuo and the resulting residue was purified using column chromatography (eluted with 0-20% ethyl acetate/DCM) to provide 5-(5-(2-(benzyloxy)-1-fluoroethyl)-6-chloropyridin-2-yl)-2-(4-fluorophenyl)-N-methyl-6-(N-methylmethylsulfonamido)benzofuran-3-carboxamide (530 mg, yield: 75%). MS (M+H)$^+$: 739.

Step 5—Synthesis of 5-(6-(4-fluoro-1H-indol-2-yl)-5-(1-fluoro-2-hydroxyethyl)pyridin-2-yl)-2-(4-fluorophenyl)-N-methyl-6-(N-methylmethylsulfonamido)benzofuran-3-carboxamide

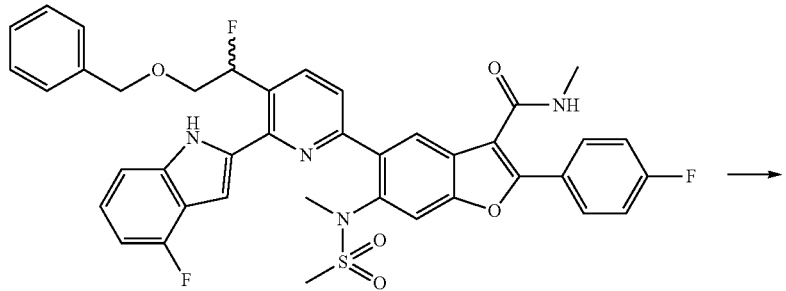

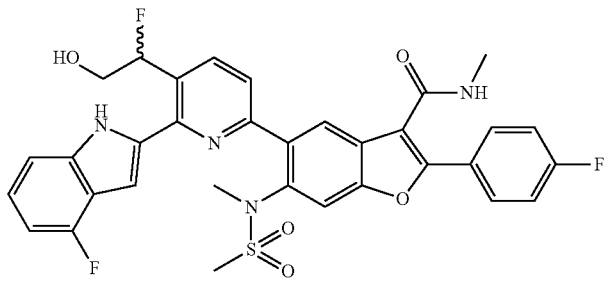

To a solution of 5-(5-(2-(benzyloxy)-1-fluoroethyl)-6-(4-fluoro-1H-indol-2-yl)pyridin-2-yl)-2-(4-fluorophenyl)-N-methyl-6-(N-methylmethylsulfonamido)benzofuran-3-carboxamide (530 mg, 0.717 mmol) in THF (10 mL) was added palladium hydroxide (101 mg, 0.717 mmol). The mixture was hydrogenated under a balloon for 2 h. Filtration through a pad of celite removed the solid. After washing with ethyl acetate, the combined filtrate was concentrated in vacuo to give 5-(6-(4-fluoro-1H-indol-2-yl)-5-(1-fluoro-2-hydroxyethyl)pyridin-2-yl)-2-(4-fluorophenyl)-N-methyl-6-(N-methylmethylsulfonamido)benzofuran-3-carboxamide (465 mg, yield: 100%). MS (M+H)$^+$: 649.

Step 6—Synthesis of 5-(5,11-difluoro-5,6-dihydroindolo[1,2-h][1,7]naphthyridin-2-yl)-2-(4-fluorophenyl)-N-methyl-6-(N-methylmethylsulfonamido)benzofuran-3-carboxamide

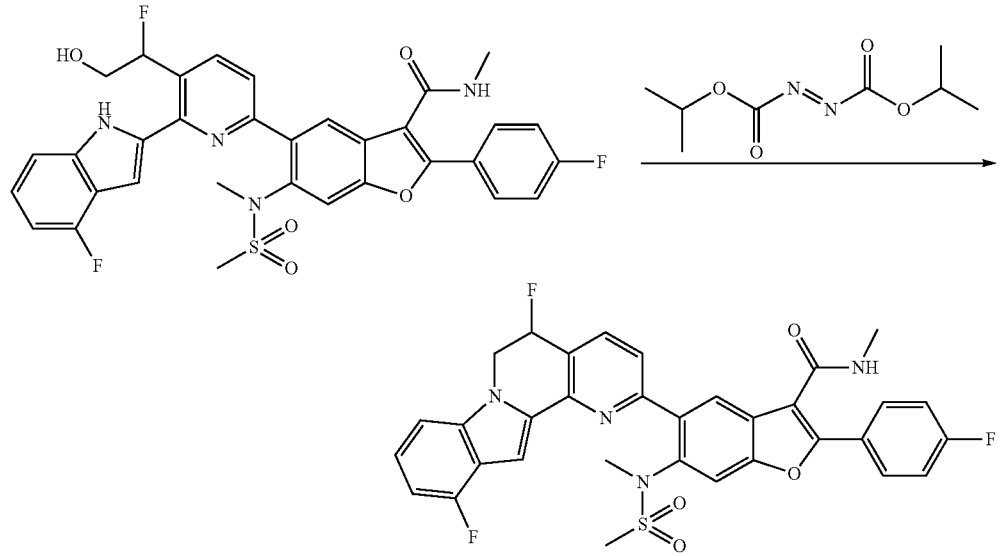

To a solution of 5-(6-(4-fluoro-1H-indol-2-yl)-5-(1-fluoro-2-hydroxyethyl)pyridin-2-yl)-2-(4-fluorophenyl)-N-methyl-6-(N-methylmethylsulfonamido)benzofuran-3-carboxamide (465 mg, 0.717 mmol) and triphenylphosphine (282 mg, 1.075 mmol) in DCM (15 mL) was added diisopropyl azodicarboxylate (217 mg, 1.075 mmol). The resulting mixture was stirred at RT overnight and concentrated in vacuo. The resulting residue was purified using column chromatography (eluted with 20-50% ethyl acetate/hexane) to provide 5-(5,11-difluoro-5,6-dihydroindolo[1,2-h][1,7]naphthyridin-2-yl)-2-(4-fluorophenyl)-N-methyl-6-(N-methylmethylsulfonamido)benzofuran-3-carboxamide (250 mg, yield: 55%). MS (M+H)$^+$: 631.

Example 90

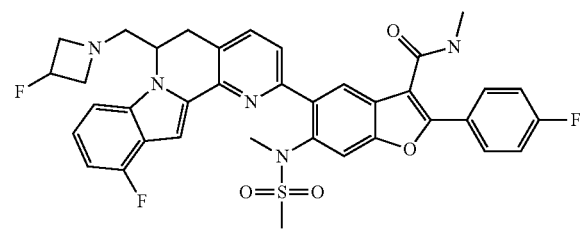 [SMILES: CNC(=O)c1c(-c2ccc(F)cc2)oc2cc(N(C)S(C)(=O)=O)c(-c3ccc4c(n3)-c3cc5c(F)cccc5n3C(CN3CC(F)C3)C4)cc12]

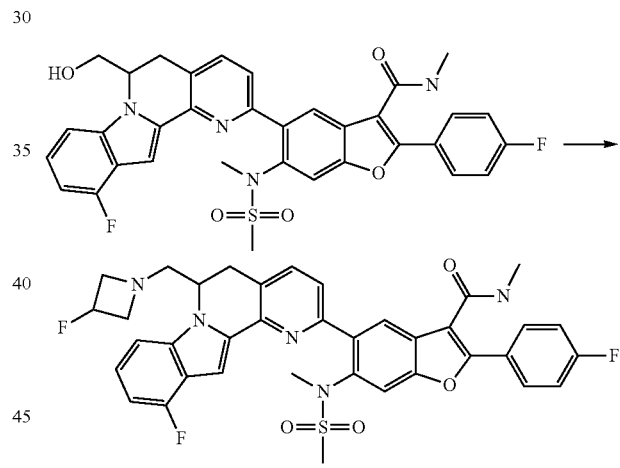

To a solution of 5-(11-fluoro-6-(hydroxymethyl)-5,6-dihydroindolo[1,2-h][1,7]naphthyridin-2-yl)-2-(4-fluorophenyl)-N-methyl-6-(N-methylmethylsulfonamido)benzofuran-3-carboxamide (180 mg, 0.280 mmol) in DCM (8 mL) at 0° C. was added trifluoromethanesulfonic anhydride in DCM (0.560 mL, 0.560 mmol). The mixture was stirred at 0° C. for 2 h, then at RT for 1 h. The mixture was evaporated in vacuo to remove the volatiles, redissolved in DMF (8 mL), followed by addition of N,N-diisopropyl ethylamine (362 mg, 2.80 mmol) and 3-fluoroazetidine hydrochloride (125 mg, 1.120 mmol). The mixture was heated to 60° C. and stirred for 3 h. 20 ml H$_2$O was added and the mixture stirred for 10 min. Filtration collected the yellow solid. After washing with additional H$_2$O, the yellow solid was purified by chromatography, and eluted with 0-70% ethyl acetate in hexane to gave 5-(11-fluoro-6-((3-fluoroazetidin-1-yl)methyl)-5,6-dihydroindolo[1,2-h][1,7]naphthyridin-2-yl)-2-(4-fluorophenyl)-N-methyl-6-(N-methylmethylsulfonamido)benzofuran-3-carboxamide (42 mg, yield: 21%). MS (M+H)$^+$: 700.

Examples 91-95

Examples 91-95, depicted in the table below, were prepared in accordance with the methods described above for Example 90.

| Example | Structure | MS M+ H)+ |
|---------|-----------|-----------|
| 91 | 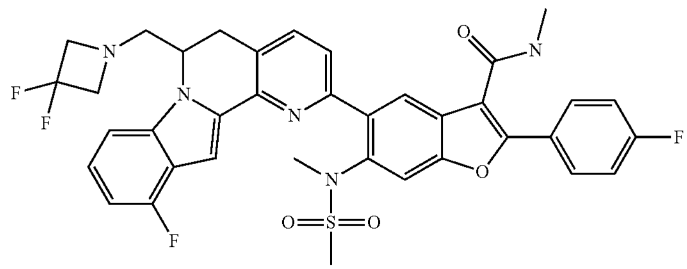 [SMILES: CNC(=O)c1c(-c2ccc(F)cc2)oc2cc(N(C)S(C)(=O)=O)c(-c3ccc4c(n3)-c3cc5c(F)cccc5n3C(CN3CC(F)(F)C3)C4)cc12] | 717 |
| 92 | 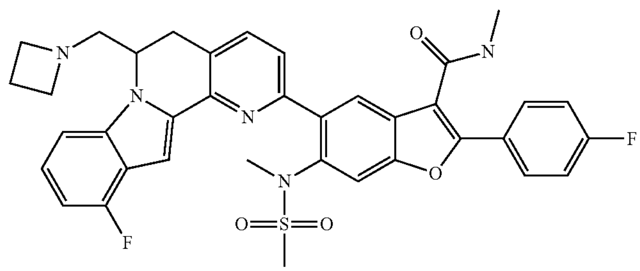 [SMILES: CNC(=O)c1c(-c2ccc(F)cc2)oc2cc(N(C)S(C)(=O)=O)c(-c3ccc4c(n3)-c3cc5c(F)cccc5n3C(CN3CCC3)C4)cc12] | 681 |
| 93 | 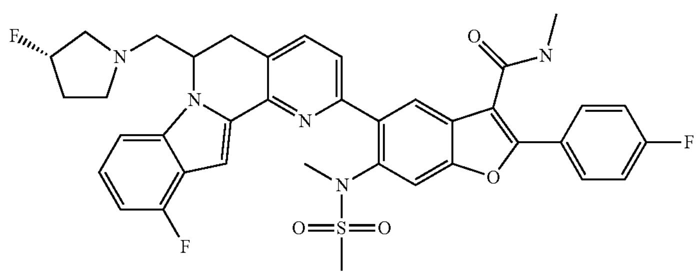 [SMILES: CNC(=O)c1c(-c2ccc(F)cc2)oc2cc(N(C)S(C)(=O)=O)c(-c3ccc4c(n3)-c3cc5c(F)cccc5n3C(CN3CC[C@H](F)C3)C4)cc12] | 713 |
| 94 | 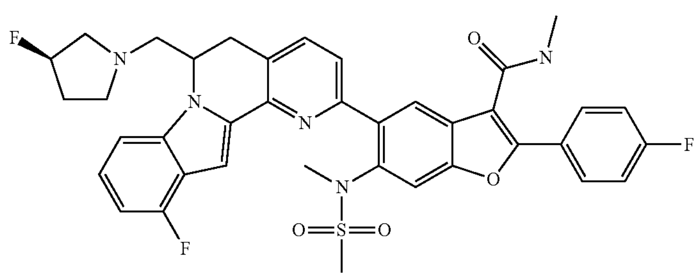 [SMILES: CNC(=O)c1c(-c2ccc(F)cc2)oc2cc(N(C)S(C)(=O)=O)c(-c3ccc4c(n3)-c3cc5c(F)cccc5n3C(CN3CC[C@@H](F)C3)C4)cc12] | 713 |
| 95 | 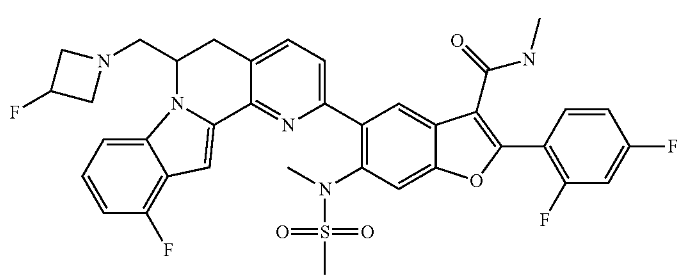 [SMILES: CNC(=O)c1c(-c2ccc(F)cc2F)oc2cc(N(C)S(C)(=O)=O)c(-c3ccc4c(n3)-c3cc5c(F)cccc5n3C(CN3CC(F)C3)C4)cc12] | 718 |

Example 96

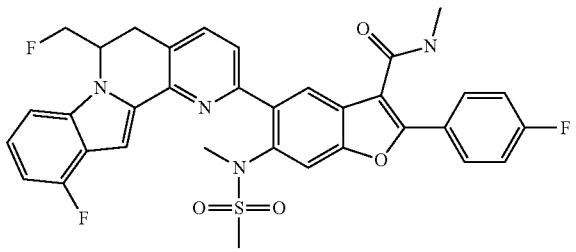 [SMILES: CNC(=O)c1c(-c2ccc(F)cc2)oc2cc(N(C)S(C)(=O)=O)c(-c3ccc4c(n3)-c3cc5c(F)cccc5n3C(CF)C4)cc12]

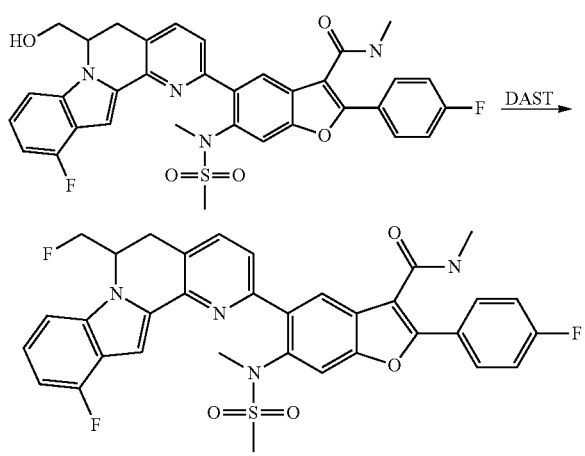

5-(11-fluoro-6-(hydroxymethyl)-5,6-dihydroindolo[1,2-h][1,7]naphthyridin-2-yl)-2-(4-fluorophenyl)-N-methyl-6-(N-methylmethylsulfonamido)benzofuran-3-carboxamide (40 mg, 0.062 mmol) was dissolved in DCM (2 ml) and cooled to 0° C., followed by addition of DAST (0.025 ml, 0.187 mmol). The mixture was stirred at 0° C. for 1 h, then at RT for 30 min and then concentrated in vacuo. Preparative TLC (50% DCM in ethyl acetate) gave 5-(11-fluoro-6-(fluoromethyl)-5,6-dihydroindolo[1,2-h][1,7]naphthyridin-2-yl)-2-(4-fluorophenyl)-N-methyl-6-(N-methylmethylsulfonamido)benzofuran-3-carboxamide (14 mg, yield: 35%). MS (M+H)$^+$: 645.

Example 97

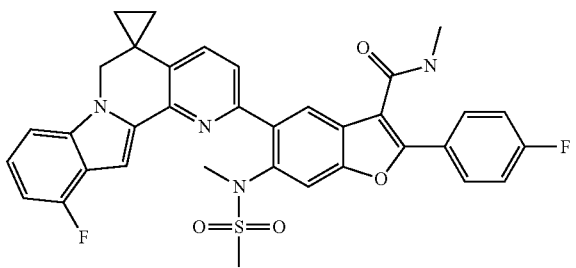 [SMILES: CNC(=O)c1c(-c2ccc(F)cc2)oc2cc(N(C)S(C)(=O)=O)c(-c3ccc4c(n3)-c3cc5c(F)cccc5n3CC43CC3)cc12]

Step 1—Synthesis of (6-bromo-2-chloropyridin-3-yl)methanol

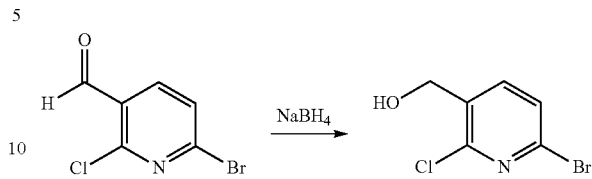

To a solution of 6-bromo-2-chloronicotinaldehyde (5.40 g, 24.50 mmol) in THF (30 ml) and MeOH (10.0 ml) at 0° C. was added NaBH$_4$ (0.927 g, 24.50 mmol). The mixture was stirred at 0° C. for 2 h. Saturated NH$_4$Cl (50 ml) was added and the mixture extracted with ethyl acetate, dried over (Na$_2$SO$_4$), filtered and concentrated in vacuo to give (6-bromo-2-chloropyridin-3-yl)methanol (5.50 mg, yield: 101%). MS (M+H)$^+$: 224.

Step 2—Synthesis of 2-(6-bromo-2-chloropyridin-3-yl)acetonitrile

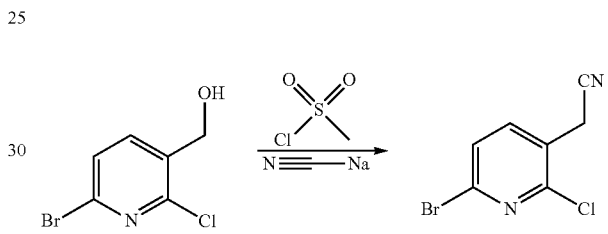

To a solution of (6-bromo-2-chloropyridin-3-yl)methanol (5.45 g, 24.50 mmol) and Et$_3$N (5.12 mL, 36.7 mmol) at 0° C. was added MsCl (2.081 mL, 26.9 mmol). The resulting mixture was stirred at 0° C. for 2 h. 30 ml diethyl ether was added and the mixture stirred for 20 min. Filtration removed the yellow solid. After washing with 2×20 ml diethyl ether, the combined filtrate was concentrated in vacuo to give the yellow solid.

The above yellow solid was dissolved in 20 ml DMSO, followed by addition of NaCN (3.72 g, 36.7 mmol). The mixture was stirred at RT for 20 hours. 100 ml H$_2$O was added and the mixture extracted with ethyl acetate, dried over (Na$_2$SO$_4$), filtered and concentrated in vacuo. The resulting residue was purified using column chromatography (eluted with 0-20% ethyl acetate in hexane) gave 2-(6-bromo-2-chloropyridin-3-yl)acetonitrile (3.8 g, yield: 67%)

Step 3—Synthesis of 1-(6-bromo-2-chloropyridin-3-yl)cyclopropanecarbonitrile

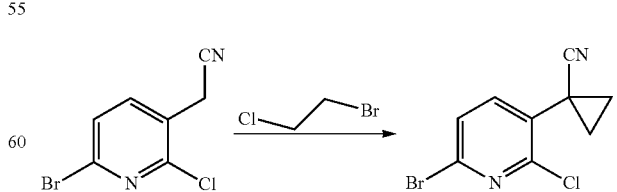

To a solution of NaOH (2.59 g, 64.8 mmol) in water (6 mL) was added 2-(6-bromo-2-chloropyridin-3-yl)acetonitrile (1.5 g, 6.48 mmol), tetrabutyl ammonium bromide (0.418 g, 1.296 mmol) and 1-bromo-2-chloroethane (1.079 mL, 12.96 mmol). The resulting mixture was heated to 50° C. and stirred for 2 h, extracted with ethyl acetate (2×30 mL), dried over Na$_2$SO$_4$, filtered and concentrated in vacuo. The residue was purified using column chromtography (eluted with 0-20% ethyl acetate in hexane) to give 1-(6-bromo-2-chloropyridin-3-yl)cyclopropanecarbonitrile (850 mg, yield: 51%) MS (M+H)$^+$: 258.

Step 4—Synthesis of (1-(6-bromo-2-chloropyridin-3-yl)cyclopropyl)methanol

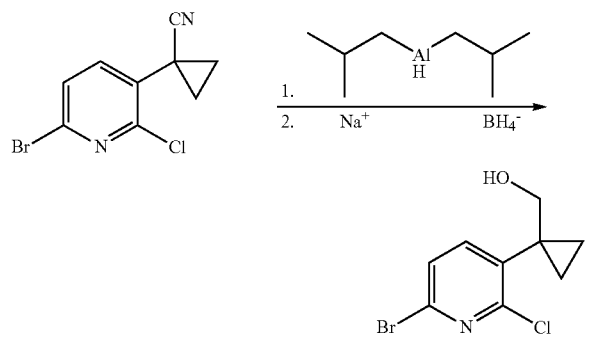

To a solution of 1-(6-bromo-2-chloropyridin-3-yl)cyclopropane carbonitrile (850 mg, 3.30 mmol) in THF (15 mL) at RT was added DIBAL-H (5.08 mL, 6.60 mmol) and stirred for 1 h. 50 ml saturated NH$_4$Cl was and the mixture extracted with ethyl acetate, dried over Na$_2$SO$_4$, filtered and concentrated in vacuo.

The above residue was dissolved in 5 ml THF/MeOH (1/1) followed by addition of NaBH$_4$ (250 mg, 6.60 mmol). The mixture was stirred at RT for 1 h. H$_2$O was added and the mixture extracted with ethyl acetate, dried over Na$_2$SO$_4$, filtered and concentrated in vacuo. Preparative TLC gave the yellow solid 100 mg. to give (1-(6-bromo-2-chloropyridin-3-yl)cyclopropyl)methanol (100 mg, yield: 12%) MS (M+H)$^+$: 263.

Step 5—Synthesis of 5-(6-chloro-5-(1-(hydroxymethyl)cyclopropyl)pyridin-2-yl)-2-(4-fluorophenyl)-N-methyl-6-(N-methylmethylsulfonamido)benzofuran-3-carboxamide

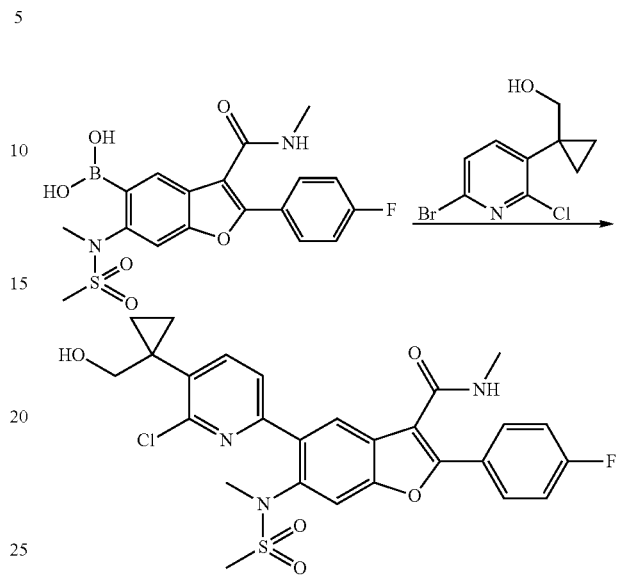

To a solution of (1-(6-bromo-2-chloropyridin-3-yl)cyclopropyl)methanol (100 mg, 0.381 mmol) and (2-(4-fluorophenyl)-3-(methylcarbamoyl)-6-(N-methylmethylsulfonamido) benzofuran-5-yl)boronic acid (160 mg, 0.381 mmol) in 1,4-Dioxane (2 mL) and water (20 μL) was added K$_2$CO$_3$ (105 mg, 0.762 mmol) and Pd(dppf)Cl$_2$ (55 mg, 0.075 mmol). The mixture was heated to 70° C. and stirred overnight. Filtration through a pad of celite removed the solid. After washing with ethyl acetate, the combined filtrate was concentrated in vacuo. Preparative TLC gave 5-(6-chloro-5-(1-(hydroxymethyl)cyclopropyl)pyridin-2-yl)-2-(4-fluorophenyl)-N-methyl-6-(N-methylmethylsulfonamido)benzofuran-3-carboxamide (80 mg, yield: 37.6%) MS (M+H)$^+$: 559.

Step 6—Synthesis of 5-(11'-fluoro-6'H-spiro[cyclopropane-1,5'-indolo[1,2-h][1,7]naphthyridin]-2'-yl)-2-(4-fluorophenyl)-N-methyl-6-(N-methylmethylsulfonamido)benzofuran-3-carboxamide

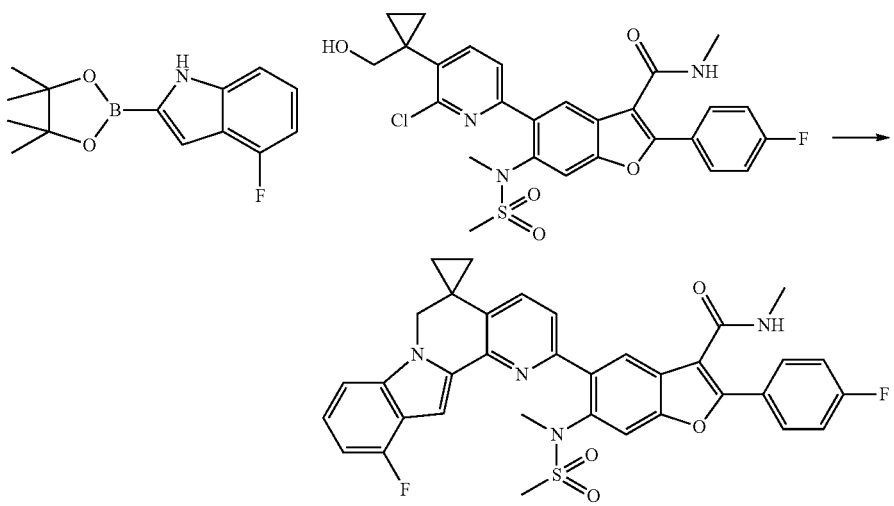

To a solution of 5-(6-chloro-5-(1-(hydroxymethyl)cyclopropyl)pyridin-2-yl)-2-(4-fluorophenyl)-N-methyl-6-(N-methylmethylsulfonamido)benzofuran-3-carboxamide (80 mg, 0.143 mmol) and 4-fluoro-2-(4,4,5,5-tetramethyl-1,3,2-dioxaborolan-2-yl)-1H-indole (56.1 mg, 0.215 mmol) in 1,4-Dioxane (2 mL) and water (20 µL) was added Cs$_2$CO$_3$ (93 mg, 0.287 mmol) and DTBPF PdCl$_2$ (21 mg, 0.032 mmol). The mixture was heated to 80° C., stirred overnight, concentrated in vacuo and dried. The residue was dissolved in DCM (2.00 mL), followed by addition of triphenylphosphine (94 mg, 0.358 mmol) and DIAD (0.070 mL, 0.358 mmol). The mixture was stirred at RT for 4 h. Preparative TLC (eluted with 20% ethyl acetate in DCM) gave 5-(11'-fluoro-6'H-spiro[cyclopropane-1,5'-indolo[1,2-h][1,7]naphthyridin]-2'-yl)-2-(4-fluorophenyl)-N-methyl-6-(N-methylmethylsulfonamido)benzofuran-3-carboxamide (4.5 mg, yield: 5%) MS (M+H)$^+$: 639.

Example 98

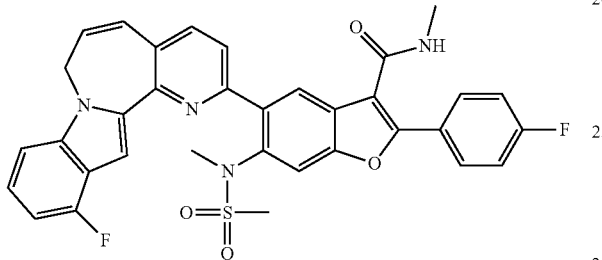

Step 1—Synthesis of 5-(5-allyl-6-chloropyridin-2-yl)-2-(4-fluorophenyl)-N-methyl-6-(N-methylmethylsulfonamido)benzofuran-3-carboxamide

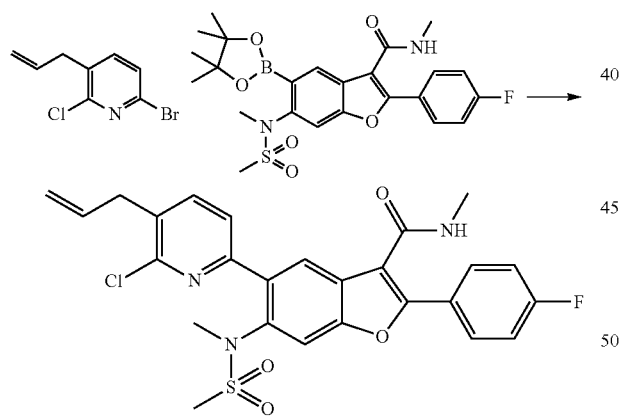

To a degassed solution of chloride (250 mg, 1.08 mmol), boronic ester (551 mg, 1.08 mmol) and Cs$_2$CO$_3$ (701 mg, 2.15 mmol) in 1,4-dioxane (5 mL) and H$_2$O (0.25 mL) was added 1,1'-bis(di-tert-butylphosphino)ferrocene palladium dichloride (70 mg, 0.11 mmol) under nitrogen atmosphere. The reaction mixture was stirred at 80° C. for 2.5 h, then cooled, filtered to remove inorganic solids and concentrated. The residue was purified on silica gel eluting with 0-100% acetone/hexane to give 5-(5-allyl-6-chloropyridin-2-yl)-2-(4-fluorophenyl)-N-methyl-6-(N-methylmethylsulfonamido)benzofuran-3-carboxamide (510 mg, 90% yield). MS (M+H)$^+$: 527.

Step 2—Synthesis of 1-allyl-4-fluoro-2-(4,4,5,5-tetramethyl-1,3,2-dioxaborolan-2-yl)-1H-indole

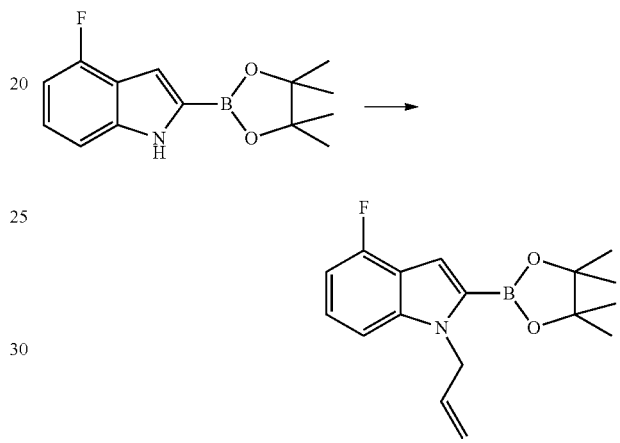

The indole (500 mg, 1.92 mmol) was added to a slurry of NaH (115 mg, 2.87 mmol, 60%) in DMF (6 mL) and cooled to 7° C. Allyl bromide (1.65 mL, 19.15) was added and the grey slurry was aged in ice bath for 1 hr. The mixture was warmed to room temperature and then another 0.5 mL allyl bromide and 188 mg NaH were added. The reaction was quenched with water and EtOAc, then a few drops 2N HCl was added until the solution was pH=10. The organic was washed with brine, dried over MgSO$_4$ and concentrated to oil. The oil was purified on silica gel eluting with 0-40% acetone/hexane and isolated 1-allyl-4-fluoro-2-(4,4,5,5-tetramethyl-1,3,2-dioxaborolan-2-yl)-1H-indole (576 mg, 10% yield).

Step 3—Synthesis of 5-(5-allyl-6-(1-allyl-4-fluoro-1H-indol-3-yl)pyridin-2-yl)-2-(4-fluorophenyl)-N-methyl-6-(N-methylmethylsulfonamido)benzofuran-3-carboxamide

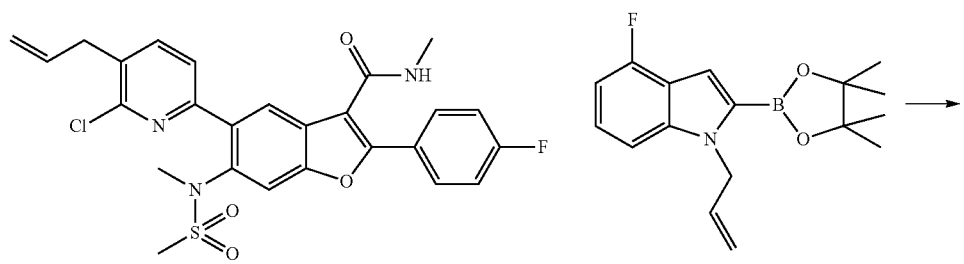

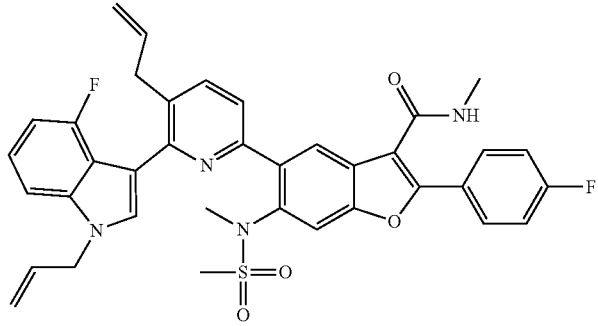

To a degassed solution of chloride (268 mg, 0.51 mmol), boronic ester (153 mg, 0.51 mmol) and $Cs_2CO_3$ (331 mg, 1.02 mmol) in 1,4-dioxane (5 mL) and $H_2O$ (0.25 mL) was added 1,1'-bis(di-tert-butylphosphino)ferrocene palladium dichloride (33 mg, 0.051 mmol) under nitrogen atmosphere. The reaction mixture was stirred at 70° C. for 2 h, then cooled and concentrated. The mixture was redissolved in DCM, washed with water and purified on silica gel eluting with 0-40% acetone/hexane to give 5-(5-allyl-6-(1-allyl-4-fluoro-1H-indol-3-yl)pyridin-2-yl)-2-(4-fluorophenyl)-N-methyl-6-(N-methylmethylsulfonamido)benzofuran-3-carboxamide (180 mg, 53% yield). MS (M+H)+: 666.

Step 4—Synthesis of 5-(12-fluoro-7H-pyrido[2',3':3,4]azepino[1,2-a]indol-2-yl)-2-(4-fluorophenyl)-N-methyl-6-(N-methylmethylsulfonamido)benzofuran-3-carboxamide

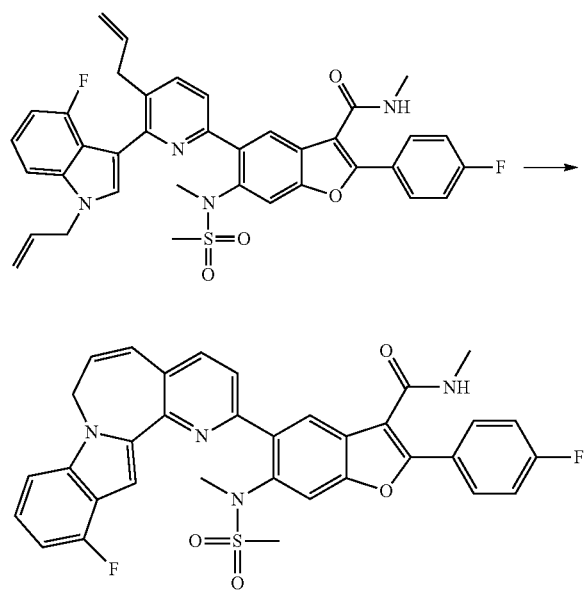

Benzylidene-bis-(tricyclohexylphosphino)dichlororuthenium (1.2 mg, 1.5 umol) was dissolved in 1 mL DCM, degassed with subsurface $N_2$ sparge and added by syringe to a similarly degassed 1 mL DCM solution of the diallyl compound and aged for 16 hours. The reaction was purified on a prep plate with 60% EtOAc/hexane to obtain 5-(12-fluoro-7H-pyrido[2',3':3,4]azepino[1,2-a]indol-2-yl)-2-(4-fluorophenyl)-N-methyl-6-(N-methylmethylsulfonamido)benzofuran-3-carboxamide (7 mg, 37% yield). MS (M+H)+: 624.

Example 99

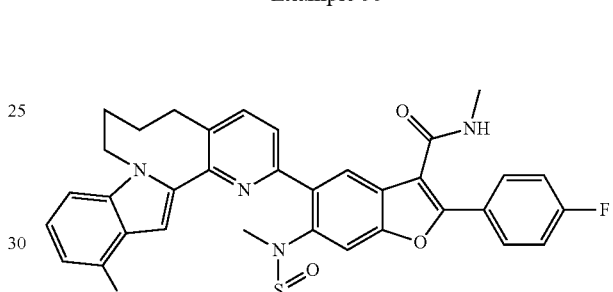

Step 1—Synthesis of (E)-3-(4-((tert-butyldimethylsilyl)oxy)but-1-en-1-yl)-2,6-dichloropyridine

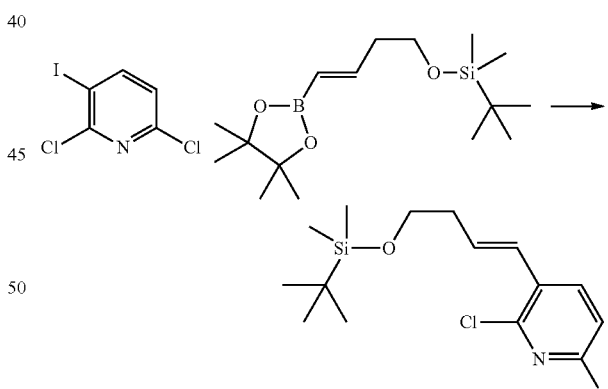

To a degassed solution of iodide (2.0 g, 7.30 mmol), boronic ester (2.70 mL, 7.30 mmol) and 1,1'-bis(di-tert-butylphosphino)ferrocene palladium dichloride (238 mg, 0.365 mmol) was added degassed aq. $K_3PO_4$ (22 mL, 22.0 mmol, 1M). The reaction mixture was stirred at room temperature for 16 h. The mixture was concentrated, diluted with EtOAc and the aqueous layer was cut. The organic layer was dried over $Mg_2SO_4$ and concentrated to a black oil. The mixture was purified on silica with DCM to obtain (E)-3-(4-((tert-butyldimethylsilyl)oxy)but-1-en-1-yl)-2,6-dichloropyridine (2.5 g, 100% yield). MS (M+H)+: 331.

193

Step 2—Synthesis of 4-(2,6-dichloropyridin-3-yl)butan-1-ol

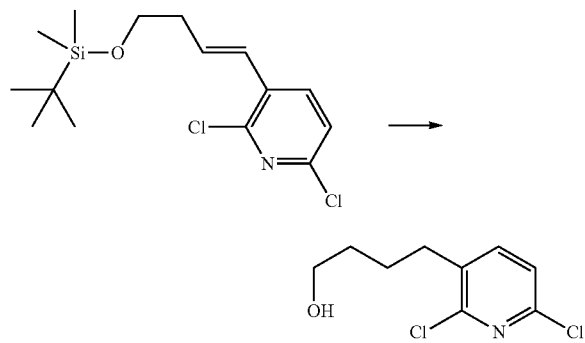

The alkene (100 mg, 0.301 mmol) was dissolved in MeOH (5 mL). The flask was evacuated and backfilled with N₂ three times. Pt/C (12 mg, 10 wt %) was added and the flask was evacuated, backfilled with N₂ three times, then evacuated and backfilled with H₂ from a balloon and aged for 2 hours. The mixture was filtered over celite, washed with methanol, and then most of the methanol was removed. HCl (1 mL, 4M in IPA) was added and the yellow solution was aged 10 minutes and then concentrated to give 4-(2,6-dichloropyridin-3-yl)butan-1-ol (45 mg, 68% yield). MS (M+H)⁺: 219.

Step 3—Synthesis of 5-(6-chloro-5-(4-hydroxybutyl)pyridin-2-yl)-2-(4-fluorophenyl)-N-methyl-6-(N-methylmethylsulfonamido)benzofuran-3-carboxamide

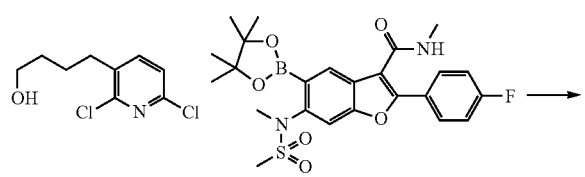

194

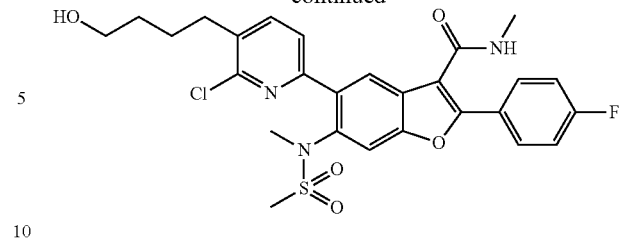

A degassed solution of chloride (45 mg, 0.175 mmol), boronic ester (106 mg, 0.201 mmol) Cs₂CO₃ (229 mg, 0.702 mmol) and Xphos pre-catalyst (16 mg, 0.018 mmol) in 1,4-dioxane (2 mL) and H₂O (0.25 mL) was heated at 70° C. for 16 h. Upon cooling the aqueous portion was removed and the organic portion was concentrated and purified on silica gel eluting with 0-10% MeOH/DCM to give 5-(6-chloro-5-(4-hydroxybutyl)pyridin-2-yl)-2-(4-fluorophenyl)-N-methyl-6-(N-methylmethylsulfonamido)benzofuran-3-carboxamide (79 mg, 80% yield). MS (M+H)⁺: 559.

Step 4—Synthesis of 5-(6-(4-fluoro-1H-indol-2-yl)-5-(4-hydroxybutyl)pyridin-2-yl)-2-(4-fluorophenyl)-N-methyl-6-(N-methylmethylsulfonamido)benzofuran-3-carboxamide

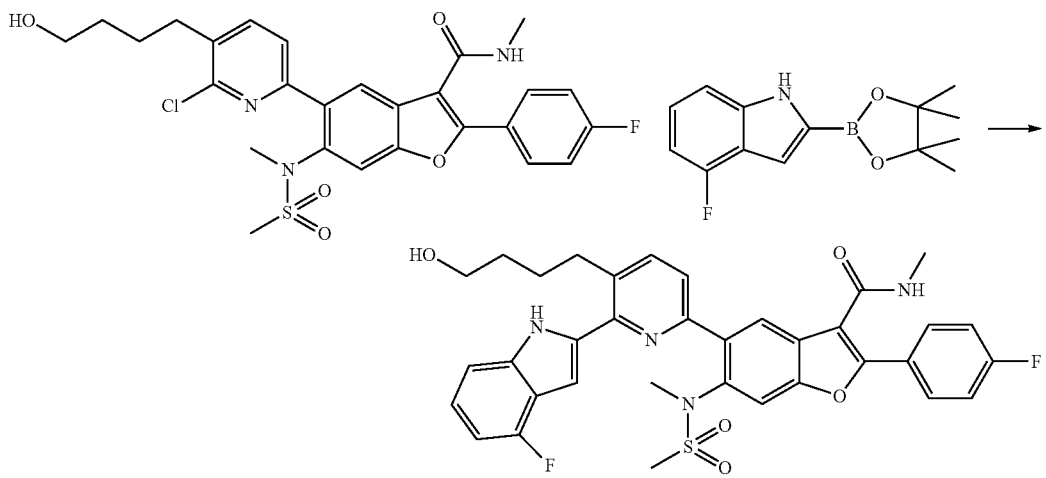

To a degassed solution of chloride (74 mg, 0.13 mmol), boronic ester (35 mg, 0.13 mmol) and Cs₂CO₃ (86 mg, 0.26 mmol) in 1,4-dioxane (5 mL) and H₂O (0.25 mL) was added 1,1'-bis(di-tert-butylphosphino)ferrocene palladium dichloride (9 mg, 0.013 mmol) under nitrogen atmosphere. The reaction mixture was stirred at 70° C. for 2 h, at which point another 8 mg catalyst and 34 mg boronate was added and the reaction aged at 70° C. for 16 h. The mixture was cooled, diluted with EtOAc, washed with water, dried over MgSO₄ and purified on silica gel eluting with 0-5% MeOH/DCM to give 5-(6-(4-fluoro-1H-indol-2-yl)-5-(4-hydroxybutyl)pyridin-2-yl)-2-(4-fluorophenyl)-N-methyl-6-(N-methylmethylsulfonamido)benzofuran-3-carboxamide (45 mg, 52% yield). MS (M+H)⁺: 658.

Step 5—Synthesis of 5-(13-fluoro-5,6,7,8-tetrahydropyrido[2',3':3,4]azocino[1,2-a]indol-2-yl)-2-(4-fluorophenyl)-N-methyl-6-(N-methylmethylsulfonamido)benzofuran-3-carboxamide

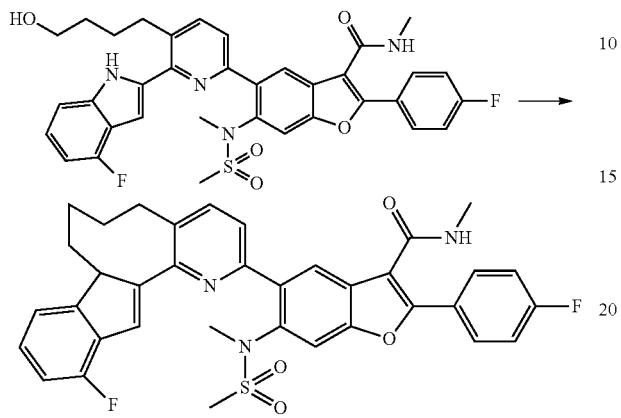

The alcohol (44 mg, 0.067 mmol) was dissolved in THF (2 mL) and then PPh$_3$ (18 mg, 0.067) and DIAD (14 mg, 0.067 mmol) were added and the mixture heated to 50° C. for 16 hours. Additional PPh$_3$ (18 mg, 0.067) and DIAD (28 mg, 0.134 mmol) were added in two more increments to get complete conversion. The reaction was then concentrated to oil and purified on silica eluting with 0-5-15% EtOAc/DCM, followed by a prep plate run in 25% acetone/hexane to obtain 5-(13-fluoro-5,6,7,8-tetrahydropyrido[2',3':3,4]azocino[1,2-a]indol-2-yl)-2-(4-fluorophenyl)-N-methyl-6-(N-methylmethylsulfonamido)benzofuran-3-carboxamide (20 mg, 46% yield). MS (M+H)$^+$: 640.

Example 100

Measuring Compound Inhibitory Potency

Measurement of inhibition by compounds was performed using the HCV replicon system. Several different replicons encoding different HCV genotypes or mutations were used. In addition, potency measurements were made using different formats of the replicon assay, including different ways of measurements and different plating formats. See Jan M. Vrolijk et al., *A replicons-based bioassay for the measurement of interferons in patients with chronic hepatitis C*, 110 J. VIROLOGICAL METHODS 201 (2003); Steven S. Carroll et al., *Inhibition of Hepatitis C Virus RNA Replication by 2'-Modified Nucleoside Analogs*, 278 (14) J. BIOLOGICAL CHEMISTRY 11979 (2003). However, the underlying principles are common to all of these determinations, and are outlined below.

Stable neomycin phosphotransferase encoding replicons-harboring cell lines were used, so all cell lines were maintained under G418 selection prior to the assay. Potency was deteremined using a cell ELISA assay with an antibody to the replicons encoded NS3/4a protease. See Caterina Trozzi et al., *In Vitro Selection and Characterization of Hepatitis C Virus Serine Protease Variants Resistant to an Active-Site Peptide Inhibitor*, 77 (6) J. Virol. 3669 (2003). To initiate an assay, replicon cells were plated in the presence of a dilution series of test compound in the absence of G418. Typically, the assays were performed in a 96-well plate formate for manual operation, or a 384-well plate format for automated assay.

Replicon cells and compound were incubated for 96 hours. At the end of the assay, cells were washed free of media and compound, and the cells were then lysed. RNA was quantified indirectly through detection of replicon-encoded NS3/4A protein levels, through an ELISA-based assay with an antibody specific for NS3/4A. IC$_{50}$ determinations were calculated as a percentage of a DMSO control by fitting the data to a four-parameter fit function and the data obtained for genotypes 1a and 1b using this method is provided in the table below.

TABLE 1

| Compound No. | 1a IC$_{50}$ (nM) | 1b IC$_{50}$ (nM) |
|---|---|---|
| 1 | 3.784 | 4.674 |
| 2 | 2.093 | 3.902 |
| 3 | 7.944 | 6.694 |
| 4 | 6.989 | 7.297 |
| 5 | 3.859 | 2.299 |
| 6 | 16.8 | 10.16 |
| 7 | 17.61 | 6.785 |
| 8 | 580.5 | 121.6 |
| 9 | 38.18 | 31.24 |
| 10 | 9.437 | 10.66 |
| 11 | 2121 | 661.1 |
| 12 | 4.59 | 10.64 |
| 13 | 17.27 | 16.5 |
| 14 | 26.39 | 24.33 |
| 15 | 3.409 | 5.087 |
| 16 | 27.02 | 14.6 |
| 17 | 372.6 | 197.4 |
| 18 | 5479 | 296 |
| 19 | 56.94 | 52.33 |
| 20 | 680.5 | 129.3 |
| 21 | 149.2 | 34.33 |
| 22 | 1454 | 162.7 |
| 23 | 212.3 | 83.2 |
| 24 | 19.97 | 18.86 |
| 25 | 287.2 | 99.41 |
| 26 | 69.35 | 84.39 |
| 27 | 9.129 | 11.1 |
| 29 | 13.54 | 15.49 |
| 30 | 2.489 | 3.805 |
| 31 | 4.534 | 4.642 |
| 32 | 10.55 | 3.952 |
| 33 | 170.5 | 23.61 |
| 34 | 5.385 | 4.657 |
| 35 | 3.28 | 5.194 |
| 36 | 10.33 | 10.25 |
| 37 | 9.827 | 14.23 |
| 38 | 21.82 | 17.03 |
| 39 | 2.71 | 2.83 |
| 40 | 16.56 | 17.07 |
| 41 | 19.27 | 6.325 |
| 42 | 3.101 | 5.474 |
| 43 | 1.735 | 3.701 |
| 44 | 1.765 | 1.867 |
| 45 | 4.288 | 8.718 |
| 46 | 2.232 | 2.401 |
| 47 | 14.54 | 8.465 |
| 48 | 1.716 | 2.642 |
| 50 | 1.154 | 3.36 |
| 51 | 4.49 | 3.424 |
| 52 | 3.346 | 2.319 |
| 53 | 8.069 | 4.028 |
| 54 | 1.56 | 2.25 |
| 55 | 0.9708 | 1.806 |
| 56 | 3.404 | 1.997 |
| 57 | 8.158 | 3.392 |
| 58 | 1.52 | 1.706 |
| 59 | 5.446 | 2.904 |
| 60 | 5 | 10.11 |
| 61 | 2.275 | 7.801 |
| 62 | 2.687 | 2.548 |
| 63 | 4.336 | 3.281 |
| 64 | 23.21 | 9.086 |
| 65 | 3.622 | 3.957 |

TABLE 1-continued

| Compound No. | 1a IC$_{50}$ (nM) | 1b IC$_{50}$ (nM) |
|---|---|---|
| 66 | 13.02 | 11.44 |
| 67 | 12.48 | 16.38 |
| 68 | 70.9 | 60.62 |
| 69 | 2.298 | 2.949 |
| 70 | 55.35 | 79.95 |
| 71 | 41.69 | 42.2 |
| 72 | 3.71 | 4.295 |
| 73 | 2.014 | 2.777 |
| 74 | 8.198 | 11.45 |
| 75 | 46.66 | 43.17 |
| 76 | 999.6 | 193.6 |
| 77 | 27.94 | 4.025 |
| 78 | 206.3 | 22.05 |
| 79 | 93.78 | 77.28 |
| 80 | 27.71 | 9.773 |
| 81 | 196.3 | 33.86 |
| 82 | 2.885 | 5.542 |
| 83 | 1.488 | 3.439 |
| 84 | 4.283 | 6.407 |
| 85 | 2.993 | 3.287 |
| 86 | 1.907 | 3.053 |
| 87 | 7.689 | 7.286 |
| 88 | 8.728 | 9.433 |
| 89 | 2.12 | 5.486 |
| 90 | 7.234 | 2.787 |
| 91 | 27.551 | 9.23 |
| 92 | 46.471 | 2.55 |
| 94 | 34 | 10.84 |
| 95 | 8.911 | 7.525 |
| 96 | 7.893 | 3.179 |
| 97 | 10.73 | 9.982 |
| 98 | 4.173 | 8.646 |
| 99 | 6.498 | 7.168 |

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A compound having structural formula I:

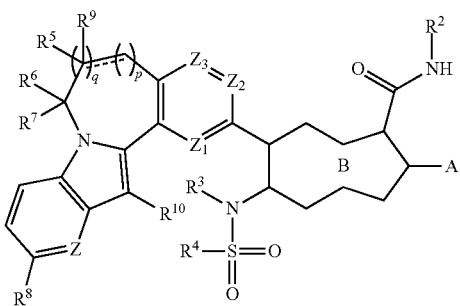

or a pharmaceutically acceptable salt thereof, wherein:
A is a $C_3$-$C_6$ cycloalkyl or an aromatic ring system selected from:
  (i) 5-6 membered monocyclic ring with 0, 1, 2 or 3 heteroatom ring atoms independently selected from N, S or O, optionally substituted with 1 or 2 substituents independently selected from $C_1$-$C_6$ alkyl, $C_1$-$C_6$ alkoxy, $C_1$-$C_6$ haloalkyl, cyano, oxo, halo, —O—$C_1$-$C_6$ haloalkyl, $C_1$-$C_6$ hydroxyalkyl, $C_3$-$C_6$ cycloalkyl, phenyl, pyrrolidinyl, and —O—$C_3$-$C_6$ cycloalkyl; and
  (ii) 8-10 membered bicyclic rings with 2 or 3 heteroatom ring atoms selected from N and O;

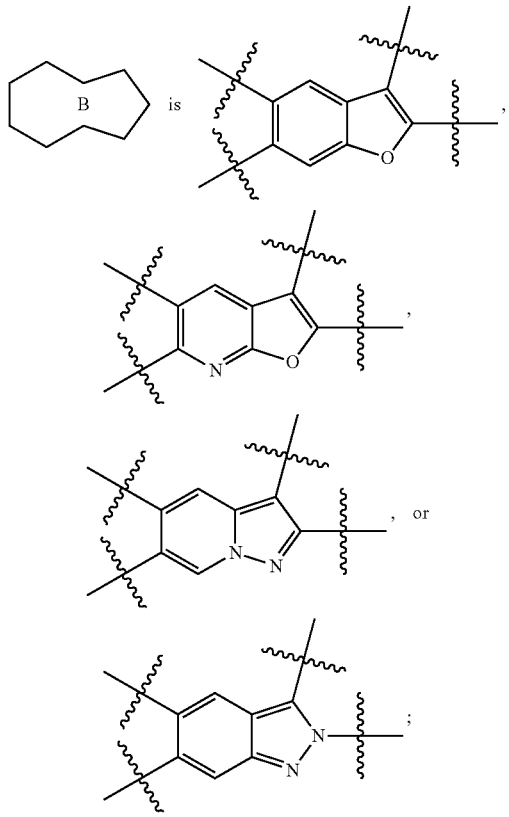

Z is N or $CR^a$;
$Z_1$, $Z_2$ and $Z_3$ are independently selected from CH and N, wherein 1 or 2 of $Z_1$, $Z_2$ and $Z_3$ are N;
p is 0, 1, or 2;
q is 0 or 1;
$R^2$ is hydrogen, $C_1$-$C_6$ alkyl or —O—$C_1$-$C_6$ alkyl;
$R^3$ is hydrogen or $C_1$-$C_6$ alkyl;
$R^4$ is $C_1$-$C_6$ alkyl or —O—$C_1$-$C_6$ alkyl;
$R^5$ is hydrogen, $C_1$-$C_6$ alkyl, —OH, halo, or a 4- to 7-membered heterocycloalkyl substituted with halo;
$R^9$ is hydrogen; or
$R^5$ and $R^9$ together with the C to which they are attached form a $C_3$-$C_6$ cycloalkyl,
$R^6$ is hydrogen, —OH, $C_1$-$C_6$ alkyl, $C_1$-$C_6$ haloalkyl, $C_1$-$C_6$ hydroxyalkyl, —$CH_2SO_2CH_3$, —$C_1$-$C_6$-(4- to 6-membered monocyclic heterocycloalkyl);
wherein the 4- to 6-membered monocyclic heterocycloalkyl is optionally substituted with one or two F substituents;
$R^7$ is hydrogen or $C_1$-$C_6$ alkyl;
or $R^6$ and $R^7$ together with the C to which they are attached form an oxo;
$R^8$ is hydrogen, halo or —$OR^b$;
$R^{10}$ is hydrogen or $C_1$-$C_6$ alkyl;
$R^a$ is hydrogen, halo, or cyano;
each $R^b$ is independently H or $C_1$-$C_6$ alkyl;

wherein
  when q is 0, p is 0 or 1;
  when q is 1 and p is 2, ----- is a single bond; and
  when ----- is a double bond, R⁷ and R⁹ are absent.

2. The compound of claim 1, wherein $R^2$ and $R^4$ are $C_1$-$C_6$ alkyl.

3. The compound of claim 1 or 2, wherein $R^2$, $R^3$ and $R^4$ are methyl.

4. The compound of any one of claims 1 to 3, wherein one of $R^a$ and $R^8$ is hydrogen.

5. The compound of any one of claims 1 to 4, wherein halo is F.

6. The compound of claim 1, or a pharmaceutically acceptable salt thereof, having the formula:

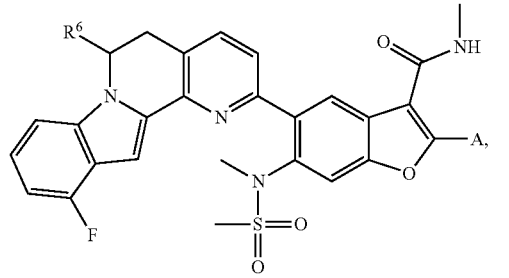
(Ia)

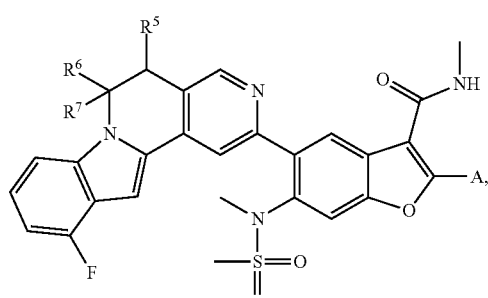
(Ib)

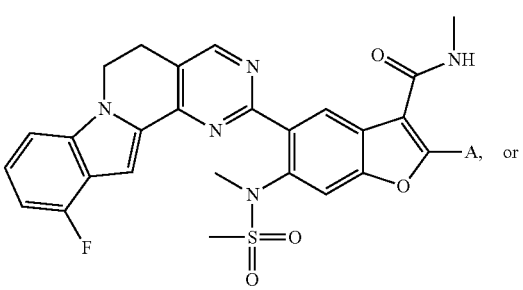
(Ic)

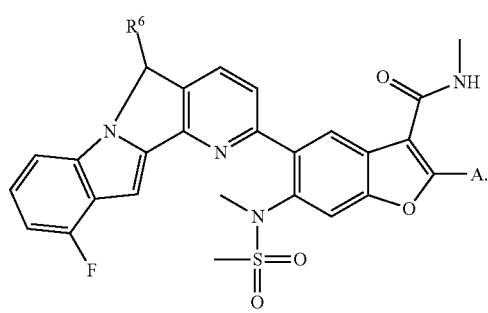
(Id)

7. The compound of claim 6 wherein $R^5$ is hydrogen or methyl;

$R^6$ is hydrogen, methyl, —CH₂OH, —CH₂CH₂OH, —CH₂SO₂CH₃,

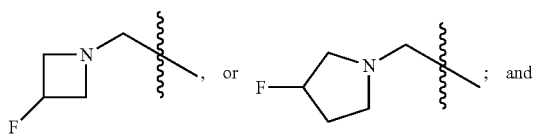 [SMILES: *CN1CC(F)C1 ; *CN1CCC(F)C1]

$R^7$ is hydrogen or methyl.

8. The compound of any one of claims 1 to 7, wherein A is $C_3$-$C_6$ cycloalkyl, or a 5-6 membered aromatic monocyclic ring with 0, 1, 2 or 3 heteroatom ring atoms selected from N and S, optionally substituted with 1 or 2 substituents independently selected from $C_1$-$C_6$ alkyl, $C_1$-$C_6$ alkoxy, $C_1$-$C_6$ haloalkyl, oxo, halo, and —O—$C_1$-$C_6$ haloalkyl.

9. The compound of any one of claims 1 to 7, wherein A is cyclopropyl,

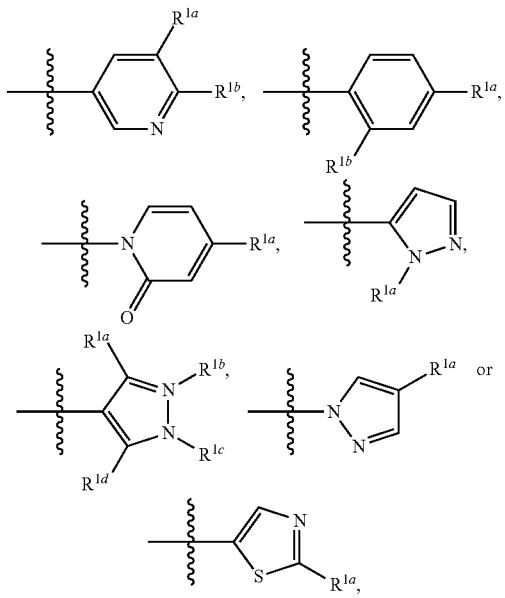

wherein $R^{1a}$, $R^{1b}$, $R^{1c}$ and $R^{1d}$ are independently selected from hydrogen, F, methyl, ethyl, hydroxymethyl, isopropyl, methoxy, ethoxy, —OCHF₂, —OCH₂CF₃, cyclopropyl, phenyl, pyrrolidinyl, —O-cyclopropyl, —CHF₂, cyano, —CF₃ and —CH₂CF₃.

10. The compound of claim 9, wherein A is

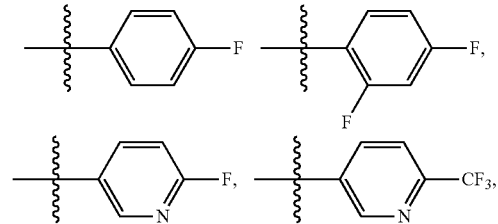

201
-continued
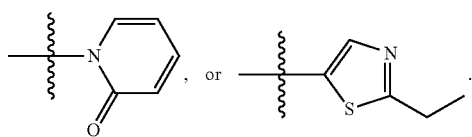
11. The compound of claim 1 which is any one of
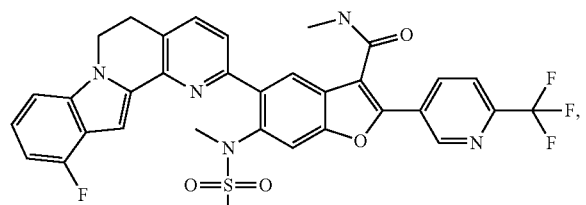
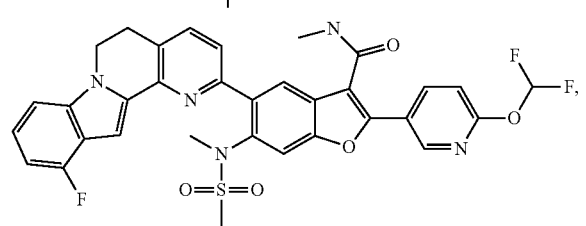
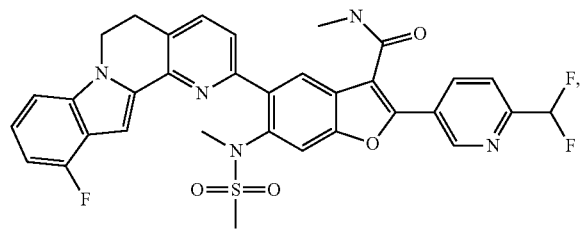
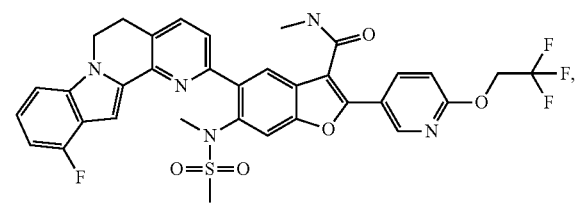
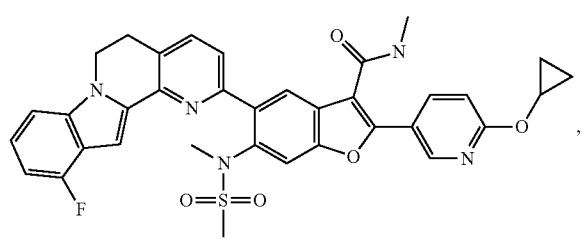
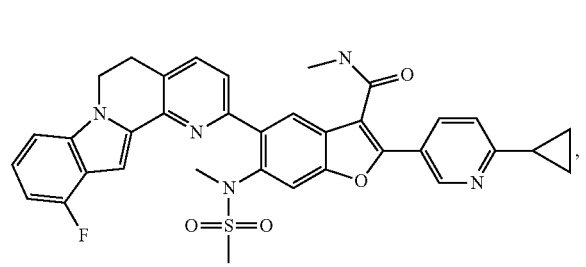
202
-continued
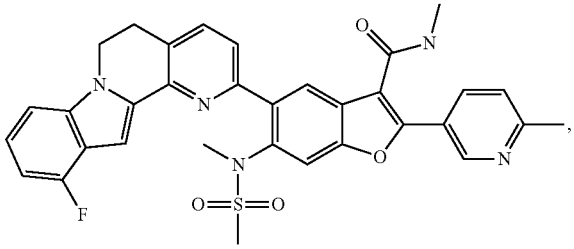
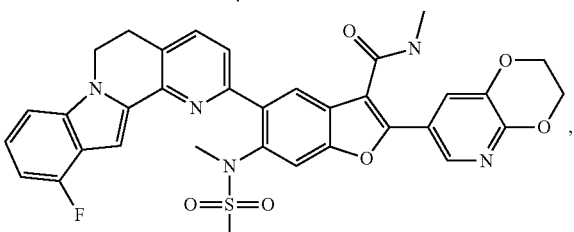
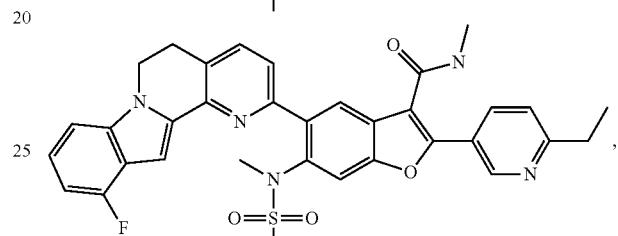
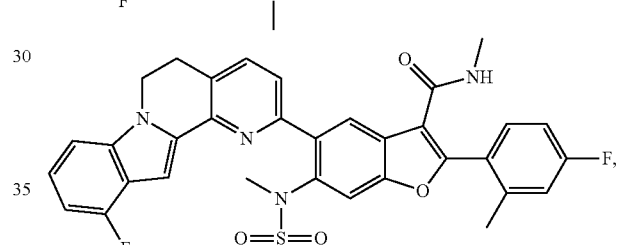
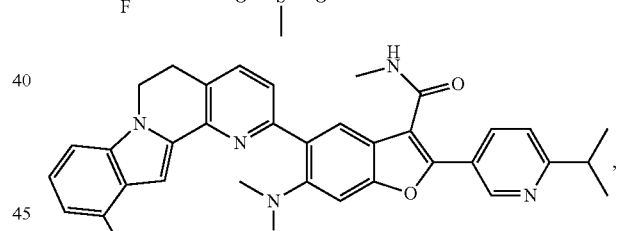
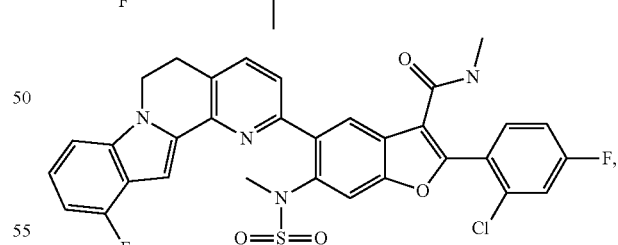
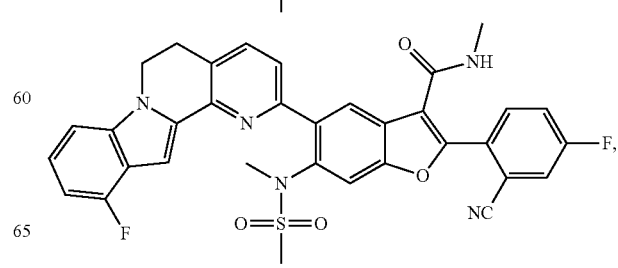

203
-continued

204
-continued

205
-continued
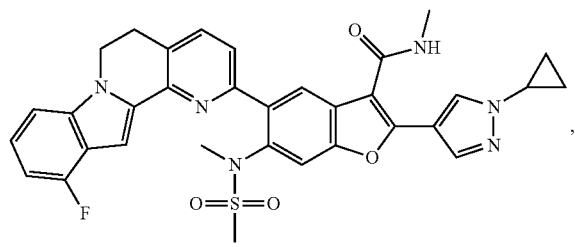
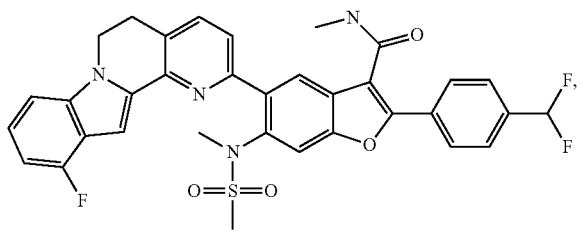
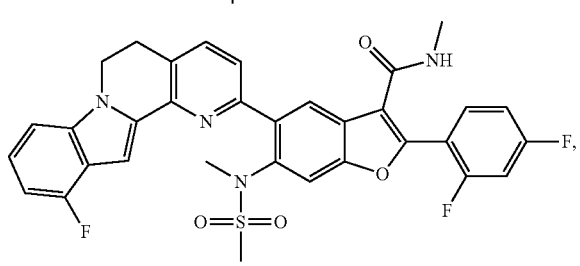
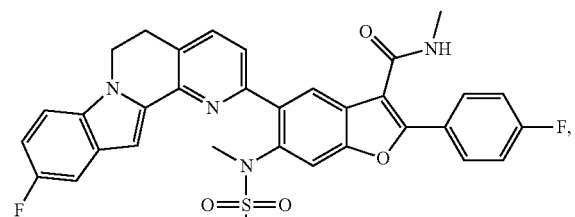
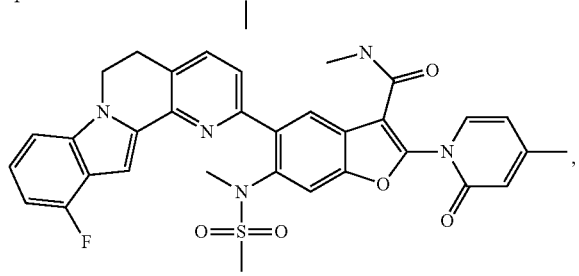
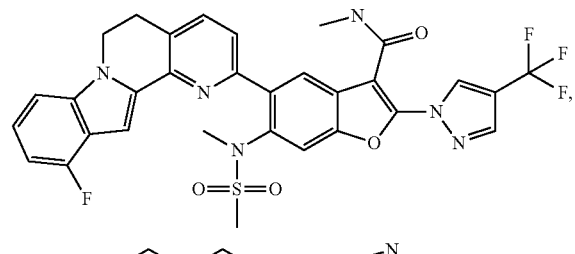
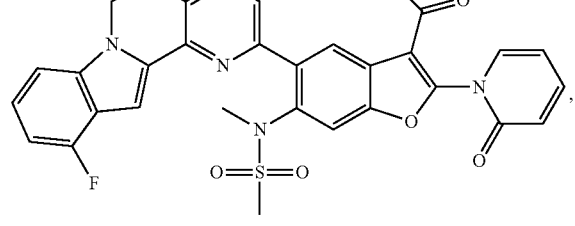
206
-continued
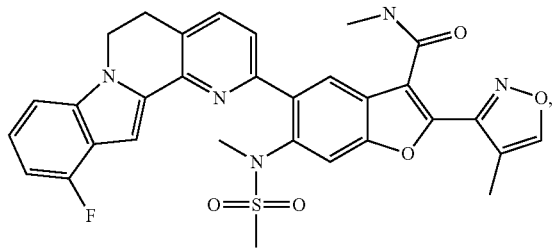
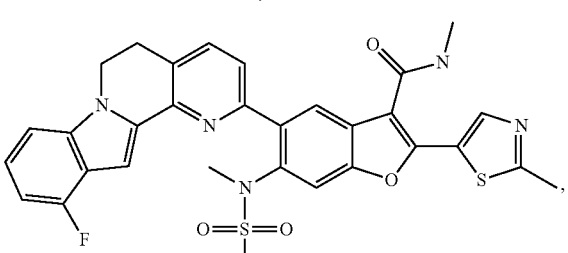
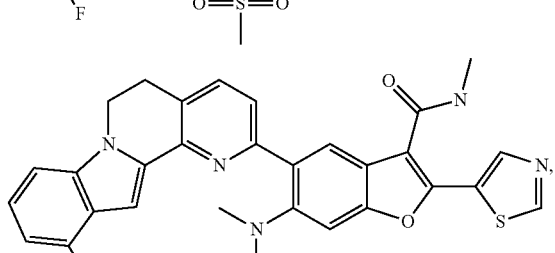
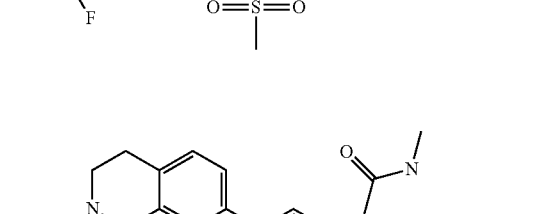
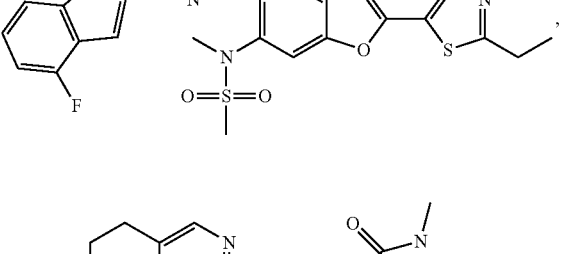
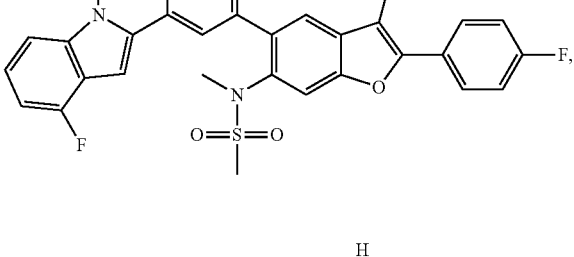
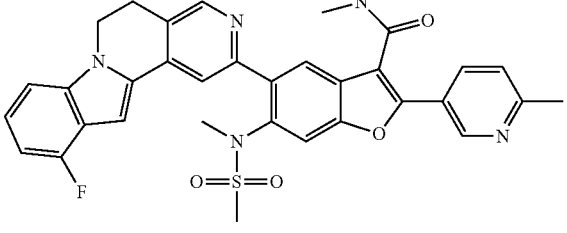

207
-continued
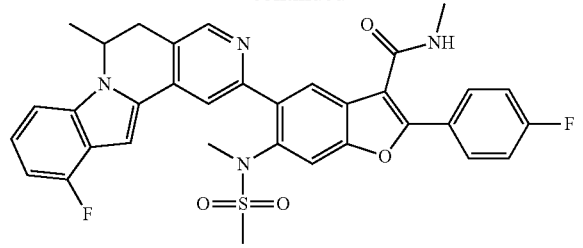
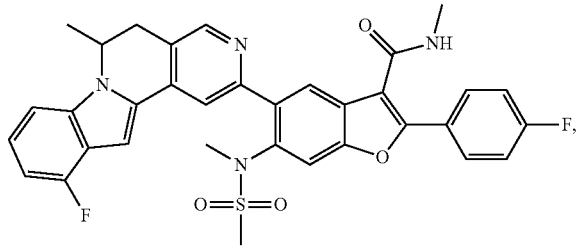
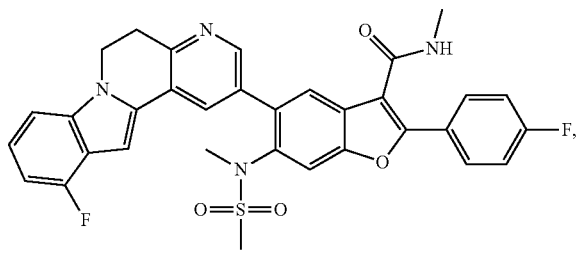
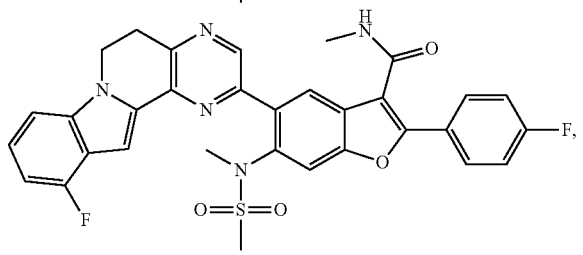
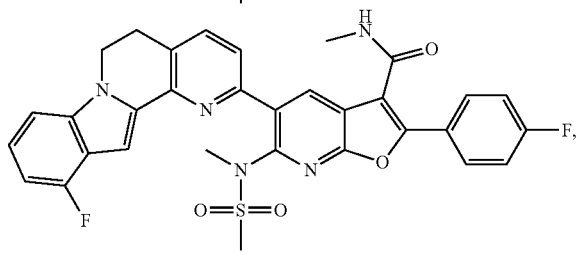
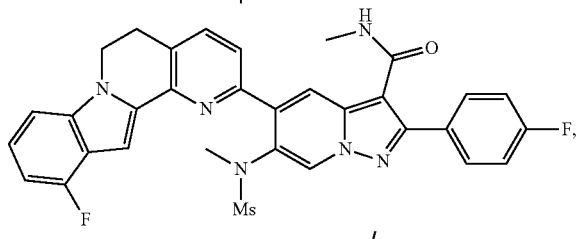
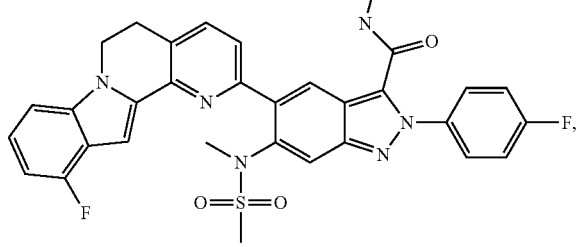
208
-continued
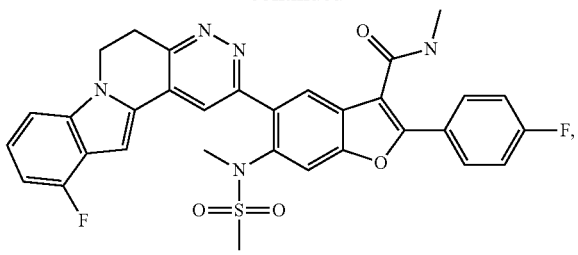
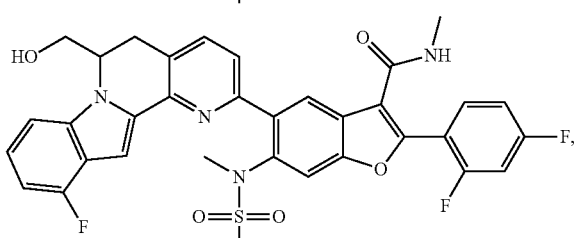
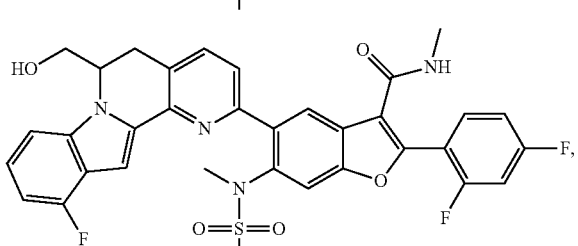
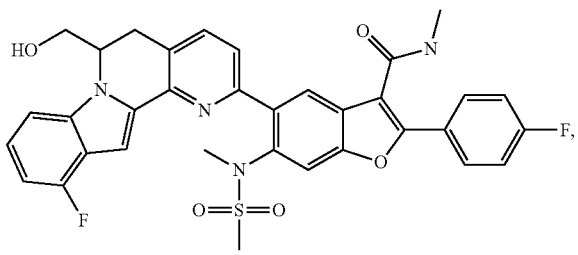
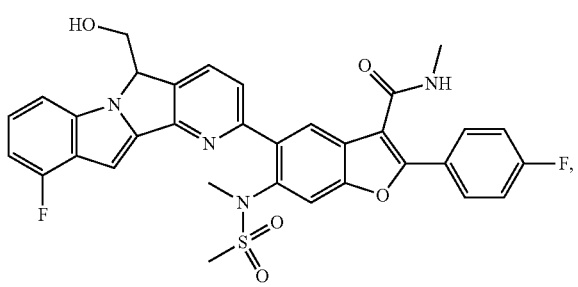
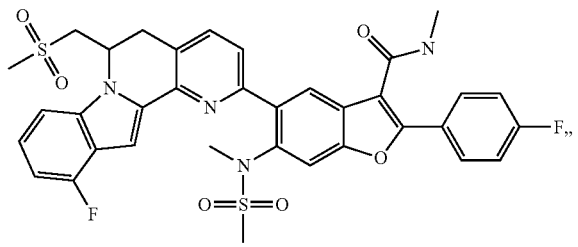

209
-continued
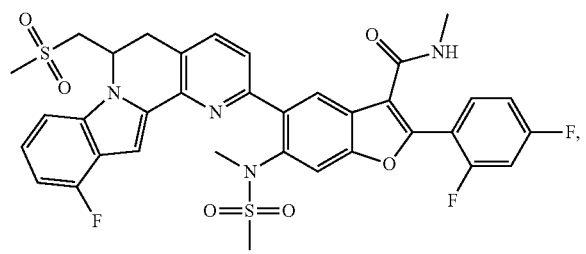
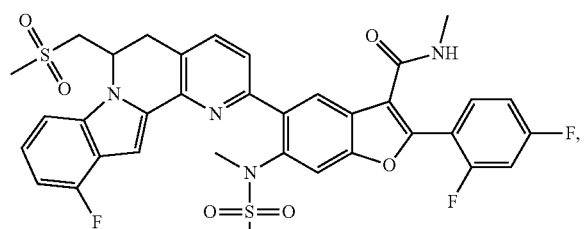
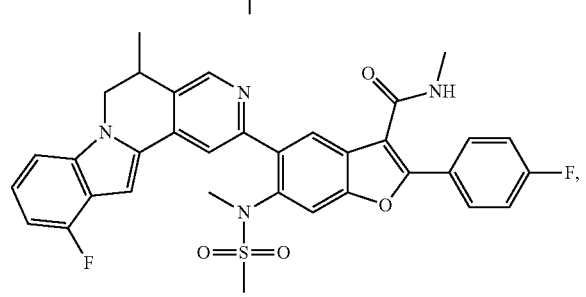
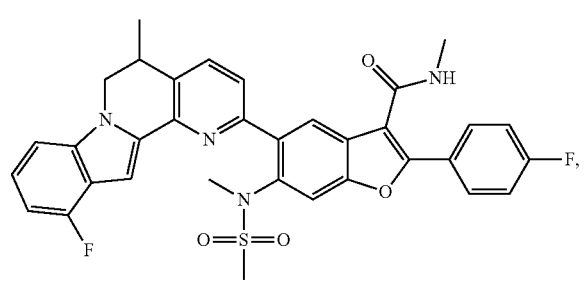
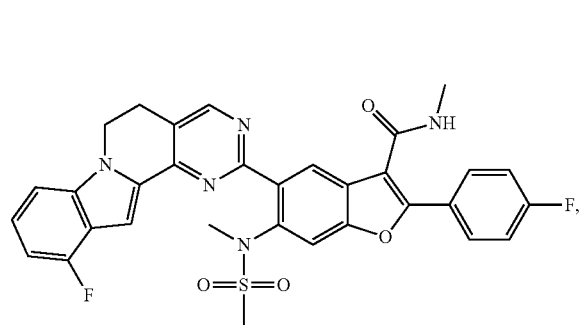
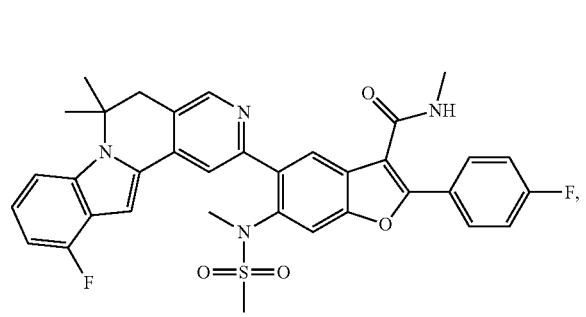
210
-continued
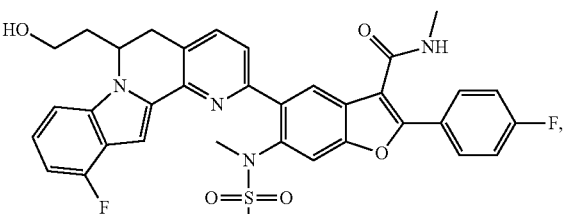
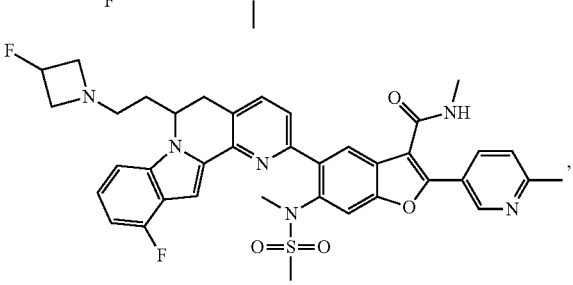
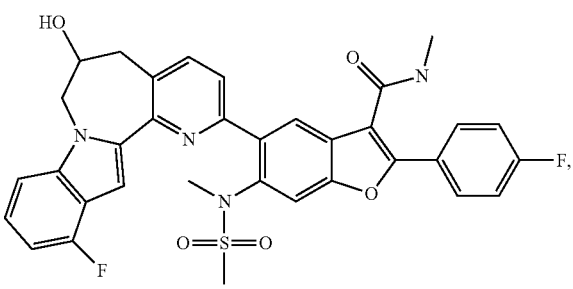
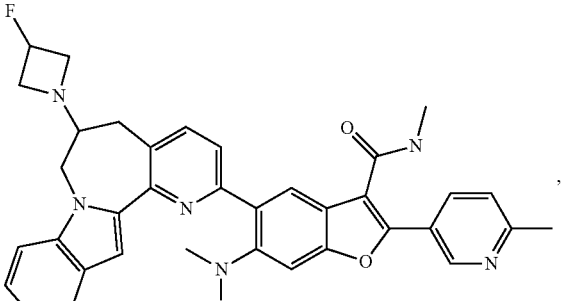
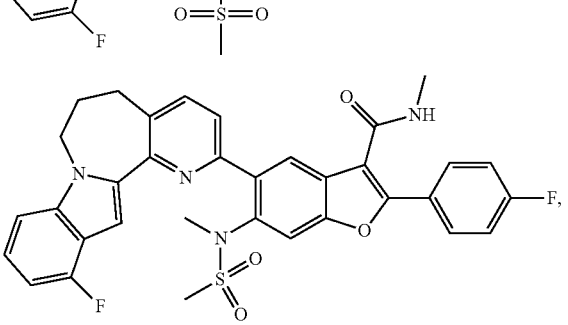
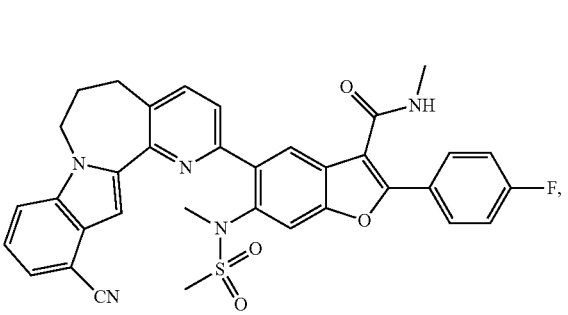

211
-continued
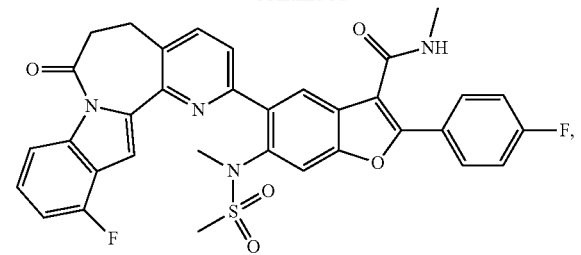
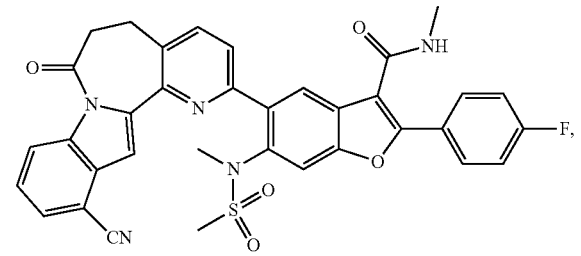
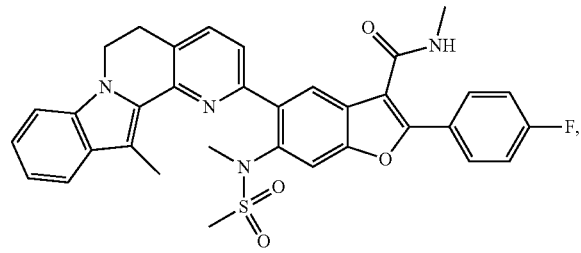 [SMILES: CNC(=O)c1c(-c2ccc(F)cc2)oc2cc(N(C)S(C)(=O)=O)c(-c3ccc4c(n3)-c3cc5c(F)cccc5n3CCCC4)cc12]
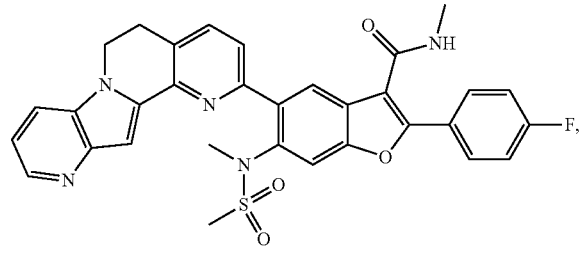
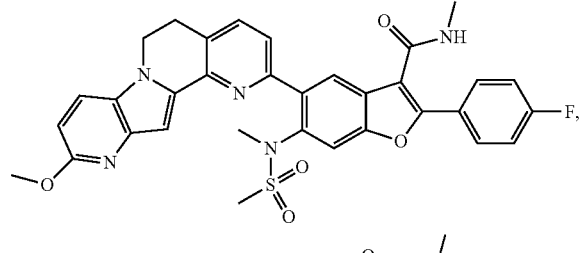
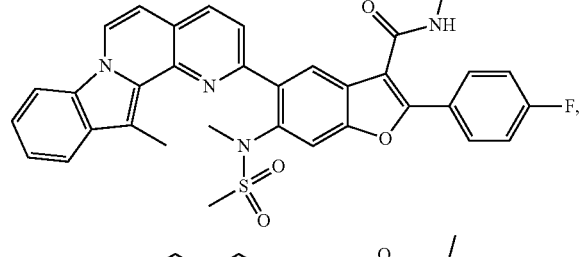
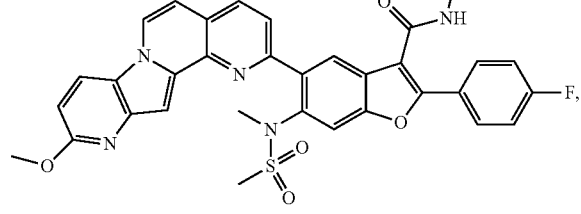
212
-continued
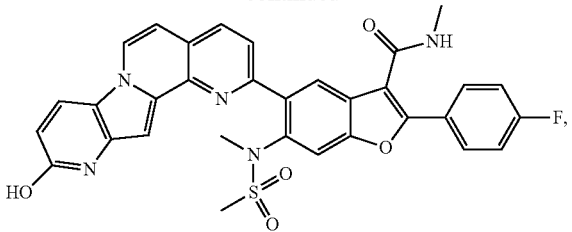
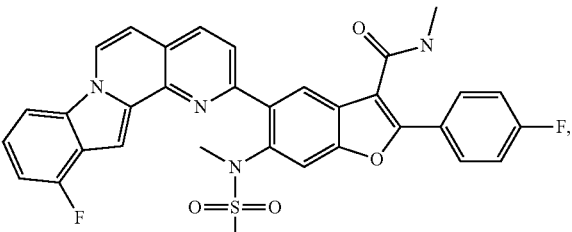
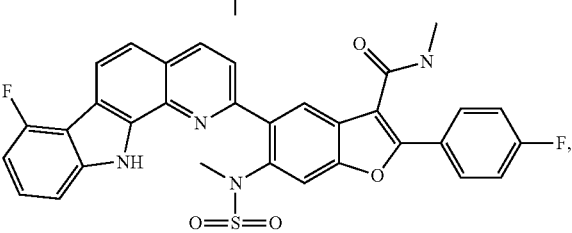
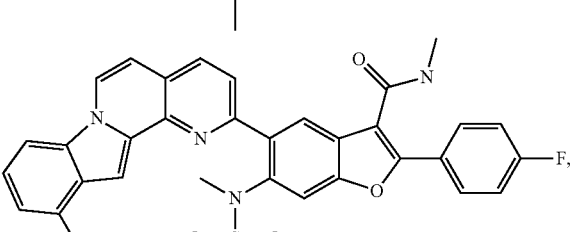
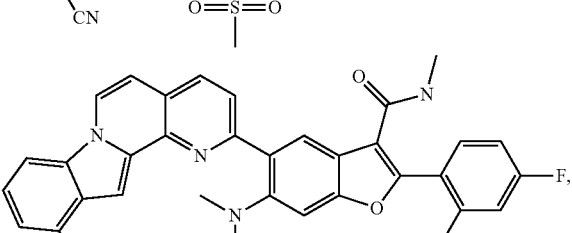
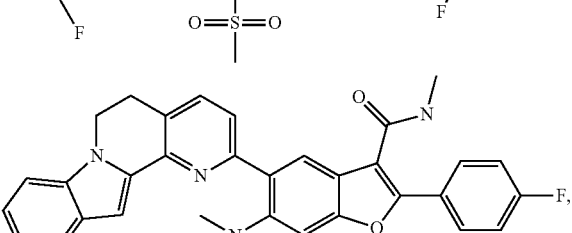
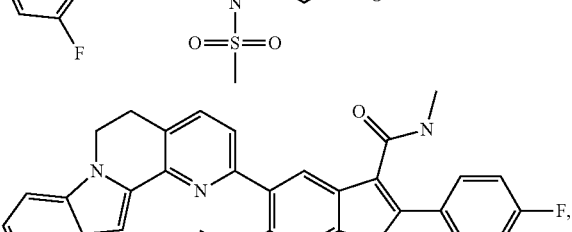

213
-continued
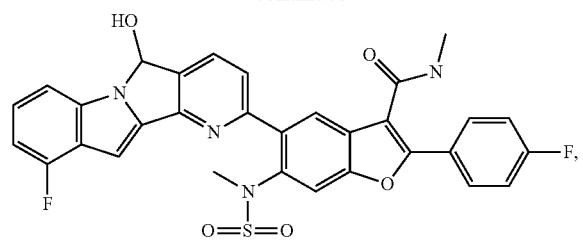
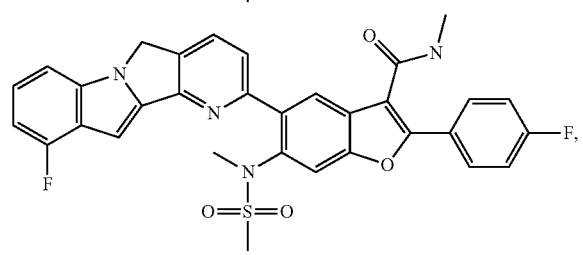
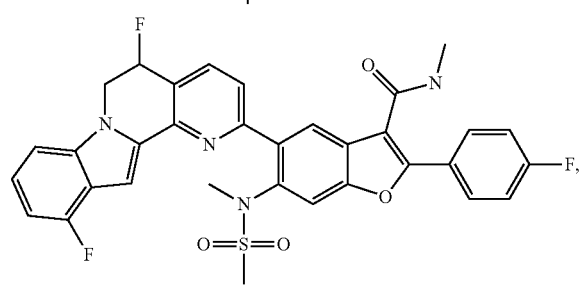
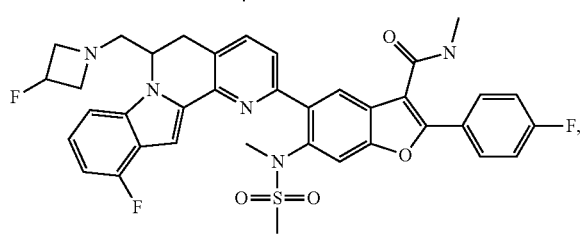
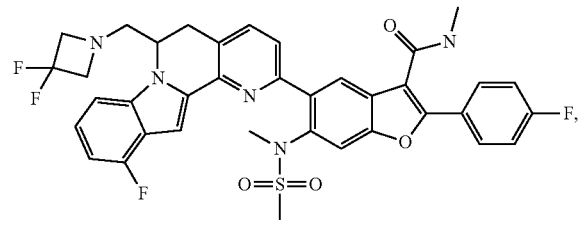
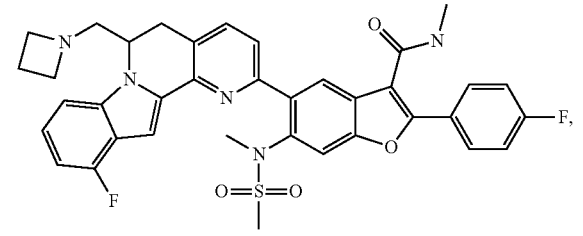
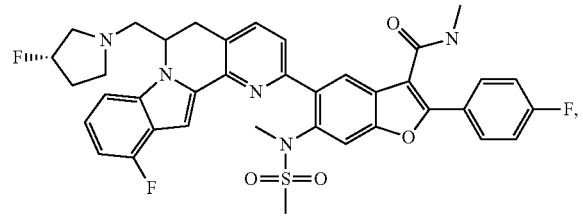
214
-continued
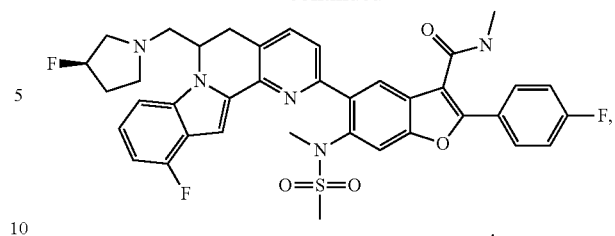
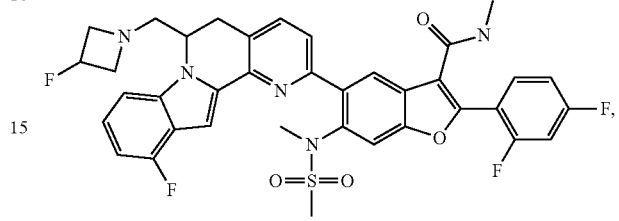
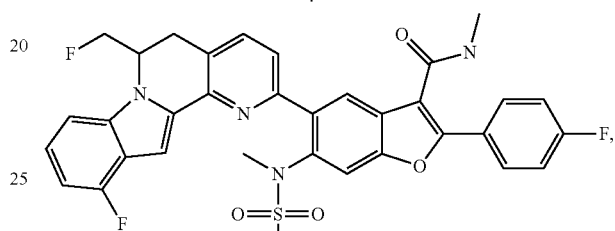
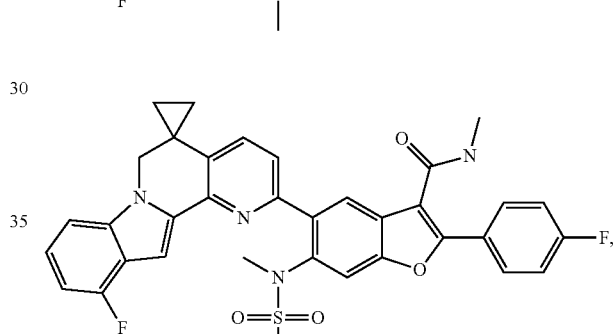
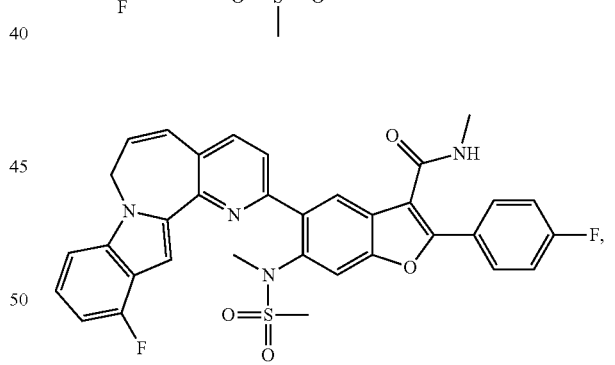
or a pharmaceutically acceptable salt thereof.

12. The compound of claim 1 which is any one of
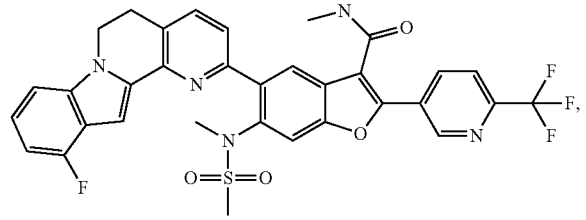
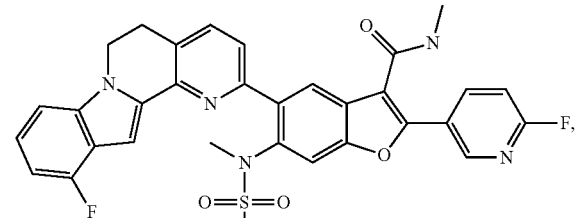
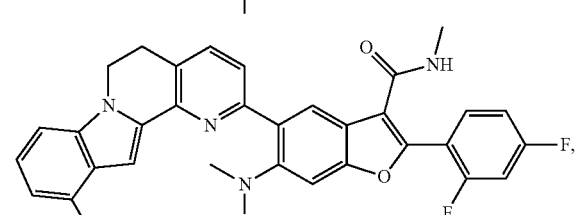
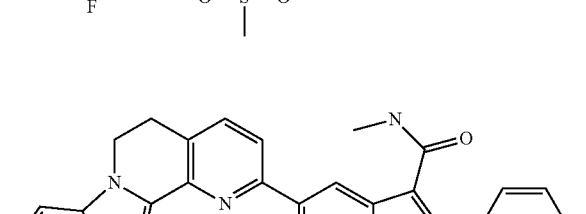
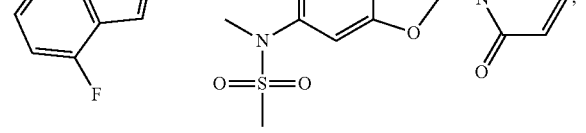
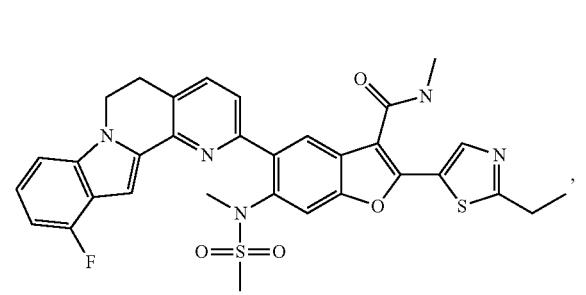
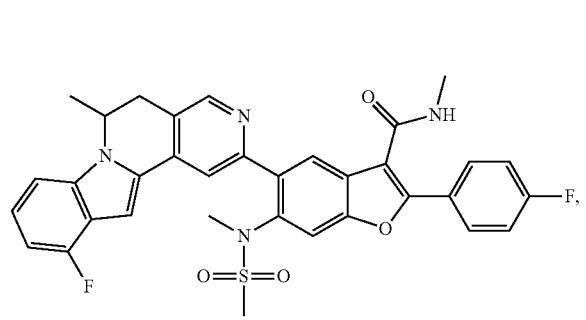
-continued
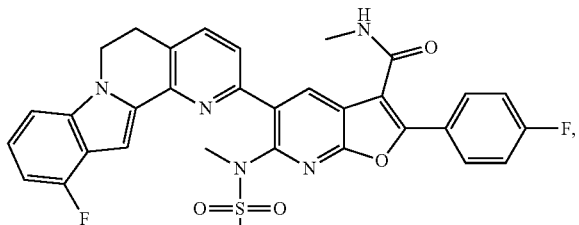
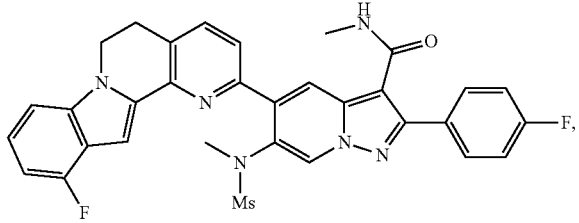
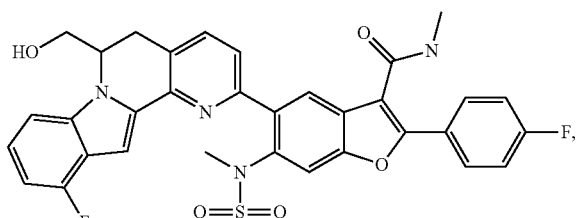
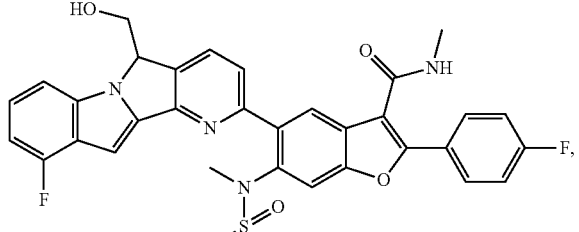
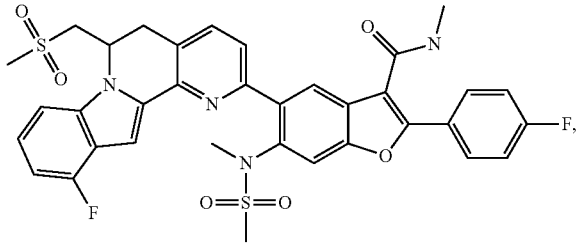
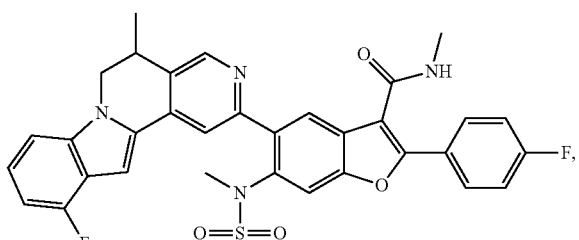

-continued

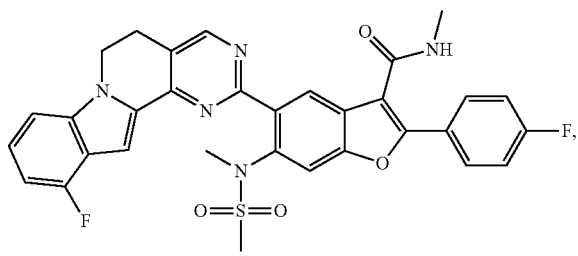

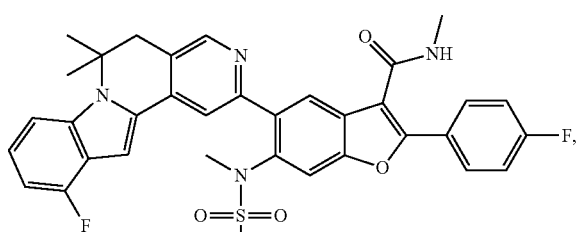

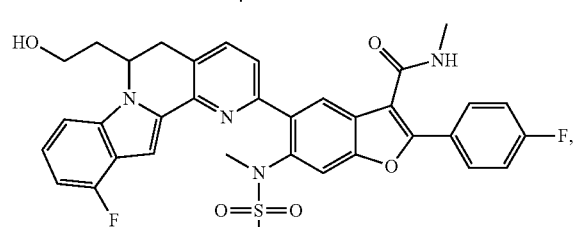

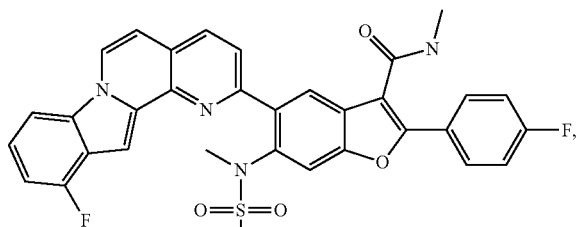

-continued

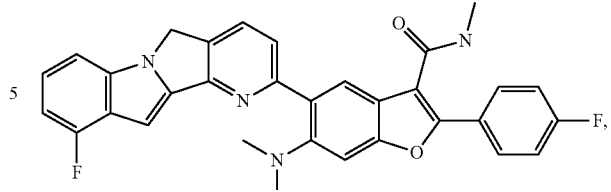

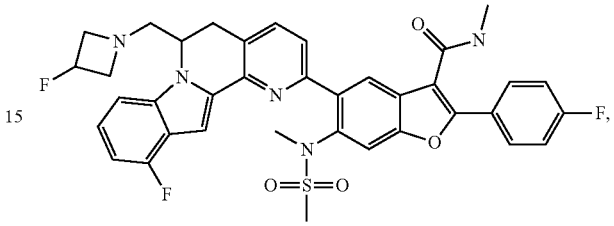

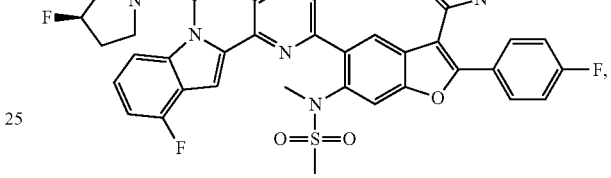

or a pharmaceutically acceptable salt thereof.

13. A pharmaceutical composition comprising (i) a pharmaceutically acceptable carrier and (ii) an effective amount of the compound of any one of claims 1-12 or a pharmaceutically acceptable salt thereof.

14. The pharmaceutical composition of claim 13, further comprising a second therapeutic agent selected from the group consisting of HCV antiviral agents, immunomodulators, and anti-infective agents.

15. The pharmaceutical composition of claim 14, wherein the second therapeutic agent is selected from the group consisting of HCV NS3 and NS3/4A protease inhibitors, HCV NS5A inhibitors and HCV NS5B polymerase inhibitors.

16. A method of treating a patient infected with HCV, the method comprising administering to the patient the compound of any one of claims 1 to 12, or a pharmaceutically acceptable salt thereof, in an amount effective to treat infection by HCV in the patient.

17. The method of claim 16, further comprising administering to said patient an effective amount of at least one second therapeutic agent selected from the group consisting of HCV NS3 and NS3/4A protease inhibitors, HCV NS5A inhibitors and HCV NS5B polymerase inhibitors.

\* \* \* \* \*